(12) United States Patent (10) Patent No.: US 8,703,778 B2
Ren et al. (45) Date of Patent: Apr. 22, 2014

(54) HETEROCYCLIC KINASE INHIBITORS

(75) Inventors: Pingda Ren, San Diego, CA (US); Yi Liu, San Diego, CA (US); Liansheng Li, San Diego, CA (US); Katrina Chan, San Diego, CA (US); Troy Edward Wilson, San Marino, CA (US)

(73) Assignee: Intellikine LLC, La Jolla, CA (US)

( * ) Notice: Subject to any disclaimer, the term of this patent is extended or adjusted under 35 U.S.C. 154(b) by 88 days.

(21) Appl. No.: 13/121,157

(22) PCT Filed: Sep. 28, 2009

(86) PCT No.: PCT/US2009/005380
§ 371 (c)(1),
(2), (4) Date: Aug. 2, 2011

(87) PCT Pub. No.: WO2010/036380
PCT Pub. Date: Apr. 1, 2010

(65) Prior Publication Data
US 2011/0281866 A1 Nov. 17, 2011

Related U.S. Application Data

(60) Provisional application No. 61/194,310, filed on Sep. 26, 2008.

(51) Int. Cl.
*A01N 43/90* (2006.01)
*A61K 31/519* (2006.01)
*C07D 487/00* (2006.01)

(52) U.S. Cl.
USPC ........................ 514/262.1; 544/262

(58) Field of Classification Search
None
See application file for complete search history.

(56) References Cited

U.S. PATENT DOCUMENTS

| | | | |
|---|---|---|---|
| 4,547,508 A | 10/1985 | Konz et al. | |
| 4,656,159 A | 4/1987 | McPherson et al. | |
| 4,704,381 A | 11/1987 | Schaumann et al. | |
| 4,795,627 A | 1/1989 | Fisher et al. | |
| 5,240,941 A | 8/1993 | Bruneau | |
| 5,294,612 A | 3/1994 | Bacon et al. | |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Karpeiskii, et. al.; Bioorganicheskaya Khimiya (1985), 11(8), 1097-104.*

Okada et al., "Essential role of phosphatidylinositol 3-kinase in insulin-induced glucose transport and antilipolysis in rat adipocytes", J. Biol. Chem., Feb. 4, 1994, vol. 269, No. 5, pp. 3568-3573.

(Continued)

*Primary Examiner* — Jeffrey H Murray
(74) *Attorney, Agent, or Firm* — Jones Day

(57) ABSTRACT

Provided herein are compounds of formula (I-A), (I-B), (I-C), or (I-D), pharmaceutical compositions comprising the compounds, and methods of use thereof. The compounds provided herein modulate kinase activity, including PI3 kinase activity, and are useful for treating diseases and conditions associated with kinase activity, including diseases and conditions associated with PI3 kinase activity.

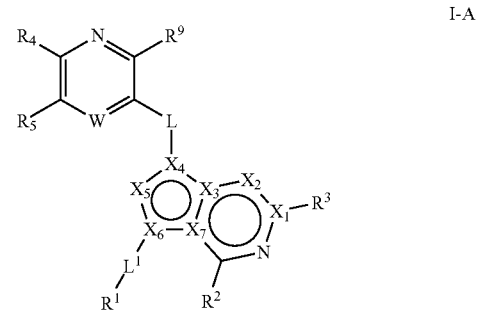

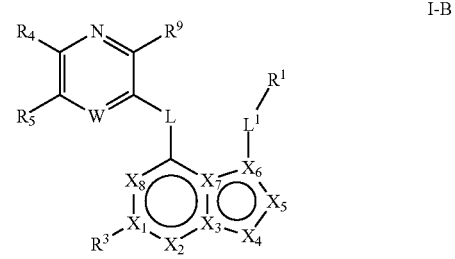

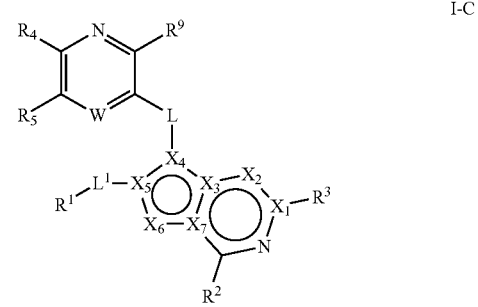

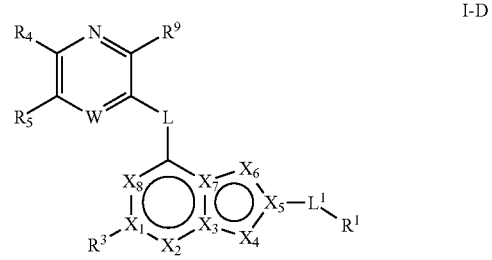

16 Claims, No Drawings

(56) References Cited

U.S. PATENT DOCUMENTS

| | | |
|---|---|---|
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,504,103 A | 4/1996 | Bonjouklian et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,106,146 B2 | 1/2012 | Benz et al. |
| 8,193,182 B2 | 6/2012 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |

(56) References Cited

U.S. PATENT DOCUMENTS

| | | |
|---|---|---|
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |

(56) References Cited

U.S. PATENT DOCUMENTS

| | | |
|---|---|---|
| 2012/0122838 A1 | 5/2012 | Ren et al. |
| 2012/0149701 A1 | 6/2012 | Ren et al. |
| 2012/0184568 A1 | 7/2012 | Ren et al. |
| 2012/0202784 A1 | 8/2012 | Aronov et al. |
| 2012/0245169 A1 | 9/2012 | Ren et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0053362 A1 | 2/2013 | Castro et al. |

FOREIGN PATENT DOCUMENTS

| | | |
|---|---|---|
| DE | 2139107 | 2/1973 |
| EP | 773023 A1 | 5/1997 |
| EP | 1020445 B1 | 7/2000 |
| GB | 812366 A | 4/1959 |
| GB | 937725 A | 9/1963 |
| JP | 61109797 A | 5/1986 |
| JP | 5256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| WO | 8301446 A1 | 4/1983 |
| WO | 9117161 A1 | 11/1991 |
| WO | 9214733 A1 | 9/1992 |
| WO | 9316091 A1 | 8/1993 |
| WO | 9316092 A1 | 8/1993 |
| WO | 9318035 A1 | 9/1993 |
| WO | 9319767 A1 | 10/1993 |
| WO | 9322443 A1 | 11/1993 |
| WO | 9413677 A1 | 6/1994 |
| WO | 9417803 A1 | 8/1994 |
| WO | 9429436 A1 | 12/1994 |
| WO | 9510628 A2 | 4/1995 |
| WO | 9512588 A1 | 5/1995 |
| WO | 9529673 A1 | 11/1995 |
| WO | 9532984 A1 | 12/1995 |
| WO | 9510628 A3 | 9/1996 |
| WO | 9640706 A1 | 12/1996 |
| WO | 9728133 A1 | 8/1997 |
| WO | 9728161 A1 | 8/1997 |
| WO | 9841525 A1 | 9/1998 |
| WO | 9852611 A1 | 11/1998 |
| WO | 9857952 A1 | 12/1998 |
| WO | 0017202 A1 | 3/2000 |
| WO | 0102369 A2 | 1/2001 |
| WO | 0116114 A2 | 3/2001 |
| WO | 0119829 A2 | 3/2001 |
| WO | 0125238 A2 | 4/2001 |
| WO | 0131063 A1 | 5/2001 |
| WO | 0138584 A2 | 5/2001 |
| WO | 0116114 A3 | 8/2001 |
| WO | 0155140 A1 | 8/2001 |
| WO | 0156988 A1 | 8/2001 |
| WO | 0119829 A3 | 9/2001 |
| WO | 0125238 A3 | 10/2001 |
| WO | 0138584 A3 | 10/2001 |
| WO | 0181346 A2 | 11/2001 |
| WO | 0206192 A1 | 1/2002 |
| WO | 0181346 A3 | 3/2002 |
| WO | 0102369 A3 | 4/2002 |
| WO | 0230944 A2 | 4/2002 |
| WO | 02057425 A2 | 7/2002 |
| WO | 02076986 A1 | 10/2002 |
| WO | 02080926 A1 | 10/2002 |
| WO | 02083143 A1 | 10/2002 |
| WO | 0288025 A1 | 11/2002 |
| WO | 02090334 A1 | 11/2002 |
| WO | 02030944 A3 | 1/2003 |
| WO | 03000187 A2 | 1/2003 |
| WO | 03016275 A1 | 2/2003 |
| WO | 03/024969 A1 | 3/2003 |
| WO | 03020880 A2 | 3/2003 |
| WO | 03028341 A2 | 4/2003 |
| WO | 03035075 A1 | 5/2003 |
| WO | 03059884 A1 | 7/2003 |
| WO | 03020880 A3 | 10/2003 |
| WO | 03082341 A1 | 10/2003 |
| WO | WO 03/082341 A1 | 10/2003 |
| WO | 03106426 A1 | 12/2003 |
| WO | 2004006906 A2 | 1/2004 |
| WO | 2004006906 A3 | 1/2004 |
| WO | 2004039774 A3 | 1/2004 |
| WO | 03000187 A3 | 3/2004 |
| WO | 2004018058 A2 | 3/2004 |
| WO | 2004031177 A1 | 4/2004 |
| WO | 2004039774 A2 | 5/2004 |
| WO | 2004018058 A3 | 7/2004 |
| WO | WO 2004/058717 A1 | 7/2004 |
| WO | 2004087053 A2 | 10/2004 |
| WO | 2004111014 A1 | 12/2004 |
| WO | 2005002585 A1 | 1/2005 |
| WO | 2005007085 A2 | 1/2005 |
| WO | 2005012323 A2 | 2/2005 |
| WO | 2005016348 A1 | 2/2005 |
| WO | 2005016349 A1 | 2/2005 |
| WO | 2005016528 A2 | 2/2005 |
| WO | 2005021533 A1 | 3/2005 |
| WO | 02057425 A3 | 4/2005 |
| WO | 2005012323 A3 | 5/2005 |
| WO | 2005016528 A3 | 5/2005 |
| WO | 2005044181 A2 | 5/2005 |
| WO | 2005047289 A1 | 5/2005 |
| WO | 2005061460 A1 | 7/2005 |
| WO | 2005063258 A1 | 7/2005 |
| WO | 2005067901 A2 | 7/2005 |
| WO | 2005074603 A2 | 8/2005 |
| WO | 2005007085 A3 | 9/2005 |
| WO | 2005097800 A1 | 10/2005 |
| WO | 2005105760 A1 | 11/2005 |
| WO | 2005067901 A3 | 12/2005 |
| WO | 2005112935 A1 | 12/2005 |
| WO | 2005113556 A1 | 12/2005 |
| WO | 2005117889 A1 | 12/2005 |
| WO | 2005120511 A1 | 12/2005 |
| WO | 2005044181 A3 | 3/2006 |
| WO | 2006030032 A1 | 3/2006 |
| WO | 2006038865 A1 | 4/2006 |
| WO | 2006050501 A2 | 5/2006 |
| WO | 2006050946 A1 | 5/2006 |
| WO | 2006068760 A2 | 6/2006 |
| WO | 2004087053 A3 | 8/2006 |
| WO | 2006089106 A2 | 8/2006 |
| WO | 2006108107 A1 | 10/2006 |
| WO | 2006112666 A1 | 10/2006 |
| WO | 2005074603 A3 | 11/2006 |
| WO | 2006114064 A2 | 11/2006 |
| WO | 2006114065 A2 | 11/2006 |
| WO | 2006068760 A3 | 12/2006 |
| WO | 2006089106 A3 | 12/2006 |
| WO | 2007002293 A2 | 1/2007 |
| WO | 20070006547 A1 | 1/2007 |
| WO | 20070020046 A1 | 2/2007 |
| WO | 2007002293 A3 | 3/2007 |
| WO | 2007025090 A2 | 3/2007 |
| WO | 2006050501 A3 | 5/2007 |
| WO | 2007061737 A2 | 5/2007 |
| WO | 2006114064 A3 | 6/2007 |
| WO | 2006114065 A3 | 6/2007 |
| WO | 2007025090 A3 | 6/2007 |
| WO | 2007075554 A2 | 7/2007 |
| WO | 2007079164 A2 | 7/2007 |
| WO | 2007079164 A3 | 9/2007 |
| WO | 2007103308 A2 | 9/2007 |
| WO | 2007112005 A2 | 10/2007 |
| WO | 2007114926 A2 | 10/2007 |
| WO | 2007121453 A2 | 10/2007 |
| WO | 2007114926 A2 | 10/2007 |
| WO | 2007121920 A2 | 11/2007 |

(56) References Cited

FOREIGN PATENT DOCUMENTS

| | | | |
|---|---|---|---|
| WO | 2007121924 A2 | 11/2007 | |
| WO | 2007124854 A1 | 11/2007 | |
| WO | 2007125310 A2 | 11/2007 | |
| WO | 2007125315 A2 | 11/2007 | |
| WO | 2007126841 A2 | 11/2007 | |
| WO | 2007134828 A1 | 11/2007 | |
| WO | 2007135380 A2 | 11/2007 | |
| WO | 2007135398 A1 | 11/2007 | |
| WO | 20070121920 A2 | 11/2007 | |
| WO | 2007061737 A3 | 12/2007 | |
| WO | 2007125315 A3 | 12/2007 | |
| WO | 2007121920 A3 | 1/2008 | |
| WO | WO 2008/001236 A1 | 1/2008 | |
| WO | WO 2008/012326 A1 | 1/2008 | |
| WO | 2007103308 A3 | 2/2008 | |
| WO | 2007112005 A3 | 2/2008 | |
| WO | WO2008118454 * | 2/2008 | C07D 471/04 |
| WO | 2007125310 A3 | 3/2008 | |
| WO | 20080025755 A1 | 3/2008 | |
| WO | 20080047821 A1 | 4/2008 | |
| WO | 2008064018 A1 | 5/2008 | |
| WO | 20080063625 A2 | 5/2008 | |
| WO | 2007121453 A3 | 7/2008 | |
| WO | 2008079028 A1 | 7/2008 | |
| WO | 2008082487 A2 | 7/2008 | |
| WO | 2008094737 A2 | 8/2008 | |
| WO | 2007121924 A3 | 9/2008 | |
| WO | 2008112715 A2 | 9/2008 | |
| WO | 2007114926 A3 | 10/2008 | |
| WO | 2008118454 A2 | 10/2008 | |
| WO | 2008118455 A1 | 10/2008 | |
| WO | 2008118468 A1 | 10/2008 | |
| WO | 2008125014 A1 | 10/2008 | |
| WO | 2008125207 A1 | 10/2008 | |
| WO | 2008127226 A2 | 10/2008 | |
| WO | 2007126841 A3 | 11/2008 | |
| WO | 2008112715 A3 | 11/2008 | |
| WO | 2008118454 A3 | 11/2008 | |
| WO | 2008136457 A1 | 11/2008 | |
| WO | 2008082487 A3 | 12/2008 | |
| WO | 2008127226 A3 | 12/2008 | |
| WO | 2009000412 A1 | 12/2008 | |
| WO | 2009004621 A1 | 1/2009 | |
| WO | 2009010925 A2 | 1/2009 | |
| WO | 2009023718 A2 | 2/2009 | |
| WO | 2008094737 A3 | 3/2009 | |
| WO | 2009023718 A3 | 4/2009 | |
| WO | 2009044707 A1 | 4/2009 | |
| WO | 2009050506 A2 | 4/2009 | |
| WO | 2009064802 A2 | 5/2009 | |
| WO | 2009010925 A3 | 7/2009 | |
| WO | 2009064802 A3 | 7/2009 | |
| WO | 2009088986 A1 | 7/2009 | |
| WO | 2009088990 A1 | 7/2009 | |
| WO | 2009100406 A2 | 8/2009 | |
| WO | 2009117157 A1 | 9/2009 | |
| WO | 2009050506 A3 | 11/2009 | |
| WO | 2009100406 A3 | 11/2009 | |
| WO | 2010006086 A2 | 1/2010 | |
| WO | 2010009207 A1 | 1/2010 | |
| WO | 2010019210 A2 | 2/2010 | |
| WO | 2010036380 A1 | 4/2010 | |
| WO | 2010039534 A2 | 4/2010 | |
| WO | 2010019210 A3 | 5/2010 | |
| WO | 2010039534 A3 | 8/2010 | |
| WO | 2011146882 A1 | 11/2011 | |
| WO | WO 2012/064973 A2 | 5/2012 | |

OTHER PUBLICATIONS

O'Shea et al., "Activaiton of human peripheral blood T lymphocytes by pharmacological induction of protein-tyrosine phosphorylation", Proc. Natl. Acad. Sci. USA, Nov. 1992, vol. 89, pp. 10306-10310.

Pérez-Blas et al., "Impaired T cell signal transduction through CD28 in a patient with idiopathic thrombocytopenia", Clin. Exp. Immunol., 1991, vol. 85, pp. 424-428.

Prasad et al., "Phosphatidylinositol (PI) 3-kinase and PI 4-kinase binding to the CD4-p56lck complex: the p56lck SH3 domain binds to PI 3-kinase but not PI 4-kinase", Molecular and Cellular Biology, Dec. 1993, vol. 13, No. 12, pp. 7708-7717.

Prasad et al., "Src-homology 3 domain of protein kinase p59fyn mediates binding phosphatidylinositol 3-kinase in T cells", Proc. Natl. Acad. Sci. USA, Aug. 1993, vol. 90, pp. 7366-7370.

Schwartz et al., "Quercetin inhibition of the induction and function of cytotoxic T lymphocytes", Immunopharmacology, 1982, vol. 4, pp. 125-138.

Schwartz, "A cell culture model for T lymphocyte clonal anergy", Science, Jun. 15, 1990, vol. 248, pp. 1349-1356.

Truitt et al., "Stimulation of CD28 triggers an association between CD 28 and phosphatidylinositol 3-kinase in Jurkat T cells", J. Exp. Med., Mar. 1994, vol. 179, pp. 1071-1076.

Vandenberghe et al., "Antibody and B7/BB1-mediated ligation of the CD28 receptor induces tyrosine phosphorylation in human T cells", J. Exp. Med., Apr. 1992, vol. 175, pp. 951-960.

Ward et al., "Ligation of CD28 receptor by B7 induces formation of D-3 phosphoinositides in T lymphocytes independently of T cell receptor/CD3 activation", Eur. J. Immunol., 1993, vol. 23, pp. 2572-2577.

Ward et al., "Regulation of D-3 phosphoinositides during T cell activation via the T cell antigen receptor/CD3 complex and CD2 antigens", Eur. J. Immunol., 1992, vol. 22, pp. 45-49.

Ward et al., "Regulation of phosphoinositide kinases in T cells", J. Biol. Chem., Nov. 25, 1992, vol. 267, No. 33, pp. 23862-23869.

Ward et al., "Inhibition of CD28-mediated T cell costimulation by the phosphoinisitide 3-kinase inhibitor wortmannin", Eur. J. Immunol., 1995, vol. 25, pp. 526-532.

Wiesinger et al., "Antiinflammatory activity of the new mold metabolite 11-desacetoxy-wortmannin and some of its derivatives", Experientia, 1974, vol. 30, pp. 135-136.

Yang et al., "A novel activation pathway for mature thymocytes", J Exp. Med., Oct. 1988, vol. 168, pp. 1457-1486.

Yano et al., "Inhibition of histamine secretion by wortmannin through the blockade of phosphatidylinositol 3-kinase in RBL-2H3 cells", J. Biol. Chem., Dec. 5, 1993, vol. 268, No. 34, pp. 25846-25856.

Yoshida et al., "Quercetin arrests human leukemic T-cells in late G1 phase of the cell cycle", 1992, vol. 52, pp. 6676-6681.

Rott et al., "Recent development in the use of biologics in psoriasis and autoimmune disorders. The role of autoantibodies", BMJ, Mar. 26, 2005, vol. 330, No. 7493, pp. 716-720.

Sykes et al., "Treatment of severe autoimmune disease by stem-cell transplantation", Nature, Jun. 2, 2005, vol. 35, No. 7042, pp. 620-627.

Bhat et al., "Pyraszolopyrimidine nucleosides. 12. Synthesis and biological activity of certain pyrazolo[3,4-d]pyrimidine nucleosides related to adenosine", J. Med. Chem., 1981, vol. 24, No. 10, pp. 1165-1172.

Pietrie et al., "Novel biotinylated adenylate analogue derived from pyrazolo[3,4-d]pyrimidine for labeling DNA probes", Bioconj. Chem., 1991, vol. 2, No. 6, pp. 441-446.

Examination Report for GB Application No. GB0819947.3 dated Oct. 27, 2010.

International Search Report dated Aug. 27, 2008 for International Applicaiton No. PCT/US07/08395.

Supplementary European Search Report dated Feb. 24, 2010, for EP Application No. 07754845.

International Search Report dated Sep. 25, 2008, for International Application No. PCT/US2007/08355.

International Search Report dated Oct. 2, 2006, for International Application No. PCT/US05/042524.

European Seach Report dated Feb. 4, 2011, for EP Application No. 05857011.0.

"Report of the Expert Committee on the diagnosis and classification of diabetes mellitus", Diabetes Care, 1992, vol. 2, Suppl. 1, pp. S5-S19.

Andrews et al., "Effects of the 11b-hydroxysteroid dehydrogenase inhibitor carbenoxolone on insulin sensitive in men with type 2 diabetes", J. Clin. Endocrinol. Metab., 2003, vol. 88, No. 1, pp. 285-291.

(56) References Cited

OTHER PUBLICATIONS

Arnold et al., "Pyrrolo[2,3-d]pyrimidines containing an extended 5-substituent as potent and selective inhibitors of Ick I", Bioorg. and Med. Chem. Lett., 2000, vol. 10, pp. 2167-2170.
Banker et al., Modern Pharmaceutics, 1996, pp. 451-593, 3ed, Marcel Dekker, New York.
Barf et al., "Arylsulfonamidothiazoles as a new class of potential antidiabetic drugs. Discovery of potent and selective inhibitors of the 11b-hydroxysteroid dehydrogenase Type 1", J. Med. Chem., 2002, vol. 45, No. 18, pp. 3813-3815.
Barnes et al., "Efficacy and Safety of Inhaled Corticosteroids in Asthma—Report of a Workshop Held in Eze, France Oct. 1992". Am. Rev. Resir. Dis., 1993, vol. 148, pp. S1-S26.
Bell et al., "Glucokinase mutations insulin secretion, and diabetes mellitus", Annu. Reb. Physiol., 1996, vol. 58, pp. 171-186.
Bishop et al., "Generation of monospecific nanomolar tyrosine kinase inhbitors via a chemical genetic approach", Journal of the American Chemical Society, 1999, vol. 121, No. 4, pp. 627-631, Washington, DC.
Bohren et al., "Expression, crystallization and preliminary crystallographic analysis of human carbonyl reductase", J. Mol. Biol., 1994, vol. 224, pp. 659-664.
Cox et al., "Human colorectal cancer cells efficiently conjugate the cyclopentenone prostaglandin, prostaglandin J2 to glutathione", Biochem. Biophys. Acta., 2002, vol. 1584, pp. 37-45.
Diederich et al., "In search for specific inhibitors of human 11b-hydroxysteroid-dehydrogenases (11bHSDs): chenodeoxycholic acid selectively inhibits 11b-HSD-I", Eur. J. Endocrinol., 2000, vol. 142, pp. 200-207.
Ding et al., "A combinatorial scaffold approach toward kinase-directed heterocycle libraries", J. Am. Chem. Soc., 2002, vol. 124, No. 8, pp. 1594-1596.
Ding et al., "A concise and traceless linker strategy toward combinatorial libraries of 2,6,9-substituted purines", J. Org. Chem., 2001, vol. 66, pp. 8273-8276.
Ding et al., "Resin-capture and release strategy toward combinatorial libraries of 2,6,9-substituted purines", J. Comb. Chem., 2002, vol. 4, pp. 183-186.
Fajans et al., "Maturity onset diabetes of the young (MODY)", Diabet. Med., 1996, vol. 13, pp. S90-S95.
Feinstein et al., "Regulation of the action of hydrocotisone in airway epithelial cells by 11b-hydroxysteroid dehydrogenase", Am. J. Resp. Cell. Mol. Biol., 1999, vol. 21, pp. 403-408.
Fingl et al., "General principles", The Pharmacological Basis of Therapeutics, 1975, Ch. 1, pp. 1-46, Fifth edition.
Forrest et al., "Carbonyl Reductase", Chem. Biol. Interact., 2000, vol. 129, pp. 21-40.
Forrest et al., "Induction of a human carbonyl reductase gene located on chromosome 21", Biochem. Biophys. Acta., 1990, vol. 1048, pp. 149-155.
Franzen, "The Suzuki, the Heck, and the Stille reaction—three versative methods for the introduction of new C-C bonds on solid support", Can. J. Chem., 2000, vol. 78, pp. 957-962.
Funder et al., "Mineralocorticoid action: target tissue specificity is enzyme, not receptor, mediated", Science, 1998, vol. 242, pp. 583-585.
Garber et al., "Diversity of gene expression in adenocarcinoma of the lung", Proc. Natl. Acad. Sci. Usa, 2001, vol. 98, No. 24, pp. 13784-13789.
Gonzalez et al., "Protection against daunorubicin cytotoxicity by expression of a cloned human carbonyl reductase cDNA in K562 leukemia cells", Cancer Res., 1995, vol. 55, pp. 4646-4650.
Haase et al., "Detection of viral nucleic acids by in situ hybridization", Methods in Virology, 1984, vol. 7, pp. 189-226.
Hanefeld et al., "One-pot synthesis of tetrasubstituted pyrazoles proof of regiochemistry", J. Chem. Soc. Perkin Trans., 1996, vol. 1, pp. 1545-1552.
Ishiyama et al., "A stoichiometric aromatic C-H borylation catalyzed by iridium(I)/2,2'-bipyridine complexes at room temperature", Angew. Chem. Int. Ed., 2002, vol. 41, No. 16, pp. 3056-3058.
Ishiyama et al., "Mild iridium-catalyzed borylation of arenes. High turnover numbers, room temperature reactions, and isolation of a potential intermediate", J. Am. Chem. Soc., 2002, vol. 124, No. 3, pp. 390-391.
Kallberg et al., "Short-chain dehydrogenase/reductase (SDR) relationships: a large family with eight clusters common to human, animal, and plant genomes", Protein Sci., 2002, vol. 11, pp. 636-641.
Kallberg et al., "Short-Chain Dehydrogenases/Reductases (SDRs)—Coenzyme-Based Functional Assignments in Completed Genomes". Eur. J. Biochem., 2002, vol. 269, pp. 4409-4417.
Knight et al., "A pharmacological map of the P13-K family defines a role for p110a in insulin signaling", Cell, 2006, vol. 125, pp. 733-747.
Kraybill et al., "Inhibitor scaffolds as new allele specific kinase substrates", Journal of the American Chemical Society, Oct. 16, 2002, vol. 124, No. 41, pp. 12118-12128, American Chemical Society, Washington, DC, US.
Kwok et al., "The anti-inflammatory natural product parthenolide from the medicinal herb feverfew directly binds to and inhibits IkB kinase", Chem. Biol., 2001, vol. 8, pp. 759-766.
Mayer et al., "Small molecule inhibitor of mitotic spindle bipolarity identified in a pheontype-cased screen", Science, 1999, vol. 286, pp. 971-974.
Miyaura et al., "Palladium-catalyzed cross-coupling reactions of organoboron compounds", Chem. Rev., 1995, vol. 95, No. 7, pp. 2457-2483.
Moon et al., "A novel microtubule destabilizing entity from orthogonal synthesis of triazine library and zebrafish embryo screening", J. Am. Chem. Soc., 2002, vol. 124, pp. 11608-11609.
Nakanishi et al., "Cloning and sequence analysis of a cDNA encoding tetrameric corbonyl reductase of pig lung", Biochem. Biophys. Acta, 1993, vol. 194, No. 3, pp. 1311-1316.
Niswender et al., "Protein engineering of protein kinase a catalytic subunits results in the acquisition of novel inhibitor sensitivity", The Journal of Biological Chemistry, 2002, vol. 277, No. 32, pp. 28916-28922.
Nobel et al., "Purification of full-length recombinant human and rat type 1 11b-hydroxysteroid dehydrogenases with retained oxidoreductase activities", Protein Expr. Purif., 2002, vol. 26, pp. 349-356.
Oppermann et al., "Forms and functions of human SDR enzymes", Chem. Biol. Interact., 2001, vol. 130-132, No. 1-3, pp. 699-705.
Persson, "Glucocorticoids for asthma—early contributions", Pulm. Pharmacol., 1989, vol. 2, pp. 163-166.
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines", J. Med. Chem., 1990, vol. 33, pp. 1984-1992.
Robertson, "Eicosandoids and human disease", Harrison's Principles of Internal Medicine, Isselbacher K.J. et al. (eds.), 1994, vol. 1, pp. 431-435, McGraw-Hill, New York City.
Romero et al., "Cloning and expression of the bovine 11b-hydroxysteroid dehydrogenase type-2", J. Steroid Biochem. Mol. Biol., 2000, vol. 72, pp. 231-237.
Singer et al., "Optimization of in situ hybridization using isotopic and non-isotopic detection methods", Biotechniques, 1986, vol. 4, No. 3, pp. 230-250.
Soldan et al., "Induction of daunorubicin carbonyl reducting enzymes by daunorubicin in sensitive and resistant pancrease carcinoma cells", Biochem. Pharmacol., 1996, vol. 51, pp. 117-123.
Tanaka et al., "An unbiased cell morphology-based screen for new, biologically active small molecules", PLoS Biology, 2005, vol. 3, No. 5, pp. 0764-0776.
Ugarkar et al., "Adenosine kinase inhibitors. 2. Synthesis, enzyme inhibition, and antiseizure activity of diaryltubercidin analogues", J. Med. Chem., 2000, vol. 43, pp. 2894-2805.
White et al., "11b-hydroxysteroid dehyrdogenase and the syndrome of apparent mineralocorticoid excess", Endocr. Rev., 1997, vol. 18, No. 1, pp. 135-156.
Widler et al., "7-alkyl- and 7-Cycloalkyl-5-aryl-pyrrolo[2,3-d]pyrimidines—potent inhibitors of the tyrosine kinase c-Src", Bioorganis and Medicinal Chemistry Letters, 2001, vol. 11, No. 6, pp. 849-852.

(56) References Cited

OTHER PUBLICATIONS

Wolff, Burger's Medicinal Chemistry, 5ed, 1995, Part 1, pp. 975-977, John Wiley & Sons.
Kost et al., "Recyclization of 3-Alkyl- and 1,3-Dialkylisoquinolinium Salts to Naphthylamines", Chemistry of Heterocyclic Compounds, Jan., 16(9): 965-970 (1981).
Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo[4,3-d] [1,2] diazepinone)", Tetrahedron Letters, Jan., 46(26): 4457-4459 (2005).
Kumar et al., "Keten Dithioacetals. Part 11. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine derivatives", Journal of the Chemical Society, Perkin Transactions 1, Chemical Society, Letchworth, Jan., 8: 857-862 (1978).
Ames et al., "Heterocyclic Synthesis from o-Halogen-acids. Part II. Thienopyridinones and Thienopyranones from 3-bromothiophene -2- and 4-Bromothiophene-3-Carboxylic Acids", Journal of the Chemical Society, Perkin Transactions 1, Jan., 14: 1390-1395 (1975).
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6): 1229-1233 (2002).
Extended European Search Report from Eureopean Application No. 09700784.3 dated Oct. 28, 2011.
International Search Report dated Oct. 26, 2011, for International Application No. PCT/US09/00038.
BASOTEST®, "Test Kit for the Quantitative Determination of the Degranulation of Basophilic Granulocytes in Heparinized Human Whole Blood", Retreived from the Internet Nov. 29, 2011.
International Preliminary Report on Patentability from International Application No. PCT/US2009/000042 issued Jul. 6, 2010.
European Seach Report dated Oct. 28, 2011, for EP Application No. 09700784.3.
J.C.S. Perkin I, 1975, 1390-1395.
Orpegen Pharma "Instructions for BASOTEST® Reagent Kit" Version 08/06, pp. 1-8.
Takeuchi et al. "Synergistic Augmentation of Rapamycin-Induced Autophagy in Malignant Glioma Cells by Phosphatidylinositol 3-Kinase/Protein Kinase B Inhibitors". Cancer Res. 65(8):3336-46. Apr. 15, 2005.
Beeram et al. Akt-Induced Endocrine Therapy Resistance is Reversed by Inhibition of mTOR Signaling. Ann Oncol. Aug. 2007. 18(8):1323-8.
Feldman et al. Active-Site Inhibitors of mTOR Target Rapamycin-Resistant Outputs of mTORC1 and mTORC2. PLoS Biol. Feb. 10, 2009. 7(2):371-383.
U.S. Appl. No. 13/016,957, filed Jan. 28, 2011.
Abdel-Mohsen. Synthesis, Reactions and Antimicrobial Activity of 2-Amino-4-(8-quinolinol-5-yl)-1-(p-toly1)-pyrrole-3-carbonitrile. Bull. Korean Chem. Soc. 2005;26(5):719-728.
Kim et al. "Activation and Function of the mTORC1 Pathway in Mast Cells". J Immunol. Apr. 1, 2008; 180(7):4586-95.
U.S. Appl. No. 13/289,540, filed Nov. 4, 2011.
International Preliminary Report on Patentability and Written Opinion for PCT/US2009/060985 dated Apr. 19, 2011.
International Preliminary Report on Patentability and Written Opinion for PCT/US2009/049969 dated Jan. 1, 2011.
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
Campora et al., "Binuclear complexes of nickel bridged by hydrocarbon ligands. Isocyanide insertion chemistry and amide formation by intramolecular coupling of acyl and imidoyl functionalities", Organometallics, Jan. 1992, vol. 11, No. 1, pp. 11-13.
Campora et al., "Isocyanide insertion chemistry. Synthesis and structural characterization of bridging imidoyl complexes of nickel and amide formation by intramolecular coupling of acyl and imidoyl functionalities", Organometallics, Oct. 1993, vol. 12, No. 10, pp. 4025-4031.
Chaisuparat et al., "Dual inhibition of P13Ka and mTOR as an alternative treatment for Kaposi's Sarcoma", Cancer Research, 2008, vol. 68, pp. 8361-8368.
Chappelow et al., "Neovascular age-related macular degeneration: potential therapies", Drugs, 2008, vol. 68, No. 8, pp. 1029-1036.
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-d imethylhydrazide", Synthetic Communications, Sep. 1997, vol. 27, No. 17, pp. 2961-2969.
Dijksman et al., "271.1: 2-dihydro-2-thianaphthalene derivatives. Part I. Preperation and reactions of 1 : 2-dihydro-1-keto-2-thianaphthalenes", J. Chem. Soc., vol. 1951, pp. 1213-1218.
Donati et al., "Emerging therapies for neovascular age-related macular degeneration: state of art", Ophthalmologica, 2007, vol. 221, pp. 366-377.
Graupera et al., "Angiogenesis selectively requires the p110 isoform of P13K to control endothelial cell migration", Nature, 2008, vol. 453, pp. 662-666.
Hellwinkel et al., "Heterocyclensynthesen mit MF/Al2O3-basensystemen; 2- arylbenzofurane and 2,3-diarylisochinolin-1(2H)-one", Synthesis, 1995, vol. 1995, No. 9, pp. 1135-1141.
International Search Report dated Mar. 11, 2009 for PCT Application No. US2009/00038.
International Search Report dated Mar. 23, 2009 for PCT/US2009/00042.
Kajita et al., "Nickel-catalyzed decarbonylative addition of phthalimides to alkynes", J. Am. Chem. Soc., May 14, 2008, vol. 130, No. 19, pp. 6058-6059.
Kundu et al., "Palladium-catalysed heteroannualation with terminal alkynes; a highly regio-and stereoselective synthesis of (Z)-3-aryl(alykl)idene isoindolin-1-ones1", Tetrahedron, Jun. 30, 2000, vol. 56, No. 27, pp. 4777-4792.
Lee et al., "All roads lead to mTOR integrating inflammation and tumor angiogenesis", Cell Cycle, 2007, vol. 6, No. 24, pp. 3011-3014.
Majumder et al., "mTOR inhibition reverses Akt-dependent prostate intraepithelial neoplasia through regulation of apoptic and HIF-1-dependent pathways", Nature Medicine, 2004, vol. 10, pp. 594-601.
Mellinghoff et al., "TORward AKTually useful mouse models", Nature Medicine, 2004, vol. 10, pp. 579-580.
Modi et al., "Isoquinolines; part IV-synthesis of methyl, 3-formyl & other 3-substituted N-arylisoquinolones", Indian J. Chem., 1979, vol. 18B, pp. 304-306.
Nemazanyi et al., "3-Amino-4aryl-1(2H)-isoquinolones", Chemistry of Heterocyclic Compounds, Mar. 1991, vol. 27, No. 3, pp. 307-308.
Oda et al., "PIK3CA cooperates with other phosphatidylinositol 3'-kinase pathway mutations to effect oncogenic transformation", Cancer Research, 2008, vol. 68, pp. 8127.
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one", Chem. Pharm. Bull., Jun. 25, 1984, vol. 32, No. 6, pp. 2160-2164.
Ozol et al., "Autoxidative transformations of 2-substituted 3-alkyl-4-hydroxy-1-oxo-1, 2-dihydroisoquinolines", Chemistry of Heterocyclic Compounds, Jun. 1978, vol. 14, No. 6, pp. 644-648.
Patel et al., "Immunopathological aspects of age-related macular degeneration", Seminars in Immunopathology, 2008, vol. 30, No. 2, pp. 97-110.
Stanoeva et al., "Homophthalic anhydrides and their application to the synthesis of heterocyclic compounds (review)", Chemistry of Heterocyclic Compounds, Dec. 1984, vol. 20, No. 12, pp. 1305-1315.
Yaguchi et al., "Antitumor activity of ZSTK474, a new phosphatidylinositol 3-kinase inhibitor", J. Natl. Cancer Inst., 2006, vol. 98, No. 8, pp. 545-556.
International Search Report dated Aug. 22, 2011for PCT Application No. PCT/US2011/37412.
Anderson et al., "Paradoxical inhibition of T-cell function in response to CTLA-4 blockade; heterogeneity within the human T-cell population", Nature, 2000, vol. 6, No. 2, pp. 211-214.

(56) References Cited

OTHER PUBLICATIONS

Arcaro et al., "Wortmannin is a potent phosphatidylinositol 3-kinase inhibitor: the role of phosphatidylinositol 3,4,5-triphosphate in neutrophil responses", Biochem. J., Dec. 1, 1993, vol. 296, Pt. 2, pp. 297-301.
Mosmann et al., "The expanding universe of T-cell subsets: Th1, Th2 and more", Immunology Today, 1996, pp. 138-146.
Bochner et al. "Immunological aspects of allergic asthma". Annual review of Immunology 1994—Annual Reviews, pp. 295-335.
Johnson et al., "Accessory cell-derived signals required for T cell activation", Immunologic Research, 1993, pp. 48-64.
Harada et al., "Novel role of phosphatidylinositol 3-kinase in CD28-mediated costimulation", J. Biol. Chem., 2001, vol. 276, No. 12, pp. 9003-9008.
Liu et al., "Costimulation of T-cell growth", Current Biology, 1992, pp. 265-270.
Augustine et al., "Interleukin 2- and polyomavirus middle T antigen-induced modification of phosphatidylinositol 3-kinase activity in activated T lymphocytes", Molecular and Cellular Biology, 1991, vol. 11, No. 9, pp. 4431-4440.
Davies et al., "The human T3y chain is phosphorylated at Serine 126 in response to T lymphocyte activation", The Journal of Biological Chemistry, 1987, vol. 262, No. 23, pp. 10918-10921.
Graber et al., "The protein tyrosine kinase inhibitor herbimycin A, but not Genistein, specifically inhibits signal transduciton by the T cell antigen receptor", International Immunology, 1992, vol. 4, No. 1, pp. 1201-1210.
June et al., "Inhibition of tyrosine phosphorylation prevents T-cell receptor mediated signal transduction", Proc. Natl. Acad. Sci. USA, 1990, vol. 87, pp. 7722-7726.
Prasad et al., "T-cell antigen CD28 interacts with the lipid kinase phosphatidylinositol 2-kinase by a cytoplasmic Tyr(P)-Met-Xaa-Met motif", Proc. Natl. Acad. Sci. USA, 1994, vol. 91, pp. 2834-2838.
Reif et al., "Divergent regulation of phosphatidylinositol 3-kinase P85a and P85b isoforms upon T cell activation", The Journal of Biological Chemistry, 1993, vol. 268, pp. No. 15, pp. 10780-10788.
Shibasaki et al., "Different properties of monomer and heterodimer forms of phosphatidylinositol 3-kinase", Biochem. J., 1993, vol. 289, pp. 227-231.
Vlahos et al., "A specific inhibitor of phosphatidylinositol 3-kinase, 2-(4-morpholinyl)-8-phenyl-4H-1-benzopyran-4-one (LY294002)", The Journal of Biological Chemistry, 1994, vol. 269, No. 7, pp. 5241-5248.
Woscholski et al., "A comparison of demthoxyviridin and wortmannin as inhibitors of phosphatidylinositol 3-kinase", FEBS letters, 1994, vol. 342, pp. 109-114.
Abe et al., "T cell receptor-mediated recognition of self-ligand induces signaling in immature thymocytes before negative selection", J. Exp. Med., Aug. 1992, vol. 176, pp. 459-468.
Baggiolini et al., "Inhibition of the phagocytosis-induced respiratory burst by the fungal metabolite wortmannin and some analogues", Experimental Cell Research, 1987, vol. 169, pp. 408-418.
Closse et al., "2,3-dihydrobenzofuran-2-ones: a new class of highly potent antiinflammatory agents", J. Med. Chem., 1981, vol. 24, pp. 1465-1471.
Gunther et al., "Acute pathological effects on rats of orally administered wortmannin-containing preparations and purified wortmannin from *Fusarium oxysporum*", Fd. Chem. Toxic., 1989, vol. 27, No. 3, pp. 173-179.
Harding et al., "CD28-mediated signalling co-stimulates murine T cells and prevents induction of anergy in T-cell clones", Nature, Apr. 16, 1992, vol. 356, pp. 607-609.
Ledbetter et al., "Crosslinking of surface antigens cause mobilization of intracellular ionized calcium in T lymphocytes", Proc. Natl. Acad. Sci. USA, Mar. 1987, vol. 84, pp. 1384-1388.
Ley et al., "The T cell receptor/CD3 complex and CD2 stimulate the tyrosine phosphorylation of indistinguishable patterns of polypeptides in the human T leukemic cell line Jurkat", Eur. J. Immunol., 1991, vol. 21, pp. 2203-2209.

Nunes et al., "Signalling Through CD28 T-Cell Activation Pathway Involves an Inositol Phospholipid-Specific Phospholipase C Activity". Biochem. J., 1993, vol. 293, pp. 835-842.
Okada et al., "Blockage of chemotactic peptide-induced stimulation of neutrophils by wortmannin as a result of selective inhibition of phosphatidylinositol 3-kinase", J. Biol. Chem., Feb. 4, 1994, vol. 269, No. 5, pp. 3568-3573.
International Preliminary Report on Patentability and Written Opinion for PCT/US2007/008395 dated Oct. 8, 2008.
International Search Report and Written Opinion for PCT/US2009/049969 dated Mar. 15, 2010.
International Search Report and Written Opinion for PCT/US2009/005380 dated Nov. 20, 2009.
International Search Report for PCT/US2010/02020 dated Nov. 2, 2010.
International Search Report for PCT/US2009/060985 dated Jun. 28, 2010.
European Search Report for EP 07873406.8 dated Mar. 1, 2010.
European Search Report and Search Opinion for EP 09700424.6 dated Oct. 26, 2011.
European Examination Report for EP 07873406.8 dated Sep. 14, 2011.
Kreutzberger et al. 5-Substituierte 4-Aminopyrimidine durch Aminomethinylierung von Acetonitrilen. Liebigs Ann. Chem. 1977: pp. 537-544.
Supplementary European Examination Report EP 07754845.1 dated Sep. 20, 2011.
Gillespie et al. "Antagonists of the Human Adenosine A2A Receptor. Part 3. Design and Synthesis of Pyrazolo [3,4-d] Pyrimidines, Pyrrolo [2, 3-d] Pyrimidines, and 6-arylpurines". Bioorganic and Medicinal Chemistry Letters. vol. 18, No. 9. Mar. 30, 2008. pp. 2924-2929.
Ballell et al. "New Thiopyrazolo[3,4-d] pryimidine derivatives as anti-mycobacterial agents". Bioorganic and Medicinal Chemistry Letters. vol. 17. Dec. 22, 2006. pp. 1736-1740.
Extended European Search Report for EP 09816603 dated Mar. 19, 2012.
Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).
Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).
Bansal et al., "The Molecular Biology of Endometrial Cancers and the Implications for Pathogenesis, Classification, and Targeted Therapies," *Cancer Control* 16(1):8-13 (2009).
Bartholomeusz et al., "Targeting the PI3K Signaling Pathway in Cancer Therapy," *Expert. Opin. Ther. Targets* 16(1):121-130 (2012).
Berndt et al., "The p110δ crystal structure uncovers mechanisms for selectivity and potency of novel PI3K inhibitors," *Nat. Chem. Biol.* 6(2):117-124 (2010).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Blunden et al., "Mycotoxins in food," *Med. Lab. Sci.* 48(4):271-282 (1991).
Bone et al., "Phosphoinositide 3-kinase signalling regulates early development and developmental haemopoiesis," *J. Cell. Sci.* 120(Pt 10):1752-1762 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).

(56) References Cited

OTHER PUBLICATIONS

Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Camps et al., "Blockade of PI3Kγ suppresses joint inflammation and damage in mouse models of rheumatoid arthritis," *Nat. Med.* 11(9):936-943 (2005).
Chang et al., "The Bruton tyrosine kinase inhibitor PCI-32765 ameliorates autoimmune arthritis by inhibition of multiple effector cells," *Arthritis Research & Therapy* 13:R115 (2011).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.*(Tokyo) 47(6):900-902 (1999).
Courtney et al., "The P13K Pathway As Drug Target in Human Cancer," *J. Clin. Oncol.* 28(6):1075-1083 (2010).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
European Search Report for EP Application No. 07754845.1 dated Sep. 20, 2011.
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Furukawa, T., "Molecular Targeting Therapy for Pancreatic Cancer: Current Knowledge and Perspectives from Bench to Bedside," *J. Gastroenterol.* 43(12):905-911 (2008).

Gunther et al., "Immunosuppressive effects of dietary wortmannin on rats and mice," *Immunopharmacol. Immunotoxicol.* 11(4):559-570 (1989).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2010/033939 dated Nov. 5, 2010.
International Search Report and Written Opinion for PCT/US2012/020831 dated May 2, 2012.
International Search Report and Written Opinion for PCT/US2012/047190 dated Oct. 2, 2012.
International Search Report for PCT/US1995/005213 dated Aug. 21, 1995.
International Search Report for PCT/US2009/000038 dated Mar. 11, 2009.
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).

(56) References Cited

OTHER PUBLICATIONS

June et al., "Evidence for the involvement of three distinct signals in the induction of IL-2 gene expression in human T lymphocytes," *J. Immunol.* 143(1):153-161 (1989).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kang et al., "Oncogenic transformation induced by the p110β, -γ, and -δ isoforms of class I phosphoinositide 3-kinase," *PNAS* 103(5):1289-1294 (2006).
Karpeiskii, *Bioorganicheskaya Khimiya* 11(8):1097-1104 (1985).
Khwaja, A., "PI3K as a Target for Therapy in Haematological Malignancies," *Curr. Top. Microbiol. Immunol.* 347:169-188 (2010).
Kong, D. and Yamori, T., "Advances in Development of Phosphatidylinositol 3-Kinase Inhibitors," *Curr. Med. Chem.* 16:2839-2854 (2009).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Ledbetter et al., "CD28 ligation in T-cell activation: evidence for two signal transduction pathways," *Blood* 75(7):1531-1539 (1990).
Lee et al., "The CD28 signal transduction pathway in T cell activation", Advances in Cell Regulation of Cell Growth, vol. 2, pp. 141-160, New York: Raven Press, Ltd. (1991).
Li et al., "Roles of PLC-beta2 and -beta3 and PI3Kgamma in chemoattractant-mediated signal transduction," *Science* 287(5455):1046-1049 (2000).
Lu et al., "CD28-induced T cell activation. Evidence for a protein-tyrosine kinase signal transduction pathway," *J. Immunol.* 149(1):24-29 (1992).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (Ash Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mazzoletti and Broggini, "PI3K/AKT/mTOR inhibitors in ovarian cancer," Curr. Med. Chem. 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals from the Microenvironment in Cellular Models of Hodgkin Lymphoma," Blood (ASH Annual Meeting Abstracts), 116:Abstract 3926 (2010).
Merida et al., "IL-2 binding activates a tyrosine-phosphorylated phosphatidylinositol-3-kinase," *J. Immunol.* 147(7): 2202-2207 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Norman, "Selective PI3K-delta Inhibitors, A Review of the Patent Literature," *Expert Opinion on Therapeutic Patents* 21(11):1773-1790 (2011).

Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Rommel et al., "PI3Kδ and PI3Kγ: partners in crime in inflammation in rheumatoid arthritis and beyond?" *Nat. Rev. Immunol.* 7:191-201 (2007).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Shapiro et al., "Phase I Dose-Escalation Study of XL147, A PI3K Inhibitor Administered Orally to Patients with Solid Tumors," *J. Clin. Oncol.* 27:146x (Suppl Abstr 3500) (2009).
Sinclair et al., "Phosphatidylinositol-3 Kinase Delta (PI3Kδ) Inhibitor AMG 319 is a Potent, Selective and Orally Bioavailable Small Molecule Inhibitor that Suppresses PI3K-Mediated Signaling and Viability in Neoplastic B Cells," *Blood (ASH Annual Meeting Abstracts)* 118:Abstract 4964 (2011).
Smith et al., "Expression of Bruton's Agammaglobulinemia Tyrosine Kinase Gene, BTK, is Selectively Down-Regulated in T Lymphocytes and Plasma Cells," *J. Immunol.* 152:557-565 (1994).
Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Search Report for EP Application No. 10800175.1 dated Nov. 7, 2012.
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).

(56) References Cited

OTHER PUBLICATIONS

Vara et al., "P13K/Akt Signalling Pathway and Cancer," *Cancer Treat. Rev.* 30(2):193-204 (2004).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (Ash Annual Meeting Abstracts)* 118: Abstract 3490 (2011).
Ward et al., "Therapeutic potential of phosphoinositide 3-kinase inhibitors," *Chem. Biol.* 10(3):207-213 (2003).
Wu et al., "Decreased immunological responses by wortmannin-containing rice culture of *Fusarium oxysporum* and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Zhao and Vogt, "Class I PI3K in oncogenic cellular transformation," *Oncogene* 27(41):5486-5496 (2008).

* cited by examiner

HETEROCYCLIC KINASE INHIBITORS

RELATED APPLICATIONS

This application is a national phase application under 35 U.S.C. §371 of International Application No. PCT/US2009/005380, filed Sep. 28, 2009, which claims the benefit under 35 USC §119(e) of U.S. Provisional Patent Application Ser. No. 61/194,310, filed Sep. 26, 2008, each of which is incorporated herein by reference in its entirety.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, ably, serine/threonine kinases which predominantly phosphorylate substrates on serine and/or threonine residues (e.g., mTor C1, mTor C2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'—OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3-Ks play a key role in intracellular trafficking through the synthesis of PI(3)P and PI(3,4)P2. The PIKKs are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

As such, kinases, particularly PI3Ks are prime targets for drug development. There remains a need for PI3K inhibitors suitable for drug development. The present invention addresses this need and provides related advantages as well by providing new classes of kinase inhibitors.

SUMMARY OF THE INVENTION

The present invention provides a compound having a structure of one of the following formulae:

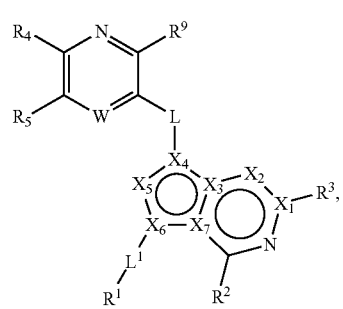

I-A

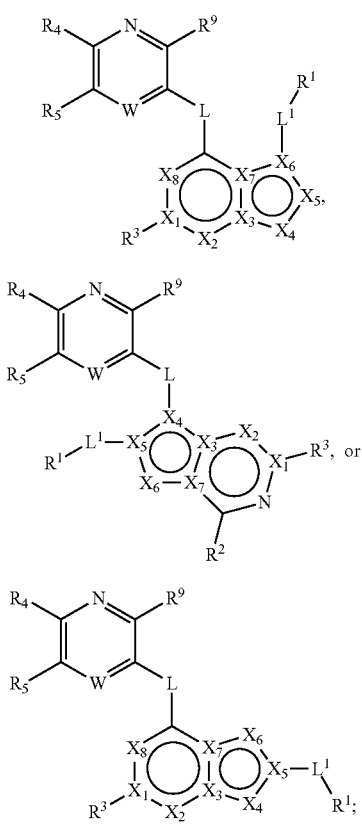

or a pharmaceutically acceptable salt thereof, wherein:
$X_5$ and $X_6$ are C—$R^6$, N, C-$L^1$-$R^1$, or N-$L^1$-$R^1$ wherein one of $X_5$ and $X_6$ is C-$L^1$-$R^1$ or N-$L^1R^1$; $X_1$ is C or N; and $X_2$ and $X_8$ are independently N or C—$R^6$; $X_3$ and $X_7$ are C or N, and at least one of $X_3$ and $X_7$ is C;

$X_4$ in Formula I-A or I-C is C or N; and $X_4$ in Formula I-B or I-D is C—$R^6$, NH, or N;

and wherein no more than two adjacent ring atoms are N or NH;

$R^1$ is hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, and n is an integer from 0 to 2;

$L^1$ is a bond, alkylene, heteroalkylene, alkenylene, alkynylene, cycloalkylene, heterocycloalkylene, arylene, or heteroarylene;

$R^2$ and $R^3$ are independently hydrogen, halogen, —CN, —$OR^{10}$, —$S(O)_nR^{11}$, —$NR^{12}R^{13}$, —$C(O)R^{14}$, alkyl, heteroalkyl, cycloalkyl, heterocycloalkyl, aryl, or heteroaryl;

$R^4$ and $R^5$ are independently hydrogen or $R^6$, or $R^4$ and $R^5$ are taken together to form a 5, 6 or 7 membered ring, wherein the 5, 6, or 7 membered ring is optionally substituted with $(R^6)_q$;

L is —NH—$CR^7R^8$—, —$(CR^7R^8)_z$—, —C=O—, or —$CR^7R^8(C=O)$—, —O—, —SO—, or —$SO_2$—;

z is an integer from 0 to 10;
q is an integer from 0 to 5;
each of $R^6$ is independently hydrogen, halogen, —CN, —$OR^{10}$, —$S(O)_nR^{11}$, —$NR^{12}R^{13}$, $C(O)R^{14}$, alkyl, alkenyl, alkynyl, heteroalkyl, cycloalkyl, heterocycloalkyl, aryl, or heteroaryl;

each of $R^7$ and $R^8$ is independently hydrogen, alkyl, heteroalkyl, cycloalkyl, heterocyclyalkyl, or $R^7$ and $R^8$ taken together form a cycloalkyl, heterocycloalkyl or aryl ring;

$R^9$ is hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl;

each $R^{10}$ is independently hydrogen, —$C(O)R^{15}$, alkyl, heteroalkyl, cycloalkyl, heterocycloalkyl, aryl, or heteroaryl;

each $R^{11}$ is independently —$NR^{16}R^{17}$, alkyl, heteroalkyl, cycloalkyl, heterocycloalkyl, aryl, or heteroaryl;

each $R^{12}$ is independently hydrogen, alkyl, heteroalkyl, cycloalkyl, heterocycloalkyl, aryl, or heteroaryl;

each $R^{13}$ is independently hydrogen, —$S(O)_nR^{18}$, —$C(O)R^{19}$, alkyl, heteroalkyl, cycloalkyl, heterocycloalkyl, aryl, or heteroaryl;

or $R^{12}$ and $R^{13}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{12}R^{13}$; and further wherein the 5, 6, 7, or 8 membered ring is optionally substituted;

each $R^{14}$ is independently —$NR^{20}R^{21}$, hydrogen, alkyl, heteroalkyl, cycloalkyl, heterocycloalkyl, aryl, or heteroaryl;

each $R^{15}$ is independently —$NR^{22}R^{23}$, hydrogen, alkyl, heteroalkyl, cycloalkyl, heterocycloalkyl, aryl, or heteroaryl;

each of $R^{16}$ and $R^{17}$ is independently hydrogen, alkyl, heteroalkyl, cycloalkyl, heterocycloalkyl, aryl, or heteroaryl; or $R^{16}$ and $R^{17}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{16}R^{17}$; and further wherein the 5, 6, 7, or 8 membered ring is optionally substituted;

each $R^{18}$ is independently hydrogen, alkyl, heteroalkyl, cycloalkyl, heterocycloalkyl, aryl, or heteroaryl;

each $R^{19}$ is independently —$NR^{24}R^{25}$, hydrogen, alkyl, heteroalkyl, cycloalkyl, heterocycloalkyl, aryl, or heteroaryl;

each of $R^{20}$ and $R^{21}$ is independently hydrogen, alkyl, heteroalkyl, cycloalkyl, heterocycloalkyl, aryl, or heteroaryl;

or $R^{20}$ and $R^{21}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{20}R^{21}$; and further wherein the 5, 6, 7, or 8 membered ring is optionally substituted;

each $R^{22}$ and $R^{23}$ are independently hydrogen, alkyl, heteroalkyl, cycloalkyl, heterocycloalkyl, aryl, or heteroaryl, or $R^{22}$ and $R^{23}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{22}R^{23}$; and further wherein the 5, 6, 7, or 8 membered ring is optionally substituted;

each $R^{24}$ and $R^{25}$ are independently hydrogen, alkyl, heteroalkyl, cycloalkyl, heterocycloalkyl, aryl, or heteroaryl, or $R^{24}$ and $R^{25}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{24}R^{25}$; and further wherein the 5, 6, 7, or 8 membered ring is optionally substituted; and W is $CR^6$ or N.

In some embodiments, the compound of Formula I-A or I-C is a compound having a structure of one of the following formulae:

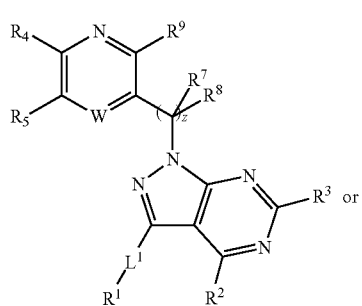

In some embodiments, the compound of Formula I-E is a compound of Formula I-J or Formula I-J-1:

In some embodiments, the compound of Formula I-A is a compound having a structure of one of the following formulae:

In some embodiments, the compound of Formula I-B or I-D, having a structure of one of the following formulae:

In another aspect, the invention provides for a compound having is a compound having a structure of the formula

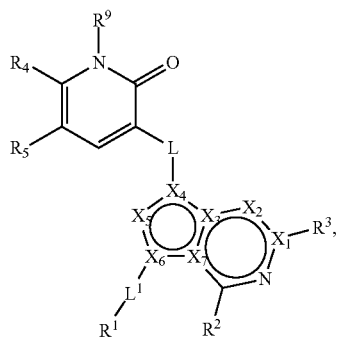

Formula V-A

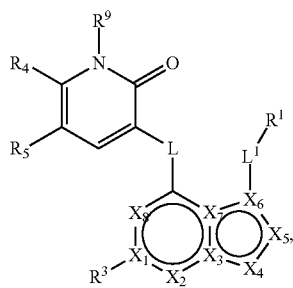

Formula V-B

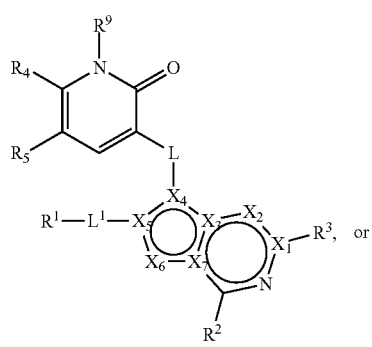

Formula V-C

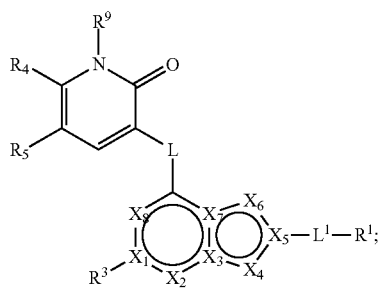

Formula V-D or a pharmaceutically acceptable salt thereof, wherein:

$X_5$ and $X_6$ are C—$R^6$, N, C-$L^1$-$R^1$, or N-$L^1$-$R^1$ wherein one and no more than one of $X_5$ and $X_6$ is C-$L^1$-$R^1$ or N-$L^1$-$R^1$;

$X_1$ is C or N; and $X_2$ and $X_8$ are independently N, or C—$R^6$;

$X_3$ and $X_7$ are C or N, at least one of $X_3$ and $X_7$ is C;

$X_4$ in Formula V-A and Formula V-C is C or N; and $X_4$ in Formula V-B and Formula V-D is C—$R^6$, NH, or N; and wherein no more than two adjacent ring atoms are N or NH;

$R^1$ is hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, and n is an integer from 0 to 2;

$L^1$ is a bond, alkylene, heteroalkylene, alkenylene, alkynylene, cycloalkylene, heterocycloalkylene, arylene, or heteroarylene;

each of $R^2$ and $R^3$ is independently hydrogen, halogen, —CN, —$OR^{10}$, —$S(O)_nR^{11}$, —$NR^{12}R^{13}$, —$C(O)R^{14}$, alkyl, heteroalkyl, cycloalkyl, heterocycloalkyl, aryl, or heteroaryl;

each of $R^4$ and $R^5$ is independently hydrogen or $R^6$, or $R^4$ and $R^5$ are taken together to form a 5, 6 or 7 membered ring, wherein the 5, 6, or 7 membered ring is optionally substituted with $(R^6)_q$;

L is —NH—$CR^7R^8$—, —$(CR^7R^8)_z$—, —C=O—, or —$CR^7R^8(C=O)$—, —O—, —SO—, or —$SO_2$—;

z is an integer from 0 to 10;

q is an integer from 0 to 5;

each $R^6$ is independently hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, wherein n is independently an integer from 0 to 2;

each of $R^7$ and $R^8$ is independently hydrogen, alkyl, heteroalkyl, cycloalkyl, heterocyclyallcyl, or $R^7$ and $R^8$ taken together form a cycloalkyl, heterocycloallcyl or aryl ring;

$R^9$ is hydrogen, —$C(O)R^{14}$, alkyl, alkenyl, alkynyl, heteroalkyl, cycloalkyl, heterocycloalkyl, aryl, or heteroaryl;

each $R^{10}$ is independently hydrogen, —$C(O)R^{15}$, alkyl, heteroalkyl, cycloalkyl, heterocycloalkyl, aryl, or heteroaryl;

each $R^{11}$ is independently —$NR^{16}R^{17}$, alkyl, heteroalkyl, cycloalkyl, heterocycloalkyl, aryl, or heteroaryl;

each $R^{12}$ is independently hydrogen, alkyl, heteroalkyl, cycloalkyl, heterocycloalkyl, aryl, or heteroaryl;

each $R^{13}$ is independently hydrogen, —$S(O)_nR^{18}$, —$C(O)R^{19}$, alkyl, heteroalkyl, cycloalkyl, heterocycloalkyl, aryl, or heteroaryl;

or $R^{12}$ and $R^{13}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{12}R^{13}$, and further wherein the 5, 6, 7, or 8 membered ring is optionally substituted;

each $R^{14}$ is independently —$NR^{20}R^{21}$, hydrogen, alkyl, heteroalkyl, cycloalkyl, heterocycloalkyl, aryl, or heteroaryl;

each $R^{15}$ is independently —$NR^{22}R^{23}$, hydrogen, alkyl, heteroalkyl, cycloalkyl, heterocycloalkyl, aryl, or heteroaryl;

each of $R^{16}$ and $R^{17}$ is independently hydrogen, alkyl, heteroalkyl, cycloalkyl, heterocycloalkyl, aryl, or heteroaryl; or $R^{16}$ and $R^{17}$ are taken together to form a 5, 6, 7 or 8 membered ring, wherein the 5, 6, 7, or 8 membered ring contains 0, 1, 2 or 3 ring heteroatoms selected from N, S, or O in addition to the nitrogen atom of —$NR^{16}R^{17}$, and further wherein the 5, 6, 7, or 8 membered ring is optionally substituted;

each $R^{18}$ is independently hydrogen, alkyl, heteroalkyl, cycloalkyl, heterocycloalkyl, aryl, or heteroaryl;

each $R^{19}$ is independently —$NR^{24}R^{25}$, hydrogen, alkyl, heteroalkyl, cycloalkyl, heterocycloalkyl, aryl, or heteroaryl;

each of $R^{20}$ and $R^{21}$ is independently hydrogen, alkyl, heteroalkyl, cycloalkyl, heterocycloalkyl, aryl, or heteroaryl, or $R^{20}$ and $R^{21}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{20}R^{21}$, and further wherein the 5, 6, 7, or 8 membered ring is optionally substituted;

each of $R^{22}$ and $R^{23}$ is independently hydrogen, alkyl, heteroalkyl, cycloalkyl, heterocycloalkyl, aryl, or heteroaryl, or $R^{22}$ and $R^{23}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{22}R^{23}$, and further wherein the 5, 6, 7, or 8 membered ring is optionally substituted; and each of $R^{24}$ and $R^{25}$ is independently hydrogen, alkyl, heteroalkyl, cycloalkyl, heterocycloallcyl, aryl, or heteroaryl, or $R^{24}$ and $R^{25}$ are taken together to form a 5, 6, 7, or 8 membered ring wherein the 5, 6, 7, or 8 membered ring contains 0, 1, 2 or 3 ring heteroatoms selected from N, S, or O in addition to the nitrogen atom of —$NR^{24}R^{25}$, and further wherein the 5, 6, 7, or 8 membered ring is optionally substituted.

In some embodiments, the compound of Formula V-A is a compound having a structure of Formula VI-A1:

Formula VI-A1

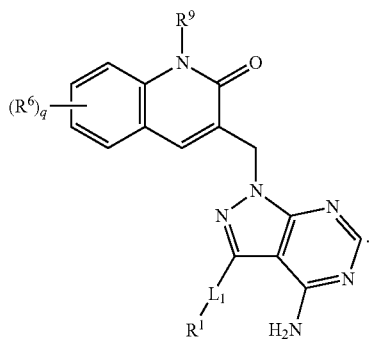

In another aspect, the invention provides for a compound having a structure of one of the following formulae Formula VII-A

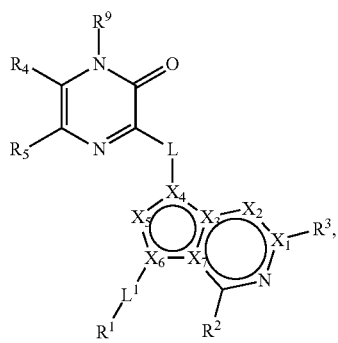

Formula VII-B

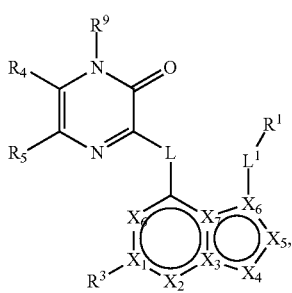

Formula VII-C

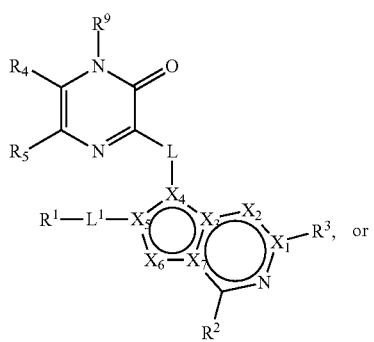

Formula VII-D

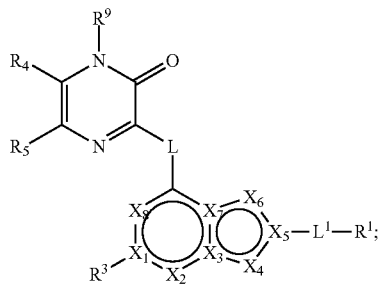

or a pharmaceutically acceptable salt thereof, wherein:
$X_5$ and $X_6$ are C—$R^6$, N, C-$L^1$-$R^1$, or N-$L^1$-$R^1$ wherein one and no more than one of $X_5$ and $X_6$ is C-$L^1$-$R^1$ or N-$L^1$-$R^1$;
$X_1$ is C or N; and $X_2$ and $X_8$ are independently N, or C—$R^6$;
$X_3$ and $X_7$ are C or N, at least one of $X_3$ and $X_7$ is C;
$X_4$ in Formula VII-A and Formula VII-C is C or N; and $X_4$ in Formula VII-B and Formula VII-D is C—$R^6$, NH, or N; and wherein no more than two adjacent ring atoms are N or NH;
$R^1$ is hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, and n is an integer from 0 to 2;
$L^1$ is a bond, alkylene, heteroalkylene, alkenylene, alkynylene, cycloalkylene, heterocycloalkylene, arylene, or heteroarylene;
each of $R^2$ and $R^3$ is independently hydrogen, halogen, —CN, —$OR^{10}$, —$S(O)_nR^{11}$, —$NR^{12}R^{13}$, —$C(O)R^{14}$, alkyl, heteroalkyl, cycloalkyl, heterocycloalkyl, aryl, or heteroaryl;
each of $R^4$ and $R^5$ is independently hydrogen or $R^6$, or $R^4$ and $R^5$ are taken together to form a 5, 6 or 7 membered ring, wherein the 5, 6, 7, or 8 membered ring is optionally substituted with $(R^6)_q$;
L is —NH—$CR^7R^8$—, —$(CR^7R^8)_z$—, —C=O—, or —$CR^7R^8(C=O)$—, —O—, —SO—, or —$SO_2$—;
z is an integer from 0 to 10;
q is an integer from 0 to 5;
each $R^6$ is independently hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, wherein n is independently an integer from 0 to 2;
each of $R^7$ and $R^8$ is independently hydrogen, alkyl, heteroalkyl, cycloalkyl, heterocyclyalkyl, or $R^7$ and $R^8$ taken together form a cycloalkyl, heterocycloalkyl or aryl ring;
$R^9$ is hydrogen, —$C(O)R^{14}$, alkyl, alkenyl, allynyl, heteroalkyl, cycloalkyl, heterocycloalkyl, aryl, or heteroaryl;
each $R^{10}$ is independently hydrogen, —$C(O)R^{15}$, alkyl, heteroalkyl, cycloalkyl, heterocycloalkyl, aryl, or heteroaryl;
each $R^{11}$ is independently —$NR^{16}R^{17}$, alkyl, heteroalkyl, cycloalkyl, heterocycloalkyl, aryl, or heteroaryl;
each $R^{12}$ is independently hydrogen, alkyl, heteroalkyl, cycloalkyl, heterocycloalkyl, aryl, or heteroaryl;
each $R^{13}$ is independently hydrogen, —$S(O)_nR^{18}$, —$C(O)R^{19}$, alkyl, heteroalkyl, cycloalkyl, heterocycloalkyl, aryl, or heteroaryl;
or $R^{12}$ and $R^{13}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{12}R^{13}$, and further wherein the 5, 6, 7, or 8 membered ring is optionally substituted;
each $R^{14}$ is independently —$NR^{20}R^{21}$, hydrogen, alkyl, heteroalkyl, cycloalkyl, heterocycloalkyl, aryl, or heteroaryl;

each $R^{15}$ is independently —$NR^{22}R^{23}$, hydrogen, alkyl, heteroalkyl, cycloalkyl, heterocycloalkyl, aryl, or heteroaryl;

each of $R^{16}$ and $R^{17}$ is independently hydrogen, alkyl, heteroalkyl, cycloalkyl, heterocycloalkyl, aryl, or heteroaryl; or $R^{16}$ and $R^{17}$ are taken together to form a 5, 6, 7, or 8 membered ring, wherein the 5, 6, 7, or 8 membered ring contains 0, 1, 2 or 3 additional ring heteroatoms selected from N, S, or O in addition to the nitrogen atom of —$NR^{16}R^{17}$, and further wherein the 5, 6, 7, or 8 membered ring is optionally substituted;

each $R^{18}$ is independently hydrogen, alkyl, heteroalkyl, cycloalkyl, heterocycloalkyl, aryl, or heteroaryl;

each $R^{19}$ is independently —$NR^{24}R^{25}$, hydrogen, alkyl, heteroalkyl, cycloalkyl, heterocycloalkyl, aryl, or heteroaryl;

each of $R^{20}$ and $R^{21}$ is independently hydrogen, alkyl, heteroalkyl, cycloalkyl, heterocycloalkyl, aryl, or heteroaryl, or $R^{20}$ and $R^{21}$ are taken together to form a 5, 6, 7, or 8 membered ring, wherein the 5, 6, 7, or 8 membered ring contains 0, 1, 2 or 3 additional ring heteroatoms selected from N, S, or O in addition to the nitrogen atom of —$NR^{20}R^{21}$, and further wherein the 5, 6, 7, or 8 membered ring is optionally substituted;

each of $R^{22}$ and $R^{23}$ is independently hydrogen, alkyl, heteroalkyl, cycloalkyl, heterocycloalkyl, aryl, or heteroaryl, or $R^{22}$ and $R^{23}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{22}R^{23}$, and further wherein the 5, 6, 7, or 8 membered ring is optionally substituted; and each of $R^{24}$ and $R^{25}$ is independently hydrogen, alkyl, heteroalkyl, cycloalkyl, heterocycloalkyl, aryl, or heteroaryl, or $R^{24}$ and $R^{25}$ are taken together to form a 5, 6, 7, or 8 membered ring wherein the 5, 6, 7, or 8 membered ring contains 0, 1, 2 or 3 ring heteroatoms selected from N, S, or O in addition to the nitrogen atom of —$NR^{24}R^{25}$, wherein the 5, 6, 7, or 8 membered ring contains 0, 1, 2 or 3 additional ring heteroatoms selected from N, S, or O, and further wherein the 5, 6, 7, or 8 membered ring is optionally substituted.

In some embodiments, compound of Formula VII-A is a compound having a structure of Formula VII-A1:

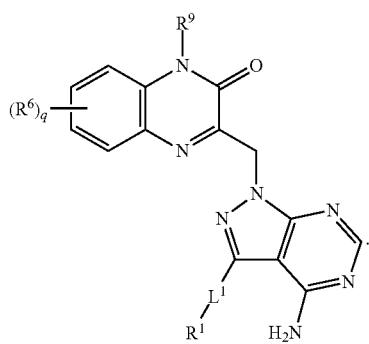

Formula VII-A1

In some embodiments of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, when L is —$(CR^7R^8)_z$— and z is 1, then $R^1$ is alkynyl, aryl, or heteroaryl. In some other embodiments, when L is —$(CR^7R^8)_z$— and z is 1, then $L^1$ is a bond, and $R^1$ is alkynyl, aryl, or heteroaryl.

In some embodiments of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^9$ is —$OR^{10}$, —$NR^{12}R^{13}$, —$C(O)R^{14}$, alkyl, alkenyl, alkynyl, heteroalkyl, cycloalkyl, heterocycloalkyl, aryl, or heteroaryl. In some embodiments, when $R^9$ is aryl, then $R^9$ is substituted with halogen, alkyl or heteroalkyl. In other embodiments, wherein when $R^9$ is —$NR^{12}R^{13}$, then $R^{12}$ and $R^{13}$ are taken together to form a 5, 6, 7 or 8 membered ring.

In some embodiments of a compound of Formula I-A, I-B, I-C, I-D, I-E, I-F, I-G, I-H, I-J, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^1$ is bicyclic heteroaryl.

In some embodiments of a compound of Formula I-A, I-B, I-C, I-D, I-E, I-F, I-G, I-H, I-J, I-J-1, I-K, II-A, II-A1, II-A2, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^4$ and $R^5$ are taken together to form a 6-membered ring.

In some embodiments of a compound of Formula I-A, I-C, I-E, I-G, I-J, I-J-1, I-K, II-A, II-A1, II-A2, III-A, IV-A, V-A, V-A1, V-C, VI-A, VI-A1, VI-A2, VI-C, VII-A, VII-A1, VII-A2, or VII-C, $R^2$ is —$NH_2$.

In some embodiments of a compound of Formula I-A, I-B, I-C, I-D, I-E, I-F, I-G, I-H, II-A, II-A1, II-A2, III-A, IV-A, V-A, V-B, V-C, V-D, VI-A, VI-A1, VI-A2, VI-B, VI-C, VI-D, VII-A, VII-A2, VII-B, VII-C, or VII-D, $R^7$ is alkyl.

In some embodiments of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-B, VI-C, VI-D, VII-A, VII-B, VII-C, or VII-D, $R^7$ and $R^8$ are hydrogen.

In some embodiments of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, or VI-D, W is CH.

In some embodiments of a compound of Formula I-A, I-B, I-C, I-D, I-E, I-F, I-G, I-H, III-A, IV-A, V-A, V-A1, V-B, V-C, V-D, VII-A, VII-B, VII-C, or VII-D, W is N.

In some embodiments of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^3$ is hydrogen.

In some embodiments of the invention, a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or WI-D is provided, wherein $R^9$ is halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, and wherein n is independently an integer from 0 to 2. In some embodiments of the invention a compound of Formula Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VU-A, VII-A1, VII-A2, VII-B, VII-C, or VII-D is provided, wherein $R^9$ is substituted heterocycloalkyl. In some embodiments of the invention a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A1, VII-A2, VII-B, VII-C, or VII-D is provided, wherein $R^9$ is substituted heterocycloalkyl. In some embodiments of the invention a compound of Formula I-A, I-B, I-C, I-D, I-E, I-F, I-G, I-H, I-J, I-J-1, I-K, II-A, II-A1, II-A2, IV-A, V-A, V-A1, V-B, V-C, V-D, VI-A, VI-A1, VI-A2, VI-B, VI-C, VI-D, VII-A, VII-A2, VII-B, VII-C, or VII-D is provided, wherein $R^9$ is unsubstituted aryl or substituted aryl. In some embodiments, $R^9$ is aryl substituted with halogen, aryl substituted with alkyl, or aryl substituted with heteroalkyl, In some embodiments of the invention a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided, wherein $R^9$ is $—NR^{12}R^{13}$. In some embodiments of the invention a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided, wherein $R^{12}$ is —H and $R^{13}$ is unsubstituted alkyl or cycloalkyl. Alternatively, $R^{12}$ and $R^{13}$ are unsubstituted alkyl or cycloalkyl. In some embodiments of the invention a compound of Formula I-A, I-B, I-C, I-D, I-E, I-F, I-G, I-H, I-J, I-J-1, I-K, II-A, II-A1, II-A2, IV-A, V-A, V-A1, V-B, V-C, V-D, VI-A, VI-A1, VI-A2, VI-B, VI-C, VI-D, VII-A, VII-A1, VII-B, VII-C, or VII-DD is provided, wherein $L^1$ is a bond.

In some embodiments of the invention a compound of Formula I-A, I-B, I-C, I-D, I-E, I-F, I-G, I-H, I-J, I-J-1, I-K, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided, wherein $R^1$ is monocyclic aryl, bicyclic aryl, monocyclic heteroaryl, or bicyclic heteroaryl. In some embodiments, $R^1$ is unsubstituted aryl, or substituted aryl. In some embodiments, $R^1$ is aryl substituted with halogen or hydroxy. In other embodiments, $R^1$ is aryl substituted with halogen and hydroxy. In yet other embodiments, $R^1$ is unsubstituted heteroaryl or substituted heteroaryl. Alternatively, $R^1$ is unsubstituted alkynyl or substituted alkynyl. In some embodiments, $R^1$ is alkynyl substituted with hydroxy. In further embodiments, $R^1$ is halogen, —CN, $—C(=O)R^{14}$, alkyl, or alkenyl.

In some embodiments of the invention a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided wherein $R^4$ and $R^5$ taken together form a 6-membered ring. The 6-membered ring can be substituted with $R^6$. In some embodiments, $R^6$ in a compound of Formula I-A, I-B, I—C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A1, VII-B, VII-C, or VII-D, is alkyl. In some embodiments of the invention a compound of Formula I-A, I-B, I-C, I-D, I-E, I-F, I-G, I-H, I-J, I-J-1, I-K, II-A2, III-A, IV-A, V-A, V-A1, V-B, V-C, V-D, VI-A, VI-A1, VI-A2, VI-B, VI—C, VI-D, VII-A, VII-A1, VII-A2, VII-B, VII-C, or VII-D is provided wherein $R^2$ is $—NR^{12}R^{13}$. In some embodiments, $R^2$ in a compound of Formula I-A, I-B, I-C, I-D, I-E, I-F, I-G, I-H, I-J, I-J-1, I-K, II-A, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, is $—NH_2$. In some embodiments of the invention a compound of Formula I-A, I-B, I-C, I-D, I-E, I-F, I-G, I-H, I-J, I-J-1, I-K, II-A, II-A1, II-A2, III-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided wherein $R^7$ is alkyl. In some embodiments of the invention a compound of Formula I-A, I-B, I-C, I-D, I-E, I-F, I-G, I-H, I-J, I-J-1, I-K, II-A, II-A1, II-A2, IV-A, V-A, V-A1, V-B, V-C, V-D, VI-A, VI-A1, VI-A2, VI-B, VI-C, VI-D, VII-A, VII-A2, VII-B, VII-C, or VII-D is provided wherein $R^7$ and $R^8$ are hydrogen. In some embodiments of the invention a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VH-D is provided wherein W is CH. In some embodiments of the invention a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided wherein z is 1. In some embodiments of the invention a compound of Formula I-A, I-B, I-C, I-D, I-E, I-F, I-G, I-H, I-J, 1-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D is provided wherein $R^3$ is hydrogen.

In some embodiments of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, the compound selectively inhibits one or more members of type I phosphatidylinositol 3-kinases (PI3-kinase) relative to other members of type I PI3-kinase, ascertained by an in vitro kinase assay. In some embodiments, the compound selectively inhibits PI3-kinase γ and PI3-kinase δ as compared to PI3-kinase β and PI3-kinase α. In other embodiments, the compound selectively inhibits PI3-kinase δ and PI3-kinase β as compared to PI3-kinase α and PI3-kinase γ.

In another aspect, the invention provides a pharmaceutical composition comprising a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, VII-D or a pharmaceutically acceptable salt of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, W-A2, VI-B, VI-C, VI-D, VII-A, VII-A1, VII-A2, VII-B, VII-C, or WI-D, and a pharmaceutically acceptable excipient.

The invention also provides a method of treating a medical condition mediated by a type I-PI3 kinase (e.g. mediated by p110δ, p110γ, p110α, or p110β kinase), comprising administering to a subject in need thereof a therapeutically effective amount of a compound of Formula I-A, I-B, I-C, I-D, I-E, I-F, I-G, I-H, I-J, I-J-1, I-K, II-A, II-A1, II-A2, IV-A, V-A, V-A1, V-B, V-C, V-D, VI-A, VI-A1, VI-A2, VI-B, VI-C, VI-D, VII-A, VII-A1, VII-A2, VII-B, VII-C, or WI-D, or a pharmaceutically acceptable salt of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D. In some embodiments, the medical condition is selected from the group consisting of hematologic malignancy, inflammation, autoimmune disease, rheumatoid arthritis, systemic lupus erythematosus, asthma, and cardiovascular disease. In other embodiments, the medical condition is selected from the group consisting of acute myelogenous leukemia, chronic myelogenous leukemia, mastocytosis, chronic lymphocytic leukemia, multiple myeloma, and myelodysplastic syndrome. In other embodiments, the method of treating a medical condition further comprises administering an anti-cancer agent.

The present invention also provides a method of inhibiting activity of a protein kinase and/or a lipid kinase present in a cell, comprising contacting said cell with an effective amount of a compound of Formula I-A, I-B, I-C, I-D, I-E, I-F, I-G, I-H, I-J, I-J-1, I-K, II-A, II-A1, II-A2, IV-A, V-A, V-A1, V-B, V-C, V-D, VI-A, VI-A1, W-A2, VI-B, VI-C, VI-D, VII-A, VII-A1, VII-A2, VII-B, VII-C, or VII-D or a pharmaceutically acceptable salt of a compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

I. Definitions

Unless otherwise stated, structures depicted herein are also meant to include compounds which differ only in the presence of one or more isotopically enriched atoms. For example, compounds having the present structures wherein hydrogen is replaced by deuterium or tritium, or wherein carbon atom is replaced by $^{13}$C- or $^{14}$C-enriched carbon, are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

"Radiation therapy" means exposing a patient, using routine methods and compositions known to the practitioner, to radiation emitters such as alpha-particle emitting radionucleotides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

"Acyl" refers to a —(C=O)R radical wherein "R" is alkyl, aryl, heteroaryl, heteroalkyl, or heterocyclyl, which are as described herein. In some embodiments, it is a $C_1$-$C_{10}$ acyl radical which refers to the total number of chain or ring atoms of the allyl, aryl, heteroaryl or heterocyclyl portion of the acyloxy group plus the carbonyl carbon of acyl, i.e three other ring or chain atoms plus carbonyl. If the R radical is heteroaryl or heterocyclyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocyclyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl. "Acyloxy" refers to a R(C=O)O— radical wherein "R" is alkyl, aryl, heteroaryl or heterocyclyl, which are as described herein. In some embodiments, it is a $C_1$-$C_4$ acyloxy radical which refers to the total number of chain or ring atoms of the alkyl, aryl, heteroaryl or heterocyclyl portion of the acyloxy group plus the carbonyl carbon of acyl, i.e three other ring or chain atoms plus carbonyl. If the R radical is heteroaryl or heterocyclyl, the hetero ring or chain atoms contribute to the total number of chain or ring atoms. Unless stated otherwise specifically in the specification, the "R" of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^8$, —C(O)O$R^a$, —C(O)N$(R^a)_2$, —N$(R^a)$C(O)O$R^a$, —N$(R^a)$C(O)$R^a$, —N$(R^a)$S(O)$_t$$R^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aralkyl" or "arylalkyl" refers to an (aryl)alkyl-radical where aryl and alkyl are as disclosed herein and which are optionally substituted by one or more of the subsituents described as suitable substituents for aryl and alkyl respectively.

"Alkoxy" refers to a (alkyl)O-radical, where alkyl is as described herein and contains 1 to 10 carbons (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. A alkoxy moiety may be substituted by one or more of the substituents described as suitable substituents for an alkyl radical.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)R$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)R$^a$, —C(O)N(R$^a$)$_2$, —N(R$^a$)C(O)R$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, unless stated otherwise specifically in the specification. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Amide" or "amido" refers to a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). In some embodiments it is a $C_1$-$C_4$ amido or amide radical, which includes the amide carbonyl in the total number of carbons in the radical. Unless stated otherwise specifically in the specification, an amino group is optionally substituted independently by one or more of the substituents as described herein for alkyl, cycloalkyl, aryl, heteroaryl, or heterocyclyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, allynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)$R^a$, —C(O)N$(R^a)_2$, —N($R^a$)C(O)$R^a$, —N($R^a$)C(O)$R^a$, —N($R^a$)S(O)$_t R^a$ (where t is 1 or 2), —S(O)$_t$ O$R^a$ (where t is 1 or 2), —S(O)$_t$N$(R^a)_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (ie. $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclohexyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)$R^a$, —C(O)N$(R^a)_2$, —N($R^a$)C(O)$R^a$, —N($R^a$)C(O) $R^a$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, allynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R)_2$, —C(O)$R^a$, —C(O)$R^a$, —C(O)N$(R^a)_2$, —N($R^a$)C (O)$R^a$, —N($R^a$)C(O)$R^a$, —N($R^a$)S(O)$_t R^a$ (where t is 1 or 2), —S(O)$_t$O$R^a$ (where t is 1 or 2), —S(O)$_t$N$(R^a)_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Heteroaryl" or, alternatively, "heteroaromatic" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a hetaryl moiety is optionally substituted by one or more subsituents which are independently: alkyl, heteroalkyl, alkenyl, allynyl, cycloalkyl, heterocycloalkyl, aryl, arylalkyl, heteroaryl, heteroarylalkyl, hydroxy, halo, cyano, nitro, oxo, thioxo, trimethylsilanyl, —SR$^a$, —OC(O)—R$^a$, —N(R$^a$)$_2$, —C(O)R$^a$, —C(O)R$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Heteroarylalkyl" or "hetarylalkyl" refers to an (heteroaryl)alkyl-radical where heteroaryl and alkyl are as disclosed herein and which are optionally substituted by one or more of the subsituents described as suitable substituents for aryl and alkyl respectively.

"Heterocyclyl" or "heterocycloalkyl" refers to a stable 3- to 18-membered non-aromatic ring (e.g., C$_3$-C$_{18}$ heterocyclyl) radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heteroaryl group may consist of 3 ring atoms, 4 ring atoms, etc., up to and including 18 ring atoms. In some embodiments, it is a C$_5$-C$_{10}$ heterocyclyl. In some embodiments, it is a C$_4$-C$_{10}$ heterocyclyl. In some embodiments, it is a C$_3$-C$_{10}$ heterocyclyl. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, a heterocyclyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)R$^a$, —N(R$^8$)C(O)R$^8$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroallcyl, carbocyclyl, carbocyclylalkyl, aryl, aralkyl, heterocyclyl, heterocyclylalkyl, heteroaryl or heteroarylalkyl.

"Heteroalicyclic" refers to a cycloalkyl radical that includes at least one heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless stated otherwise specifically in the specification, a heteroalicyclic group is optionally substituted by one or more of substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)R$^a$, —N(R$^a$)C(O)R$^a$, —N(R$^a$)S(O)$_t$R$^a$ (where t is 1 or 2), —S(O)$_t$R$^a$ (where t is 1 or 2), —S(O)$_t$N(R$^a$)$_2$ (where t is 1 or 2), —OPO$_3$WY (where W and Y are hydrogen, methyl, ethyl, alkyl, lithium, sodium or potassiun) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Imino" refers to the =N—H radical.

"Isocyanato" refers to a —NCO radical.

"Isothiocyanato" refers to a —NCS radical.

"Mercaptyl" refers to a (alkyl)S— or (H)S— radical.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Sulfinyl" refers to a —S(=O)—R radical, where R is selected from the group consisting of alkyl, cycloallcyl, aryl, heteroaryl (bonded through a ring carbon) and heteroalicyclic (bonded through a ring carbon).

"Sulfonyl" refers to a —S(=O)$_2$—R radical, where R is selected from the group consisting of alkyl, cycloalkyl, aryl, heteroaryl (bonded through a ring carbon) and heteroalicyclic (bonded through a ring carbon).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). In some embodiments, it is a C$_1$-C$_4$ sulfonamido, wherein each R in sulfonamido contains 1 carbon, 2 carbons, 3 carbons, or 4 carbons total. A sulfonamido group is optionally substituted by one or more of the subsituents described for alkyl, cycloalkyl, aryl, heteroaryl respectively "Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonategroup is optionally substituted on R by one or more of the subsituents described for alkyl, cycloallyl, aryl, heteroaryl respectively.

"Thiocyanato" refers to a —CNS radical.

"Thioxo" refers to the =S radical.

"Substituted" means that the referenced group may be substituted with one or more additional group(s) individually and independently selected from acyl, alkyl, alkylaryl, cycloalkyl, aralkyl, aryl, carbohydrate, heteroaryl, heterocyclic, hydroxy, alkoxy, aryloxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamidyl, sulfoxyl, sulfonate, and amino, including mono- and di-substituted amino groups, and the protected derivatives thereof. The substituents themselves may be substituted, for example, a cycloakyl substituent may have a halide substituted at one or more ring carbons, and the like. The protecting groups that may form the protective derivatives of the above substituents are known to those of skill in the art and may be found in references such as Greene and Wuts, above.

The compounds presented herein may possess one or more chiral centers and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

The methods and formulations described herein include the use of N-oxides, crystalline forms (also known as polymorphs), or pharmaceutically acceptable salts of compounds having the structure of Formula (I), as well as active metabolites of these compounds having the same type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

The term "selective inhibition" or "selectively inhibit" as referred to a biologically active agent refers to the agent's ability to preferentially reduce the target signaling activity as compared to off-target signaling activity, via direct or interact interaction with the target.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. All formulae disclosed here are shown without a definitive stereochemistry at certain positions. The present invention includes all stereoisomers of the shown formulae and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

"Isomers" are different compounds that have the same molecular formula. "Stereoisomers" are isomers that differ only in the way the atoms are arranged in space, i.e. having a different stereochemical configuration. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)- isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

II. Compositions

In one aspect, the present invention provides a compound of the formula:

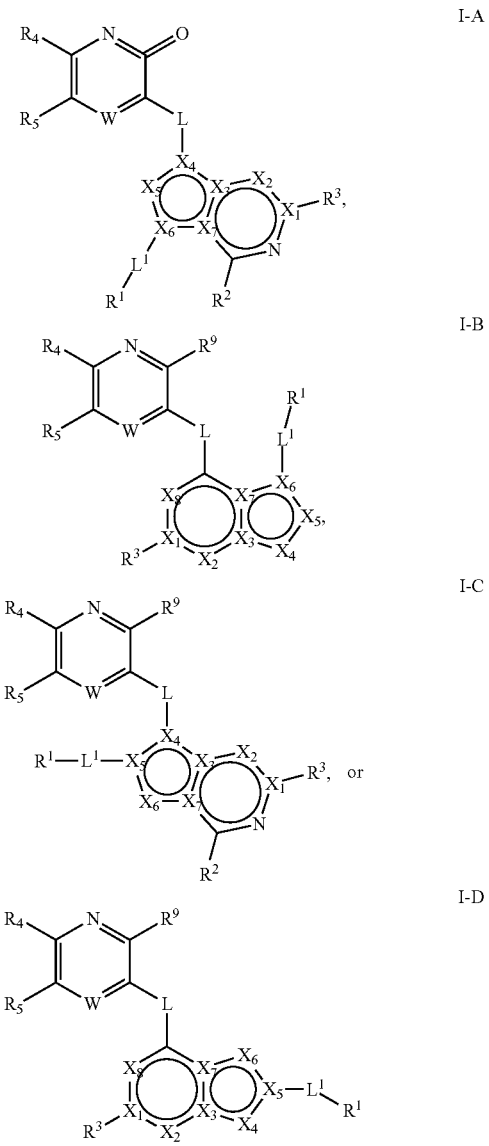

or a pharmaceutically acceptable salt thereof, wherein:
$X_5$ and $X_6$ are C—$R^6$, N, C-$L^1$-$R^1$, or N-$L^1$-$R^1$ wherein one of $X_5$ and $X_6$ is C-$L^1$-$R^1$ or N-$L^1$-$R^1$;
$X_1$ is C or N; and $X_2$ and $X_8$ are independently N or C—$R^6$;
$X_3$ and $X_7$ are C or N, and at least one of $X_3$ and $X_7$ is C;
$X_4$ in Formula I-A or I-C is C or N; and $X_4$ in Formula I-B or I-D is C—$R^6$, NH, or N; and no more than two adjacent ring atoms are N or NH;
$R^1$ is hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, and n is an integer from 0 to 2;
$L^1$ is a bond, alkylene, heteroalkylene, alkenylene, alkynylene, cycloalkylene, heterocycloalkylene, arylene, or heteroarylene;
$R^2$ and $R^3$ are independently hydrogen, halogen, —CN, —$OR^{10}$, —$S(O)_nR^{11}$, —$NR^{12}R^{13}$, —$C(O)R^{14}$, alkyl, heteroalkyl, cycloalkyl, heterocyclyalkyl, aryl, or heteroaryl;
$R^4$ and $R^5$ are independently hydrogen or $R^6$, or $R^4$ and $R^5$ are taken together to form a 5, 6 or 7-membered ring, wherein the 5, 6, or 7 membered ring is optionally substituted with $(R^6)_q$;

L is —NH—CR⁷R⁸—, —(CR⁷R⁸)$_z$—, —C=O—, or —CR⁷R⁸(C=O)—, —O—, —SO—, or —SO$_2$—;
z is an integer from 0 to 10;
q is an integer from 0 to 5;
each of $R^6$ is independently hydrogen, halogen, —CN, —OR$^{10}$, —S(O)$_n$R$^{11}$, —NR$^{12}$R$^{13}$, —C(O)R$^{14}$, alkyl, alkenyl, alkynyl, heteroalkyl, cycloalkyl, heterocycloalkyl, aryl, or heteroaryl;
each of $R^7$ and $R^8$ is independently hydrogen, alkyl, heteroalkyl, cycloalkyl, heterocyclyalkyl, or $R^7$ and $R^8$ taken together form a cycloalkyl, heterocycloalkyl or aryl ring;
$R^9$ is hydrogen, halogen, —CN, —OR$^{10}$, —S(O)$_n$R$^{11}$, —NR$^{12}$R$^{13}$, —C(O)R$^{14}$, alkyl, alkenyl, alkynyl, heteroalkyl, cycloalkyl, heterocycloalkyl, aryl, or heteroaryl;
each $R^{10}$ is independently hydrogen, —C(O)R$^{15}$, alkyl, heteroalkyl, cycloalkyl, heterocycloalkyl, aryl, or heteroaryl;
each $R^{11}$ is independently —NR$^{16}$R$^{17}$, alkyl, heteroalkyl, cycloalkyl, heterocycloalkyl, aryl, or heteroaryl;
each $R^{12}$ is independently hydrogen, alkyl, heteroalkyl, cycloalkyl, heterocycloalkyl, aryl, or heteroaryl;
each $R^{13}$ is independently hydrogen, —S(O)$_n$R$^{18}$, —C(O)R$^{19}$, alkyl, heteroalkyl, cycloalkyl, heterocycloalkyl, aryl, or heteroaryl;
or $R^{12}$ and $R^{13}$ are taken together to form a 5, 6 or 7-membered ring, wherein the 5, 6, 7, or 8 membered ring contains 0, 1, 2 or 3 ring heteroatoms selected from N, S, or O in addition to the nitrogen atom of —NR$^{12}$R$^{13}$; and further wherein the 5, 6, 7, or 8 membered ring is optionally substituted;
each $R^{14}$ is independently —NR$^{20}$R$^{21}$, hydrogen, alkyl, heteroalkyl, cycloalkyl, heterocycloalkyl, aryl, or heteroaryl;
each $R^{15}$ is independently —NR$^{22}$R$^{23}$, hydrogen, alkyl, heteroalkyl, cycloalkyl, heterocycloalkyl, aryl, or heteroaryl;
each of $R^{16}$ and $R^{17}$ is independently hydrogen, alkyl, heteroalkyl, cycloalkyl, heterocycloalkyl, aryl, or heteroaryl;
or $R^{16}$ and $R^{17}$ are taken together to form a 5, 6 or 7-membered ring, wherein the 5, 6, 7, or 8 membered ring contains 0, 1, 2 or 3 ring heteroatoms selected from N, S, or O in addition to the nitrogen atom of —NR$^{16}$R$^{17}$; and further wherein the 5, 6, 7, or 8 membered ring is optionally substituted;
each $R^{18}$ is independently hydrogen, alkyl, heteroalkyl, cycloalkyl, heterocycloalkyl, aryl, or heteroaryl;
each $R^{19}$ is independently —NR$^{24}$R$^{25}$, hydrogen, alkyl, heteroalkyl, cycloalkyl, heterocycloalkyl, aryl, or heteroaryl;
each of $R^{20}$ and $R^{21}$ is independently hydrogen, alkyl, heteroalkyl, cycloalkyl, heterocycloalkyl, aryl, or heteroaryl, or $R^{20}$ and $R^{21}$ are taken together to form a 5, 6 or 7-membered ring, wherein the 5, 6, 7, or 8 membered ring contains 0, 1, 2 or 3 ring heteroatoms selected from N, S, or O in addition to the nitrogen atom of —NR$^{20}$R$^{21}$; and further wherein the 5, 6, 7, or 8 membered ring is optionally substituted;
each of $R^{22}$ and $R^{23}$ is independently hydrogen, alkyl, heteroalkyl, cycloalkyl, heterocycloalkyl, aryl, or heteroaryl, or $R^{22}$ and $R^{23}$ are taken together to form a 5, 6 or 7-membered ring, wherein the 5, 6, 7, or 8 membered ring contains 0, 1, 2 or 3 ring heteroatoms selected from N, S, or O in addition to the nitrogen atom of —NR$^{22}$R$^{23}$; and further wherein the 5, 6, 7, or 8 membered ring is optionally substituted;
each of $R^{24}$ and $R^{25}$ is independently hydrogen, alkyl, heteroalkyl, cycloalkyl, heterocycloalkyl, aryl, or heteroaryl, or $R^{24}$ and $R^{25}$ are taken together to form a 5, 6 or 7-membered ring, wherein the 5, 6, 7, or 8 membered ring contains 0, 1, 2 or 3 ring heteroatoms selected from N, S, or O in addition to the nitrogen atom of —NR$^{24}$R$^{25}$; and further wherein the 5, 6, 7, or 8 membered ring is optionally substituted; and
W is C—R$^6$ or N.

In some embodiments, a compound of one of Formula I-A, I-B, I-C, or I-D has a structure of one of the following formulae:

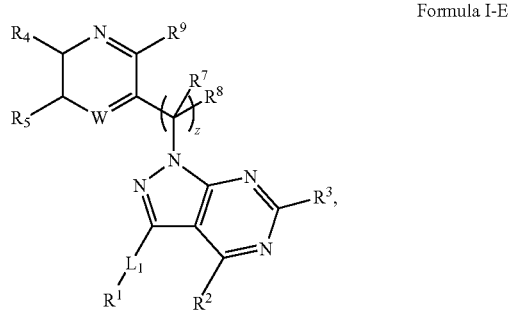

Formula I-E

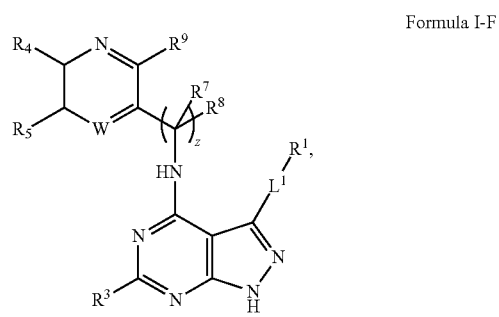

Formula I-F

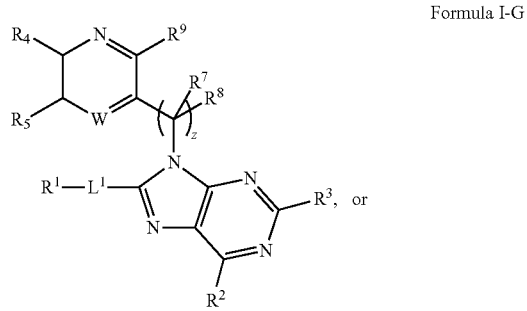

Formula I-G

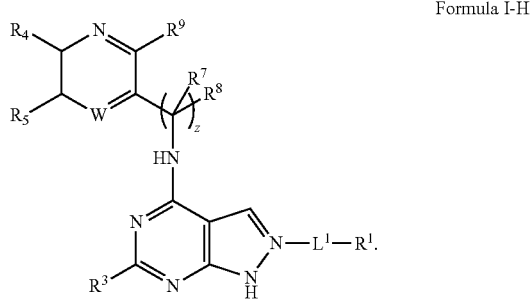

Formula I-H

In some embodiments of the invention, the compound of Formula I-E has a structure of Formula I-J or Formula I-K:

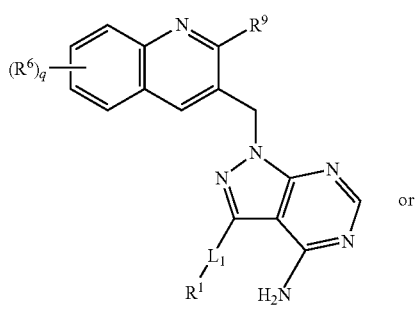

Formula I-J or

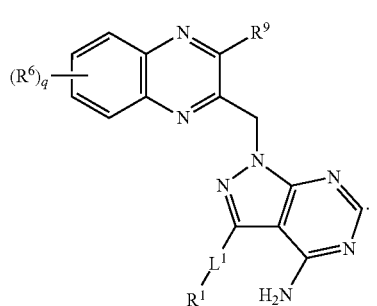

Formula I-K

In some embodiments, the compound of FormulaI-J is a compound of Formula I-J-1:

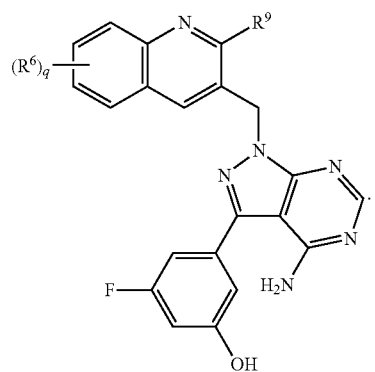

Formula I-J-1

In some embodiments, the compound of Formula I-E is a compound of Formula II-A, Formula II-A1 or Formula II-A2:

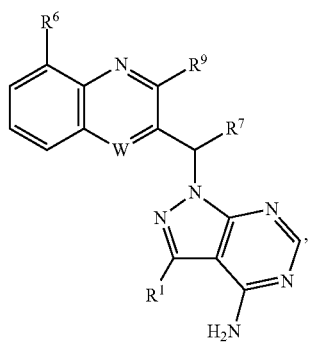

Formula II-A

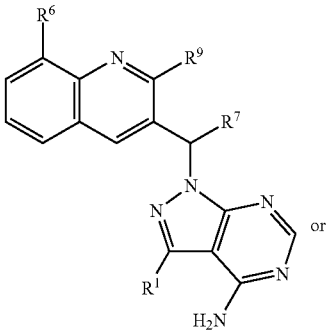

Formula II-A1 or

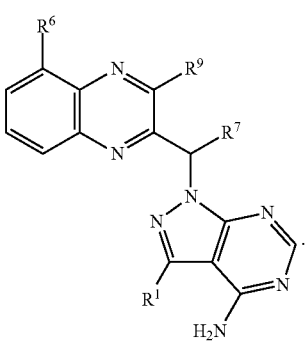

Formula II-A2

In other embodiments, a compound of Formula I-E has a structure of Formula III-A:

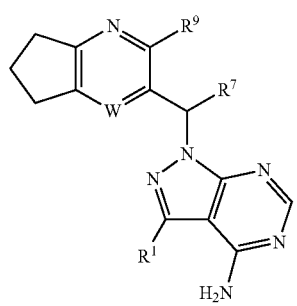

Formula III-A

In other embodiments, a compound of Formula I-E has a structure of Formula IV-A:

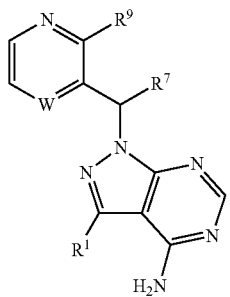

Formula IV-A

In some embodiments, W is C—$R^6$. In other embodiments, W is CH. In yet other embodiments W is N.

In another aspect, a compound of the invention has a structure of one of the following formulae:

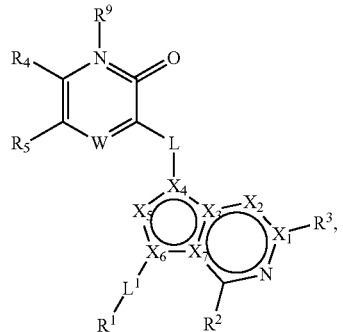
Formula V-A

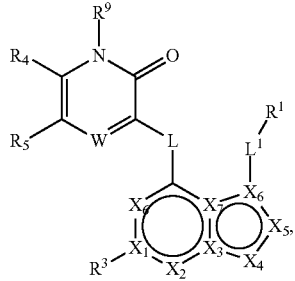
Formula V-B

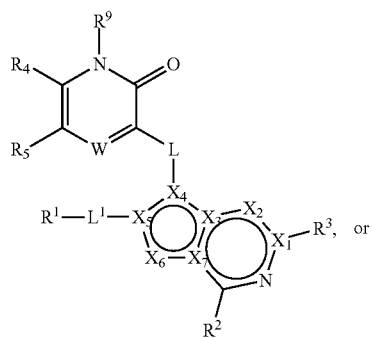
Formula V-C, or

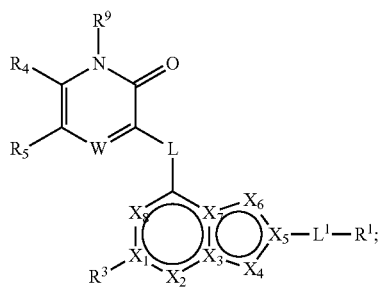
Formula V-D or a pharmaceutically acceptable salt thereof, wherein:
W is C—$R^6$ or N;
$X_5$ and $X_6$ are C—$R^6$, N, C-$L^1$-$R^1$, or N-$L^1$-$R^1$ wherein one and no more than one of $X_5$ and $X_6$ is C-$L^1$-$R^1$ or N-$L^1$-$R^1$;
$X_1$ is C or N; and $X_2$ and $X_8$ are independently N, or C—$R^6$;
$X_3$ and $X_7$ are C or N, at least one of $X_3$ and $X_7$ is C;
$X_4$ in Formula V-A and Formula V-C is C or N; and $X_4$ in Formula V-B and Formula V-D is C—$R^6$, NH, or N; and wherein no more than two adjacent ring atoms are N or NH;
$R^1$ is hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, and n is an integer from 0 to 2;
$L^1$ is a bond, alkylene, heteroalkylene, alkenylene, alkynylene, cycloalkylene, heterocycloalkylene, arylene, or heteroarylene;
each of $R^2$ and $R^3$ is independently hydrogen, halogen, —CN, —$OR^{10}$, —$S(O)_nR^{11}$, —$NR^{12}R^{13}$, —$C(O)R^{14}$, alkyl, heteroalkyl, cycloalkyl, heterocycloallyl, aryl, or heteroaryl;
each of $R^4$ and $R^5$ is independently hydrogen or $R^6$, or $R^4$ and $R^5$ are taken together to form a 5, 6 or 7 membered ring, wherein the 5, 6, or 7 membered ring is optionally substituted with $(R^6)_q$;
L is —NH—$CR^7R^8$—, —$(CR^7R^8)_z$—, —C=O—, or —$CR^7R^8(C=O)$—, —O—, —SO—, or —$SO_2$—;
z is an integer from 0 to 10;
q is an integer from 0 to 5;
each $R^6$ is independently hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, wherein n is independently an integer from 0 to 2;
each of $R^7$ and $R^8$ is independently hydrogen, alkyl, heteroalkyl, cycloalkyl, heterocyclyalkyl, or $R^7$ and $R^8$ taken together form a cycloalkyl, heterocycloalkyl or aryl ring;
$R^9$ is hydrogen, —$C(O)R^{14}$, alkyl, alkenyl, alkynyl, heteroalkyl, cycloalkyl, heterocycloalkyl, aryl, or heteroaryl;
each $R^{10}$ is independently hydrogen, —$C(O)R^{15}$, alkyl, heteroalkyl, cycloalkyl, heterocycloalkyl, aryl, or heteroaryl;
each $R^{11}$ is independently —$NR^{16}R^{17}$, alkyl, heteroalkyl, cycloalkyl, heterocycloalkyl, aryl, or heteroaryl;
each $R^{12}$ is independently hydrogen, alkyl, heteroalkyl, cycloalkyl, heterocycloalkyl, aryl, or heteroaryl;
each $R^{13}$ is independently hydrogen, —$S(O)_nR^{18}$, —$C(O)R^{19}$, alkyl, heteroalkyl, cycloalkyl, heterocycloalkyl, aryl, or heteroaryl;
or $R^{12}$ and $R^{13}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{12}R^{13}$, and further wherein the 5, 6, 7, or 8 membered ring is optionally substituted;
each $R^{14}$ is independently —$NR^{20}R^{21}$, hydrogen, alkyl, heteroalkyl, cycloalkyl, heterocycloalkyl, aryl, or heteroaryl;
each $R^{15}$ is independently —$NR^{22}R^{23}$, hydrogen, alkyl, heteroalkyl, cycloalkyl, heterocycloalkyl, aryl, or heteroaryl;
each of $R^{16}$ and $R^{17}$ is independently hydrogen, alkyl, heteroalkyl, cycloalkyl, heterocycloalkyl, aryl, or heteroaryl; or $R^{16}$ and $R^{17}$ are taken together to form a 5, 6, 7 or 8 membered ring, wherein the 5, 6, 7, or 8 membered ring contains 0, 1, 2 or 3 ring heteroatoms selected from N, S, or O in addition to the nitrogen atom of —$NR^{16}R^{17}$, and further wherein the 5, 6, 7, or 8 membered ring is optionally substituted;
each $R^{18}$ is independently hydrogen, alkyl, heteroalkyl, cycloalkyl, heterocycloalkyl, aryl, or heteroaryl;
each $R^{19}$ is independently —$NR^{24}R^{25}$, hydrogen, alkyl, heteroalkyl, cycloalkyl, heterocycloalkyl, aryl, or heteroaryl;
each of $R^{20}$ and $R^{21}$ is independently hydrogen, alkyl, heteroalkyl, cycloalkyl, heterocycloalkyl, aryl, or heteroaryl, or $R^{20}$ and $R^{21}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{20}R^{21}$, and further wherein the 5, 6, 7, or 8 membered ring is optionally substituted;
each of $R^{22}$ and $R^{23}$ is independently hydrogen, alkyl, heteroalkyl, cycloalkyl, heterocycloalkyl, aryl, or heteroaryl, or $R^{22}$ and $R^{23}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —NR$^{22}$R$^{23}$, and further wherein the 5, 6, 7, or 8 membered ring is optionally substituted; and each of R$^{24}$ and R$^{25}$ is independently hydrogen, alkyl, heteroalkyl, cycloalkyl, heterocycloalkyl, aryl, or heteroaryl, or R$^{24}$ and R$^{25}$ are taken together to form a 5, 6, 7, or 8 membered ring wherein the 5, 6, 7, or 8 membered ring contains 0, 1, 2 or 3 ring heteroatoms selected from N, S, or O in addition to the nitrogen atom of —NR$^{24}$R$^{25}$, and further wherein the 5, 6, 7, or 8 membered ring is optionally substituted.

In some embodiments, the compound of Formula V-A is a compound having the structure of Formula V-A1:

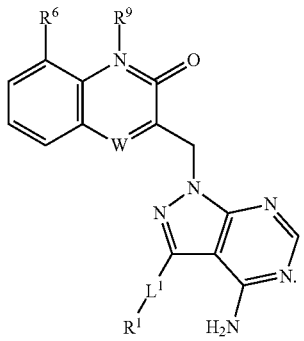

Formula V-A1

In some embodiments, the compound of Formula V-A, Formula V-B, Formula V-C or Formula V-D is a compound having a structure of one of the following formulae:

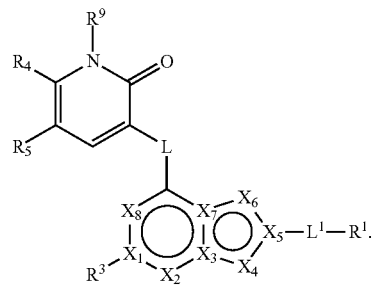

Formula VI-A

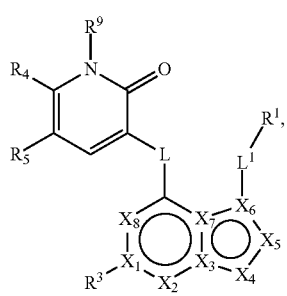

Formula VI-B

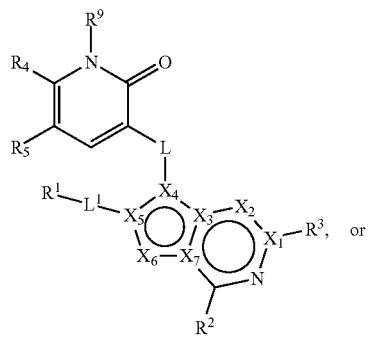

Formula VI-C

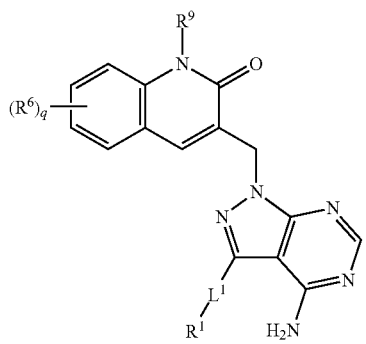

Formula VI-D

In some embodiments, a compound of Formula VI-A is a compound having a structure of Formula VI-A1 or Formula VI-A2:

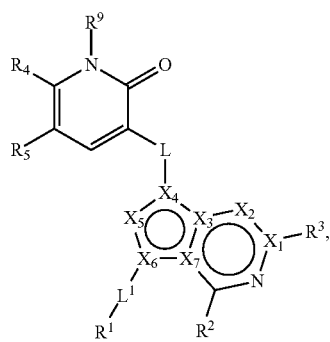

Formula VI-A1

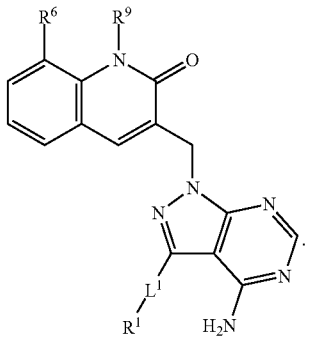

Formula VI-A2

In some other embodiments, the compound of Formula V-A, Formula V-B, Formula V-C or Formula V-D is a compound having a structure of one of the following formulae:

Formula VII-A

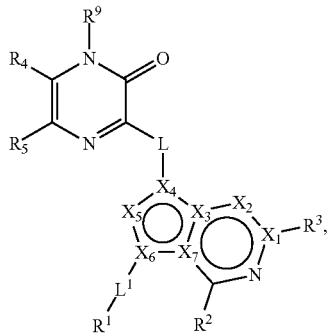

Formula VII-B

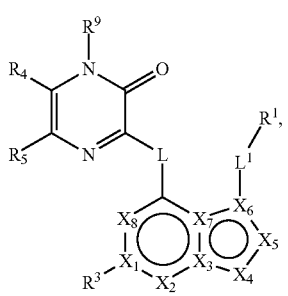

Formula VII-C

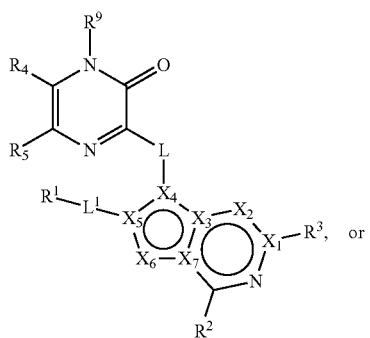

Formula VII-D

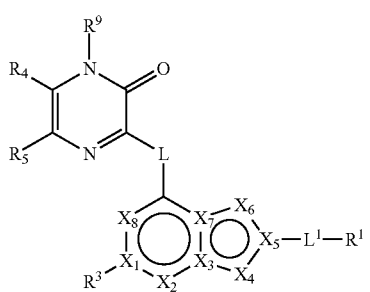

In some embodiments, a compound of Formula VI-A is a compound having a structure of Formula VI-A1 or Formula VI-A2:

Formula VII-A1

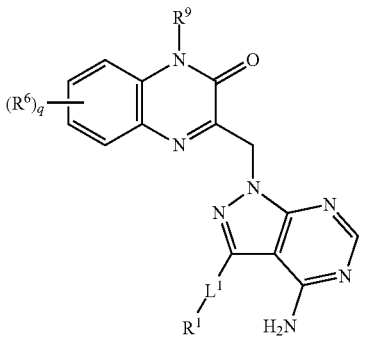

or

Formula VII-A2

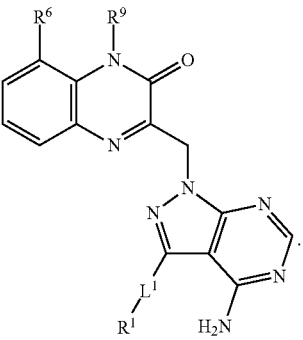

In some embodiments of the compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A1, VII-A2, VII-B, VII-C, or VII-D, L is a group of the formula —$(CR^7R^8)_z$—, where z is an integer from 0 to 10. In some embodiments, z is 1, 2 or 3. For example, z may be 1. Each $R^7$ and $R^8$ is independently hydrogen, alkyl, heteroalkyl, cycloalkyl, heterocyclyalkyl, or $R^7$ and $R^8$ taken together form a cycloalkyl, heterocycloalkyl or aryl ring. In some embodiments, L is methylene or ethylene. In other embodiments, L is methylene or ethylene substituted with additional alkyl groups such as methyl, ethyl or isopropyl.

In some embodiments of the compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^1$ is halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl, wherein n is independently an integer from 0 to 2. For example, $R^1$ may be an monocyclic aryl group, that can be substituted or is unsubstituted; a bicyclic aryl group, that can be substituted or unsubstituted; a monocyclic heteroaryl group, that can be substituted or is unsubstituted; or a bicyclic heteroaryl group, that can be substituted or is unsubstituted. In other embodiments, $R^1$ may be a monocyclic heterocycloalkyl group, that can be substituted or is unsubstituted; a bicyclic heterocycloalkyl group, that can be substituted or is unsubstituted; a heteroalkyl group, that can be substituted or is unsubstituted; or an alkyl group, that can be substituted or is unsubstituted. In some embodiments, $R^1$ is substituted with halogen, —CN, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl. In some embodiments, $R^1$ is an aryl group substituted with —$C(O)R^{14}$. In other embodiments, $R^1$ is a heteroaryl group substituted with halogen or —$NR^{12}R^{13}$. When $R^1$ is a monocyclic aromatic or heteroaryl group, substitutions on $R^1$ may be effected, for example, at the ortho, meta and/or para positions. In some embodiments, $R^1$ is monocyclic aryl. In other embodiments, R' is bicyclic aryl.
Additional examples of $R^1$ groups are illustrated below:
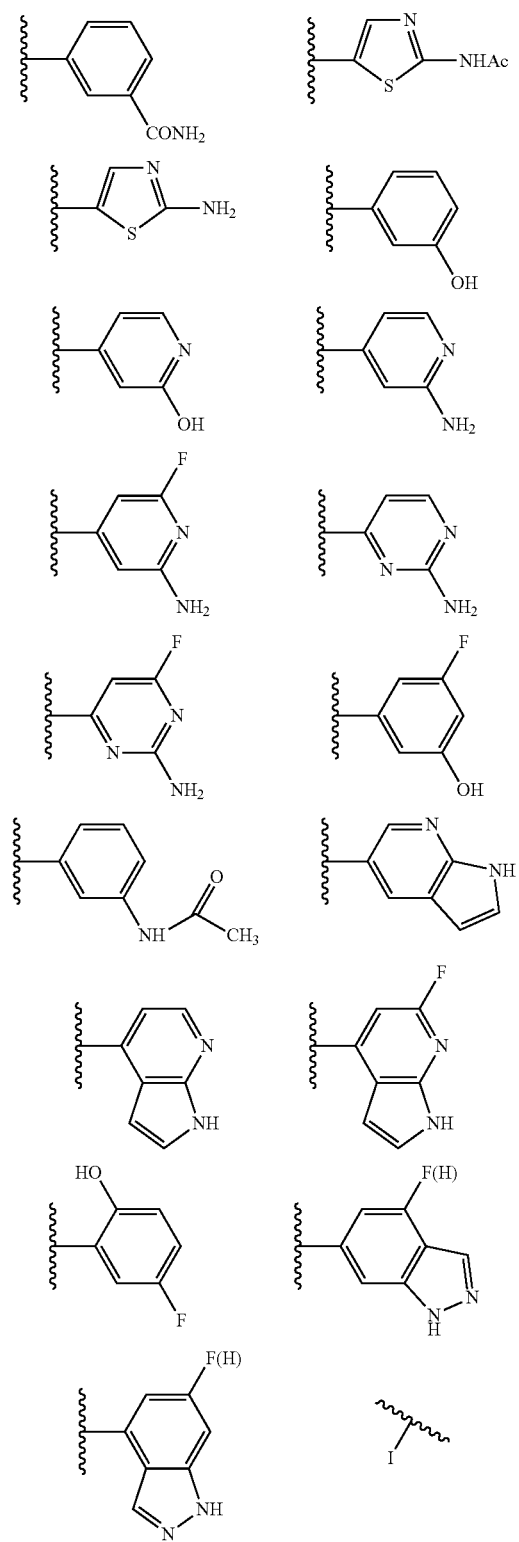
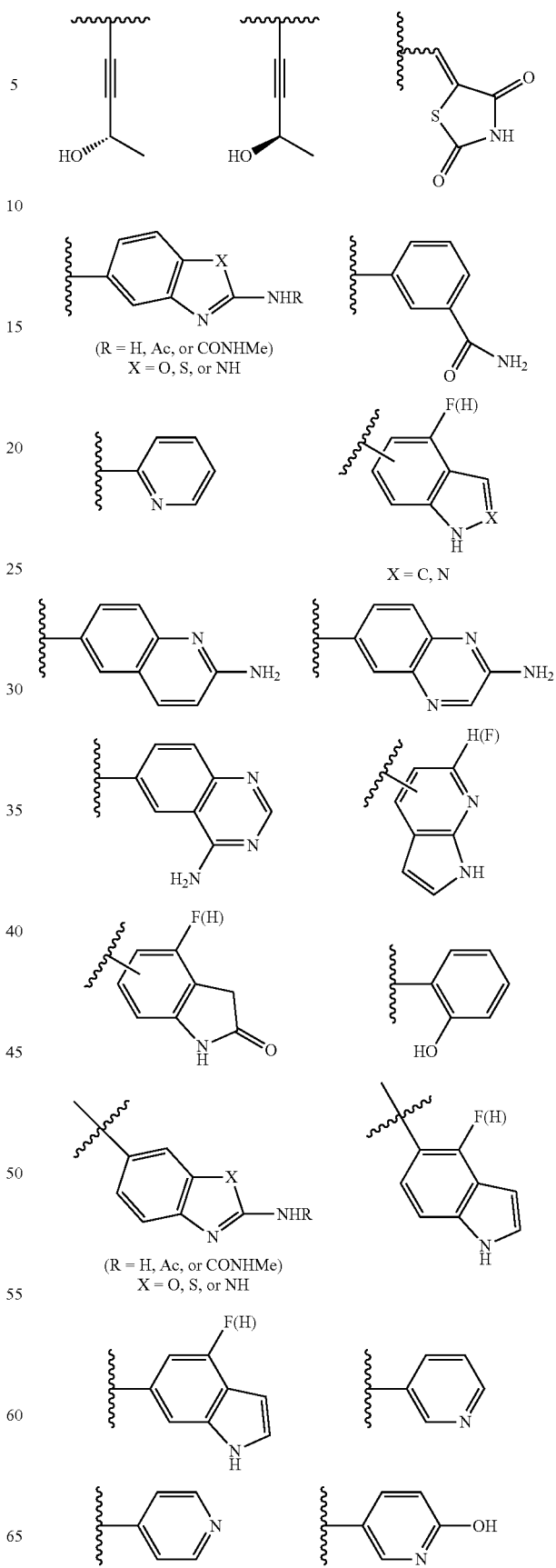

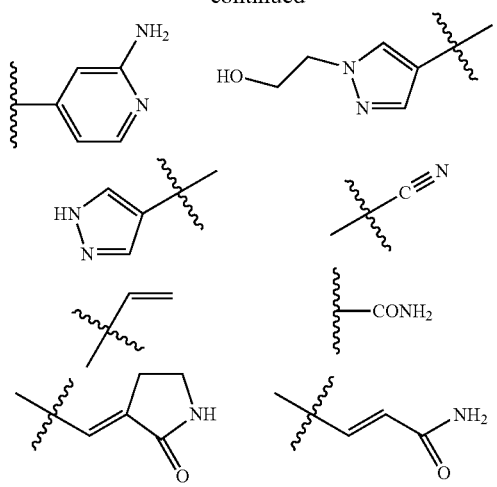

In some embodiments of the compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $L^1$ may be a bond or a linker connecting $R^1$ to a heterocyclic moiety of the compounds of the invention. In some embodiments, $L^1$ is a bond. In other embodiments, $L^1$ is an alkylene group.

In some embodiments of the compound of Formula I-A, I-B, I-C, I-D, I-E, I-F, I-G, I-H, I-J, I-J-1, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^4$ and $R^5$ are independently hydrogen. Alternatively, $R^4$ and $R^5$ taken together form a 5, 6 or 7-membered ring, unsubstituted or substituted with $(R^6)_q$. In some embodiments, $R^4$ and $R^5$ taken together form a 5 or 6-membered unsubstituted or substituted with $(R^6)_q$. The ring may be saturated, unsaturated, or partially unsaturated, and may be aromatic or nonaromatic. In some embodiments, the ring is aromatic and substituted by $R^6$. In some embodiments, $R^4$ and $R^5$ taken together form a group having a structure of one of the following formulae:

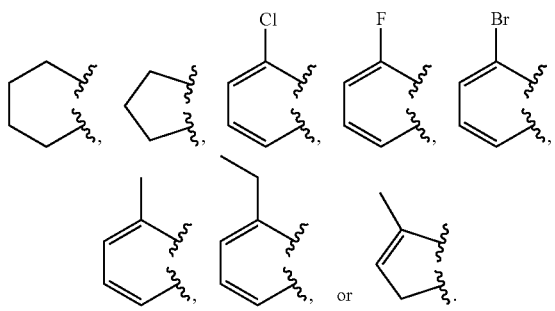

In some embodiments of the compound of Formula I-A, I-B, I-C, I-D, I-E, I-F, I-G, I-H, I-J, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^6$ may be any substituent such as halogen, —CN, —OR$^{10}$, —S(O)$_n$R$^{11}$, —NR$^{12}$R$^{13}$, —C(O)R$^{14}$, alkyl, alkenyl, alkynyl, heteroalkyl, cycloalkyl, heterocycloalkyl, aryl, or heteroaryl, wherein n is independently an integer from 0 to 2. In some embodiments, $R^6$ is halogen. Alternatively, $R^6$ is an alkyl group such as methyl. In further embodiments, $R^6$ is a substituted alkyl group such as $CF_3$.

In some embodiments of the compound of Formula I-A, I-B, I-C, I-D, I-E, I-F, I-G, I-H, I-J, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^9$ may be any cyclic, linear or branched substituent. In some embodiments, $R^9$ is halogen, —CN, —S(O)$_n$R$^{11}$, —NR$^{12}$R$^{13}$, —C(O)R$^{14}$, alkyl, alkenyl, alkynyl, heteroalkyl, cycloalkyl, heterocycloalkyl, aryl, or heteroaryl, wherein n is independently an integer from 0 to 2. For example, $R^9$ may be an monocyclic aryl group, substituted or unsubstituted; a bicyclic aryl group, substituted or unsubstituted; a monocyclic heteroaryl group, substituted or unsubstituted; a bicyclic heteroaryl group, substituted or unsubstituted; a monocyclic heterocycloalkyl group, substituted or unsubstituted; a bicyclic heterocycloalkyl group, substituted or unsubstituted; a heteroalkyl group, substituted or unsubstituted; an alkyl group, substituted or unsubstituted. In some embodiments, $R^9$ is substituted with halogen, —CN, OR$^{10}$, —S(O)$_n$R$^{11}$, —NR$^{12}$R$^{13}$, —C(O)R$^{14}$, alkyl, alkenyl, alkynyl, heteroalkyl, cycloalkyl, heterocycloalkyl, aryl, or heteroaryl.

In some embodiments, $R^9$ is any of the groups shown below:

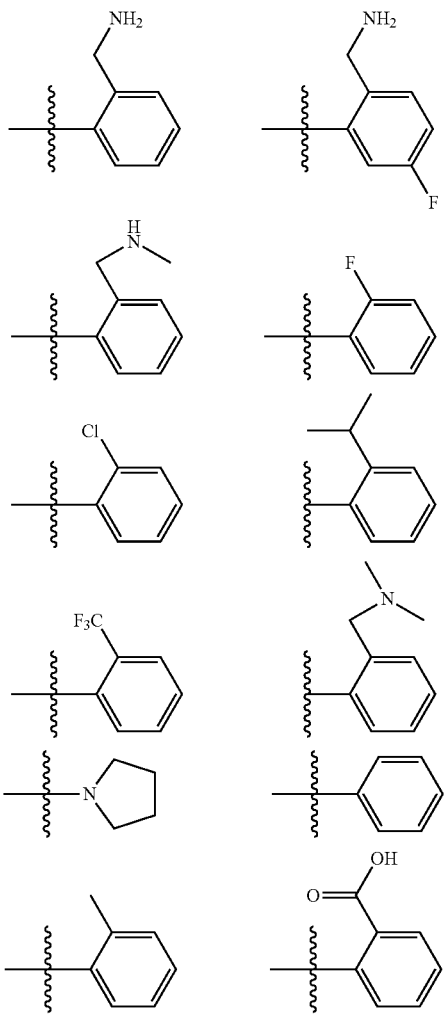

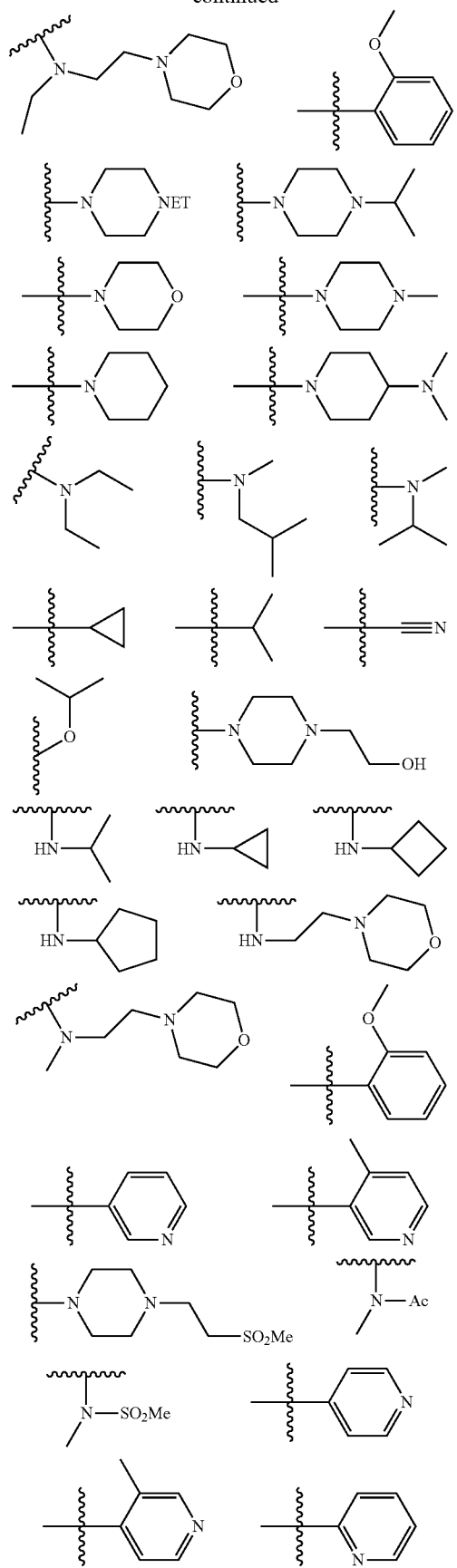
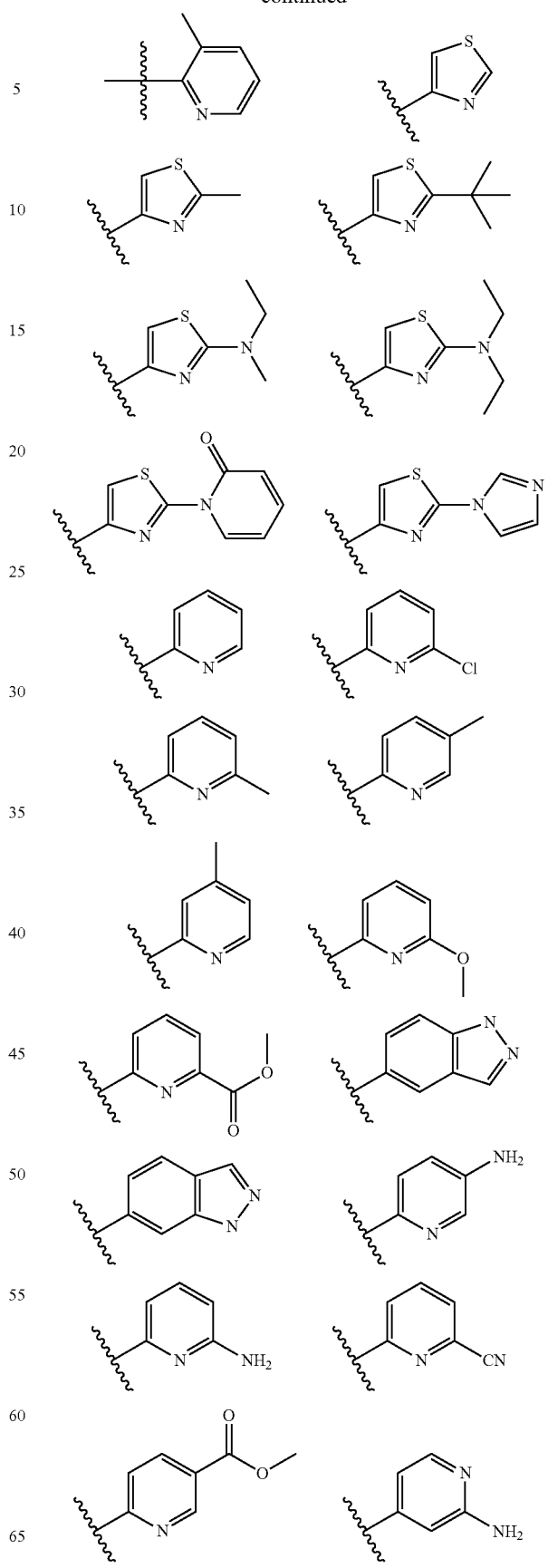

-continued
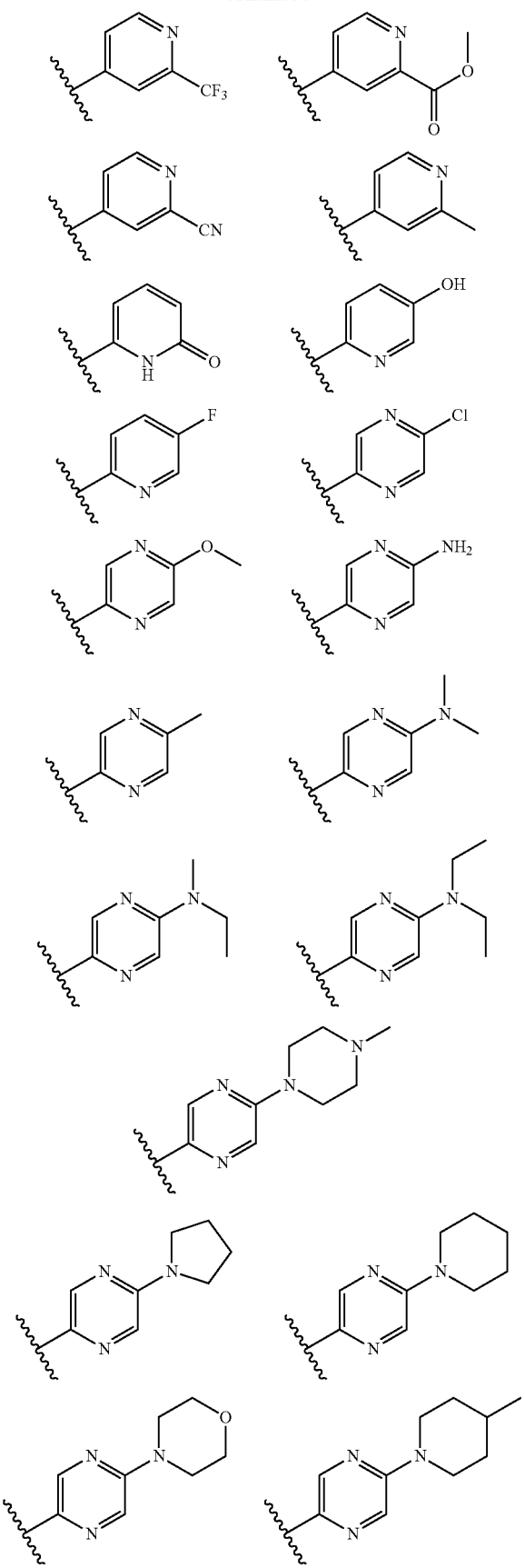
-continued
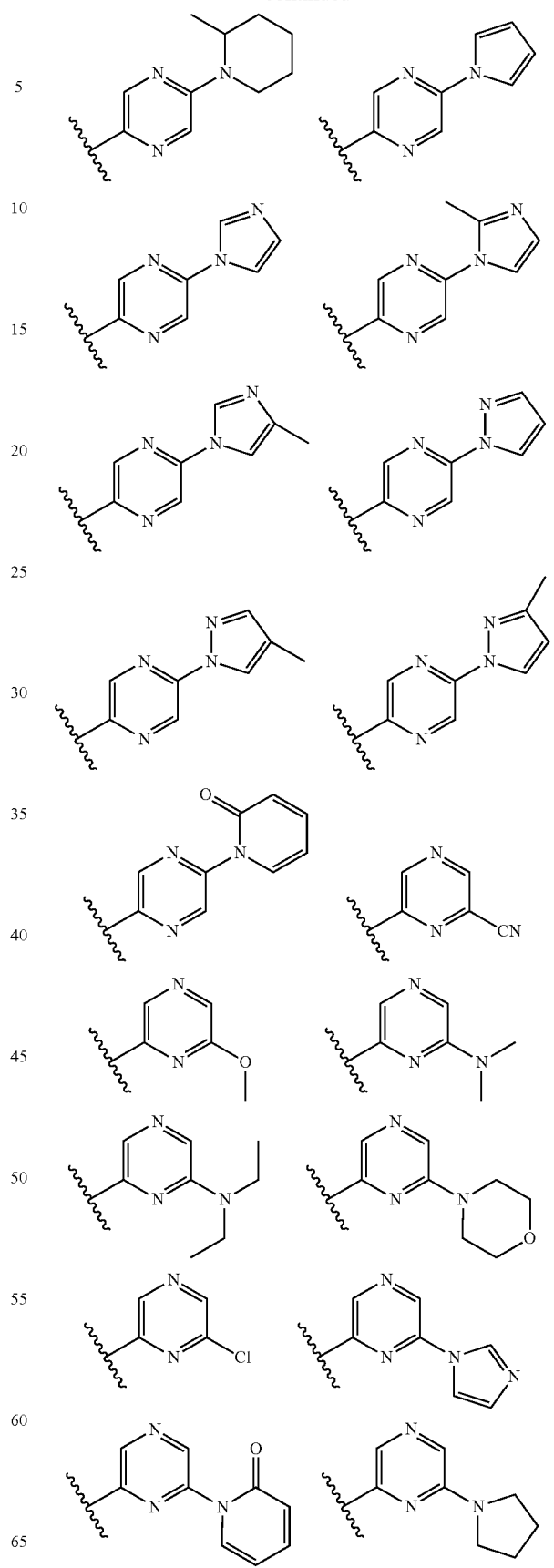

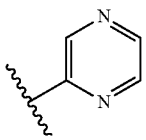

In some embodiments of the compound Formula I-A, I-B, I-C, I-D, I-E, I-F, I-G, I-H, I-J, I-K, II-A, II-A1, II-A2, III-A, IV-A, V-A, V-A1, V-B, V-C, V-D, VI-A, VI-A1, VI-A2, VI-B, VI-C, VI-D, VII-A, VII-A1, VII-A2, VII-B, VII-C, or VII-D, $R^{12}$ and $R^{13}$ in —$NR^{12}R^{13}$, $R^{16}$ an $R^{17}$ in —$NR^{16}R^{17}$, $R^{20}$ and $R^{21}$ in —$NR^{20}R^{21}$, $R^{22}$ and $R^{23}$ in —$NR^{22}R^{23}$, or $R^{24}$ and $R^{25}$ in —$NR^{24}R^{25}$, are taken together with the nitrogen atom to which they are attached to form a 5-8 membered saturated or unsaturated ring; wherein said ring is independently unsubstituted or is substituted by one or more —$NR^{12}R^{13}$, hydroxyl, halogen, oxo, aryl, hetaryl, $C_1$ alkyl, —C(=O)$OC_{1-6}$alkyl, —$OPO_3H_2$ or —O-aryl, and wherein said 5-8 membered saturated or unsaturated ring independently contains 0, 1, or 2 more heteroatoms selected from N, O, or S in addition to the nitrogen.

In some embodiments, $R^{12}$ and $R^{13}$ in —$NR^{12}R^{13}$, $R^{16}$ and $R^{17}$ in —$NR^{16}R^{17}$, $R^{20}$ and $R^{21}$ in —$NR^{20}R^{21}$, $R^{22}$ and $R^{23}$ in —$NR^{22}R^{23}$, or $R^{24}$ and $R^{25}$ in —$NR^{24}R^{25}$, are taken together with the nitrogen atom to which they are attached to form a moiety of one of the following formulae:

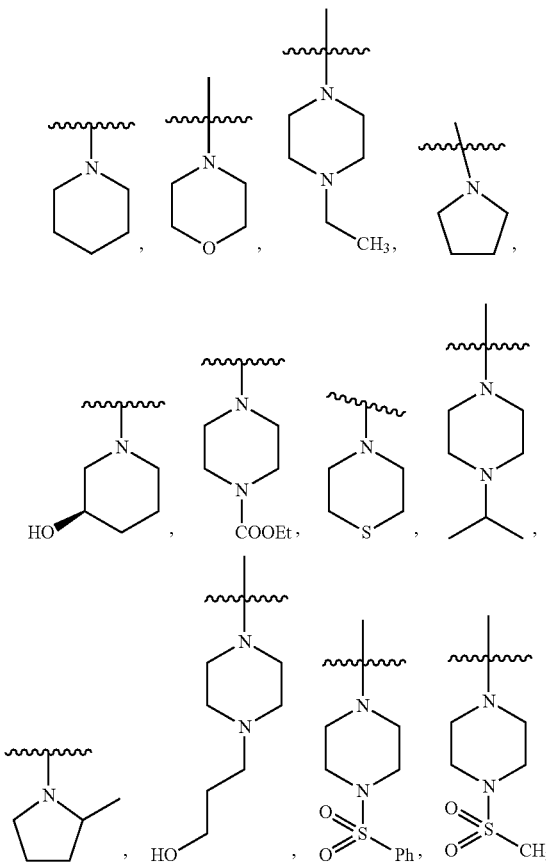

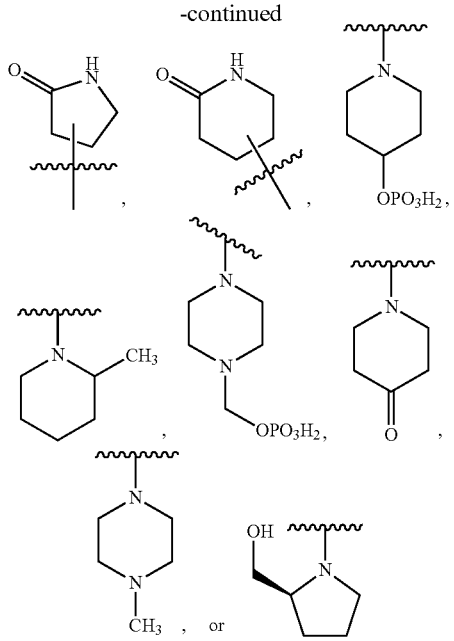

In some embodiments, the compound of the invention comprises a heterocyclic subunit of the formulas Za or Zb shown below. The symbol ⨍ represents the point of attachment to the linker L. In specific embodiments, the point of attachment to the linker L is $X^4$ or the exocyclic amine moiety. Additional substituents may be present at any or several of the $X^1$, $X^2$, $X^4$, $X^5$, and $X^6$ positions. For example, an R' group as defined above may be connected to $X^6$.

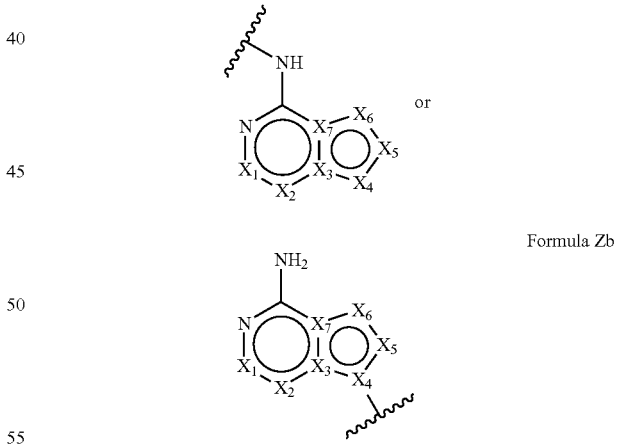

Formula Za

Formula Zb

| Core | $X_1$ | $X_2$ | $X_3$ | $X_4$ | $X_5$ | $X_6$ | $X_7$ |
|------|-------|-------|-------|-------|-------|-------|-------|
| Z-1  | C | C | C | C | C | C | C |
| Z-2  | C | C | C | N | C | C | C |
| Z-3  | C | C | C | C | C | N | C |
| Z-4  | C | C | C | C | N | C | C |
| Z-5  | C | C | N | C | C | C | C |
| Z-6  | C | C | C | C | C | C | N |
| Z-7  | C | N | C | N | C | C | C |
| Z-8  | C | N | C | C | C | N | C |
| Z-9  | C | N | C | C | N | C | C |
| Z-10 | C | N | N | C | C | C | C |
| Z-11 | C | N | C | C | C | C | N |

-continued

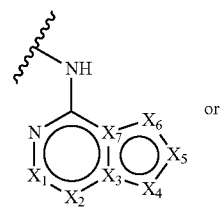

Formula Za

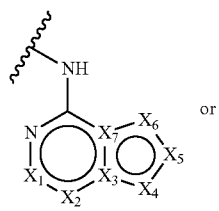

Formula Za

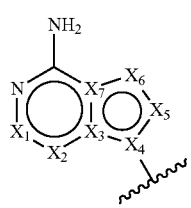

Formula Zb

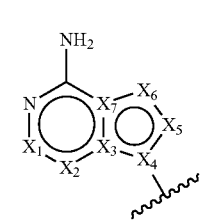

Formula Zb

| Core | X₁ | X₂ | X₃ | X₄ | X₅ | X₆ | X₇ |
|---|---|---|---|---|---|---|---|
| Z-12 | N | C | C | N | C | C | C |
| Z-13 | N | C | C | C | C | N | C |
| Z-14 | N | C | C | C | N | C | C |
| Z-15 | N | C | N | C | C | C | C |
| Z-16 | N | C | C | C | C | C | N |
| Z-17 | C | C | C | C | N | N | C |
| Z-18 | C | C | C | N | N | C | C |
| Z-19 | C | N | C | C | N | N | C |
| Z-20 | C | N | C | N | N | C | C |
| Z-21 | N | C | C | C | N | N | C |

| Core | X₁ | X₂ | X₃ | X₄ | X₅ | X₆ | X₇ |
|---|---|---|---|---|---|---|---|
| Z-22 | N | C | C | N | N | C | C |
| Z-23 | N | C | C | C | N | C | N |
| Z-24 | C | N | C | C | N | C | N |
| Z-25 | C | C | C | C | N | C | N |
| Z-26 | C | C | N | C | N | C | C |
| Z-27 | N | C | N | C | N | C | C |
| Z-28 | C | C | N | N | C | C | C |

Non-limiting examples of compounds of the invention are described in more detail in Tables 2-5 below.

TABLE 2

Exemplary compounds of Formula II-A, wherein X represents Cl, Br, or F.

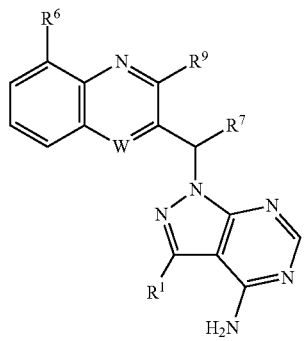

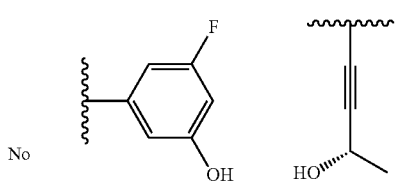
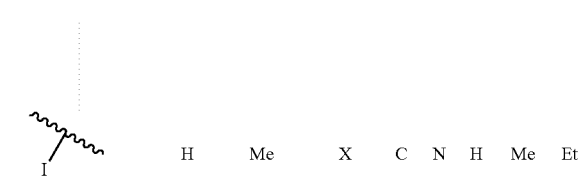

| No | (fluorophenol) | (HO-alkyne) | (I) | H | Me | X | C | N | H | Me | Et |
|---|---|---|---|---|---|---|---|---|---|---|---|
| 2-1 | X | | | X | | | X | | X | | |
| 2-2 | X | | | X | | | X | | X | | |
| 2-3 | X | | | X | | | X | | X | | |
| 2-4 | X | | | X | | | X | | X | | |
| 2-5 | X | | | X | | | X | | X | | |
| 2-6 | X | | | X | | | X | | | X | |
| 2-7 | X | | | X | | | X | | | X | |
| 2-8 | X | | | X | | | X | | | X | |
| 2-9 | X | | | X | | | X | | | X | |
| 2-10 | X | | | X | | | X | | | X | |
| 2-11 | X | | | X | | | X | | | | X |
| 2-12 | X | | | X | | | X | | | | X |

TABLE 2-continued

Exemplary compounds of Formula II-A, wherein X represents Cl, Br, or F.

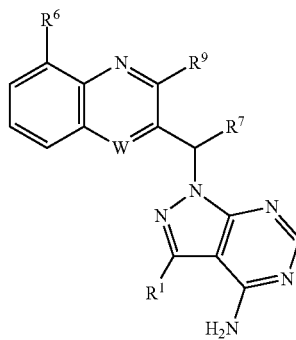

| # | c1 | c2 | c3 | c4 | c5 | c6 | c7 |
|---|---|---|---|---|---|---|---|
| 2-13 | X |  | X |  | X |  | X |
| 2-14 | X |  | X |  | X |  | X |
| 2-15 | X |  | X |  | X |  | X |
| 2-16 | X |  | X |  | X | X |  |
| 2-17 | X |  | X |  | X | X |  |
| 2-18 | X |  | X |  | X | X |  |
| 2-19 | X |  | X |  | X | X |  |
| 2-20 | X |  | X |  | X | X |  |
| 2-21 | X |  | X |  | X |  | X |
| 2-22 | X |  | X |  | X |  | X |
| 2-23 | X |  | X |  | X |  | X |
| 2-24 | X |  | X |  | X |  | X |
| 2-25 | X |  | X |  | X |  | X |
| 2-26 | X |  | X |  | X |  |  | X |
| 2-27 | X |  | X |  | X |  |  | X |
| 2-28 | X |  | X |  | X |  |  | X |
| 2-29 | X |  | X |  | X |  |  | X |
| 2-30 | X |  | X |  | X |  |  | X |
| 2-31 | X |  |  | X | X | X |  |
| 2-32 | X |  |  | X | X | X |  |
| 2-33 | X |  |  | X | X | X |  |
| 2-34 | X |  |  | X | X | X |  |
| 2-35 | X |  |  | X | X | X |  |
| 2-36 | X |  |  | X | X |  | X |
| 2-37 | X |  |  | X | X |  | X |
| 2-38 | X |  |  | X | X |  | X |
| 2-39 | X |  |  | X | X |  | X |
| 2-40 | X |  |  | X | X |  | X |
| 2-41 | X |  |  | X | X |  |  | X |
| 2-42 | X |  |  | X | X |  |  | X |
| 2-43 | X |  |  | X | X |  |  | X |
| 2-44 | X |  |  | X | X |  |  | X |
| 2-45 | X |  |  | X | X |  |  | X |
| 2-46 | X |  |  | X | X | X |  |
| 2-47 | X |  |  | X | X | X |  |
| 2-48 | X |  |  | X | X | X |  |
| 2-49 | X |  |  | X | X | X |  |
| 2-50 | X |  |  | X | X | X |  |
| 2-51 | X |  |  | X | X |  | X |
| 2-52 | X |  |  | X | X |  | X |
| 2-53 | X |  |  | X | X |  | X |
| 2-54 | X |  |  | X | X |  | X |
| 2-55 | X |  |  | X | X |  | X |
| 2-56 | X |  |  | X | X |  |  | X |
| 2-57 | X |  |  | X | X |  |  | X |
| 2-58 | X |  |  | X | X |  |  | X |
| 2-59 | X |  |  | X | X |  |  | X |
| 2-60 | X |  |  | X | X |  |  | X |
| 2-61 | X |  |  |  | X | X | X |
| 2-62 | X |  |  |  | X | X | X |
| 2-63 | X |  |  |  | X | X | X |
| 2-64 | X |  |  |  | X | X | X |
| 2-65 | X |  |  |  | X | X | X |
| 2-66 | X |  |  |  | X | X |  | X |
| 2-67 | X |  |  |  | X | X |  | X |
| 2-68 | X |  |  |  | X | X |  | X |
| 2-69 | X |  |  |  | X | X |  | X |
| 2-70 | X |  |  |  | X | X |  | X |
| 2-71 | X |  |  |  | X | X |  |  | X |
| 2-72 | X |  |  |  | X | X |  |  | X |

TABLE 2-continued

Exemplary compounds of Formula II-A, wherein X represents Cl, Br, or F.

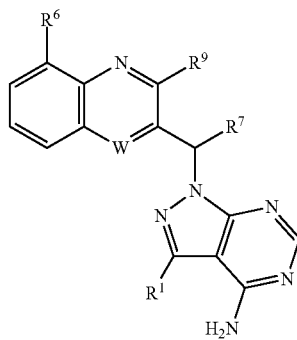

| | C1 | C2 | C3 | C4 | C5 | C6 | C7 | C8 | C9 |
|---|---|---|---|---|---|---|---|---|---|
| 2-73 | X | | | | | X | X | | X |
| 2-74 | X | | | | | X | X | | X |
| 2-75 | X | | | | | X | X | | X |
| 2-76 | X | | | | | X | X | X | |
| 2-77 | X | | | | | X | X | X | |
| 2-78 | X | | | | | X | X | X | |
| 2-79 | X | | | | | X | X | X | |
| 2-80 | X | | | | | X | X | X | |
| 2-81 | X | | | | | X | X | | X |
| 2-82 | X | | | | | X | X | | X |
| 2-83 | X | | | | | X | X | | X |
| 2-84 | X | | | | | X | X | | X |
| 2-85 | X | | | | | X | X | | X |
| 2-86 | X | | | | | X | X | | | X |
| 2-87 | X | | | | | X | X | | | X |
| 2-88 | X | | | | | X | X | | | X |
| 2-89 | X | | | | | X | X | | | X |
| 2-90 | | | | | | | | | |
| 2-91 | | X | | X | | X | X | | |
| 2-92 | | X | | X | | X | X | | |
| 2-93 | | X | | X | | X | X | | |
| 2-94 | | X | | X | | X | X | | |
| 2-95 | | X | | X | | X | X | | |
| 2-96 | | X | | X | | X | | X | |
| 2-97 | | X | | X | | X | | X | |
| 2-98 | | X | | X | | X | | X | |
| 2-99 | | X | | X | | X | | X | |
| 2-100 | | X | | X | | X | | X | |
| 2-101 | | X | | X | | X | | | X |
| 2-102 | | X | | X | | X | | | X |
| 2-103 | | X | | X | | X | | | X |
| 2-104 | | X | | X | | X | | | X |
| 2-105 | | X | | X | | X | | | X |
| 2-106 | | X | | X | | | X | X | |
| 2-107 | | X | | X | | | X | X | |
| 2-108 | | X | | X | | | X | X | |
| 2-109 | | X | | X | | | X | X | |
| 2-110 | | X | | X | | | X | X | |
| 2-111 | | X | | X | | | X | | X |
| 2-112 | | X | | X | | | X | | X |
| 2-113 | | X | | X | | | X | | X |
| 2-114 | | X | | X | | | X | | X |
| 2-115 | | X | | X | | | X | | X |
| 2-116 | | X | | X | | | X | | | X |
| 2-117 | | X | | X | | | X | | | X |
| 2-118 | | X | | X | | | X | | | X |
| 2-119 | | X | | X | | | X | | | X |
| 2-120 | | X | | X | | | X | | | X |
| 2-121 | | X | | | X | X | X | | |
| 2-122 | | X | | | X | X | X | | |
| 2-123 | | X | | | X | X | X | | |
| 2-124 | | X | | | X | X | X | | |
| 2-125 | | X | | | X | X | X | | |
| 2-126 | | X | | | X | X | | X | |
| 2-127 | | X | | | X | X | | X | |
| 2-128 | | X | | | X | X | | X | |
| 2-129 | | X | | | X | X | | X | |
| 2-130 | | X | | | X | X | | X | |
| 2-131 | | X | | | X | X | | | X |
| 2-132 | | X | | | X | X | | | X |

TABLE 2-continued

Exemplary compounds of Formula II-A, wherein X represents Cl, Br, or F.

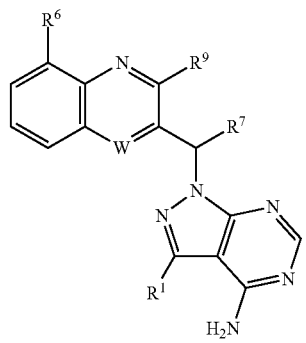

| | Col1 | Col2 | Col3 | Col4 | Col5 | Col6 | Col7 |
|---|---|---|---|---|---|---|---|
| 2-133 | X | | | X | X | | X |
| 2-134 | X | | | X | X | | X |
| 2-135 | X | | | X | X | | X |
| 2-136 | X | | | X | | X | X |
| 2-137 | X | | | X | | X | X |
| 2-138 | X | | | X | | X | X |
| 2-139 | X | | | X | | X | X |
| 2-140 | X | | | X | | X | X |
| 2-141 | X | | | X | | X | X |
| 2-142 | X | | | X | | X | X |
| 2-143 | X | | | X | | X | X |
| 2-144 | X | | | X | | X | X |
| 2-145 | X | | | X | | X | X |
| 2-146 | X | | | X | | X | | X |
| 2-147 | X | | | X | | X | | X |
| 2-148 | X | | | X | | X | | X |
| 2-149 | X | | | X | | X | | X |
| 2-150 | X | | | X | | X | | X |
| 2-151 | X | | | | X | X | X |
| 2-152 | X | | | | X | X | X |
| 2-153 | X | | | | X | X | X |
| 2-154 | X | | | | X | X | X |
| 2-155 | X | | | | X | X | X |
| 2-156 | X | | | | X | X | | X |
| 2-157 | X | | | | X | X | | X |
| 2-158 | X | | | | X | X | | X |
| 2-159 | X | | | | X | X | | X |
| 2-160 | X | | | | X | X | | X |
| 2-161 | X | | | | X | X | | | X |
| 2-162 | X | | | | X | X | | | X |
| 2-163 | X | | | | X | X | | | X |
| 2-164 | X | | | | X | X | | | X |
| 2-165 | X | | | | X | X | | | X |
| 2-166 | X | | | | X | | X | X |
| 2-167 | X | | | | X | | X | X |
| 2-168 | X | | | | X | | X | X |
| 2-169 | X | | | | X | | X | X |
| 2-170 | X | | | | X | | X | X |
| 2-171 | X | | | | X | | X | | X |
| 2-172 | X | | | | X | | X | | X |
| 2-173 | X | | | | X | | X | | X |
| 2-174 | X | | | | X | | X | | X |
| 2-175 | X | | | | X | | X | | X |
| 2-176 | X | | | | X | | X | | | X |
| 2-177 | X | | | | X | | X | | | X |
| 2-178 | X | | | | X | | X | | | X |
| 2-179 | X | | | | X | | X | | | X |
| 2-180 | X | | | | X | | X | | | X |
| 2-181 | | X | X | | X | X | |
| 2-182 | | X | X | | X | X | |
| 2-183 | | X | X | | X | X | |
| 2-184 | | X | X | | X | X | |
| 2-185 | | X | X | | X | X | |
| 2-186 | | X | X | | X | | X |
| 2-187 | | X | X | | X | | X |
| 2-188 | | X | X | | X | | X |
| 2-189 | | X | X | | X | | X |
| 2-190 | | X | X | | X | | X |
| 2-191 | | X | X | | X | | | X |
| 2-192 | | X | X | | X | | | X |

TABLE 2-continued

Exemplary compounds of Formula II-A, wherein X represents Cl, Br, or F.

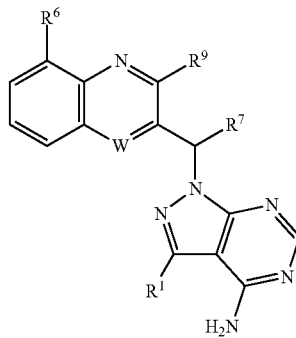

| # | C1 | C2 | C3 | C4 | C5 | C6 |
|---|---|---|---|---|---|---|
| 2-193 | | X | X | | X | | X |
| 2-194 | | X | X | | X | | X |
| 2-195 | | X | X | | X | | X |
| 2-196 | | X | X | | | X | X |
| 2-197 | | X | X | | | X | X |
| 2-198 | | X | X | | | X | X |
| 2-199 | | X | X | | | X | X |
| 2-200 | | X | X | | | X | X |
| 2-201 | | X | X | | X | X | |
| 2-202 | | X | X | | X | X | |
| 2-203 | | X | X | | X | X | |
| 2-204 | | X | X | | X | X | |
| 2-205 | | X | X | | X | X | |
| 2-206 | | X | X | | X | | X |
| 2-207 | | X | X | | X | | X |
| 2-208 | | X | X | | X | | X |
| 2-209 | | X | X | | X | | X |
| 2-210 | | X | X | | X | | X |
| 2-211 | | X | | X | X | X | |
| 2-212 | | X | | X | X | X | |
| 2-213 | | X | | X | X | X | |
| 2-214 | | X | | X | X | X | |
| 2-215 | | X | | X | X | X | |
| 2-216 | | X | | X | X | X | |
| 2-217 | | X | | X | X | X | |
| 2-218 | | X | | X | X | X | |
| 2-219 | | X | | X | X | X | |
| 2-220 | | X | | X | X | X | |
| 2-221 | | X | | X | X | | X |
| 2-222 | | X | | X | X | | X |
| 2-223 | | X | | X | X | | X |
| 2-224 | | X | | X | X | | X |
| 2-225 | | X | | X | X | | X |
| 2-226 | | X | | X | | X | X |
| 2-227 | | X | | X | | X | X |
| 2-228 | | X | | X | | X | X |
| 2-229 | | X | | X | | X | X |
| 2-230 | | X | | X | | X | X |
| 2-231 | | X | | X | X | X | |
| 2-232 | | X | | X | X | X | |
| 2-233 | | X | | X | X | X | |
| 2-234 | | X | | X | X | X | |
| 2-235 | | X | | X | X | X | |
| 2-236 | | X | | X | X | | X |
| 2-237 | | X | | X | X | | X |
| 2-238 | | X | | X | X | | X |
| 2-239 | | X | | X | X | | X |
| 2-240 | | X | | X | X | | X |
| 2-241 | | X | | | X | X | X |
| 2-242 | | X | | | X | X | X |
| 2-243 | | X | | | X | X | X |
| 2-244 | | X | | | X | X | X |
| 2-245 | | X | | | X | X | X |
| 2-246 | | X | | | X | X | X |
| 2-247 | | X | | | X | X | X |
| 2-248 | | X | | | X | X | X |
| 2-249 | | X | | | X | X | X |
| 2-250 | | X | | | X | X | X |
| 2-251 | | X | | | X | X | | X |
| 2-252 | | X | | | X | X | | X |

TABLE 2-continued

Exemplary compounds of Formula II-A, wherein X represents Cl, Br, or F.

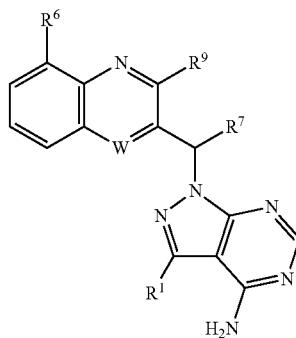

| No. | C1 | C2 | C3 | C4 | C5 | C6 | C7 |
|---|---|---|---|---|---|---|---|
| 2-253 |  | X |  | X | X |  | X |
| 2-254 |  | X |  | X | X |  | X |
| 2-255 |  | X |  | X | X |  | X |
| 2-256 |  | X |  | X | X | X |  |
| 2-257 |  | X |  | X | X | X |  |
| 2-258 |  | X |  | X | X | X |  |
| 2-259 |  | X |  | X | X | X |  |
| 2-260 |  | X |  | X | X | X |  |
| 2-261 |  | X |  | X | X | X |  |
| 2-262 |  | X |  | X | X | X |  |
| 2-263 |  | X |  | X | X | X |  |
| 2-264 |  | X |  | X | X | X |  |
| 2-265 |  | X |  | X | X | X |  |
| 2-266 |  | X |  | X | X |  | X |
| 2-267 |  | X |  | X | X |  | X |
| 2-268 |  | X |  | X | X |  | X |
| 2-269 |  | X |  | X | X |  | X |
| 2-270 |  | X |  | X | X |  | X |
| 2-271 | X |  |  | X | X | X |  |
| 2-272 | X |  |  | X | X | X |  |
| 2-273 | X |  |  | X | X | X |  |
| 2-274 | X |  |  | X | X | X |  |
| 2-275 | X |  |  | X | X | X |  |
| 2-276 | X |  |  | X | X | X |  |
| 2-277 | X |  |  | X | X | X |  |
| 2-278 | X |  |  | X | X | X |  |
| 2-279 | X |  |  | X | X | X |  |
| 2-280 | X |  |  | X | X | X |  |
| 2-281 | X |  |  | X | X |  | X |
| 2-282 | X |  |  | X | X |  | X |
| 2-283 | X |  |  | X | X |  | X |
| 2-284 | X |  |  | X | X |  | X |
| 2-285 | X |  |  | X | X |  | X |
| 2-286 | X |  |  | X | X | X |  |
| 2-287 | X |  |  | X | X | X |  |
| 2-288 | X |  |  | X | X | X |  |
| 2-289 | X |  |  | X | X | X |  |
| 2-290 | X |  |  | X | X | X |  |
| 2-291 | X |  |  | X | X | X |  |
| 2-292 | X |  |  | X | X | X |  |
| 2-293 | X |  |  | X | X | X |  |
| 2-294 | X |  |  | X | X | X |  |
| 2-295 | X |  |  | X | X | X |  |
| 2-296 | X |  |  | X | X |  | X |
| 2-297 | X |  |  | X | X |  | X |
| 2-298 | X |  |  | X | X |  | X |
| 2-299 | X |  |  | X | X |  | X |
| 2-300 | X |  |  | X | X |  | X |
| 2-301 | X |  | X |  | X | X |  |
| 2-302 | X |  | X |  | X | X |  |
| 2-303 | X |  | X |  | X | X |  |
| 2-304 | X |  | X |  | X | X |  |
| 2-305 | X |  | X |  | X | X |  |
| 2-306 | X |  | X |  | X | X |  |
| 2-307 | X |  | X |  | X | X |  |
| 2-308 | X |  | X |  | X | X |  |
| 2-309 | X |  | X |  | X | X |  |
| 2-310 | X |  | X |  | X | X |  |
| 2-311 | X |  | X |  | X |  | X |
| 2-312 | X |  | X |  | X |  | X |

TABLE 2-continued

Exemplary compounds of Formula II-A, wherein X represents Cl, Br, or F.

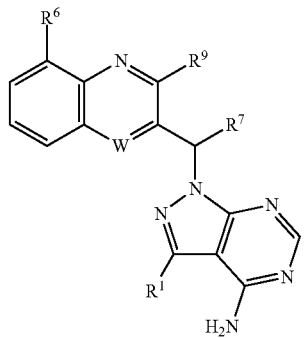

| Cmpd | C1 | C2 | C3 | C4 | C5 | C6 | C7 | C8 |
|---|---|---|---|---|---|---|---|---|
| 2-313 | X |  |  |  | X | X |  | X |
| 2-314 | X |  |  |  | X | X |  | X |
| 2-315 | X |  |  |  | X | X |  | X |
| 2-316 | X |  |  |  | X |  | X | X |
| 2-317 | X |  |  |  | X |  | X | X |
| 2-318 | X |  |  |  | X |  | X | X |
| 2-319 | X |  |  |  | X |  | X | X |
| 2-320 | X |  |  |  | X |  | X | X |
| 2-321 | X |  |  |  | X |  | X |  |
| 2-322 | X |  |  |  | X |  | X |  |
| 2-323 | X |  |  |  | X |  | X |  |
| 2-324 | X |  |  |  | X |  | X |  |
| 2-325 | X |  |  |  | X |  | X |  |
| 2-326 | X |  |  |  | X |  | X | X |
| 2-327 | X |  |  |  | X |  | X | X |
| 2-328 | X |  |  |  | X |  | X | X |
| 2-329 | X |  |  |  | X |  | X | X |
| 2-330 | X |  |  |  | X |  | X | X |
| 2-331 | X |  |  |  |  | X | X | X |
| 2-332 | X |  |  |  |  | X | X | X |
| 2-333 | X |  |  |  |  | X | X | X |
| 2-334 | X |  |  |  |  | X | X | X |
| 2-335 | X |  |  |  |  | X | X | X |
| 2-336 | X |  |  |  |  | X | X | X |
| 2-337 | X |  |  |  |  | X | X | X |
| 2-338 | X |  |  |  |  | X | X | X |
| 2-339 | X |  |  |  |  | X | X | X |
| 2-340 | X |  |  |  |  | X | X | X |
| 2-341 | X |  |  |  |  | X | X | X |
| 2-342 | X |  |  |  |  | X | X | X |
| 2-343 | X |  |  |  |  | X | X | X |
| 2-344 | X |  |  |  |  | X | X | X |
| 2-345 | X |  |  |  |  | X | X | X |
| 2-346 | X |  |  |  |  | X |  | X X |
| 2-347 | X |  |  |  |  | X |  | X X |
| 2-348 | X |  |  |  |  | X |  | X X |
| 2-349 | X |  |  |  |  | X |  | X X |
| 2-350 | X |  |  |  |  | X |  | X X |
| 2-351 | X |  |  |  |  | X | X | X |
| 2-352 | X |  |  |  |  | X | X | X |
| 2-353 | X |  |  |  |  | X | X | X |
| 2-354 | X |  |  |  |  | X | X | X |
| 2-355 | X |  |  |  |  | X | X | X |
| 2-356 | X |  |  |  |  | X | X | X |
| 2-357 | X |  |  |  |  | X | X | X |
| 2-358 | X |  |  |  |  | X | X | X |
| 2-359 | X |  |  |  |  | X | X | X |
| 2-360 | X |  |  |  |  | X | X | X |
| 2-361 |  | X |  | X |  | X | X |  |
| 2-362 |  | X |  | X |  | X | X |  |
| 2-363 |  | X |  | X |  | X | X |  |
| 2-364 |  | X |  | X |  | X | X |  |
| 2-365 |  | X |  | X |  | X | X |  |
| 2-366 |  | X |  | X |  | X |  | X |
| 2-367 |  | X |  | X |  | X |  | X |
| 2-368 |  | X |  | X |  | X |  | X |
| 2-369 |  | X |  | X |  | X |  | X |
| 2-370 |  | X |  | X |  | X |  | X |
| 2-371 |  | X |  | X |  | X |  | X |
| 2-372 |  | X |  | X |  | X |  | X |

TABLE 2-continued

Exemplary compounds of Formula II-A, wherein X represents Cl, Br, or F.

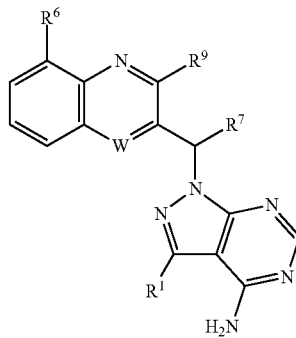

| Compound | 1 | 2 | 3 | 4 | 5 | 6 | 7 |
|---|---|---|---|---|---|---|---|
| 2-373 | X |   | X |   | X |   | X |
| 2-374 | X |   | X |   | X |   | X |
| 2-375 | X |   | X |   | X |   | X |
| 2-376 | X |   | X |   | X | X |   |
| 2-377 | X |   | X |   | X | X |   |
| 2-378 | X |   | X |   | X | X |   |
| 2-379 | X |   | X |   | X | X |   |
| 2-380 | X |   | X |   | X | X |   |
| 2-381 | X |   | X |   | X |   | X |
| 2-382 | X |   | X |   | X |   | X |
| 2-383 | X |   | X |   | X |   | X |
| 2-384 | X |   | X |   | X |   | X |
| 2-385 | X |   | X |   | X |   | X |
| 2-386 | X |   | X |   | X |   | X |
| 2-387 | X |   | X |   | X |   | X |
| 2-388 | X |   | X |   | X |   | X |
| 2-389 | X |   | X |   | X |   | X |
| 2-390 | X |   | X |   | X |   | X |
| 2-391 | X |   |   | X | X | X |   |
| 2-392 | X |   |   | X | X | X |   |
| 2-393 | X |   |   | X | X | X |   |
| 2-394 | X |   |   | X | X | X |   |
| 2-395 | X |   |   | X | X | X |   |
| 2-396 | X |   |   | X | X |   | X |
| 2-397 | X |   |   | X | X |   | X |
| 2-398 | X |   |   | X | X |   | X |
| 2-399 | X |   |   | X | X |   | X |
| 2-400 | X |   |   | X | X |   | X |
| 2-401 | X |   |   | X | X |   | X |
| 2-402 | X |   |   | X | X |   | X |
| 2-403 | X |   |   | X | X |   | X |
| 2-404 | X |   |   | X | X |   | X |
| 2-405 | X |   |   | X | X |   | X |
| 2-406 | X |   |   | X |   | X | X |
| 2-407 | X |   |   | X |   | X | X |
| 2-408 | X |   |   | X |   | X | X |
| 2-409 | X |   |   | X |   | X | X |
| 2-410 | X |   |   | X |   | X | X |
| 2-411 | X |   |   | X |   | X | X |
| 2-412 | X |   |   | X |   | X | X |
| 2-413 | X |   |   | X |   | X | X |
| 2-414 | X |   |   | X |   | X | X |
| 2-415 | X |   |   | X |   | X | X |
| 2-416 | X |   |   | X |   | X | X |
| 2-417 | X |   |   | X |   | X | X |
| 2-418 | X |   |   | X |   | X | X |
| 2-419 | X |   |   | X |   | X | X |
| 2-420 | X |   |   | X |   | X | X |
| 2-421 | X |   |   |   | X | X | X |
| 2-422 | X |   |   |   | X | X | X |
| 2-423 | X |   |   |   | X | X | X |
| 2-424 | X |   |   |   | X | X | X |
| 2-425 | X |   |   |   | X | X | X |
| 2-426 | X |   |   |   | X | X | X |
| 2-427 | X |   |   |   | X | X | X |
| 2-428 | X |   |   |   | X | X | X |
| 2-429 | X |   |   |   | X | X | X |
| 2-430 | X |   |   |   | X | X | X |
| 2-431 | X |   |   |   | X | X | X |
| 2-432 | X |   |   |   | X | X | X |

TABLE 2-continued

Exemplary compounds of Formula II-A, wherein X represents Cl, Br, or F.

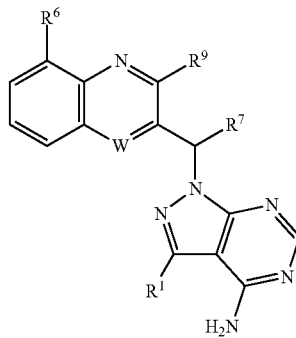

| Cmpd | C1 | C2 | C3 | C4 | C5 | C6 | C7 |
|---|---|---|---|---|---|---|---|
| 2-433 | X |   |   | X | X |   | X |
| 2-434 | X |   |   | X | X |   | X |
| 2-435 | X |   |   | X | X |   | X |
| 2-436 | X |   |   | X | X | X |   |
| 2-437 | X |   |   | X | X | X |   |
| 2-438 | X |   |   | X | X | X |   |
| 2-439 | X |   |   | X | X | X |   |
| 2-440 | X |   |   | X | X | X |   |
| 2-441 | X |   |   | X | X | X |   |
| 2-442 | X |   |   | X | X | X |   |
| 2-443 | X |   |   | X | X | X |   |
| 2-444 | X |   |   | X | X | X |   |
| 2-445 | X |   |   | X | X | X |   |
| 2-446 | X |   |   | X | X |   | X |
| 2-447 | X |   |   | X | X |   | X |
| 2-448 | X |   |   | X | X |   | X |
| 2-449 | X |   |   | X | X |   | X |
| 2-450 | X |   |   | X | X |   | X |
| 2-451 |   | X | X | X | X |   |   |
| 2-452 |   | X | X | X | X |   |   |
| 2-453 |   | X | X | X | X |   |   |
| 2-454 |   | X | X | X | X |   |   |
| 2-455 |   | X | X | X | X |   |   |
| 2-456 |   | X | X | X | X |   |   |
| 2-457 |   | X | X | X | X |   |   |
| 2-458 |   | X | X | X | X |   |   |
| 2-459 |   | X | X | X | X |   |   |
| 2-460 |   | X | X | X | X |   |   |
| 2-461 |   | X | X | X |   |   | X |
| 2-462 |   | X | X | X |   |   | X |
| 2-463 |   | X | X | X |   |   | X |
| 2-464 |   | X | X | X |   |   | X |
| 2-465 |   | X | X | X |   |   | X |
| 2-466 |   | X | X |   | X | X |   |
| 2-467 |   | X | X |   | X | X |   |
| 2-468 |   | X | X |   | X | X |   |
| 2-469 |   | X | X |   | X | X |   |
| 2-470 |   | X | X |   | X | X |   |
| 2-471 |   | X | X |   | X | X |   |
| 2-472 |   | X | X |   | X | X |   |
| 2-473 |   | X | X |   | X | X |   |
| 2-474 |   | X | X |   | X | X |   |
| 2-475 |   | X | X |   | X | X |   |
| 2-476 |   | X | X |   | X |   | X |
| 2-477 |   | X | X |   | X |   | X |
| 2-478 |   | X | X |   | X |   | X |
| 2-479 |   | X | X |   | X |   | X |
| 2-480 |   | X | X |   | X |   | X |
| 2-481 |   | X |   | X | X | X |   |
| 2-482 |   | X |   | X | X | X |   |
| 2-483 |   | X |   | X | X | X |   |
| 2-484 |   | X |   | X | X | X |   |
| 2-485 |   | X |   | X | X | X |   |
| 2-486 |   | X |   | X | X |   | X |
| 2-487 |   | X |   | X | X |   | X |
| 2-488 |   | X |   | X | X |   | X |
| 2-489 |   | X |   | X | X |   | X |
| 2-490 |   | X |   | X | X |   | X |
| 2-491 |   | X |   | X | X |   | X |
| 2-492 |   | X |   | X | X |   | X |

TABLE 2-continued
Exemplary compounds of Formula II-A, wherein X represents Cl, Br, or F.
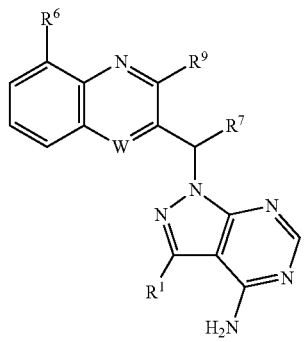
| | C1 | C2 | C3 | C4 | C5 |
|---|---|---|---|---|---|
| 2-493 | X | X | X | | X |
| 2-494 | X | X | X | | X |
| 2-495 | X | X | X | | X |
| 2-496 | X | X | | X | X |
| 2-497 | X | X | | X | X |
| 2-498 | X | X | | X | X |
| 2-499 | X | X | | X | X |
| 2-500 | X | X | | X | X |
| 2-501 | X | X | | X | X |
| 2-502 | X | X | | X | X |
| 2-503 | X | X | | X | X |
| 2-504 | X | X | | X | X |
| 2-505 | X | X | | X | X |
| 2-506 | X | X | | X | | X |
| 2-507 | X | X | | X | | X |
| 2-508 | X | X | | X | | X |
| 2-509 | X | X | | X | | X |
| 2-510 | X | X | | X | | X |
| 2-511 | X | | X | X | X |
| 2-512 | X | | X | X | X |
| 2-513 | X | | X | X | X |
| 2-514 | X | | X | X | X |
| 2-515 | X | | X | X | X |
| 2-516 | X | | X | X | X |
| 2-517 | X | | X | X | X |
| 2-518 | X | | X | X | X |
| 2-519 | X | | X | X | X |
| 2-520 | X | | X | X | X |
| 2-521 | X | | X | X | | X |
| 2-522 | X | | X | X | | X |
| 2-523 | X | | X | X | | X |
| 2-524 | X | | X | X | | X |
| 2-525 | X | | X | X | | X |
| 2-526 | X | | X | X | X |
| 2-527 | X | | X | X | X |
| 2-528 | X | | X | X | X |
| 2-529 | X | | X | X | X |
| 2-530 | X | | X | X | X |
| 2-531 | X | | X | X | X |
| 2-532 | X | | X | X | X |
| 2-533 | X | | X | X | X |
| 2-534 | X | | X | X | X |
| 2-535 | X | | X | X | X |
| 2-536 | X | | X | X | | X |
| 2-537 | X | | X | X | | X |
| 2-538 | X | | X | X | | X |
| 2-539 | X | | X | X | | X |
| 2-540 | X | | X | X | | X |

TABLE 2-continued
Exemplary compounds of Formula II-A, wherein X represents Cl, Br, or F.
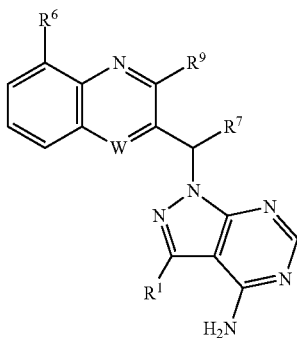
Exemplary compounds of Formula II-A, wherein X represents Cl, Br, or F.
| No | pyrrolidinyl | isopropylphenyl | N-methylpiperazinyl | isopropylamino | methoxyphenyl |
|---|---|---|---|---|---|
| 2-1 | X | | | | |
| 2-2 | | X | | | |
| 2-3 | | | X | | |
| 2-4 | | | | X | |
| 2-5 | | | | | X |
| 2-6 | X | | | | |
| 2-7 | | X | | | |
| 2-8 | | | X | | |
| 2-9 | | | | X | |
| 2-10 | | | | | X |
| 2-11 | X | | | | |
| 2-12 | | X | | | |
| 2-13 | | | X | | |
| 2-14 | | | | X | |
| 2-15 | | | | | X |
| 2-16 | X | | | | |
| 2-17 | | X | | | |
| 2-18 | | | X | | |
| 2-19 | | | | X | |
| 2-20 | | | | | X |
| 2-21 | X | | | | |
| 2-22 | | X | | | |
| 2-23 | | | X | | |
| 2-24 | | | | X | |
| 2-25 | | | | | X |
| 2-26 | X | | | | |
| 2-27 | | X | | | |
| 2-28 | | | X | | |
| 2-29 | | | | X | |
| 2-30 | | | | | X |
| 2-31 | X | | | | |
| 2-32 | | X | | | |
| 2-33 | | | X | | |
| 2-34 | | | | X | |
| 2-35 | | | | | X |
| 2-36 | X | | | | |
| 2-37 | | X | | | |
| 2-38 | | | X | | |
| 2-39 | | | | X | |
| 2-40 | | | | | X |
| 2-41 | X | | | | |
| 2-42 | | X | | | |
| 2-43 | | | X | | |
| 2-44 | | | | X | |
| 2-45 | | | | | X |
| 2-46 | X | | | | |
| 2-47 | | X | | | |
| 2-48 | | | X | | |

TABLE 2-continued
Exemplary compounds of Formula II-A, wherein X represents Cl, Br, or F.
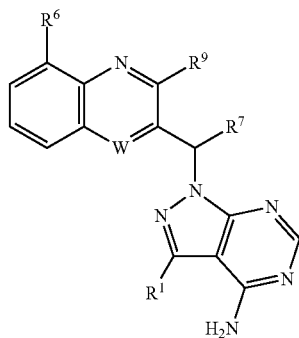
| Compound | R1 | R7 | R9 | R6 | W |
|---|---|---|---|---|---|
| 2-49 | | | | X | |
| 2-50 | | | | | X |
| 2-51 | X | | | | |
| 2-52 | | X | | | |
| 2-53 | | | X | | |
| 2-54 | | | | X | |
| 2-55 | | | | | X |
| 2-56 | X | | | | |
| 2-57 | | X | | | |
| 2-58 | | | X | | |
| 2-59 | | | | X | |
| 2-60 | | | | | X |
| 2-61 | X | | | | |
| 2-62 | | X | | | |
| 2-63 | | | X | | |
| 2-64 | | | | X | |
| 2-65 | | | | | X |
| 2-66 | X | | | | |
| 2-67 | | X | | | |
| 2-68 | | | X | | |
| 2-69 | | | | X | |
| 2-70 | | | | | X |
| 2-71 | X | | | | |
| 2-72 | | X | | | |
| 2-73 | | | X | | |
| 2-74 | | | | X | |
| 2-75 | | | | | X |
| 2-76 | X | | | | |
| 2-77 | | X | | | |
| 2-78 | | | X | | |
| 2-79 | | | | X | |
| 2-80 | | | | | X |
| 2-81 | X | | | | |
| 2-82 | | X | | | |
| 2-83 | | | X | | |
| 2-84 | | | | X | |
| 2-85 | | | | | X |
| 2-86 | X | | | | |
| 2-87 | | X | | | |
| 2-88 | | | X | | |
| 2-89 | | | | X | |
| 2-90 | | | | | X |
| 2-91 | X | | | | |
| 2-92 | | X | | | |
| 2-93 | | | X | | |
| 2-94 | | | | X | |
| 2-95 | | | | | X |
| 2-96 | X | | | | |
| 2-97 | | X | | | |
| 2-98 | | | X | | |
| 2-99 | | | | X | |
| 2-100 | | | | | X |
| 2-101 | X | | | | |
| 2-102 | | X | | | |
| 2-103 | | | X | | |
| 2-104 | | | | X | |
| 2-105 | | | | | X |
| 2-106 | X | | | | |
| 2-107 | | X | | | |
| 2-108 | | | X | | |

TABLE 2-continued
Exemplary compounds of Formula II-A, wherein X represents Cl, Br, or F.
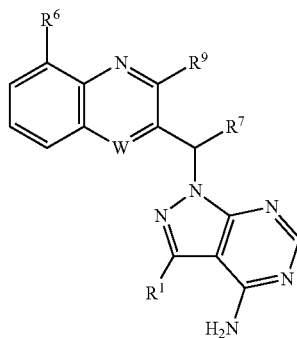
| # | | | | | |
|---|---|---|---|---|---|
| 2-109 | | | | X | |
| 2-110 | | | | | X |
| 2-111 | X | | | | |
| 2-112 | | X | | | |
| 2-113 | | | X | | |
| 2-114 | | | | X | |
| 2-115 | | | | | X |
| 2-116 | X | | | | |
| 2-117 | | X | | | |
| 2-118 | | | X | | |
| 2-119 | | | | X | |
| 2-120 | | | | | X |
| 2-121 | X | | | | |
| 2-122 | | X | | | |
| 2-123 | | | X | | |
| 2-124 | | | | X | |
| 2-125 | | | | | X |
| 2-126 | X | | | | |
| 2-127 | | X | | | |
| 2-128 | | | X | | |
| 2-129 | | | | X | |
| 2-130 | | | | | X |
| 2-131 | X | | | | |
| 2-132 | | X | | | |
| 2-133 | | | X | | |
| 2-134 | | | | X | |
| 2-135 | | | | | X |
| 2-136 | X | | | | |
| 2-137 | | X | | | |
| 2-138 | | | X | | |
| 2-139 | | | | X | |
| 2-140 | | | | | X |
| 2-141 | X | | | | |
| 2-142 | | X | | | |
| 2-143 | | | X | | |
| 2-144 | | | | X | |
| 2-145 | | | | | X |
| 2-146 | X | | | | |
| 2-147 | | X | | | |
| 2-148 | | | X | | |
| 2-149 | | | | X | |
| 2-150 | | | | | X |
| 2-151 | X | | | | |
| 2-152 | | X | | | |
| 2-153 | | | X | | |
| 2-154 | | | | X | |
| 2-155 | | | | | X |
| 2-156 | X | | | | |
| 2-157 | | X | | | |
| 2-158 | | | X | | |
| 2-159 | | | | X | |
| 2-160 | | | | | X |
| 2-161 | X | | | | |
| 2-162 | | X | | | |
| 2-163 | | | X | | |
| 2-164 | | | | X | |
| 2-165 | | | | | X |
| 2-166 | X | | | | |
| 2-167 | | X | | | |
| 2-168 | | | X | | |

TABLE 2-continued
Exemplary compounds of Formula II-A, wherein X represents Cl, Br, or F.
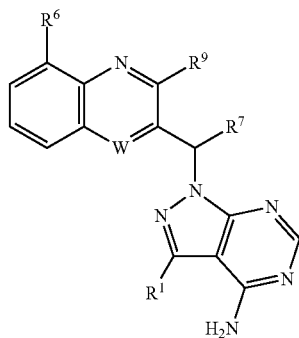
| # | R1 | R6 | R7 | R9 | W |
|---|---|---|---|---|---|
| 2-169 | | | | X | |
| 2-170 | | | | | X |
| 2-171 | X | | | | |
| 2-172 | | X | | | |
| 2-173 | | | X | | |
| 2-174 | | | | X | |
| 2-175 | | | | | X |
| 2-176 | X | | | | |
| 2-177 | | X | | | |
| 2-178 | | | X | | |
| 2-179 | | | | X | |
| 2-180 | | | | | X |
| 2-181 | X | | | | |
| 2-182 | | X | | | |
| 2-183 | | | X | | |
| 2-184 | | | | X | |
| 2-185 | | | | | X |
| 2-186 | X | | | | |
| 2-187 | | X | | | |
| 2-188 | | | X | | |
| 2-189 | | | | X | |
| 2-190 | | | | | X |
| 2-191 | X | | | | |
| 2-192 | | X | | | |
| 2-193 | | | X | | |
| 2-194 | | | | X | |
| 2-195 | | | | | X |
| 2-196 | X | | | | |
| 2-197 | | X | | | |
| 2-198 | | | X | | |
| 2-199 | | | | X | |
| 2-200 | | | | | X |
| 2-201 | X | | | | |
| 2-202 | | X | | | |
| 2-203 | | | X | | |
| 2-204 | | | | X | |
| 2-205 | | | | | X |
| 2-206 | X | | | | |
| 2-207 | | X | | | |
| 2-208 | | | X | | |
| 2-209 | | | | X | |
| 2-210 | | | | | X |
| 2-211 | X | | | | |
| 2-212 | | X | | | |
| 2-213 | | | X | | |
| 2-214 | | | | X | |
| 2-215 | | | | | X |
| 2-216 | X | | | | |
| 2-217 | | X | | | |
| 2-218 | | | X | | |
| 2-219 | | | | X | |
| 2-220 | | | | | X |
| 2-221 | X | | | | |
| 2-222 | | X | | | |
| 2-223 | | | X | | |
| 2-224 | | | | X | |
| 2-225 | | | | | X |
| 2-226 | X | | | | |
| 2-227 | | X | | | |
| 2-228 | | | X | | |

TABLE 2-continued
Exemplary compounds of Formula II-A, wherein X represents Cl, Br, or F.
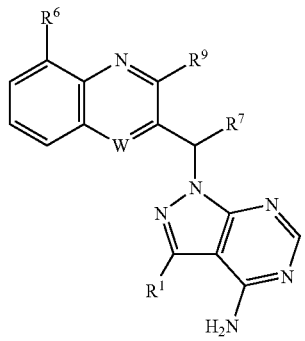
| | | | | | | |
|---|---|---|---|---|---|---|
| 2-229 | | | | | X | |
| 2-230 | | | | | | X |
| 2-231 | X | | | | | |
| 2-232 | | X | | | | |
| 2-233 | | | | X | | |
| 2-234 | | | | | X | |
| 2-235 | | | | | | X |
| 2-236 | X | | | | | |
| 2-237 | | X | | | | |
| 2-238 | | | | X | | |
| 2-239 | | | | | X | |
| 2-240 | | | | | | X |
| 2-241 | X | | | | | |
| 2-242 | | X | | | | |
| 2-243 | | | | X | | |
| 2-244 | | | | | X | |
| 2-245 | | | | | | X |
| 2-246 | X | | | | | |
| 2-247 | | X | | | | |
| 2-248 | | | | X | | |
| 2-249 | | | | | X | |
| 2-250 | | | | | | X |
| 2-251 | X | | | | | |
| 2-252 | | X | | | | |
| 2-253 | | | | X | | |
| 2-254 | | | | | X | |
| 2-255 | | | | | | X |
| 2-256 | X | | | | | |
| 2-257 | | X | | | | |
| 2-258 | | | | X | | |
| 2-259 | | | | | X | |
| 2-260 | | | | | | X |
| 2-261 | X | | | | | |
| 2-262 | | X | | | | |
| 2-263 | | | | X | | |
| 2-264 | | | | | X | |
| 2-265 | | | | | | X |
| 2-266 | X | | | | | |
| 2-267 | | X | | | | |
| 2-268 | | | | X | | |
| 2-269 | | | | | X | |
| 2-270 | | | | | | X |

TABLE 2-continued
Exemplary compounds of Formula II-A, wherein X represents Cl, Br, or F.
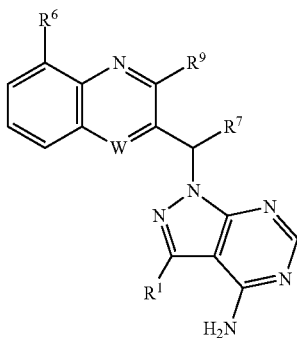
Exemplary compounds of Formula II-A, wherein X represents Cl, Br, or F.
| No | 2-methylphenyl | phenyl | 2-carboxyphenyl | 2-pyridyl | isopropyl |
|---|---|---|---|---|---|
| 2-271 | X | | | | |
| 2-272 | | X | | | |
| 2-273 | | | X | | |
| 2-274 | | | | X | |
| 2-275 | | | | | X |
| 2-276 | X | | | | |
| 2-277 | | X | | | |
| 2-278 | | | X | | |
| 2-279 | | | | X | |
| 2-280 | | | | | X |
| 2-281 | X | | | | |
| 2-282 | | X | | | |
| 2-283 | | | X | | |
| 2-284 | | | | X | |
| 2-285 | | | | | X |
| 2-286 | X | | | | |
| 2-287 | | X | | | |
| 2-288 | | | X | | |
| 2-289 | | | | X | |
| 2-290 | | | | | X |
| 2-291 | X | | | | |
| 2-292 | | X | | | |
| 2-293 | | | X | | |
| 2-294 | | | | X | |
| 2-295 | | | | | X |
| 2-296 | X | | | | |
| 2-297 | | X | | | |
| 2-298 | | | X | | |
| 2-299 | | | | X | |
| 2-300 | | | | | X |
| 2-301 | X | | | | |
| 2-302 | | X | | | |
| 2-303 | | | X | | |
| 2-304 | | | | X | |
| 2-305 | | | | | X |
| 2-306 | X | | | | |
| 2-307 | | X | | | |
| 2-308 | | | X | | |
| 2-309 | | | | X | |
| 2-310 | | | | | X |
| 2-311 | X | | | | |
| 2-312 | | X | | | |
| 2-313 | | | X | | |
| 2-314 | | | | X | |
| 2-315 | | | | | X |
| 2-316 | X | | | | |
| 2-317 | | X | | | |
| 2-318 | | | X | | |

TABLE 2-continued
Exemplary compounds of Formula II-A, wherein X represents Cl, Br, or F.
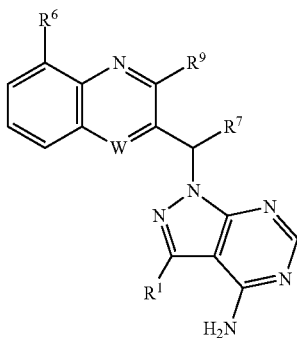
| | | | | | |
|---|---|---|---|---|---|
| 2-319 | | | | X | |
| 2-320 | | | | | X |
| 2-321 | X | | | | |
| 2-322 | | X | | | |
| 2-323 | | | X | | |
| 2-324 | | | | X | |
| 2-325 | | | | | X |
| 2-326 | X | | | | |
| 2-327 | | X | | | |
| 2-328 | | | X | | |
| 2-329 | | | | X | |
| 2-330 | | | | | X |
| 2-331 | X | | | | |
| 2-332 | | X | | | |
| 2-333 | | | X | | |
| 2-334 | | | | X | |
| 2-335 | | | | | X |
| 2-336 | X | | | | |
| 2-337 | | X | | | |
| 2-338 | | | X | | |
| 2-339 | | | | X | |
| 2-340 | | | | | X |
| 2-341 | X | | | | |
| 2-342 | | X | | | |
| 2-343 | | | X | | |
| 2-344 | | | | X | |
| 2-345 | | | | | X |
| 2-346 | X | | | | |
| 2-347 | | X | | | |
| 2-348 | | | X | | |
| 2-349 | | | | X | |
| 2-350 | | | | | X |
| 2-351 | X | | | | |
| 2-352 | | X | | | |
| 2-353 | | | X | | |
| 2-354 | | | | X | |
| 2-355 | | | | | X |
| 2-356 | X | | | | |
| 2-357 | | X | | | |
| 2-358 | | | X | | |
| 2-359 | | | | X | |
| 2-360 | | | | | X |
| 2-361 | X | | | | |
| 2-362 | | X | | | |
| 2-363 | | | X | | |
| 2-364 | | | | X | |
| 2-365 | | | | | X |
| 2-366 | X | | | | |
| 2-367 | | X | | | |
| 2-368 | | | X | | |
| 2-369 | | | | X | |
| 2-370 | | | | | X |
| 2-371 | X | | | | |
| 2-372 | | X | | | |
| 2-373 | | | X | | |
| 2-374 | | | | X | |
| 2-375 | | | | | X |
| 2-376 | X | | | | |
| 2-377 | | X | | | |
| 2-378 | | | X | | |

TABLE 2-continued
Exemplary compounds of Formula II-A, wherein X represents Cl, Br, or F.
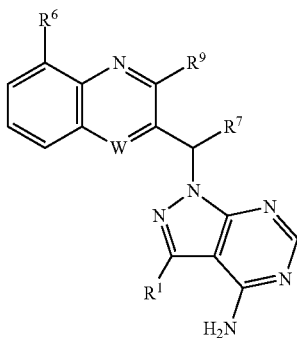
| Compound | | | | | |
|---|---|---|---|---|---|
| 2-379 | | | | X | |
| 2-380 | | | | | X |
| 2-381 | X | | | | |
| 2-382 | | X | | | |
| 2-383 | | | X | | |
| 2-384 | | | | X | |
| 2-385 | | | | | X |
| 2-386 | X | | | | |
| 2-387 | | X | | | |
| 2-388 | | | X | | |
| 2-389 | | | | X | |
| 2-390 | | | | | X |
| 2-391 | X | | | | |
| 2-392 | | X | | | |
| 2-393 | | | X | | |
| 2-394 | | | | X | |
| 2-395 | | | | | X |
| 2-396 | X | | | | |
| 2-397 | | X | | | |
| 2-398 | | | X | | |
| 2-399 | | | | X | |
| 2-400 | | | | | X |
| 2-401 | X | | | | |
| 2-402 | | X | | | |
| 2-403 | | | X | | |
| 2-404 | | | | X | |
| 2-405 | | | | | X |
| 2-406 | X | | | | |
| 2-407 | | X | | | |
| 2-408 | | | X | | |
| 2-409 | | | | X | |
| 2-410 | | | | | X |
| 2-411 | X | | | | |
| 2-412 | | X | | | |
| 2-413 | | | X | | |
| 2-414 | | | | X | |
| 2-415 | | | | | X |
| 2-416 | X | | | | |
| 2-417 | | X | | | |
| 2-418 | | | X | | |
| 2-419 | | | | X | |
| 2-420 | | | | | X |
| 2-421 | X | | | | |
| 2-422 | | X | | | |
| 2-423 | | | X | | |
| 2-424 | | | | X | |
| 2-425 | | | | | X |
| 2-426 | X | | | | |
| 2-427 | | X | | | |
| 2-428 | | | X | | |
| 2-429 | | | | X | |
| 2-430 | | | | | X |
| 2-431 | X | | | | |
| 2-432 | | X | | | |
| 2-433 | | | X | | |
| 2-434 | | | | X | |
| 2-435 | | | | | X |
| 2-436 | X | | | | |
| 2-437 | | X | | | |
| 2-438 | | | X | | |

TABLE 2-continued
Exemplary compounds of Formula II-A, wherein X represents Cl, Br, or F.
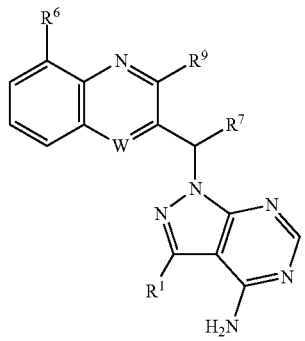
| Cpd | | | | | |
|---|---|---|---|---|---|
| 2-439 | | | | X | |
| 2-440 | | | | | X |
| 2-441 | X | | | | |
| 2-442 | | X | | | |
| 2-443 | | | X | | |
| 2-444 | | | | X | |
| 2-445 | | | | | X |
| 2-446 | X | | | | |
| 2-447 | | X | | | |
| 2-448 | | | X | | |
| 2-449 | | | | X | |
| 2-450 | | | | | X |
| 2-451 | X | | | | |
| 2-452 | | X | | | |
| 2-453 | | | X | | |
| 2-454 | | | | X | |
| 2-455 | | | | | X |
| 2-456 | X | | | | |
| 2-457 | | X | | | |
| 2-458 | | | X | | |
| 2-459 | | | | X | |
| 2-460 | | | | | X |
| 2-461 | X | | | | |
| 2-462 | | X | | | |
| 2-463 | | | X | | |
| 2-464 | | | | X | |
| 2-465 | | | | | X |
| 2-466 | X | | | | |
| 2-467 | | X | | | |
| 2-468 | | | X | | |
| 2-469 | | | | X | |
| 2-470 | | | | | X |
| 2-471 | X | | | | |
| 2-472 | | X | | | |
| 2-473 | | | X | | |
| 2-474 | | | | X | |
| 2-475 | | | | | X |
| 2-476 | X | | | | |
| 2-477 | | X | | | |
| 2-478 | | | X | | |
| 2-479 | | | | X | |
| 2-480 | | | | | X |
| 2-481 | X | | | | |
| 2-482 | | X | | | |
| 2-483 | | | X | | |
| 2-484 | | | | X | |
| 2-485 | | | | | X |
| 2-486 | X | | | | |
| 2-487 | | X | | | |
| 2-488 | | | X | | |
| 2-489 | | | | X | |
| 2-490 | | | | | X |
| 2-491 | X | | | | |
| 2-492 | | X | | | |
| 2-493 | | | X | | |
| 2-494 | | | | X | |
| 2-495 | | | | | X |
| 2-496 | X | | | | |
| 2-497 | | X | | | |
| 2-498 | | | X | | |

TABLE 2-continued
Exemplary compounds of Formula II-A, wherein X represents Cl, Br, or F.
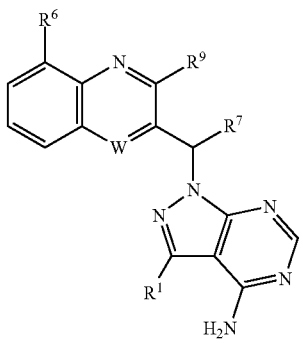
| | | | | | |
|---|---|---|---|---|---|
| 2-499 | | | | X | |
| 2-500 | | | | | X |
| 2-501 | X | | | | |
| 2-502 | | X | | | |
| 2-503 | | | X | | |
| 2-504 | | | | X | |
| 2-505 | | | | | X |
| 2-506 | X | | | | |
| 2-507 | | X | | | |
| 2-508 | | | X | | |
| 2-509 | | | | X | |
| 2-510 | | | | | X |
| 2-511 | X | | | | |
| 2-512 | | X | | | |
| 2-513 | | | X | | |
| 2-514 | | | | X | |
| 2-515 | | | | | X |
| 2-516 | X | | | | |
| 2-517 | | X | | | |
| 2-518 | | | X | | |
| 2-519 | | | | X | |
| 2-520 | | | | | X |
| 2-521 | X | | | | |
| 2-522 | | X | | | |
| 2-523 | | | X | | |
| 2-524 | | | | X | |
| 2-525 | | | | | X |
| 2-526 | X | | | | |
| 2-527 | | X | | | |
| 2-528 | | | X | | |
| 2-529 | | | | X | |
| 2-530 | | | | | X |
| 2-531 | X | | | | |
| 2-532 | | X | | | |
| 2-533 | | | X | | |
| 2-534 | | | | X | |
| 2-535 | | | | | X |
| 2-536 | X | | | | |
| 2-537 | | X | | | |
| 2-538 | | | X | | |
| 2-539 | | | | X | |
| 2-540 | | | | | X |

TABLE 3

Formula III-A

|  | R¹ | | | W | | R⁷ | | |
|---|---|---|---|---|---|---|---|---|
| No | F/OH-phenyl | HO-alkyne | I | C | N | H | Me | Et |
| 3-1 | X | | | X | | X | | |
| 3-2 | X | | | X | | X | | |
| 3-3 | X | | | X | | X | | |
| 3-4 | X | | | X | | X | | |
| 3-5 | X | | | X | | X | | |
| 3-6 | X | | | X | | | X | |
| 3-7 | X | | | X | | | X | |
| 3-8 | X | | | X | | | X | |
| 3-9 | X | | | X | | | X | |
| 3-10 | X | | | X | | | X | |
| 3-11 | X | | | X | | | | X |
| 3-12 | X | | | X | | | | X |
| 3-13 | X | | | X | | | | X |
| 3-14 | X | | | X | | | | X |
| 3-15 | X | | | X | | | | X |
| 3-16 | X | | | | X | X | | |
| 3-17 | X | | | | X | X | | |
| 3-18 | X | | | | X | X | | |
| 3-19 | X | | | | X | X | | |
| 3-20 | X | | | | X | X | | |
| 3-21 | X | | | | X | | X | |
| 3-22 | X | | | | X | | X | |
| 3-23 | X | | | | X | | X | |
| 3-24 | X | | | | X | | X | |
| 3-25 | X | | | | X | | X | |
| 3-26 | X | | | | X | | | X |
| 3-27 | X | | | | X | | | X |
| 3-28 | X | | | | X | | | X |
| 3-29 | X | | | | X | | | X |
| 3-30 | X | | | | X | | | X |
| 3-31 | X | | | X | | X | | |
| 3-32 | X | | | X | | X | | |
| 3-33 | X | | | X | | X | | |
| 3-34 | X | | | X | | X | | |
| 3-35 | X | | | X | | X | | |
| 3-36 | X | | | X | | | X | |
| 3-37 | X | | | X | | | X | |
| 3-38 | X | | | X | | | X | |
| 3-39 | X | | | X | | | X | |
| 3-40 | X | | | X | | | X | |
| 3-41 | X | | | X | | | | X |
| 3-42 | X | | | X | | | | X |
| 3-43 | X | | | X | | | | X |
| 3-44 | X | | | X | | | | X |
| 3-45 | X | | | X | | | | X |
| 3-46 | X | | | | X | X | | |
| 3-47 | X | | | | X | X | | |
| 3-48 | X | | | | X | X | | |
| 3-49 | X | | | | X | X | | |
| 3-50 | X | | | | X | X | | |
| 3-51 | X | | | | X | | X | |

TABLE 3-continued

| | C1 | C2 | C3 | C4 | C5 | C6 |
|---|---|---|---|---|---|---|
| 3-52 | X | | | X | X | |
| 3-53 | X | | | X | X | |
| 3-54 | X | | | X | X | |
| 3-55 | X | | | X | X | |
| 3-56 | X | | | X | | X |
| 3-57 | X | | | X | | X |
| 3-58 | X | | | X | | X |
| 3-59 | X | | | X | | X |
| 3-60 | X | | | X | | X |
| 3-61 | X | | X | | X | |
| 3-62 | X | | X | | X | |
| 3-63 | X | | X | | X | |
| 3-64 | X | | X | | X | |
| 3-65 | X | | X | | X | |
| 3-66 | X | | X | | | X |
| 3-67 | X | | X | | | X |
| 3-68 | X | | X | | | X |
| 3-69 | X | | X | | | X |
| 3-70 | X | | X | | | X |
| 3-71 | X | | X | | | X |
| 3-72 | X | | X | | | X |
| 3-73 | X | | X | | | X |
| 3-74 | X | | X | | | X |
| 3-75 | X | | X | | | X |
| 3-76 | X | | | X | X | |
| 3-77 | X | | | X | X | |
| 3-78 | X | | | X | X | |
| 3-79 | X | | | X | X | |
| 3-80 | X | | | X | X | |
| 3-81 | X | | | X | | X |
| 3-82 | X | | | X | | X |
| 3-83 | X | | | X | | X |
| 3-84 | X | | | X | | X |
| 3-85 | X | | | X | | X |
| 3-86 | X | | | X | | X |
| 3-87 | X | | | X | | X |
| 3-88 | X | | | X | | X |
| 3-89 | X | | | X | | X |
| 3-90 | X | | | X | | X |
| 3-91 | | X | X | | X | |
| 3-92 | | X | X | | X | |
| 3-93 | | X | X | | X | |
| 3-94 | | X | X | | X | |
| 3-95 | | X | X | | X | |
| 3-96 | | X | X | | X | |
| 3-97 | | X | X | | X | |
| 3-98 | | X | X | | X | |
| 3-99 | | X | X | | X | |
| 3-100 | | X | X | | X | |
| 3-101 | | X | X | | | X |
| 3-102 | | X | X | | | X |
| 3-103 | | X | X | | | X |
| 3-104 | | X | X | | | X |
| 3-105 | | X | X | | | X |
| 3-106 | | X | | X | X | |
| 3-107 | | X | | X | X | |
| 3-108 | | X | | X | X | |
| 3-109 | | X | | X | X | |
| 3-110 | | X | | X | X | |
| 3-111 | | X | | X | | X |
| 3-112 | | X | | X | | X |
| 3-113 | | X | | X | | X |
| 3-114 | | X | | X | | X |
| 3-115 | | X | | X | | X |
| 3-116 | | X | | X | | X |
| 3-117 | | X | | X | | X |
| 3-118 | | X | | X | | X |
| 3-119 | | X | | X | | X |
| 3-120 | | X | | X | | X |
| 3-121 | | X | X | | X | |
| 3-122 | | X | X | | X | |
| 3-123 | | X | X | | X | |
| 3-124 | | X | X | | X | |
| 3-125 | | X | X | | X | |
| 3-126 | | X | X | | | X |
| 3-127 | | X | X | | | X |
| 3-128 | | X | X | | | X |
| 3-129 | | X | X | | | X |
| 3-130 | | X | X | | | X |
| 3-131 | | X | X | | | X |

TABLE 3-continued

| | | | | | |
|---|---|---|---|---|---|
| 3-132 | X | | X | | X |
| 3-133 | X | | X | | X |
| 3-134 | X | | X | | X |
| 3-135 | X | | X | | X |
| 3-136 | X | | | X | X |
| 3-137 | X | | | X | X |
| 3-138 | X | | | X | X |
| 3-139 | X | | | X | X |
| 3-140 | X | | | X | X |
| 3-141 | X | | | X | | X |
| 3-142 | X | | | X | | X |
| 3-143 | X | | | X | | X |
| 3-144 | X | | | X | | X |
| 3-145 | X | | | X | | X |
| 3-146 | X | | | X | | | X |
| 3-147 | X | | | X | | | X |
| 3-148 | X | | | X | | | X |
| 3-149 | X | | | X | | | X |
| 3-150 | X | | | X | | | X |
| 3-151 | X | | X | | X |
| 3-152 | X | | X | | X |
| 3-153 | X | | X | | X |
| 3-154 | X | | X | | X |
| 3-155 | X | | X | | X |
| 3-156 | X | | X | | | X |
| 3-157 | X | | X | | | X |
| 3-158 | X | | X | | | X |
| 3-159 | X | | X | | | X |
| 3-160 | X | | X | | | X |
| 3-161 | X | | X | | | | X |
| 3-162 | X | | X | | | | X |
| 3-163 | X | | X | | | | X |
| 3-164 | X | | X | | | | X |
| 3-165 | X | | X | | | | X |
| 3-166 | X | | | X | X |
| 3-167 | X | | | X | X |
| 3-168 | X | | | X | X |
| 3-169 | X | | | X | X |
| 3-170 | X | | | X | X |
| 3-171 | X | | | X | | X |
| 3-172 | X | | | X | | X |
| 3-173 | X | | | X | | X |
| 3-174 | X | | | X | | X |
| 3-175 | X | | | X | | X |
| 3-176 | X | | | X | | | X |
| 3-177 | X | | | X | | | X |
| 3-178 | X | | | X | | | X |
| 3-179 | X | | | X | | | X |
| 3-180 | X | | | X | | | X |
| 3-181 | | X | X | | X |
| 3-182 | | X | X | | X |
| 3-183 | | X | X | | X |
| 3-184 | | X | X | | X |
| 3-185 | | X | X | | X |
| 3-186 | | X | X | | | X |
| 3-187 | | X | X | | | X |
| 3-188 | | X | X | | | X |
| 3-189 | | X | X | | | X |
| 3-190 | | X | X | | | X |
| 3-191 | | X | X | | | | X |
| 3-192 | | X | X | | | | X |
| 3-193 | | X | X | | | | X |
| 3-194 | | X | X | | | | X |
| 3-195 | | X | X | | | | X |
| 3-196 | | X | | X | X |
| 3-197 | | X | | X | X |
| 3-198 | | X | | X | X |
| 3-199 | | X | | X | X |
| 3-200 | | X | | X | X |
| 3-201 | | X | | X | | X |
| 3-202 | | X | | X | | X |
| 3-203 | | X | | X | | X |
| 3-204 | | X | | X | | X |
| 3-205 | | X | | X | | X |
| 3-206 | | X | | X | | | X |
| 3-207 | | X | | X | | | X |
| 3-208 | | X | | X | | | X |
| 3-209 | | X | | X | | | X |
| 3-210 | | X | | X | | | X |
| 3-211 | | X | X | | X |

TABLE 3-continued

| | | | | | | | |
|---|---|---|---|---|---|---|---|
| 3-212 | | X | X | | X | | |
| 3-213 | | X | X | | X | | |
| 3-214 | | X | X | | X | | |
| 3-215 | | X | X | | X | | |
| 3-216 | | X | X | | | X | |
| 3-217 | | X | X | | | X | |
| 3-218 | | X | X | | | X | |
| 3-219 | | X | X | | | X | |
| 3-220 | | X | X | | | X | |
| 3-221 | | X | X | | | | X |
| 3-222 | | X | X | | | | X |
| 3-223 | | X | X | | | | X |
| 3-224 | | X | X | | | | X |
| 3-225 | | X | X | | | | X |
| 3-226 | | X | | X | X | | |
| 3-227 | | X | | X | X | | |
| 3-228 | | X | | X | X | | |
| 3-229 | | X | | X | X | | |
| 3-230 | | X | | X | X | | |
| 3-231 | | X | | X | | X | |
| 3-232 | | X | | X | | X | |
| 3-233 | | X | | X | | X | |
| 3-234 | | X | | X | | X | |
| 3-235 | | X | | X | | X | |
| 3-236 | | X | | X | | | X |
| 3-237 | | X | | X | | | X |
| 3-238 | | X | | X | | | X |
| 3-239 | | X | | X | | | X |
| 3-240 | | X | | X | | | X |
| 3-241 | | X | X | | X | | |
| 3-242 | | X | X | | X | | |
| 3-243 | | X | X | | X | | |
| 3-244 | | X | X | | X | | |
| 3-245 | | X | X | | X | | |
| 3-246 | | X | X | | | X | |
| 3-247 | | X | X | | | X | |
| 3-248 | | X | X | | | X | |
| 3-249 | | X | X | | | X | |
| 3-250 | | X | X | | | X | |
| 3-251 | | X | X | | | | X |
| 3-252 | | X | X | | | | X |
| 3-253 | | X | X | | | | X |
| 3-254 | | X | X | | | | X |
| 3-255 | | X | X | | | | X |
| 3-256 | | X | | X | X | | |
| 3-257 | | X | | X | X | | |
| 3-258 | | X | | X | X | | |
| 3-259 | | X | | X | X | | |
| 3-260 | | X | | X | X | | |
| 3-261 | | X | | X | | X | |
| 3-262 | | X | | X | | X | |
| 3-263 | | X | | X | | X | |
| 3-264 | | X | | X | | X | |
| 3-265 | | X | | X | | X | |
| 3-266 | | X | | X | | | X |
| 3-267 | | X | | X | | | X |
| 3-268 | | X | | X | | | X |
| 3-269 | | X | | X | | | X |
| 3-270 | | X | | X | | | X |
| 3-271 | X | | | X | X | | |
| 3-272 | X | | | X | X | | |
| 3-273 | X | | | X | X | | |
| 3-274 | X | | | X | X | | |
| 3-275 | X | | | X | X | | |
| 3-276 | X | | | X | | X | |
| 3-277 | X | | | X | | X | |
| 3-278 | X | | | X | | X | |
| 3-279 | X | | | X | | X | |
| 3-280 | X | | | X | | X | |
| 3-281 | X | | | X | | | X |
| 3-282 | X | | | X | | | X |
| 3-283 | X | | | X | | | X |
| 3-284 | X | | | X | | | X |
| 3-285 | X | | | X | | | X |
| 3-286 | X | | | X | X | | |
| 3-287 | X | | | X | X | | |
| 3-288 | X | | | X | X | | |
| 3-289 | X | | | X | X | | |
| 3-290 | X | | | X | X | | |
| 3-291 | X | | | X | | X | |

TABLE 3-continued

| | | | | | |
|---|---|---|---|---|---|
| 3-292 | X | | | X | X |
| 3-293 | X | | | X | X |
| 3-294 | X | | | X | X |
| 3-295 | X | | | X | X |
| 3-296 | X | | | X | | X |
| 3-297 | X | | | X | | X |
| 3-298 | X | | | X | | X |
| 3-299 | X | | | X | | X |
| 3-300 | X | | | X | | X |
| 3-301 | X | | X | | X |
| 3-302 | X | | X | | X |
| 3-303 | X | | X | | X |
| 3-304 | X | | X | | X |
| 3-305 | X | | X | | X |
| 3-306 | X | | X | | | X |
| 3-307 | X | | X | | | X |
| 3-308 | X | | X | | | X |
| 3-309 | X | | X | | | X |
| 3-310 | X | | X | | | X |
| 3-311 | X | | X | | | | X |
| 3-312 | X | | X | | | | X |
| 3-313 | X | | X | | | | X |
| 3-314 | X | | X | | | | X |
| 3-315 | X | | X | | | | X |
| 3-316 | X | | | X | X |
| 3-317 | X | | | X | X |
| 3-318 | X | | | X | X |
| 3-319 | X | | | X | X |
| 3-320 | X | | | X | X |
| 3-321 | X | | | X | | X |
| 3-322 | X | | | X | | X |
| 3-323 | X | | | X | | X |
| 3-324 | X | | | X | | X |
| 3-325 | X | | | X | | X |
| 3-326 | X | | | X | | | X |
| 3-327 | X | | | X | | | X |
| 3-328 | X | | | X | | | X |
| 3-329 | X | | | X | | | X |
| 3-330 | X | | | X | | | X |
| 3-331 | X | | X | | X |
| 3-332 | X | | X | | X |
| 3-333 | X | | X | | X |
| 3-334 | X | | X | | X |
| 3-335 | X | | X | | X |
| 3-336 | X | | X | | | X |
| 3-337 | X | | X | | | X |
| 3-338 | X | | X | | | X |
| 3-339 | X | | X | | | X |
| 3-340 | X | | X | | | X |
| 3-341 | X | | X | | | | X |
| 3-342 | X | | X | | | | X |
| 3-343 | X | | X | | | | X |
| 3-344 | X | | X | | | | X |
| 3-345 | X | | X | | | | X |
| 3-346 | X | | | X | X |
| 3-347 | X | | | X | X |
| 3-348 | X | | | X | X |
| 3-349 | X | | | X | X |
| 3-350 | X | | | X | X |
| 3-351 | X | | | X | | X |
| 3-352 | X | | | X | | X |
| 3-353 | X | | | X | | X |
| 3-354 | X | | | X | | X |
| 3-355 | X | | | X | | X |
| 3-356 | X | | | X | | | X |
| 3-357 | X | | | X | | | X |
| 3-358 | X | | | X | | | X |
| 3-359 | X | | | X | | | X |
| 3-360 | X | | | X | | | X |
| 3-361 | | X | | X | | X |
| 3-362 | | X | | X | | X |
| 3-363 | | X | | X | | X |
| 3-364 | | X | | X | | X |
| 3-365 | | X | | X | | X |
| 3-366 | | X | | X | | | X |
| 3-367 | | X | | X | | | X |
| 3-368 | | X | | X | | | X |
| 3-369 | | X | | X | | | X |
| 3-370 | | X | | X | | | X |
| 3-371 | | X | | X | | | | X |

TABLE 3-continued

| | | | | | | |
|---|---|---|---|---|---|---|
| 3-372 | X | X | | | | X |
| 3-373 | X | X | | | | X |
| 3-374 | X | X | | | | X |
| 3-375 | X | X | | | | X |
| 3-376 | X | | X | X | | |
| 3-377 | X | | X | X | | |
| 3-378 | X | | X | X | | |
| 3-379 | X | | X | X | | |
| 3-380 | X | | X | X | | |
| 3-381 | X | | X | | X | |
| 3-382 | X | | X | | X | |
| 3-383 | X | | X | | X | |
| 3-384 | X | | X | | X | |
| 3-385 | X | | X | | X | |
| 3-386 | X | | X | | | X |
| 3-387 | X | | X | | | X |
| 3-388 | X | | X | | | X |
| 3-389 | X | | X | | | X |
| 3-390 | X | | X | | | X |
| 3-391 | X | X | X | | | |
| 3-392 | X | X | X | | | |
| 3-393 | X | X | X | | | |
| 3-394 | X | X | X | | | |
| 3-395 | X | X | X | | | |
| 3-396 | X | X | | X | | |
| 3-397 | X | X | | X | | |
| 3-398 | X | X | | X | | |
| 3-399 | X | X | | X | | |
| 3-400 | X | X | | X | | |
| 3-401 | X | X | | | | X |
| 3-402 | X | X | | | | X |
| 3-403 | X | X | | | | X |
| 3-404 | X | X | | | | X |
| 3-405 | X | X | | | | X |
| 3-406 | X | | X | X | | |
| 3-407 | X | | X | X | | |
| 3-408 | X | | X | X | | |
| 3-409 | X | | X | X | | |
| 3-410 | X | | X | X | | |
| 3-411 | X | | X | | X | |
| 3-412 | X | | X | | X | |
| 3-413 | X | | X | | X | |
| 3-414 | X | | X | | X | |
| 3-415 | X | | X | | X | |
| 3-416 | X | | X | | | X |
| 3-417 | X | | X | | | X |
| 3-418 | X | | X | | | X |
| 3-419 | X | | X | | | X |
| 3-420 | X | | X | | | X |
| 3-421 | X | X | X | | | |
| 3-422 | X | X | X | | | |
| 3-423 | X | X | X | | | |
| 3-424 | X | X | X | | | |
| 3-425 | X | X | X | | | |
| 3-426 | X | X | | X | | |
| 3-427 | X | X | | X | | |
| 3-428 | X | X | | X | | |
| 3-429 | X | X | | X | | |
| 3-430 | X | X | | X | | |
| 3-431 | X | X | | | | X |
| 3-432 | X | X | | | | X |
| 3-433 | X | X | | | | X |
| 3-434 | X | X | | | | X |
| 3-435 | X | X | | | | X |
| 3-436 | X | | X | X | | |
| 3-437 | X | | X | X | | |
| 3-438 | X | | X | X | | |
| 3-439 | X | | X | X | | |
| 3-440 | X | | X | X | | |
| 3-441 | X | | X | | X | |
| 3-442 | X | | X | | X | |
| 3-443 | X | | X | | X | |
| 3-444 | X | | X | | X | |
| 3-445 | X | | X | | X | |
| 3-446 | X | | X | | | X |
| 3-447 | X | | X | | | X |
| 3-448 | X | | X | | | X |
| 3-449 | X | | X | | | X |
| 3-450 | X | | X | | | X |
| 3-451 | | X | X | | X | |

TABLE 3-continued

| | | | | | |
|---|---|---|---|---|---|
| 3-452 | X | X | | X | |
| 3-453 | X | X | | X | |
| 3-454 | X | X | | X | |
| 3-455 | X | X | | X | |
| 3-456 | X | X | | | X |
| 3-457 | X | X | | | X |
| 3-358 | X | X | | | X |
| 3-459 | X | X | | | X |
| 3-460 | X | X | | | X |
| 3-461 | X | X | | | | X |
| 3-462 | X | X | | | | X |
| 3-463 | X | X | | | | X |
| 3-464 | X | X | | | | X |
| 3-465 | X | X | | | | X |
| 3-466 | X | | X | X | |
| 3-467 | X | | X | X | |
| 3-468 | X | | X | X | |
| 3-469 | X | | X | X | |
| 3-470 | X | | X | X | |
| 3-471 | X | | X | | X |
| 3-472 | X | | X | | X |
| 3-473 | X | | X | | X |
| 3-474 | X | | X | | X |
| 3-475 | X | | X | | X |
| 3-476 | X | | X | | | X |
| 3-477 | X | | X | | | X |
| 3-478 | X | | X | | | X |
| 3-479 | X | | X | | | X |
| 3-480 | X | | X | | | X |
| 3-481 | X | X | | X | |
| 3-482 | X | X | | X | |
| 3-483 | X | X | | X | |
| 3-484 | X | X | | X | |
| 3-485 | X | X | | X | |
| 3-486 | X | X | | | X |
| 3-487 | X | X | | | X |
| 3-488 | X | X | | | X |
| 3-489 | X | X | | | X |
| 3-490 | X | X | | | X |
| 3-491 | X | X | | | | X |
| 3-492 | X | X | | | | X |
| 3-493 | X | X | | | | X |
| 3-494 | X | X | | | | X |
| 3-495 | X | X | | | | X |
| 3-496 | X | | X | X | |
| 3-497 | X | | X | X | |
| 3-498 | X | | X | X | |
| 3-499 | X | | X | X | |
| 3-500 | X | | X | X | |
| 3-501 | X | | X | | X |
| 3-502 | X | | X | | X |
| 3-503 | X | | X | | X |
| 3-504 | X | | X | | X |
| 3-505 | X | | X | | X |
| 3-506 | X | | X | | | X |
| 3-507 | X | | X | | | X |
| 3-508 | X | | X | | | X |
| 3-509 | X | | X | | | X |
| 3-510 | X | | X | | | X |
| 3-511 | X | X | | X | |
| 3-512 | X | X | | X | |
| 3-513 | X | X | | X | |
| 3-514 | X | X | | X | |
| 3-515 | X | X | | X | |
| 3-516 | X | X | | | X |
| 3-517 | X | X | | | X |
| 3-518 | X | X | | | X |
| 3-519 | X | X | | | X |
| 3-520 | X | X | | | X |
| 3-521 | X | X | | | | X |
| 3-522 | X | X | | | | X |
| 3-523 | X | X | | | | X |
| 3-524 | X | X | | | | X |
| 3-525 | X | X | | | | X |
| 3-526 | X | | X | X | |
| 3-527 | X | | X | X | |
| 3-528 | X | | X | X | |
| 3-529 | X | | X | X | |
| 3-530 | X | | X | X | |
| 3-531 | X | | X | | X |

TABLE 3-continued
| No | | | | | |
|---|---|---|---|---|---|
| 3-532 | X | X | X | | |
| 3-533 | X | X | X | | |
| 3-534 | X | X | X | | |
| 3-535 | X | X | X | | |
| 3-536 | X | X | | X | |
| 3-537 | X | X | | X | |
| 3-538 | X | X | | X | |
| 3-539 | X | X | | X | |
| 3-540 | X | X | | X | |
Formula III-A
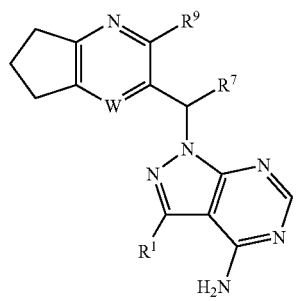
R⁹
| No | pyrrolidine | isopropylphenyl | N-methylpiperazine | HN-isopropyl | methoxyphenyl |
|---|---|---|---|---|---|
| 3-1 | X | | | | |
| 3-2 | | X | | | |
| 3-3 | | | X | | |
| 3-4 | | | | X | |
| 3-5 | | | | | X |
| 3-6 | X | | | | |
| 3-7 | | X | | | |
| 3-8 | | | X | | |
| 3-9 | | | | X | |
| 3-10 | | | | | X |
| 3-11 | X | | | | |
| 3-12 | | X | | | |
| 3-13 | | | X | | |
| 3-14 | | | | X | |
| 3-15 | | | | | X |
| 3-16 | X | | | | |
| 3-17 | | X | | | |
| 3-18 | | | X | | |
| 3-19 | | | | X | |
| 3-20 | | | | | X |
| 3-21 | X | | | | |
| 3-22 | | X | | | |
| 3-23 | | | X | | |
| 3-24 | | | | X | |
| 3-25 | | | | | X |
| 3-26 | X | | | | |
| 3-27 | | X | | | |
| 3-28 | | | X | | |
| 3-29 | | | | X | |
| 3-30 | | | | | X |
| 3-31 | X | | | | |
| 3-32 | | X | | | |
| 3-33 | | | X | | |
| 3-34 | | | | X | |
| 3-35 | | | | | X |
| 3-36 | X | | | | |
| 3-37 | | X | | | |
| 3-38 | | | X | | |
| 3-39 | | | | X | |
| 3-40 | | | | | X |
| 3-41 | X | | | | |
| 3-42 | | X | | | |
| 3-43 | | | X | | |

TABLE 3-continued

|   | C1 | C2 | C3 | C4 | C5 |
|---|---|---|---|---|---|
| 3-44 |  |  |  | X |  |
| 3-45 |  |  |  |  | X |
| 3-46 | X |  |  |  |  |
| 3-47 |  | X |  |  |  |
| 3-48 |  |  | X |  |  |
| 3-49 |  |  |  | X |  |
| 3-50 |  |  |  |  | X |
| 3-51 | X |  |  |  |  |
| 3-52 |  | X |  |  |  |
| 3-53 |  |  | X |  |  |
| 3-54 |  |  |  | X |  |
| 3-55 |  |  |  |  | X |
| 3-56 | X |  |  |  |  |
| 3-57 |  | X |  |  |  |
| 3-58 |  |  | X |  |  |
| 3-59 |  |  |  | X |  |
| 3-60 |  |  |  |  | X |
| 3-61 | X |  |  |  |  |
| 3-62 |  | X |  |  |  |
| 3-63 |  |  | X |  |  |
| 3-64 |  |  |  | X |  |
| 3-65 |  |  |  |  | X |
| 3-66 | X |  |  |  |  |
| 3-67 |  | X |  |  |  |
| 3-68 |  |  | X |  |  |
| 3-69 |  |  |  | X |  |
| 3-70 |  |  |  |  | X |
| 3-71 | X |  |  |  |  |
| 3-72 |  | X |  |  |  |
| 3-73 |  |  | X |  |  |
| 3-74 |  |  |  | X |  |
| 3-75 |  |  |  |  | X |
| 3-76 | X |  |  |  |  |
| 3-77 |  | X |  |  |  |
| 3-78 |  |  | X |  |  |
| 3-79 |  |  |  | X |  |
| 3-80 |  |  |  |  | X |
| 3-81 | X |  |  |  |  |
| 3-82 |  | X |  |  |  |
| 3-83 |  |  | X |  |  |
| 3-84 |  |  |  | X |  |
| 3-85 |  |  |  |  | X |
| 3-86 | X |  |  |  |  |
| 3-87 |  | X |  |  |  |
| 3-88 |  |  | X |  |  |
| 3-89 |  |  |  | X |  |
| 3-90 |  |  |  |  | X |
| 3-91 | X |  |  |  |  |
| 3-92 |  | X |  |  |  |
| 3-93 |  |  | X |  |  |
| 3-94 |  |  |  | X |  |
| 3-95 |  |  |  |  | X |
| 3-96 | X |  |  |  |  |
| 3-97 |  | X |  |  |  |
| 3-98 |  |  | X |  |  |
| 3-99 |  |  |  | X |  |
| 3-100 |  |  |  |  | X |
| 3-101 | X |  |  |  |  |
| 3-102 |  | X |  |  |  |
| 3-103 |  |  | X |  |  |
| 3-104 |  |  |  | X |  |
| 3-105 |  |  |  |  | X |
| 3-106 | X |  |  |  |  |
| 3-107 |  | X |  |  |  |
| 3-108 |  |  | X |  |  |
| 3-109 |  |  |  | X |  |
| 3-110 |  |  |  |  | X |
| 3-111 | X |  |  |  |  |
| 3-112 |  | X |  |  |  |
| 3-113 |  |  | X |  |  |
| 3-114 |  |  |  | X |  |
| 3-115 |  |  |  |  | X |
| 3-116 | X |  |  |  |  |
| 3-117 |  | X |  |  |  |
| 3-118 |  |  | X |  |  |
| 3-119 |  |  |  | X |  |
| 3-120 |  |  |  |  | X |
| 3-121 | X |  |  |  |  |
| 3-122 |  | X |  |  |  |
| 3-123 |  |  | X |  |  |

TABLE 3-continued

| | | | | | |
|---|---|---|---|---|---|
| 3-124 | | | | X | |
| 3-125 | | | | | X |
| 3-126 | X | | | | |
| 3-127 | | X | | | |
| 3-128 | | | X | | |
| 3-129 | | | | X | |
| 3-130 | | | | | X |
| 3-131 | X | | | | |
| 3-132 | | X | | | |
| 3-133 | | | X | | |
| 3-134 | | | | X | |
| 3-135 | | | | | X |
| 3-136 | X | | | | |
| 3-137 | | X | | | |
| 3-138 | | | X | | |
| 3-139 | | | | X | |
| 3-140 | | | | | X |
| 3-141 | X | | | | |
| 3-142 | | X | | | |
| 3-143 | | | X | | |
| 3-144 | | | | X | |
| 3-145 | | | | | X |
| 3-146 | X | | | | |
| 3-147 | | X | | | |
| 3-148 | | | X | | |
| 3-149 | | | | X | |
| 3-150 | | | | | X |
| 3-151 | X | | | | |
| 3-152 | | X | | | |
| 3-153 | | | X | | |
| 3-154 | | | | X | |
| 3-155 | | | | | X |
| 3-156 | X | | | | |
| 3-157 | | X | | | |
| 3-158 | | | X | | |
| 3-159 | | | | X | |
| 3-160 | | | | | X |
| 3-161 | X | | | | |
| 3-162 | | X | | | |
| 3-163 | | | X | | |
| 3-164 | | | | X | |
| 3-165 | | | | | X |
| 3-166 | X | | | | |
| 3-167 | | X | | | |
| 3-168 | | | X | | |
| 3-169 | | | | X | |
| 3-170 | | | | | X |
| 3-171 | X | | | | |
| 3-172 | | X | | | |
| 3-173 | | | X | | |
| 3-174 | | | | X | |
| 3-175 | | | | | X |
| 3-176 | X | | | | |
| 3-177 | | X | | | |
| 3-178 | | | X | | |
| 3-179 | | | | X | |
| 3-180 | | | | | X |
| 3-181 | X | | | | |
| 3-182 | | X | | | |
| 3-183 | | | X | | |
| 3-184 | | | | X | |
| 3-185 | | | | | X |
| 3-186 | X | | | | |
| 3-187 | | X | | | |
| 3-188 | | | X | | |
| 3-189 | | | | X | |
| 3-190 | | | | | X |
| 3-191 | X | | | | |
| 3-192 | | X | | | |
| 3-193 | | | X | | |
| 3-194 | | | | X | |
| 3-195 | | | | | X |
| 3-196 | X | | | | |
| 3-197 | | X | | | |
| 3-198 | | | X | | |
| 3-199 | | | | X | |
| 3-200 | | | | | X |
| 3-201 | X | | | | |
| 3-202 | | X | | | |
| 3-203 | | | X | | |

TABLE 3-continued

| | | | | | |
|---|---|---|---|---|---|
| 3-204 | | | | X | |
| 3-205 | | | | | X |
| 3-206 | X | | | | |
| 3-207 | | X | | | |
| 3-208 | | | X | | |
| 3-209 | | | | X | |
| 3-210 | | | | | X |
| 3-211 | X | | | | |
| 3-212 | | X | | | |
| 3-213 | | | X | | |
| 3-214 | | | | X | |
| 3-215 | | | | | X |
| 3-216 | X | | | | |
| 3-217 | | X | | | |
| 3-218 | | | X | | |
| 3-219 | | | | X | |
| 3-220 | | | | | X |
| 3-221 | X | | | | |
| 3-222 | | X | | | |
| 3-223 | | | X | | |
| 3-224 | | | | X | |
| 3-225 | | | | | X |
| 3-226 | X | | | | |
| 3-227 | | X | | | |
| 3-228 | | | X | | |
| 3-229 | | | | X | |
| 3-230 | | | | | X |
| 3-231 | X | | | | |
| 3-232 | | X | | | |
| 3-233 | | | X | | |
| 3-234 | | | | X | |
| 3-235 | | | | | X |
| 3-236 | X | | | | |
| 3-237 | | X | | | |
| 3-238 | | | X | | |
| 3-239 | | | | X | |
| 3-240 | | | | | X |
| 3-241 | X | | | | |
| 3-242 | | X | | | |
| 3-243 | | | X | | |
| 3-244 | | | | X | |
| 3-245 | | | | | X |
| 3-246 | X | | | | |
| 3-247 | | X | | | |
| 3-248 | | | X | | |
| 3-249 | | | | X | |
| 3-250 | | | | | X |
| 3-251 | X | | | | |
| 3-252 | | X | | | |
| 3-253 | | | X | | |
| 3-254 | | | | X | |
| 3-255 | | | | | X |
| 3-256 | X | | | | |
| 3-257 | | X | | | |
| 3-258 | | | X | | |
| 3-259 | | | | X | |
| 3-260 | | | | | X |
| 3-261 | X | | | | |
| 3-262 | | X | | | |
| 3-263 | | | X | | |
| 3-264 | | | | X | |
| 3-265 | | | | | X |
| 3-266 | X | | | | |
| 3-267 | | X | | | |
| 3-268 | | | X | | |
| 3-269 | | | | X | |
| 3-270 | | | | | X |

TABLE 3-continued
Formula III-A
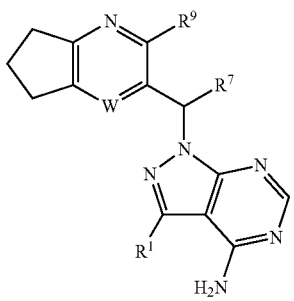
| No | 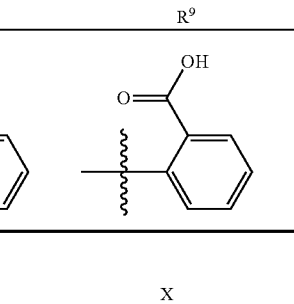 | 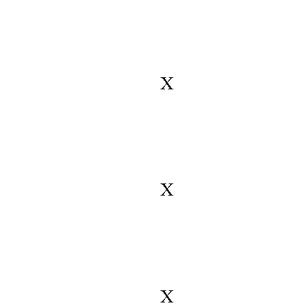 |  | 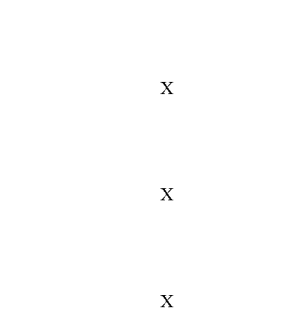 | |
|---|---|---|---|---|---|
| 3-271 | X | | | | |
| 3-272 | | X | | | |
| 3-273 | | | X | | |
| 3-274 | | | | X | |
| 3-275 | | | | | X |
| 3-276 | X | | | | |
| 3-277 | | X | | | |
| 3-278 | | | X | | |
| 3-279 | | | | X | |
| 3-280 | | | | | X |
| 3-281 | X | | | | |
| 3-282 | | X | | | |
| 3-283 | | | X | | |
| 3-284 | | | | X | |
| 3-285 | | | | | X |
| 3-286 | X | | | | |
| 3-287 | | X | | | |
| 3-288 | | | X | | |
| 3-289 | | | | X | |
| 3-290 | | | | | X |
| 3-291 | X | | | | |
| 3-292 | | X | | | |
| 3-293 | | | X | | |
| 3-294 | | | | X | |
| 3-295 | | | | | X |
| 3-296 | X | | | | |
| 3-297 | | X | | | |
| 3-298 | | | X | | |
| 3-299 | | | | X | |
| 3-300 | | | | | X |
| 3-301 | X | | | | |
| 3-302 | | X | | | |
| 3-303 | | | X | | |
| 3-304 | | | | X | |
| 3-305 | | | | | X |
| 3-306 | X | | | | |
| 3-307 | | X | | | |
| 3-308 | | | X | | |
| 3-309 | | | | X | |
| 3-310 | | | | | X |
| 3-311 | X | | | | |
| 3-312 | | X | | | |
| 3-313 | | | X | | |
| 3-314 | | | | X | |
| 3-315 | | | | | X |
| 3-316 | X | | | | |
| 3-317 | | X | | | |
| 3-318 | | | X | | |
| 3-319 | | | | X | |
| 3-320 | | | | | X |
| 3-321 | X | | | | |
| 3-322 | | X | | | |
| 3-323 | | | X | | |

TABLE 3-continued

| | | | | | |
|---|---|---|---|---|---|
| 3-324 | | | | X | |
| 3-325 | | | | | X |
| 3-326 | X | | | | |
| 3-327 | | X | | | |
| 3-328 | | | X | | |
| 3-329 | | | | X | |
| 3-330 | | | | | X |
| 3-331 | X | | | | |
| 3-332 | | X | | | |
| 3-333 | | | X | | |
| 3-334 | | | | X | |
| 3-335 | | | | | X |
| 3-336 | X | | | | |
| 3-337 | | X | | | |
| 3-338 | | | X | | |
| 3-339 | | | | X | |
| 3-340 | | | | | X |
| 3-341 | X | | | | |
| 3-342 | | X | | | |
| 3-343 | | | X | | |
| 3-344 | | | | X | |
| 3-345 | | | | | X |
| 3-346 | X | | | | |
| 3-347 | | X | | | |
| 3-348 | | | X | | |
| 3-349 | | | | X | |
| 3-350 | | | | | X |
| 3-351 | X | | | | |
| 3-352 | | X | | | |
| 3-353 | | | X | | |
| 3-354 | | | | X | |
| 3-355 | | | | | X |
| 3-356 | X | | | | |
| 3-357 | | X | | | |
| 3-358 | | | X | | |
| 3-359 | | | | X | |
| 3-360 | | | | | X |
| 3-361 | X | | | | |
| 3-362 | | X | | | |
| 3-363 | | | X | | |
| 3-364 | | | | X | |
| 3-365 | | | | | X |
| 3-366 | X | | | | |
| 3-367 | | X | | | |
| 3-368 | | | X | | |
| 3-369 | | | | X | |
| 3-370 | | | | | X |
| 3-371 | X | | | | |
| 3-372 | | X | | | |
| 3-373 | | | X | | |
| 3-374 | | | | X | |
| 3-375 | | | | | X |
| 3-376 | X | | | | |
| 3-377 | | X | | | |
| 3-378 | | | X | | |
| 3-379 | | | | X | |
| 3-380 | | | | | X |
| 3-381 | X | | | | |
| 3-382 | | X | | | |
| 3-383 | | | X | | |
| 3-384 | | | | X | |
| 3-385 | | | | | X |
| 3-386 | X | | | | |
| 3-387 | | X | | | |
| 3-388 | | | X | | |
| 3-389 | | | | X | |
| 3-390 | | | | | X |
| 3-391 | X | | | | |
| 3-392 | | X | | | |
| 3-393 | | | X | | |
| 3-394 | | | | X | |
| 3-395 | | | | | X |
| 3-396 | X | | | | |
| 3-397 | | X | | | |
| 3-398 | | | X | | |
| 3-399 | | | | X | |
| 3-400 | | | | | X |
| 3-401 | X | | | | |
| 3-402 | | X | | | |
| 3-403 | | | X | | |

TABLE 3-continued

| | | | | | |
|---|---|---|---|---|---|
| 3-404 | | | | X | |
| 3-405 | | | | | X |
| 3-406 | X | | | | |
| 3-407 | | X | | | |
| 3-408 | | | X | | |
| 3-409 | | | | X | |
| 3-410 | | | | | X |
| 3-411 | X | | | | |
| 3-412 | | X | | | |
| 3-413 | | | X | | |
| 3-414 | | | | X | |
| 3-415 | | | | | X |
| 3-416 | X | | | | |
| 3-417 | | X | | | |
| 3-418 | | | X | | |
| 3-419 | | | | X | |
| 3-420 | | | | | X |
| 3-421 | X | | | | |
| 3-422 | | X | | | |
| 3-423 | | | X | | |
| 3-424 | | | | X | |
| 3-425 | | | | | X |
| 3-426 | X | | | | |
| 3-427 | | X | | | |
| 3-428 | | | X | | |
| 3-429 | | | | X | |
| 3-430 | | | | | X |
| 3-431 | X | | | | |
| 3-432 | | X | | | |
| 3-433 | | | X | | |
| 3-434 | | | | X | |
| 3-435 | | | | | X |
| 3-436 | X | | | | |
| 3-437 | | X | | | |
| 3-438 | | | X | | |
| 3-439 | | | | X | |
| 3-440 | | | | | X |
| 3-441 | X | | | | |
| 3-442 | | X | | | |
| 3-443 | | | X | | |
| 3-444 | | | | X | |
| 3-445 | | | | | X |
| 3-446 | X | | | | |
| 3-447 | | X | | | |
| 3-448 | | | X | | |
| 3-449 | | | | X | |
| 3-450 | | | | | X |
| 3-451 | X | | | | |
| 3-452 | | X | | | |
| 3-453 | | | X | | |
| 3-454 | | | | X | |
| 3-455 | | | | | X |
| 3-456 | X | | | | |
| 3-457 | | X | | | |
| 3-358 | | | X | | |
| 3-459 | | | | X | |
| 3-460 | | | | | X |
| 3-461 | X | | | | |
| 3-462 | | X | | | |
| 3-463 | | | X | | |
| 3-464 | | | | X | |
| 3-465 | | | | | X |
| 3-466 | X | | | | |
| 3-467 | | X | | | |
| 3-468 | | | X | | |
| 3-469 | | | | X | |
| 3-470 | | | | | X |
| 3-471 | X | | | | |
| 3-472 | | X | | | |
| 3-473 | | | X | | |
| 3-474 | | | | X | |
| 3-475 | | | | | X |
| 3-476 | X | | | | |
| 3-477 | | X | | | |
| 3-478 | | | X | | |
| 3-479 | | | | X | |
| 3-480 | | | | | X |
| 3-481 | X | | | | |
| 3-482 | | X | | | |
| 3-483 | | | X | | |

TABLE 3-continued

| | | | | | |
|---|---|---|---|---|---|
| 3-484 | | | | X | |
| 3-485 | | | | | X |
| 3-486 | X | | | | |
| 3-487 | | X | | | |
| 3-488 | | | X | | |
| 3-489 | | | | X | |
| 3-490 | | | | | X |
| 3-491 | X | | | | |
| 3-492 | | X | | | |
| 3-493 | | | X | | |
| 3-494 | | | | X | |
| 3-495 | | | | | X |
| 3-496 | X | | | | |
| 3-497 | | X | | | |
| 3-498 | | | X | | |
| 3-499 | | | | X | |
| 3-500 | | | | | X |
| 3-501 | X | | | | |
| 3-502 | | X | | | |
| 3-503 | | | X | | |
| 3-504 | | | | X | |
| 3-505 | | | | | X |
| 3-506 | X | | | | |
| 3-507 | | X | | | |
| 3-508 | | | X | | |
| 3-509 | | | | X | |
| 3-510 | | | | | X |
| 3-511 | X | | | | |
| 3-512 | | X | | | |
| 3-513 | | | X | | |
| 3-514 | | | | X | |
| 3-515 | | | | | X |
| 3-516 | X | | | | |
| 3-517 | | X | | | |
| 3-518 | | | X | | |
| 3-519 | | | | X | |
| 3-520 | | | | | X |
| 3-521 | X | | | | |
| 3-522 | | X | | | |
| 3-523 | | | X | | |
| 3-524 | | | | X | |
| 3-525 | | | | | X |
| 3-526 | X | | | | |
| 3-527 | | X | | | |
| 3-528 | | | X | | |
| 3-529 | | | | X | |
| 3-530 | | | | | X |
| 3-531 | X | | | | |
| 3-532 | | X | | | |
| 3-533 | | | X | | |
| 3-534 | | | | X | |
| 3-535 | | | | | X |
| 3-536 | X | | | | |
| 3-537 | | X | | | |
| 3-538 | | | X | | |
| 3-539 | | | | X | |
| 3-540 | | | | | X |

Exemplary compounds of the invention of Formula III-A, wherein X represents a halo group (Cl, Br, I or F).

TABLE 4

Formula IV-A

| No | R1 (F-phenol-OH) | R1 (HO-alkyne) | R1 (I) | W: C | W: N | R7: H | R7: Me | R7: Et |
|---|---|---|---|---|---|---|---|---|
| 4-1 | X | | | X | | X | | |
| 4-2 | X | | | X | | X | | |
| 4-3 | X | | | X | | X | | |
| 4-4 | X | | | X | | X | | |
| 4-5 | X | | | X | | X | | |
| 4-6 | X | | | X | | | X | |
| 4-7 | X | | | X | | | X | |
| 4-8 | X | | | X | | | X | |
| 4-9 | X | | | X | | | X | |
| 4-10 | X | | | X | | | X | |
| 4-11 | X | | | X | | | | X |
| 4-12 | X | | | X | | | | X |
| 4-13 | X | | | X | | | | X |
| 4-14 | X | | | X | | | | X |
| 4-15 | X | | | X | | | | X |
| 4-16 | X | | | | X | X | | |
| 4-17 | X | | | | X | X | | |
| 4-18 | X | | | | X | X | | |
| 4-19 | X | | | | X | X | | |
| 4-20 | X | | | | X | X | | |
| 4-21 | X | | | | X | | X | |
| 4-22 | X | | | | X | | X | |
| 4-23 | X | | | | X | | X | |
| 4-24 | X | | | | X | | X | |
| 4-25 | X | | | | X | | X | |
| 4-26 | X | | | | X | | | X |
| 4-27 | X | | | | X | | | X |
| 4-28 | X | | | | X | | | X |
| 4-29 | X | | | | X | | | X |
| 4-30 | X | | | | X | | | X |
| 4-31 | X | | | X | | X | | |
| 4-32 | X | | | X | | X | | |
| 4-33 | X | | | X | | X | | |
| 4-34 | X | | | X | | X | | |
| 4-35 | X | | | X | | X | | |
| 4-36 | X | | | X | | | X | |
| 4-37 | X | | | X | | | X | |
| 4-38 | X | | | X | | | X | |
| 4-39 | X | | | X | | | X | |
| 4-40 | X | | | X | | | X | |
| 4-41 | X | | | X | | | | X |
| 4-42 | X | | | X | | | | X |
| 4-43 | X | | | X | | | | X |
| 4-44 | X | | | X | | | | X |
| 4-45 | X | | | X | | | | X |
| 4-46 | X | | | | X | X | | |
| 4-47 | X | | | | X | X | | |
| 4-48 | X | | | | X | X | | |
| 4-49 | X | | | | X | X | | |
| 4-50 | X | | | | X | X | | |
| 4-51 | X | | | | X | | X | |
| 4-52 | X | | | | X | | X | |
| 4-53 | X | | | | X | | X | |

TABLE 4-continued

| | | | | | | |
|---|---|---|---|---|---|---|
| 4-54 | X | | | X | X | |
| 4-55 | X | | | X | X | |
| 4-56 | X | | | X | | X |
| 4-57 | X | | | X | | X |
| 4-58 | X | | | X | | X |
| 4-59 | X | | | X | | X |
| 4-60 | X | | | X | | X |
| 4-61 | X | | X | | X | |
| 4-62 | X | | X | | X | |
| 4-63 | X | | X | | X | |
| 4-64 | X | | X | | X | |
| 4-65 | X | | X | | X | |
| 4-66 | X | | X | | X | |
| 4-67 | X | | X | | X | |
| 4-68 | X | | X | | X | |
| 4-69 | X | | X | | X | |
| 4-70 | X | | X | | X | |
| 4-71 | X | | X | | | X |
| 4-72 | X | | X | | | X |
| 4-73 | X | | X | | | X |
| 4-74 | X | | X | | | X |
| 4-75 | X | | X | | | X |
| 4-76 | X | | | X | X | |
| 4-77 | X | | | X | X | |
| 4-78 | X | | | X | X | |
| 4-79 | X | | | X | X | |
| 4-80 | X | | | X | X | |
| 4-81 | X | | | X | X | |
| 4-82 | X | | | X | X | |
| 4-83 | X | | | X | X | |
| 4-84 | X | | | X | X | |
| 4-85 | X | | | X | X | |
| 4-86 | X | | | X | | X |
| 4-87 | X | | | X | | X |
| 4-88 | X | | | X | | X |
| 4-89 | X | | | X | | X |
| 4-90 | X | | | X | | X |
| 4-91 | | X | X | | X | |
| 4-92 | | X | X | | X | |
| 4-93 | | X | X | | X | |
| 4-94 | | X | X | | X | |
| 4-95 | | X | X | | X | |
| 4-96 | | X | X | | X | |
| 4-97 | | X | X | | X | |
| 4-98 | | X | X | | X | |
| 4-99 | | X | X | | X | |
| 4-100 | | X | X | | X | |
| 4-101 | | X | X | | | X |
| 4-102 | | X | X | | | X |
| 4-103 | | X | X | | | X |
| 4-104 | | X | X | | | X |
| 4-105 | | X | X | | | X |
| 4-106 | | X | | X | X | |
| 4-107 | | X | | X | X | |
| 4-108 | | X | | X | X | |
| 4-109 | | X | | X | X | |
| 4-110 | | X | | X | X | |
| 4-111 | | X | | X | X | |
| 4-112 | | X | | X | X | |
| 4-113 | | X | | X | X | |
| 4-114 | | X | | X | X | |
| 4-115 | | X | | X | X | |
| 4-116 | | X | | X | | X |
| 4-117 | | X | | X | | X |
| 4-118 | | X | | X | | X |
| 4-119 | | X | | X | | X |
| 4-120 | | X | | X | | X |
| 4-121 | | X | X | | X | |
| 4-122 | | X | X | | X | |
| 4-123 | | X | X | | X | |
| 4-124 | | X | X | | X | |
| 4-125 | | X | X | | X | |
| 4-126 | | X | X | | X | |
| 4-127 | | X | X | | X | |
| 4-128 | | X | X | | X | |
| 4-129 | | X | X | | X | |
| 4-130 | | X | X | | X | |
| 4-131 | | X | X | | | X |
| 4-132 | | X | X | | | X |
| 4-133 | | X | X | | | X |

TABLE 4-continued

| | | | | | |
|---|---|---|---|---|---|
| 4-134 | X | | X | | X |
| 4-135 | X | | X | | X |
| 4-136 | X | | | X | X |
| 4-137 | X | | | X | X |
| 4-138 | X | | | X | X |
| 4-139 | X | | | X | X |
| 4-140 | X | | | X | X |
| 4-141 | X | | | X | X |
| 4-142 | X | | | X | X |
| 4-143 | X | | | X | X |
| 4-144 | X | | | X | X |
| 4-145 | X | | | X | X |
| 4-146 | X | | | X | X |
| 4-147 | X | | | X | X |
| 4-148 | X | | | X | X |
| 4-149 | X | | | X | X |
| 4-150 | X | | | X | X |
| 4-151 | X | | X | | X |
| 4-152 | X | | X | | X |
| 4-153 | X | | X | | X |
| 4-154 | X | | X | | X |
| 4-155 | X | | X | | X |
| 4-156 | X | | X | X | |
| 4-157 | X | | X | X | |
| 4-158 | X | | X | X | |
| 4-159 | X | | X | X | |
| 4-160 | X | | X | X | |
| 4-161 | X | | X | | X |
| 4-162 | X | | X | | X |
| 4-163 | X | | X | | X |
| 4-164 | X | | X | | X |
| 4-165 | X | | X | | X |
| 4-166 | X | | | X | X |
| 4-167 | X | | | X | X |
| 4-168 | X | | | X | X |
| 4-169 | X | | | X | X |
| 4-170 | X | | | X | X |
| 4-171 | X | | | X | X |
| 4-172 | X | | | X | X |
| 4-173 | X | | | X | X |
| 4-174 | X | | | X | X |
| 4-175 | X | | | X | X |
| 4-176 | X | | | X | X |
| 4-177 | X | | | X | X |
| 4-178 | X | | | X | X |
| 4-179 | X | | | X | X |
| 4-180 | X | | | X | X |
| 4-181 | | X | X | X | |
| 4-182 | | X | X | X | |
| 4-183 | | X | X | X | |
| 4-184 | | X | X | X | |
| 4-185 | | X | X | X | |
| 4-186 | | X | X | X | |
| 4-187 | | X | X | X | |
| 4-188 | | X | X | X | |
| 4-189 | | X | X | X | |
| 4-190 | | X | X | X | |
| 4-191 | | X | X | | X |
| 4-192 | | X | X | | X |
| 4-193 | | X | X | | X |
| 4-194 | | X | X | | X |
| 4-195 | | X | X | | X |
| 4-196 | | X | | X | X |
| 4-197 | | X | | X | X |
| 4-198 | | X | | X | X |
| 4-199 | | X | | X | X |
| 4-200 | | X | | X | X |
| 4-201 | | X | | X | X |
| 4-202 | | X | | X | X |
| 4-203 | | X | | X | X |
| 4-204 | | X | | X | X |
| 4-205 | | X | | X | X |
| 4-206 | | X | | X | X |
| 4-207 | | X | | X | X |
| 4-208 | | X | | X | X |
| 4-209 | | X | | X | X |
| 4-210 | | X | | X | X |
| 4-211 | | X | X | X | |
| 4-212 | | X | X | X | |
| 4-213 | | X | X | X | |

TABLE 4-continued

| No. | | | | | |
|---|---|---|---|---|---|
| 4-214 | | X | X | X | |
| 4-215 | | X | X | X | |
| 4-216 | | X | X | | X |
| 4-217 | | X | X | | X |
| 4-218 | | X | X | | X |
| 4-219 | | X | X | | X |
| 4-220 | | X | X | | X |
| 4-221 | | X | X | | X |
| 4-222 | | X | X | | X |
| 4-223 | | X | X | | X |
| 4-224 | | X | X | | X |
| 4-225 | | X | X | | X |
| 4-226 | | X | | X | X |
| 4-227 | | X | | X | X |
| 4-228 | | X | | X | X |
| 4-229 | | X | | X | X |
| 4-230 | | X | | X | X |
| 4-231 | | X | | X | X |
| 4-232 | | X | | X | X |
| 4-233 | | X | | X | X |
| 4-234 | | X | | X | X |
| 4-235 | | X | | X | X |
| 4-236 | | X | | X | X |
| 4-237 | | X | | X | X |
| 4-238 | | X | | X | X |
| 4-239 | | X | | X | X |
| 4-240 | | X | | X | X |
| 4-241 | | X | X | X | |
| 4-242 | | X | X | X | |
| 4-243 | | X | X | X | |
| 4-244 | | X | X | X | |
| 4-245 | | X | X | X | |
| 4-246 | | X | X | | X |
| 4-247 | | X | X | | X |
| 4-248 | | X | X | | X |
| 4-249 | | X | X | | X |
| 4-250 | | X | X | | X |
| 4-251 | | X | X | | X |
| 4-252 | | X | X | | X |
| 4-253 | | X | X | | X |
| 4-254 | | X | X | | X |
| 4-255 | | X | X | | X |
| 4-256 | | X | | X | X |
| 4-257 | | X | | X | X |
| 4-258 | | X | | X | X |
| 4-259 | | X | | X | X |
| 4-260 | | X | | X | X |
| 4-261 | | X | | X | X |
| 4-262 | | X | | X | X |
| 4-263 | | X | | X | X |
| 4-264 | | X | | X | X |
| 4-265 | | X | | X | X |
| 4-266 | | X | | X | X |
| 4-267 | | X | | X | X |
| 4-268 | | X | | X | X |
| 4-269 | | X | | X | X |
| 4-270 | | X | | X | X |
| 4-271 | X | | | X | X |
| 4-272 | X | | | X | X |
| 4-273 | X | | | X | X |
| 4-274 | X | | | X | X |
| 4-275 | X | | | X | X |
| 4-276 | X | | | X | X |
| 4-277 | X | | | X | X |
| 4-278 | X | | | X | X |
| 4-279 | X | | | X | X |
| 4-280 | X | | | X | X |
| 4-281 | X | | | X | X |
| 4-282 | X | | | X | X |
| 4-283 | X | | | X | X |
| 4-284 | X | | | X | X |
| 4-285 | X | | | X | X |
| 4-286 | X | | | X | X |
| 4-287 | X | | | X | X |
| 4-288 | X | | | X | X |
| 4-289 | X | | | X | X |
| 4-290 | X | | | X | X |
| 4-291 | X | | | X | X |
| 4-292 | X | | | X | X |
| 4-293 | X | | | X | X |

TABLE 4-continued

| No. | | | | | | |
|---|---|---|---|---|---|---|
| 4-294 | X | | | X | X | |
| 4-295 | X | | | X | X | |
| 4-296 | X | | | X | | X |
| 4-297 | X | | | X | | X |
| 4-298 | X | | | X | | X |
| 4-299 | X | | | X | | X |
| 4-300 | X | | | X | | X |
| 4-301 | X | | X | | X | |
| 4-302 | X | | X | | X | |
| 4-303 | X | | X | | X | |
| 4-304 | X | | X | | X | |
| 4-305 | X | | X | | X | |
| 4-306 | X | | X | | | X |
| 4-307 | X | | X | | | X |
| 4-308 | X | | X | | | X |
| 4-309 | X | | X | | | X |
| 4-310 | X | | X | | | X |
| 4-311 | X | | X | | | X |
| 4-312 | X | | X | | | X |
| 4-313 | X | | X | | | X |
| 4-314 | X | | X | | | X |
| 4-315 | X | | X | | | X |
| 4-316 | X | | | X | X | |
| 4-317 | X | | | X | X | |
| 4-318 | X | | | X | X | |
| 4-319 | X | | | X | X | |
| 4-320 | X | | | X | X | |
| 4-321 | X | | | X | | X |
| 4-322 | X | | | X | | X |
| 4-323 | X | | | X | | X |
| 4-324 | X | | | X | | X |
| 4-325 | X | | | X | | X |
| 4-326 | X | | | X | | X |
| 4-327 | X | | | X | | X |
| 4-328 | X | | | X | | X |
| 4-329 | X | | | X | | X |
| 4-330 | X | | | X | | X |
| 4-331 | X | | X | | X | |
| 4-332 | X | | X | | X | |
| 4-333 | X | | X | | X | |
| 4-334 | X | | X | | X | |
| 4-335 | X | | X | | X | |
| 4-336 | X | | X | | | X |
| 4-337 | X | | X | | | X |
| 4-338 | X | | X | | | X |
| 4-339 | X | | X | | | X |
| 4-340 | X | | X | | | X |
| 4-341 | X | | X | | | X |
| 4-342 | X | | X | | | X |
| 4-343 | X | | X | | | X |
| 4-344 | X | | X | | | X |
| 4-345 | X | | X | | | X |
| 4-346 | X | | | X | X | |
| 4-347 | X | | | X | X | |
| 4-348 | X | | | X | X | |
| 4-349 | X | | | X | X | |
| 4-350 | X | | | X | X | |
| 4-351 | X | | | X | | X |
| 4-352 | X | | | X | | X |
| 4-353 | X | | | X | | X |
| 4-354 | X | | | X | | X |
| 4-355 | X | | | X | | X |
| 4-356 | X | | | X | | X |
| 4-357 | X | | | X | | X |
| 4-358 | X | | | X | | X |
| 4-359 | X | | | X | | X |
| 4-360 | X | | | X | | X |
| 4-361 | | X | | X | | X |
| 4-362 | | X | | X | | X |
| 4-363 | | X | | X | | X |
| 4-364 | | X | | X | | X |
| 4-365 | | X | | X | | X |
| 4-366 | | X | | X | | X |
| 4-367 | | X | | X | | X |
| 4-368 | | X | | X | | X |
| 4-369 | | X | | X | | X |
| 4-370 | | X | | X | | X |
| 4-371 | | X | | X | | X |
| 4-372 | | X | | X | | X |
| 4-373 | | X | | X | | X |

TABLE 4-continued

| | C1 | C2 | C3 | C4 | C5 |
|---|---|---|---|---|---|
| 4-374 | X | | X | | X |
| 4-375 | X | | X | | X |
| 4-376 | X | | X | X | |
| 4-377 | X | | X | X | |
| 4-378 | X | | X | X | |
| 4-379 | X | | X | X | |
| 4-380 | X | | X | X | |
| 4-381 | X | | | X | X |
| 4-382 | X | | | X | X |
| 4-383 | X | | | X | X |
| 4-384 | X | | | X | X |
| 4-385 | X | | | X | X |
| 4-386 | X | | X | | X |
| 4-387 | X | | X | | X |
| 4-388 | X | | X | | X |
| 4-389 | X | | X | | X |
| 4-390 | X | | X | | X |
| 4-391 | X | X | | X | |
| 4-392 | X | X | | X | |
| 4-393 | X | X | | X | |
| 4-394 | X | X | | X | |
| 4-395 | X | X | | X | |
| 4-396 | X | X | | | X |
| 4-397 | X | X | | | X |
| 4-398 | X | X | | | X |
| 4-399 | X | X | | | X |
| 4-400 | X | X | | | X |
| 4-401 | X | X | | | X |
| 4-402 | X | X | | | X |
| 4-403 | X | X | | | X |
| 4-404 | X | X | | | X |
| 4-405 | X | X | | | X |
| 4-406 | X | | | X | X |
| 4-407 | X | | | X | X |
| 4-408 | X | | | X | X |
| 4-409 | X | | | X | X |
| 4-410 | X | | | X | X |
| 4-411 | X | | | X | X |
| 4-412 | X | | | X | X |
| 4-413 | X | | | X | X |
| 4-414 | X | | | X | X |
| 4-415 | X | | | X | X |
| 4-416 | X | | | X | X |
| 4-417 | X | | | X | X |
| 4-418 | X | | | X | X |
| 4-419 | X | | | X | X |
| 4-420 | X | | | X | X |
| 4-421 | X | X | | X | |
| 4-422 | X | X | | X | |
| 4-423 | X | X | | X | |
| 4-424 | X | X | | X | |
| 4-425 | X | X | | X | |
| 4-426 | X | X | | | X |
| 4-427 | X | X | | | X |
| 4-428 | X | X | | | X |
| 4-429 | X | X | | | X |
| 4-430 | X | X | | | X |
| 4-431 | X | X | | | X |
| 4-432 | X | X | | | X |
| 4-433 | X | X | | | X |
| 4-434 | X | X | | | X |
| 4-435 | X | X | | | X |
| 4-436 | X | | | X | X |
| 4-437 | X | | | X | X |
| 4-438 | X | | | X | X |
| 4-439 | X | | | X | X |
| 4-440 | X | | | X | X |
| 4-441 | X | | | X | X |
| 4-442 | X | | | X | X |
| 4-443 | X | | | X | X |
| 4-444 | X | | | X | X |
| 4-445 | X | | | X | X |
| 4-446 | X | | | X | X |
| 4-447 | X | | | X | X |
| 4-448 | X | | | X | X |
| 4-449 | X | | | X | X |
| 4-450 | X | | | X | X |
| 4-451 | | X | X | | X |
| 4-452 | | X | X | | X |
| 4-453 | | X | X | | X |

TABLE 4-continued

| | | | | |
|---|---|---|---|---|
| 4-454 | X | X | X | |
| 4-455 | X | X | X | |
| 4-456 | X | X | | X |
| 4-457 | X | X | | X |
| 4-458 | X | X | | X |
| 4-459 | X | X | | X |
| 4-460 | X | X | | X |
| 4-461 | X | X | | | X |
| 4-462 | X | X | | | X |
| 4-463 | X | X | | | X |
| 4-464 | X | X | | | X |
| 4-465 | X | X | | | X |
| 4-466 | X | | X | X | |
| 4-467 | X | | X | X | |
| 4-468 | X | | X | X | |
| 4-469 | X | | X | X | |
| 4-470 | X | | X | X | |
| 4-471 | X | | X | | X |
| 4-472 | X | | X | | X |
| 4-473 | X | | X | | X |
| 4-474 | X | | X | | X |
| 4-475 | X | | X | | X |
| 4-476 | X | | X | | | X |
| 4-477 | X | | X | | | X |
| 4-478 | X | | X | | | X |
| 4-479 | X | | X | | | X |
| 4-480 | X | | X | | | X |
| 4-481 | X | X | | X | |
| 4-482 | X | X | | X | |
| 4-483 | X | X | | X | |
| 4-484 | X | X | | X | |
| 4-485 | X | X | | X | |
| 4-486 | X | X | | | X |
| 4-487 | X | X | | | X |
| 4-488 | X | X | | | X |
| 4-489 | X | X | | | X |
| 4-490 | X | X | | | X |
| 4-491 | X | X | | | | X |
| 4-492 | X | X | | | | X |
| 4-493 | X | X | | | | X |
| 4-494 | X | X | | | | X |
| 4-495 | X | X | | | | X |
| 4-496 | X | | X | X | |
| 4-497 | X | | X | X | |
| 4-498 | X | | X | X | |
| 4-499 | X | | X | X | |
| 4-500 | X | | X | X | |
| 4-501 | X | | X | | X |
| 4-502 | X | | X | | X |
| 4-503 | X | | X | | X |
| 4-504 | X | | X | | X |
| 4-505 | X | | X | | X |
| 4-506 | X | | X | | | X |
| 4-507 | X | | X | | | X |
| 4-508 | X | | X | | | X |
| 4-509 | X | | X | | | X |
| 4-510 | X | | X | | | X |
| 4-511 | X | X | | X | |
| 4-512 | X | X | | X | |
| 4-513 | X | X | | X | |
| 4-514 | X | X | | X | |
| 4-515 | X | X | | X | |
| 4-516 | X | X | | | X |
| 4-517 | X | X | | | X |
| 4-518 | X | X | | | X |
| 4-519 | X | X | | | X |
| 4-520 | X | X | | | X |
| 4-521 | X | X | | | | X |
| 4-522 | X | X | | | | X |
| 4-523 | X | X | | | | X |
| 4-524 | X | X | | | | X |
| 4-525 | X | X | | | | X |
| 4-526 | X | | X | X | |
| 4-527 | X | | X | X | |
| 4-528 | X | | X | X | |
| 4-529 | X | | X | X | |
| 4-530 | X | | X | X | |
| 4-531 | X | | X | | X |
| 4-532 | X | | X | | X |
| 4-533 | X | | X | | X |

TABLE 4-continued
| No | | | | | |
|------|---|---|---|---|---|
| 4-534 | | X | X | X | |
| 4-535 | | X | X | X | |
| 4-536 | | X | X | | X |
| 4-537 | | X | X | | X |
| 4-538 | | X | X | | X |
| 4-539 | | X | X | | X |
| 4-540 | | X | X | | X |
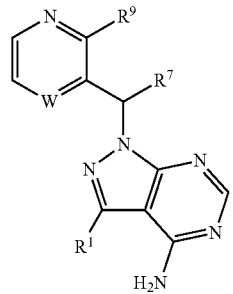
Formula IV-A
| No | R⁹ pyrrolidinyl | 2-isopropylphenyl | 4-methylpiperazinyl | isopropylamino | 2-methoxyphenyl |
|------|---|---|---|---|---|
| 4-1 | X | | | | |
| 4-2 | | X | | | |
| 4-3 | | | X | | |
| 4-4 | | | | X | |
| 4-5 | | | | | X |
| 4-6 | X | | | | |
| 4-7 | | X | | | |
| 4-8 | | | X | | |
| 4-9 | | | | X | |
| 4-10 | | | | | X |
| 4-11 | X | | | | |
| 4-12 | | X | | | |
| 4-13 | | | X | | |
| 4-14 | | | | X | |
| 4-15 | | | | | X |
| 4-16 | X | | | | |
| 4-17 | | X | | | |
| 4-18 | | | X | | |
| 4-19 | | | | X | |
| 4-20 | | | | | X |
| 4-21 | X | | | | |
| 4-22 | | X | | | |
| 4-23 | | | X | | |
| 4-24 | | | | X | |
| 4-25 | | | | | X |
| 4-26 | X | | | | |
| 4-27 | | X | | | |
| 4-28 | | | X | | |
| 4-29 | | | | X | |
| 4-30 | | | | | X |
| 4-31 | X | | | | |
| 4-32 | | X | | | |
| 4-33 | | | X | | |
| 4-34 | | | | X | |
| 4-35 | | | | | X |
| 4-36 | X | | | | |
| 4-37 | | X | | | |
| 4-38 | | | X | | |
| 4-39 | | | | X | |
| 4-40 | | | | | X |
| 4-41 | X | | | | |
| 4-42 | | X | | | |
| 4-43 | | | X | | |
| 4-44 | | | | X | |
| 4-45 | | | | | X |

TABLE 4-continued

| | | | | | |
|---|---|---|---|---|---|
| 4-46 | X | | | | |
| 4-47 | | X | | | |
| 4-48 | | | X | | |
| 4-49 | | | | X | |
| 4-50 | | | | | X |
| 4-51 | X | | | | |
| 4-52 | | X | | | |
| 4-53 | | | X | | |
| 4-54 | | | | X | |
| 4-55 | | | | | X |
| 4-56 | X | | | | |
| 4-57 | | X | | | |
| 4-58 | | | X | | |
| 4-59 | | | | X | |
| 4-60 | | | | | X |
| 4-61 | X | | | | |
| 4-62 | | X | | | |
| 4-63 | | | X | | |
| 4-64 | | | | X | |
| 4-65 | | | | | X |
| 4-66 | X | | | | |
| 4-67 | | X | | | |
| 4-68 | | | X | | |
| 4-69 | | | | X | |
| 4-70 | | | | | X |
| 4-71 | X | | | | |
| 4-72 | | X | | | |
| 4-73 | | | X | | |
| 4-74 | | | | X | |
| 4-75 | | | | | X |
| 4-76 | X | | | | |
| 4-77 | | X | | | |
| 4-78 | | | X | | |
| 4-79 | | | | X | |
| 4-80 | | | | | X |
| 4-81 | X | | | | |
| 4-82 | | X | | | |
| 4-83 | | | X | | |
| 4-84 | | | | X | |
| 4-85 | | | | | X |
| 4-86 | X | | | | |
| 4-87 | | X | | | |
| 4-88 | | | X | | |
| 4-89 | | | | X | |
| 4-90 | | | | | X |
| 4-91 | X | | | | |
| 4-92 | | X | | | |
| 4-93 | | | X | | |
| 4-94 | | | | X | |
| 4-95 | | | | | X |
| 4-96 | X | | | | |
| 4-97 | | X | | | |
| 4-98 | | | X | | |
| 4-99 | | | | X | |
| 4-100 | | | | | X |
| 4-101 | X | | | | |
| 4-102 | | X | | | |
| 4-103 | | | X | | |
| 4-104 | | | | X | |
| 4-105 | | | | | X |
| 4-106 | X | | | | |
| 4-107 | | X | | | |
| 4-108 | | | X | | |
| 4-109 | | | | X | |
| 4-110 | | | | | X |
| 4-111 | X | | | | |
| 4-112 | | X | | | |
| 4-113 | | | X | | |
| 4-114 | | | | X | |
| 4-115 | | | | | X |
| 4-116 | X | | | | |
| 4-117 | | X | | | |
| 4-118 | | | X | | |
| 4-119 | | | | X | |
| 4-120 | | | | | X |
| 4-121 | X | | | | |
| 4-122 | | X | | | |
| 4-123 | | | X | | |
| 4-124 | | | | X | |
| 4-125 | | | | | X |

TABLE 4-continued

| | | | | | |
|---|---|---|---|---|---|
| 4-126 | X | | | | |
| 4-127 | | X | | | |
| 4-128 | | | X | | |
| 4-129 | | | | X | |
| 4-130 | | | | | X |
| 4-131 | X | | | | |
| 4-132 | | X | | | |
| 4-133 | | | X | | |
| 4-134 | | | | X | |
| 4-135 | | | | | X |
| 4-136 | X | | | | |
| 4-137 | | X | | | |
| 4-138 | | | X | | |
| 4-139 | | | | X | |
| 4-140 | | | | | X |
| 4-141 | X | | | | |
| 4-142 | | X | | | |
| 4-143 | | | X | | |
| 4-144 | | | | X | |
| 4-145 | | | | | X |
| 4-146 | X | | | | |
| 4-147 | | X | | | |
| 4-148 | | | X | | |
| 4-149 | | | | X | |
| 4-150 | | | | | X |
| 4-151 | X | | | | |
| 4-152 | | X | | | |
| 4-153 | | | X | | |
| 4-154 | | | | X | |
| 4-155 | | | | | X |
| 4-156 | X | | | | |
| 4-157 | | X | | | |
| 4-158 | | | X | | |
| 4-159 | | | | X | |
| 4-160 | | | | | X |
| 4-161 | X | | | | |
| 4-162 | | X | | | |
| 4-163 | | | X | | |
| 4-164 | | | | X | |
| 4-165 | | | | | X |
| 4-166 | X | | | | |
| 4-167 | | X | | | |
| 4-168 | | | X | | |
| 4-169 | | | | X | |
| 4-170 | | | | | X |
| 4-171 | X | | | | |
| 4-172 | | X | | | |
| 4-173 | | | X | | |
| 4-174 | | | | X | |
| 4-175 | | | | | X |
| 4-176 | X | | | | |
| 4-177 | | X | | | |
| 4-178 | | | X | | |
| 4-179 | | | | X | |
| 4-180 | | | | | X |
| 4-181 | X | | | | |
| 4-182 | | X | | | |
| 4-183 | | | X | | |
| 4-184 | | | | X | |
| 4-185 | | | | | X |
| 4-186 | X | | | | |
| 4-187 | | X | | | |
| 4-188 | | | X | | |
| 4-189 | | | | X | |
| 4-190 | | | | | X |
| 4-191 | X | | | | |
| 4-192 | | X | | | |
| 4-193 | | | X | | |
| 4-194 | | | | X | |
| 4-195 | | | | | X |
| 4-196 | X | | | | |
| 4-197 | | X | | | |
| 4-198 | | | X | | |
| 4-199 | | | | X | |
| 4-200 | | | | | X |
| 4-201 | X | | | | |
| 4-202 | | X | | | |
| 4-203 | | | X | | |
| 4-204 | | | | X | |
| 4-205 | | | | | X |

TABLE 4-continued

| | | | | | |
|---|---|---|---|---|---|
| 4-206 | X | | | | |
| 4-207 | | X | | | |
| 4-208 | | | X | | |
| 4-209 | | | | X | |
| 4-210 | | | | | X |
| 4-211 | X | | | | |
| 4-212 | | X | | | |
| 4-213 | | | X | | |
| 4-214 | | | | X | |
| 4-215 | | | | | X |
| 4-216 | X | | | | |
| 4-217 | | X | | | |
| 4-218 | | | X | | |
| 4-219 | | | | X | |
| 4-220 | | | | | X |
| 4-221 | X | | | | |
| 4-222 | | X | | | |
| 4-223 | | | X | | |
| 4-224 | | | | X | |
| 4-225 | | | | | X |
| 4-226 | X | | | | |
| 4-227 | | X | | | |
| 4-228 | | | X | | |
| 4-229 | | | | X | |
| 4-230 | | | | | X |
| 4-231 | X | | | | |
| 4-232 | | X | | | |
| 4-233 | | | X | | |
| 4-234 | | | | X | |
| 4-235 | | | | | X |
| 4-236 | X | | | | |
| 4-237 | | X | | | |
| 4-238 | | | X | | |
| 4-239 | | | | X | |
| 4-240 | | | | | X |
| 4-241 | X | | | | |
| 4-242 | | X | | | |
| 4-243 | | | X | | |
| 4-244 | | | | X | |
| 4-245 | | | | | X |
| 4-246 | X | | | | |
| 4-247 | | X | | | |
| 4-248 | | | X | | |
| 4-249 | | | | X | |
| 4-250 | | | | | X |
| 4-251 | X | | | | |
| 4-252 | | X | | | |
| 4-253 | | | X | | |
| 4-254 | | | | X | |
| 4-255 | | | | | X |
| 4-256 | X | | | | |
| 4-257 | | X | | | |
| 4-258 | | | X | | |
| 4-259 | | | | X | |
| 4-260 | | | | | X |
| 4-261 | X | | | | |
| 4-262 | | X | | | |
| 4-263 | | | X | | |
| 4-264 | | | | X | |
| 4-265 | | | | | X |
| 4-266 | X | | | | |
| 4-267 | | X | | | |
| 4-268 | | | X | | |
| 4-269 | | | | X | |
| 4-270 | | | | | X |

TABLE 4-continued
Formula IV-A
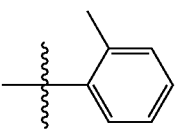 [SMILES: *c1ccccc1C]
| No | 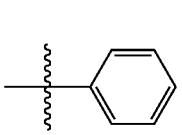 o-tolyl | phenyl | 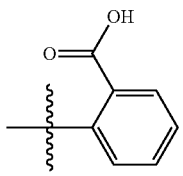 [SMILES: *c1ccccc1C(=O)O] 2-carboxyphenyl | 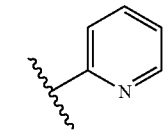 [SMILES: *c1ccccn1] 2-pyridyl | 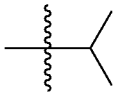 [SMILES: *C(C)C] isopropyl |
|---|---|---|---|---|---|
| 4-271 | X | | | | |
| 4-272 | | X | | | |
| 4-273 | | | X | | |
| 4-274 | | | | X | |
| 4-275 | | | | | X |
| 4-276 | X | | | | |
| 4-277 | | X | | | |
| 4-278 | | | X | | |
| 4-279 | | | | X | |
| 4-280 | | | | | X |
| 4-281 | X | | | | |
| 4-282 | | X | | | |
| 4-283 | | | X | | |
| 4-284 | | | | X | |
| 4-285 | | | | | X |
| 4-286 | X | | | | |
| 4-287 | | X | | | |
| 4-288 | | | X | | |
| 4-289 | | | | X | |
| 4-290 | | | | | X |
| 4-291 | X | | | | |
| 4-292 | | X | | | |
| 4-293 | | | X | | |
| 4-294 | | | | X | |
| 4-295 | | | | | X |
| 4-296 | X | | | | |
| 4-297 | | X | | | |
| 4-298 | | | X | | |
| 4-299 | | | | X | |
| 4-300 | | | | | X |
| 4-301 | X | | | | |
| 4-302 | | X | | | |
| 4-303 | | | X | | |
| 4-304 | | | | X | |
| 4-305 | | | | | X |
| 4-306 | X | | | | |
| 4-307 | | X | | | |
| 4-308 | | | X | | |
| 4-309 | | | | X | |
| 4-310 | | | | | X |
| 4-311 | X | | | | |
| 4-312 | | X | | | |
| 4-313 | | | X | | |
| 4-314 | | | | X | |
| 4-315 | | | | | X |
| 4-316 | X | | | | |
| 4-317 | | X | | | |
| 4-318 | | | X | | |
| 4-319 | | | | X | |
| 4-320 | | | | | X |
| 4-321 | X | | | | |
| 4-322 | | X | | | |
| 4-323 | | | X | | |

TABLE 4-continued

| | | | | | |
|---|---|---|---|---|---|
| 4-324 | | | | X | |
| 4-325 | | | | | X |
| 4-326 | X | | | | |
| 4-327 | | X | | | |
| 4-328 | | | X | | |
| 4-329 | | | | X | |
| 4-330 | | | | | X |
| 4-331 | X | | | | |
| 4-332 | | X | | | |
| 4-333 | | | X | | |
| 4-334 | | | | X | |
| 4-335 | | | | | X |
| 4-336 | X | | | | |
| 4-337 | | X | | | |
| 4-338 | | | X | | |
| 4-339 | | | | X | |
| 4-340 | | | | | X |
| 4-341 | X | | | | |
| 4-342 | | X | | | |
| 4-343 | | | X | | |
| 4-344 | | | | X | |
| 4-345 | | | | | X |
| 4-346 | X | | | | |
| 4-347 | | X | | | |
| 4-348 | | | X | | |
| 4-349 | | | | X | |
| 4-350 | | | | | X |
| 4-351 | X | | | | |
| 4-352 | | X | | | |
| 4-353 | | | X | | |
| 4-354 | | | | X | |
| 4-355 | | | | | X |
| 4-356 | X | | | | |
| 4-357 | | X | | | |
| 4-358 | | | X | | |
| 4-359 | | | | X | |
| 4-360 | | | | | X |
| 4-361 | X | | | | |
| 4-362 | | X | | | |
| 4-363 | | | X | | |
| 4-364 | | | | X | |
| 4-365 | | | | | X |
| 4-366 | X | | | | |
| 4-367 | | X | | | |
| 4-368 | | | X | | |
| 4-369 | | | | X | |
| 4-370 | | | | | X |
| 4-371 | X | | | | |
| 4-372 | | X | | | |
| 4-373 | | | X | | |
| 4-374 | | | | X | |
| 4-375 | | | | | X |
| 4-376 | X | | | | |
| 4-377 | | X | | | |
| 4-378 | | | X | | |
| 4-379 | | | | X | |
| 4-380 | | | | | X |
| 4-381 | X | | | | |
| 4-382 | | X | | | |
| 4-383 | | | X | | |
| 4-384 | | | | X | |
| 4-385 | | | | | X |
| 4-386 | X | | | | |
| 4-387 | | X | | | |
| 4-388 | | | X | | |
| 4-389 | | | | X | |
| 4-390 | | | | | X |
| 4-391 | X | | | | |
| 4-392 | | X | | | |
| 4-393 | | | X | | |
| 4-394 | | | | X | |
| 4-395 | | | | | X |
| 4-396 | X | | | | |
| 4-397 | | X | | | |
| 4-398 | | | X | | |
| 4-399 | | | | X | |
| 4-400 | | | | | X |
| 4-401 | X | | | | |
| 4-402 | | X | | | |
| 4-403 | | | X | | |

TABLE 4-continued

| | | | | | |
|---|---|---|---|---|---|
| 4-404 | | | | X | |
| 4-405 | | | | | X |
| 4-406 | X | | | | |
| 4-407 | | X | | | |
| 4-408 | | | X | | |
| 4-409 | | | | X | |
| 4-410 | | | | | X |
| 4-411 | X | | | | |
| 4-412 | | X | | | |
| 4-413 | | | X | | |
| 4-414 | | | | X | |
| 4-415 | | | | | X |
| 4-416 | X | | | | |
| 4-417 | | X | | | |
| 4-418 | | | X | | |
| 4-419 | | | | X | |
| 4-420 | | | | | X |
| 4-421 | X | | | | |
| 4-422 | | X | | | |
| 4-423 | | | X | | |
| 4-424 | | | | X | |
| 4-425 | | | | | X |
| 4-426 | X | | | | |
| 4-427 | | X | | | |
| 4-428 | | | X | | |
| 4-429 | | | | X | |
| 4-430 | | | | | X |
| 4-431 | X | | | | |
| 4-432 | | X | | | |
| 4-433 | | | X | | |
| 4-434 | | | | X | |
| 4-435 | | | | | X |
| 4-436 | X | | | | |
| 4-437 | | X | | | |
| 4-438 | | | X | | |
| 4-439 | | | | X | |
| 4-440 | | | | | X |
| 4-441 | X | | | | |
| 4-442 | | X | | | |
| 4-443 | | | X | | |
| 4-444 | | | | X | |
| 4-445 | | | | | X |
| 4-446 | X | | | | |
| 4-447 | | X | | | |
| 4-448 | | | X | | |
| 4-449 | | | | X | |
| 4-450 | | | | | X |
| 4-451 | X | | | | |
| 4-452 | | X | | | |
| 4-453 | | | X | | |
| 4-454 | | | | X | |
| 4-455 | | | | | X |
| 4-456 | X | | | | |
| 4-457 | | X | | | |
| 4-458 | | | X | | |
| 4-459 | | | | X | |
| 4-460 | | | | | X |
| 4-461 | X | | | | |
| 4-462 | | X | | | |
| 4-463 | | | X | | |
| 4-464 | | | | X | |
| 4-465 | | | | | X |
| 4-466 | X | | | | |
| 4-467 | | X | | | |
| 4-468 | | | X | | |
| 4-469 | | | | X | |
| 4-470 | | | | | X |
| 4-471 | X | | | | |
| 4-472 | | X | | | |
| 4-473 | | | X | | |
| 4-474 | | | | X | |
| 4-475 | | | | | X |
| 4-476 | X | | | | |
| 4-477 | | X | | | |
| 4-478 | | | X | | |
| 4-479 | | | | X | |
| 4-480 | | | | | X |
| 4-481 | X | | | | |
| 4-482 | | X | | | |
| 4-483 | | | X | | |

TABLE 4-continued

| | | | | | |
|---|---|---|---|---|---|
| 4-484 | | | | X | |
| 4-485 | | | | | X |
| 4-486 | X | | | | |
| 4-487 | | X | | | |
| 4-488 | | | X | | |
| 4-489 | | | | X | |
| 4-490 | | | | | X |
| 4-491 | X | | | | |
| 4-492 | | X | | | |
| 4-493 | | | X | | |
| 4-494 | | | | X | |
| 4-495 | | | | | X |
| 4-496 | X | | | | |
| 4-497 | | X | | | |
| 4-498 | | | X | | |
| 4-499 | | | | X | |
| 4-500 | | | | | X |
| 4-501 | X | | | | |
| 4-502 | | X | | | |
| 4-503 | | | X | | |
| 4-504 | | | | X | |
| 4-505 | | | | | X |
| 4-506 | X | | | | |
| 4-507 | | X | | | |
| 4-508 | | | X | | |
| 4-509 | | | | X | |
| 4-510 | | | | | X |
| 4-511 | X | | | | |
| 4-512 | | X | | | |
| 4-513 | | | X | | |
| 4-514 | | | | X | |
| 4-515 | | | | | X |
| 4-516 | X | | | | |
| 4-517 | | X | | | |
| 4-518 | | | X | | |
| 4-519 | | | | X | |
| 4-520 | | | | | X |
| 4-521 | X | | | | |
| 4-522 | | X | | | |
| 4-523 | | | X | | |
| 4-524 | | | | X | |
| 4-525 | | | | | X |
| 4-526 | X | | | | |
| 4-527 | | X | | | |
| 4-528 | | | X | | |
| 4-529 | | | | X | |
| 4-530 | | | | | X |
| 4-531 | X | | | | |
| 4-532 | | X | | | |
| 4-533 | | | X | | |
| 4-534 | | | | X | |
| 4-535 | | | | | X |
| 4-536 | X | | | | |
| 4-537 | | X | | | |
| 4-538 | | | X | | |
| 4-539 | | | | X | |
| 4-540 | | | | | X |

Exemplary compounds of the invention of Formula IV-A. X represents a halo group (Cl, Br, I or F).

TABLE 5

Exemplary compounds of the invention of Formula V-A1.

Formula V-A1

| No | R¹ (3-F-5-OH-phenyl) | R¹ (HO-alkyne) | R¹ (I) | R⁶ H | R⁶ Me | R⁶ X | W C | W N | R⁷ H | R⁷ Me | R⁷ Et | R⁹ H | R⁹ Me | R⁹ Et | R⁹ i-Pr |
|---|---|---|---|---|---|---|---|---|---|---|---|---|---|---|---|
| 5-1 | X | | | X | | | X | | X | | | X | | | |
| 5-2 | X | | | X | | | X | | X | | | | X | | |
| 5-3 | X | | | X | | | X | | X | | | | | X | |
| 5-4 | X | | | X | | | X | | X | | | | | | X |
| 5-5 | X | | | X | | | X | | X | | | | | | |
| 5-6 | X | | | X | | | X | | | X | | X | | | |
| 5-7 | X | | | X | | | X | | | X | | | X | | |
| 5-8 | X | | | X | | | X | | | X | | | | X | |
| 5-9 | X | | | X | | | X | | | X | | | | | X |
| 5-10 | X | | | X | | | X | | | X | | | | | |
| 5-11 | X | | | X | | | X | | | | X | X | | | |
| 5-12 | X | | | X | | | X | | | | X | | X | | |
| 5-13 | X | | | X | | | X | | | | X | | | X | |
| 5-14 | X | | | X | | | X | | | | X | | | | X |
| 5-15 | X | | | X | | | X | | | | X | | | | |
| 5-16 | X | | | | X | | X | | X | | | X | | | |
| 5-17 | X | | | | X | | X | | X | | | | X | | |
| 5-18 | X | | | | X | | X | | X | | | | | X | |
| 5-19 | X | | | | X | | X | | X | | | | | | X |
| 5-20 | X | | | | X | | X | | X | | | | | | |
| 5-21 | X | | | | X | | X | | | X | | X | | | |
| 5-22 | X | | | | X | | X | | | X | | | X | | |
| 5-23 | X | | | | X | | X | | | X | | | | X | |
| 5-24 | X | | | | X | | X | | | X | | | | | X |
| 5-25 | X | | | | X | | X | | | X | | | | | |
| 5-26 | X | | | | X | | X | | | | X | X | | | |
| 5-27 | X | | | | X | | X | | | | X | | X | | |
| 5-28 | X | | | | X | | X | | | | X | | | X | |
| 5-29 | X | | | | X | | X | | | | X | | | | X |
| 5-30 | X | | | | X | | X | | | | X | | | | |
| 5-31 | X | | | | | X | X | | X | | | X | | | |
| 5-32 | X | | | | | X | X | | X | | | | X | | |
| 5-33 | X | | | | | X | X | | X | | | | | X | |
| 5-34 | X | | | | | X | X | | X | | | | | | X |
| 5-35 | X | | | | | X | X | | X | | | | | | |
| 5-36 | X | | | | | X | X | | | X | | X | | | |
| 5-37 | X | | | | | X | X | | | X | | | X | | |
| 5-38 | X | | | | | X | X | | | X | | | | X | |
| 5-39 | X | | | | | X | X | | | X | | | | | X |
| 5-40 | X | | | | | X | X | | | X | | | | | |
| 5-41 | X | | | | | X | X | | | | X | X | | | |
| 5-42 | X | | | | | X | X | | | | X | | X | | |
| 5-43 | X | | | | | X | X | | | | X | | | X | |
| 5-44 | X | | | | | X | X | | | | X | | | | X |
| 5-45 | X | | | | | X | X | | | | X | | | | |
| 5-46 | X | | | X | | | | X | X | | | X | | | |
| 5-47 | X | | | X | | | | X | X | | | | X | | |
| 5-48 | X | | | X | | | | X | X | | | | | X | |
| 5-49 | X | | | X | | | | X | X | | | | | | X |

TABLE 5-continued

Exemplary compounds of the invention of Formula V-A1.

Formula V-A1

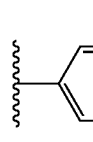

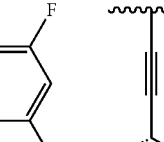

| | R1 | | | | R6 | | | W | | R7 | | | R9 | | | |
|---|---|---|---|---|---|---|---|---|---|---|---|---|---|---|---|---|
| No | OH | HO | I | | H | Me | X | C | N | H | Me | Et | H | Me | Et | i-Pr |
| 5-50 | X | | | | | X | | X | | X | | | X | | | |
| 5-51 | X | | | | | X | | X | | X | | | | X | | |
| 5-52 | X | | | | | X | | X | | X | | | | | X | |
| 5-53 | X | | | | | X | | X | | X | | | | | | X |
| 5-54 | X | | | | | X | | X | | | X | | X | | | |
| 5-55 | X | | | | | X | | X | | | X | | | X | | |
| 5-56 | X | | | | | X | | X | | | X | | | | X | |
| 5-57 | X | | | | | X | | X | | | X | | | | | X |
| 5-58 | X | | | | | X | | X | | | | X | X | | | |
| 5-59 | X | | | | | X | | X | | | | X | | X | | |
| 5-60 | X | | | | | X | | X | | | | X | | | X | |
| 5-61 | X | | | | | | X | X | | X | | | X | | | |
| 5-62 | X | | | | | | X | X | | X | | | | X | | |
| 5-63 | X | | | | | | X | X | | X | | | | | X | |
| 5-64 | X | | | | | | X | X | | X | | | | | | X |
| 5-65 | X | | | | | | X | X | | | X | | X | | | |
| 5-66 | X | | | | | | X | X | | | X | | | X | | |
| 5-67 | X | | | | | | X | X | | | X | | | | X | |
| 5-68 | X | | | | | | X | X | | | X | | | | | X |
| 5-69 | X | | | | | | X | X | | | | X | X | | | |
| 5-70 | X | | | | | | X | X | | | | X | | X | | |
| 5-71 | X | | | | | | X | X | | | | X | | | X | |
| 5-72 | X | | | | | | X | X | | | | X | | | | X |
| 5-73 | X | | | | | | X | X | | X | | | X | | | |
| 5-74 | X | | | | | | X | X | | X | | | | X | | |
| 5-75 | X | | | | | | X | X | | X | | | | | X | |
| 5-76 | X | | | | | | X | | X | X | | | X | | | |
| 5-77 | X | | | | | | X | | X | X | | | | X | | |
| 5-78 | X | | | | | | X | | X | X | | | | | X | |
| 5-79 | X | | | | | | X | | X | X | | | | | | X |
| 5-80 | X | | | | | | X | | X | | X | | X | | | |
| 5-81 | X | | | | | | X | | X | | X | | | X | | |
| 5-82 | X | | | | | | X | | X | | X | | | | X | |
| 5-83 | X | | | | | | X | | X | | X | | | | | X |
| 5-84 | X | | | | | | X | | X | | | X | X | | | |
| 5-85 | X | | | | | | X | | X | | | X | | X | | |
| 5-86 | X | | | | | | X | | X | | | X | | | X | |
| 5-87 | X | | | | | | X | | X | | | X | | | | X |
| 5-88 | X | | | | | | X | | X | X | | | X | | | |
| 5-89 | X | | | | | | X | | X | X | | | | X | | |
| 5-90 | X | | | | | | X | | X | X | | | | | X | |
| 5-91 | | X | | | | | X | | X | X | | | X | | | |
| 5-92 | | X | | | | | X | | X | X | | | | X | | |
| 5-93 | | X | | | | | X | | X | X | | | | | X | |
| 5-94 | | X | | | | | X | | X | X | | | | | | X |
| 5-95 | | X | | | | | X | | X | | X | | X | | | |
| 5-96 | | X | | | | | X | | X | | X | | | X | | |
| 5-97 | | X | | | | | X | | X | | X | | | | X | |
| 5-98 | | X | | | | | X | | X | | X | | | | | X |

TABLE 5-continued

Exemplary compounds of the invention of Formula V-A1.

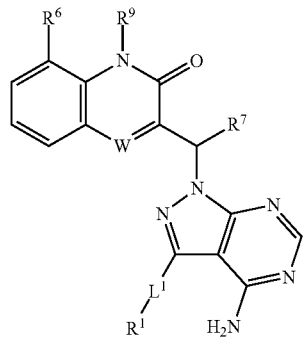

Formula V-A1

| No | R¹-OH | R¹-HO | R¹-I | R⁶-H | R⁶-Me | R⁶-X | W-C | W-N | R⁷-H | R⁷-Me | R⁷-Et | R⁹-H | R⁹-Me | R⁹-Et | R⁹-i-Pr |
|---|---|---|---|---|---|---|---|---|---|---|---|---|---|---|---|
| 5-99 | | X | | | X | | X | | | X | | | | | X |
| 5-100 | | X | | | X | | X | | | X | | | | | |
| 5-101 | | X | | | X | | X | | | | X | X | | | |
| 5-102 | | X | | | X | | X | | | | X | | X | | |
| 5-103 | | X | | | X | | X | | | | X | | | X | |
| 5-104 | | X | | | X | | X | | | | X | | | | X |
| 5-105 | | X | | | X | | X | | | | X | | | | |
| 5-106 | | X | | | X | | | X | X | | | X | | | |
| 5-107 | | X | | | X | | | X | X | | | | X | | |
| 5-108 | | X | | | X | | | X | X | | | | | X | |
| 5-109 | | X | | | X | | | X | X | | | | | | X |
| 5-110 | | X | | | X | | | X | X | | | | | | |
| 5-111 | | X | | | X | | | X | | X | | X | | | |
| 5-112 | | X | | | X | | | X | | X | | | X | | |
| 5-113 | | X | | | X | | | X | | X | | | | X | |
| 5-114 | | X | | | X | | | X | | X | | | | | X |
| 5-115 | | X | | | X | | | X | | X | | | | | |
| 5-116 | | X | | | X | | | X | | | X | X | | | |
| 5-117 | | X | | | X | | | X | | | X | | X | | |
| 5-118 | | X | | | X | | | X | | | X | | | X | |
| 5-119 | | X | | | X | | | X | | | X | | | | X |
| 5-120 | | X | | | X | | | X | | | X | | | | |
| 5-121 | | X | | | | X | X | | X | | | X | | | |
| 5-122 | | X | | | | X | X | | X | | | | X | | |
| 5-123 | | X | | | | X | X | | X | | | | | X | |
| 5-124 | | X | | | | X | X | | X | | | | | | X |
| 5-125 | | X | | | | X | X | | X | | | | | | |
| 5-126 | | X | | | | X | X | | | X | | X | | | |
| 5-127 | | X | | | | X | X | | | X | | | X | | |
| 5-128 | | X | | | | X | X | | | X | | | | X | |
| 5-129 | | X | | | | X | X | | | X | | | | | X |
| 5-130 | | X | | | | X | X | | | X | | | | | |
| 5-131 | | X | | | | X | X | | | | X | X | | | |
| 5-132 | | X | | | | X | X | | | | X | | X | | |
| 5-133 | | X | | | | X | X | | | | X | | | X | |
| 5-134 | | X | | | | X | X | | | | X | | | | X |
| 5-135 | | X | | | | X | X | | | | X | | | | |
| 5-136 | | X | | | | X | | X | X | | | X | | | |
| 5-137 | | X | | | | X | | X | X | | | | X | | |
| 5-138 | | X | | | | X | | X | X | | | | | X | |
| 5-139 | | X | | | | X | | X | X | | | | | | X |
| 5-140 | | X | | | | X | | X | X | | | | | | |
| 5-141 | | X | | | | X | | X | | X | | X | | | |
| 5-142 | | X | | | | X | | X | | X | | | X | | |
| 5-143 | | X | | | | X | | X | | X | | | | X | |
| 5-144 | | X | | | | X | | X | | X | | | | | X |
| 5-145 | | X | | | | X | | X | | X | | | | | |
| 5-146 | | X | | | | X | | X | | | X | X | | | |
| 5-147 | | X | | | | X | | X | | | X | | X | | |

TABLE 5-continued

Exemplary compounds of the invention of Formula V-A1.

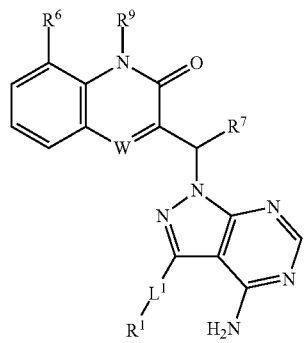

Formula V-A1

| No | R¹: OH | R¹: HO (alkyne) | R¹: I | R⁶ H | R⁶ Me | R⁶ X | W C | W N | R⁷ H | R⁷ Me | R⁷ Et | R⁹ H | R⁹ Me | R⁹ Et | R⁹ i-Pr |
|---|---|---|---|---|---|---|---|---|---|---|---|---|---|---|---|
| 5-148 | X |  |  |  | X |  | X |  | X |  |  |  | X |  |  |
| 5-149 | X |  |  |  | X |  | X |  | X |  |  |  |  | X |  |
| 5-150 | X |  |  |  | X |  | X |  | X |  |  |  |  |  | X |
| 5-151 | X |  |  |  |  | X | X |  | X |  |  | X |  |  |  |
| 5-152 | X |  |  |  |  | X | X |  | X |  |  |  | X |  |  |
| 5-153 | X |  |  |  |  | X | X |  | X |  |  |  |  | X |  |
| 5-154 | X |  |  |  |  | X | X |  | X |  |  |  |  |  | X |
| 5-155 | X |  |  |  |  | X | X |  | X |  |  |  |  |  |  |
| 5-156 | X |  |  |  |  | X | X |  |  | X |  | X |  |  |  |
| 5-157 | X |  |  |  |  | X | X |  |  | X |  |  | X |  |  |
| 5-158 | X |  |  |  |  | X | X |  |  | X |  |  |  | X |  |
| 5-159 | X |  |  |  |  | X | X |  |  | X |  |  |  |  | X |
| 5-160 | X |  |  |  |  | X | X |  |  | X |  |  |  |  |  |
| 5-161 | X |  |  |  |  | X | X |  |  |  | X | X |  |  |  |
| 5-162 | X |  |  |  |  | X | X |  |  |  | X |  | X |  |  |
| 5-163 | X |  |  |  |  | X | X |  |  |  | X |  |  | X |  |
| 5-164 | X |  |  |  |  | X | X |  |  |  | X |  |  |  | X |
| 5-165 | X |  |  |  |  | X | X |  |  |  | X |  |  |  |  |
| 5-166 | X |  |  |  |  | X |  | X | X |  |  | X |  |  |  |
| 5-167 | X |  |  |  |  | X |  | X | X |  |  |  | X |  |  |
| 5-168 | X |  |  |  |  | X |  | X | X |  |  |  |  | X |  |
| 5-169 | X |  |  |  |  | X |  | X | X |  |  |  |  |  | X |
| 5-170 | X |  |  |  |  | X |  | X | X |  |  |  |  |  |  |
| 5-171 | X |  |  |  |  | X |  | X |  | X |  | X |  |  |  |
| 5-172 | X |  |  |  |  | X |  | X |  | X |  |  | X |  |  |
| 5-173 | X |  |  |  |  | X |  | X |  | X |  |  |  | X |  |
| 5-174 | X |  |  |  |  | X |  | X |  | X |  |  |  |  | X |
| 5-175 | X |  |  |  |  | X |  | X |  | X |  |  |  |  |  |
| 5-176 | X |  |  |  |  | X |  | X |  |  | X | X |  |  |  |
| 5-177 | X |  |  |  |  | X |  | X |  |  | X |  | X |  |  |
| 5-178 | X |  |  |  |  | X |  | X |  |  | X |  |  | X |  |
| 5-179 | X |  |  |  |  | X |  | X |  |  | X |  |  |  | X |
| 5-180 | X |  |  |  |  | X |  | X |  |  | X |  |  |  |  |
| 5-181 |  | X |  |  |  | X | X |  | X |  |  | X |  |  |  |
| 5-182 |  | X |  |  |  | X | X |  | X |  |  |  | X |  |  |
| 5-183 |  | X |  |  |  | X | X |  | X |  |  |  |  | X |  |
| 5-184 |  | X |  |  |  | X | X |  | X |  |  |  |  |  | X |
| 5-185 |  | X |  |  |  | X | X |  | X |  |  |  |  |  |  |
| 5-186 |  | X |  |  |  | X | X |  |  | X |  | X |  |  |  |
| 5-187 |  | X |  |  |  | X | X |  |  | X |  |  | X |  |  |
| 5-188 |  | X |  |  |  | X | X |  |  | X |  |  |  | X |  |
| 5-189 |  | X |  |  |  | X | X |  |  | X |  |  |  |  | X |
| 5-190 |  | X |  |  |  | X | X |  |  | X |  |  |  |  |  |
| 5-191 |  | X |  |  |  | X | X |  |  |  | X | X |  |  |  |
| 5-192 |  | X |  |  |  | X | X |  |  |  | X |  | X |  |  |
| 5-193 |  | X |  |  |  | X | X |  |  |  | X |  |  | X |  |
| 5-194 |  | X |  |  |  | X | X |  |  |  | X |  |  |  | X |
| 5-195 |  | X |  |  |  | X | X |  |  |  | X |  |  |  |  |
| 5-196 |  | X |  |  |  | X |  | X | X |  |  | X |  |  |  |

TABLE 5-continued

Exemplary compounds of the invention of Formula V-A1.

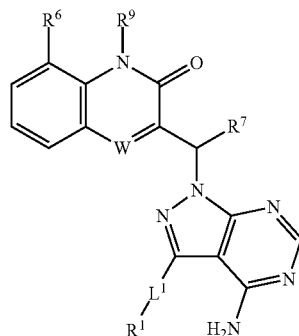

Formula V-A1

| No | R¹ (F-phenyl-OH) | R¹ (HO-alkyne) | R¹ (I) | R⁶ H | R⁶ Me | R⁶ X | W C | W N | R⁷ H | R⁷ Me | R⁷ Et | R⁹ H | R⁹ Me | R⁹ Et | R⁹ i-Pr |
|---|---|---|---|---|---|---|---|---|---|---|---|---|---|---|---|
| 5-197 | | | X | X | | | X | X | | | | | X | | |
| 5-198 | | | X | X | | | X | X | | | | | | X | |
| 5-199 | | | X | X | | | X | X | | | | | | | X |
| 5-200 | | | X | X | | | X | X | | | | | | | |
| 5-201 | | | X | X | | | X | | X | | | X | | | |
| 5-202 | | | X | X | | | X | | X | | | | X | | |
| 5-203 | | | X | X | | | X | | X | | | | | X | |
| 5-204 | | | X | X | | | X | | X | | | | | | X |
| 5-205 | | | X | X | | | X | | X | | | | | | |
| 5-206 | | | X | X | | | X | | | X | | X | | | |
| 5-207 | | | X | X | | | X | | | X | | | X | | |
| 5-208 | | | X | X | | | X | | | X | | | | X | |
| 5-209 | | | X | X | | | X | | | X | | | | | X |
| 5-210 | | | X | X | | | X | | | X | | | | | |
| 5-211 | | | X | | X | | X | | X | | | X | | | |
| 5-212 | | | X | | X | | X | | X | | | | X | | |
| 5-213 | | | X | | X | | X | | X | | | | | X | |
| 5-214 | | | X | | X | | X | | X | | | | | | X |
| 5-215 | | | X | | X | | X | | X | | | | | | |
| 5-216 | | | X | | X | | X | | | X | | X | | | |
| 5-217 | | | X | | X | | X | | | X | | | X | | |
| 5-218 | | | X | | X | | X | | | X | | | | X | |
| 5-219 | | | X | | X | | X | | | X | | | | | X |
| 5-220 | | | X | | X | | X | | | X | | | | | |
| 5-221 | | | X | | X | | X | | | | X | X | | | |
| 5-222 | | | X | | X | | X | | | | X | | X | | |
| 5-223 | | | X | | X | | X | | | | X | | | X | |
| 5-224 | | | X | | X | | X | | | | X | | | | X |
| 5-225 | | | X | | X | | X | | | | X | | | | |
| 5-226 | | | X | | X | | X | X | | | | X | | | |
| 5-227 | | | X | | X | | X | X | | | | | X | | |
| 5-228 | | | X | | X | | X | X | | | | | | X | |
| 5-229 | | | X | | X | | X | X | | | | | | | X |
| 5-230 | | | X | | X | | X | X | | | | | | | |
| 5-231 | | | X | | X | | X | | X | | | X | | | |
| 5-232 | | | X | | X | | X | | X | | | | X | | |
| 5-233 | | | X | | X | | X | | X | | | | | X | |
| 5-234 | | | X | | X | | X | | X | | | | | | X |
| 5-235 | | | X | | X | | X | | X | | | | | | |
| 5-236 | | | X | | X | | X | | | X | | X | | | |
| 5-237 | | | X | | X | | X | | | X | | | X | | |
| 5-238 | | | X | | X | | X | | | X | | | | X | |
| 5-239 | | | X | | X | | X | | | X | | | | | X |
| 5-240 | | | X | | X | | X | | | X | | | | | |
| 5-241 | | | X | | | X | X | | X | | | X | | | |
| 5-242 | | | X | | | X | X | | X | | | | X | | |
| 5-243 | | | X | | | X | X | | X | | | | | X | |
| 5-244 | | | X | | | X | X | | X | | | | | | X |
| 5-245 | | | X | | | X | X | | X | | | | | | |

TABLE 5-continued

Exemplary compounds of the invention of Formula V-A1.

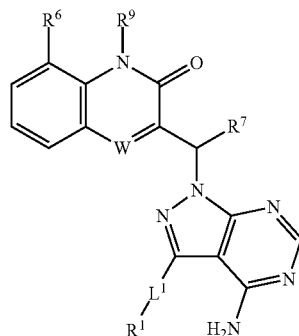

Formula V-A1

| No | R1: F-phenyl-OH | R1: HO-alkyne | R1: I | R6: H | R6: Me | R6: X | W: C | W: N | R7: H | R7: Me | R7: Et | R9: H | R9: Me | R9: Et | R9: i-Pr |
|---|---|---|---|---|---|---|---|---|---|---|---|---|---|---|---|
| 5-246 | | | X | | X | | X | | X | | | X | | | |
| 5-247 | | | X | | X | | X | | X | | | | X | | |
| 5-248 | | | X | | X | | X | | X | | | | | X | |
| 5-249 | | | X | | X | | X | | X | | | | | | X |
| 5-250 | | | X | | X | | X | | X | | | | | | |
| 5-251 | | | X | | X | | X | | | X | | X | | | |
| 5-252 | | | X | | X | | X | | | X | | | X | | |
| 5-253 | | | X | | X | | X | | | X | | | | X | |
| 5-254 | | | X | | X | | X | | | X | | | | | X |
| 5-255 | | | X | | X | | X | | | X | | | | | |
| 5-256 | | | X | | X | | | X | X | | | X | | | |
| 5-257 | | | X | | X | | | X | X | | | | X | | |
| 5-258 | | | X | | X | | | X | X | | | | | X | |
| 5-259 | | | X | | X | | | X | X | | | | | | X |
| 5-260 | | | X | | X | | | X | X | | | | | | |
| 5-261 | | | X | | X | | | X | | X | | X | | | |
| 5-262 | | | X | | X | | | X | | X | | | X | | |
| 5-263 | | | X | | X | | | X | | X | | | | X | |
| 5-264 | | | X | | X | | | X | | X | | | | | X |
| 5-265 | | | X | | X | | | X | | X | | | | | |
| 5-266 | | | X | | X | | X | | | | X | X | | | |
| 5-267 | | | X | | X | | X | | | | X | | X | | |
| 5-268 | | | X | | X | | X | | | | X | | | X | |
| 5-269 | | | X | | X | | X | | | | X | | | | X |
| 5-270 | | | X | | X | | X | | | | X | | | | |
| 5-271 | X | | | | | X | X | | X | | | X | | | |
| 5-272 | X | | | | | X | X | | X | | | | X | | |
| 5-273 | X | | | | | X | X | | X | | | | | X | |
| 5-274 | X | | | | | X | X | | X | | | | | | X |
| 5-275 | X | | | | | X | X | | X | | | | | | |
| 5-276 | X | | | | | X | X | | | X | | X | | | |
| 5-277 | X | | | | | X | X | | | X | | | X | | |
| 5-278 | X | | | | | X | X | | | X | | | | X | |
| 5-279 | X | | | | | X | X | | | X | | | | | X |
| 5-280 | X | | | | | X | X | | | X | | | | | |
| 5-281 | X | | | | | X | X | | | | X | X | | | |
| 5-282 | X | | | | | X | X | | | | X | | X | | |
| 5-283 | X | | | | | X | X | | | | X | | | X | |
| 5-284 | X | | | | | X | X | | | | X | | | | X |
| 5-285 | X | | | | | X | X | | | | X | | | | |
| 5-286 | X | | | | | X | | X | X | | | X | | | |
| 5-287 | X | | | | | X | | X | X | | | | X | | |
| 5-288 | X | | | | | X | | X | X | | | | | X | |
| 5-289 | X | | | | | X | | X | X | | | | | | X |
| 5-290 | X | | | | | X | | X | X | | | | | | |
| 5-291 | X | | | | | X | | X | | X | | X | | | |
| 5-292 | X | | | | | X | | X | | X | | | X | | |
| 5-293 | X | | | | | X | | X | | X | | | | X | |
| 5-294 | X | | | | | X | | X | | X | | | | | X |

TABLE 5-continued

Exemplary compounds of the invention of Formula V-A1.

Formula V-A1

| No | R¹ 3-F-5-OH-phenyl | R¹ HO-pentynyl | R¹ I | R⁶ H | R⁶ Me | R⁶ X | W C | W N | R⁷ H | R⁷ Me | R⁷ Et | R⁹ H | R⁹ Me | R⁹ Et | R⁹ i-Pr |
|---|---|---|---|---|---|---|---|---|---|---|---|---|---|---|---|
| 5-295 | X | | | X | | | | X | X | | | X | | | |
| 5-296 | X | | | X | | | | X | X | | | | X | | |
| 5-297 | X | | | X | | | | X | X | | | | | X | |
| 5-298 | X | | | X | | | | X | X | | | | | | X |
| 5-299 | X | | | X | | | | X | X | | | | | | X |
| 5-300 | X | | | X | | | | X | | X | | | | | |
| 5-301 | X | | | | X | | | X | X | | | X | | | |
| 5-302 | X | | | | X | | | X | X | | | | X | | |
| 5-303 | X | | | | X | | | X | X | | | | | X | |
| 5-304 | X | | | | X | | | X | X | | | | | | X |
| 5-305 | X | | | | X | | | X | X | | | | | | |
| 5-306 | X | | | | X | | | X | | X | | X | | | |
| 5-307 | X | | | | X | | | X | | X | | | X | | |
| 5-308 | X | | | | X | | | X | | X | | | | X | |
| 5-309 | X | | | | X | | | X | | X | | | | | X |
| 5-310 | X | | | | X | | | X | | X | | | | | |
| 5-311 | X | | | | X | | | X | | | X | X | | | |
| 5-312 | X | | | | X | | | X | | | X | | X | | |
| 5-313 | X | | | | X | | | X | | | X | | | X | |
| 5-314 | X | | | | X | | | X | | | X | | | | X |
| 5-315 | X | | | | X | | X | | | | X | | | | |
| 5-316 | X | | | | X | | X | X | | | | X | | | |
| 5-317 | X | | | | X | | X | X | | | | | X | | |
| 5-318 | X | | | | X | | X | X | | | | | | X | |
| 5-319 | X | | | | X | | X | X | | | | | | | X |
| 5-320 | X | | | | X | | X | X | | | | | | | |
| 5-321 | X | | | | X | | | X | X | | | X | | | |
| 5-322 | X | | | | X | | | X | X | | | | X | | |
| 5-323 | X | | | | X | | | X | X | | | | | X | |
| 5-324 | X | | | | X | | | X | X | | | | | | X |
| 5-325 | X | | | | X | | | X | X | | | | | | |
| 5-326 | X | | | | X | | | X | | X | | X | | | |
| 5-327 | X | | | | X | | | X | | X | | | X | | |
| 5-328 | X | | | | X | | | X | | X | | | | X | |
| 5-329 | X | | | | X | | | X | | X | | | | | X |
| 5-330 | X | | | | X | | | X | | X | | | | | |
| 5-331 | X | | | | | X | X | | X | | | X | | | |
| 5-332 | X | | | | | X | X | | X | | | | X | | |
| 5-333 | X | | | | | X | X | | X | | | | | X | |
| 5-334 | X | | | | | X | X | | X | | | | | | X |
| 5-335 | X | | | | | X | X | | X | | | | | | |
| 5-336 | X | | | | | X | X | | | X | | X | | | |
| 5-337 | X | | | | | X | X | | | X | | | X | | |
| 5-338 | X | | | | | X | X | | | X | | | | X | |
| 5-339 | X | | | | | X | X | | | X | | | | | X |
| 5-340 | X | | | | | X | X | | | X | | | | | |
| 5-341 | X | | | | | X | X | | | | X | X | | | |
| 5-342 | X | | | | | X | X | | | | X | | X | | |
| 5-343 | X | | | | | X | X | | | | X | | | X | |

TABLE 5-continued

Exemplary compounds of the invention of Formula V-A1.

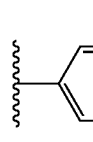

Formula V-A1

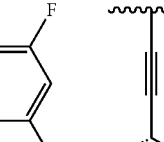

| No | R¹: F-phenyl-OH | R¹: HO-alkyne | R¹: I | R⁶: H | R⁶: Me | R⁶: X | W: C | W: N | R⁷: H | R⁷: Me | R⁷: Et | R⁹: H | R⁹: Me | R⁹: Et | R⁹: i-Pr |
|---|---|---|---|---|---|---|---|---|---|---|---|---|---|---|---|
| 5-344 | X | | | X | | | X | | X | | | | | | X |
| 5-345 | X | | | X | | | X | | X | | | | | X | |
| 5-346 | X | | | | X | | X | | X | | | X | | | |
| 5-347 | X | | | | X | | X | | X | | | | X | | |
| 5-348 | X | | | | X | | X | | X | | | | | X | |
| 5-349 | X | | | | X | | X | | X | | | | | | X |
| 5-350 | X | | | | X | | X | | X | | | | | | |
| 5-351 | X | | | | X | | X | | | X | | X | | | |
| 5-352 | X | | | | X | | X | | | X | | | X | | |
| 5-353 | X | | | | X | | X | | | X | | | | X | |
| 5-354 | X | | | | X | | X | | | X | | | | | X |
| 5-355 | X | | | | X | | X | | | X | | | | | |
| 5-356 | X | | | | X | | X | | | | X | X | | | |
| 5-357 | X | | | | X | | X | | | | X | | X | | |
| 5-358 | X | | | | X | | X | | | | X | | | X | |
| 5-359 | X | | | | X | | X | | | | X | | | | X |
| 5-360 | X | | | | X | | X | | | | X | | | | |
| 5-361 | | X | | | | X | X | | X | | | X | | | |
| 5-362 | | X | | | | X | X | | X | | | | X | | |
| 5-363 | | X | | | | X | X | | X | | | | | X | |
| 5-364 | | X | | | | X | X | | X | | | | | | X |
| 5-365 | | X | | | | X | X | | X | | | | | | |
| 5-366 | | X | | | | X | X | | | X | | X | | | |
| 5-367 | | X | | | | X | X | | | X | | | X | | |
| 5-368 | | X | | | | X | X | | | X | | | | X | |
| 5-369 | | X | | | | X | X | | | X | | | | | X |
| 5-370 | | X | | | | X | X | | | X | | | | | |
| 5-371 | | X | | | | X | X | | | | X | X | | | |
| 5-372 | | X | | | | X | X | | | | X | | X | | |
| 5-373 | | X | | | | X | X | | | | X | | | X | |
| 5-374 | | X | | | | X | X | | | | X | | | | X |
| 5-375 | | X | | | | X | X | | | | X | | | | |
| 5-376 | | X | | | | X | | X | X | | | X | | | |
| 5-377 | | X | | | | X | | X | X | | | | X | | |
| 5-378 | | X | | | | X | | X | X | | | | | X | |
| 5-379 | | X | | | | X | | X | X | | | | | | X |
| 5-380 | | X | | | | X | | X | X | | | | | | |
| 5-381 | | X | | | | X | | X | | X | | X | | | |
| 5-382 | | X | | | | X | | X | | X | | | X | | |
| 5-383 | | X | | | | X | | X | | X | | | | X | |
| 5-384 | | X | | | | X | | X | | X | | | | | X |
| 5-385 | | X | | | | X | | X | | X | | | | | |
| 5-386 | | X | | | | X | | X | | | X | X | | | |
| 5-387 | | X | | | | X | | X | | | X | | X | | |
| 5-388 | | X | | | | X | | X | | | X | | | X | |
| 5-389 | | X | | | | X | | X | | | X | | | | X |
| 5-390 | | X | | | | X | | X | | | X | | | | |
| 5-391 | | X | | | X | | X | | X | | | X | | | |
| 5-392 | | X | | | X | | X | | X | | | | X | | |

TABLE 5-continued

Exemplary compounds of the invention of Formula V-A1.

Formula V-A1

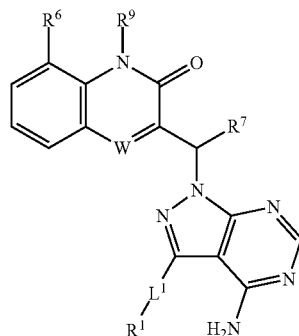

| No | R¹ (OH-F-phenyl) | R¹ (HO-alkyne) | R¹ (I) | R⁶ H | R⁶ Me | R⁶ X | W C | W N | R⁷ H | R⁷ Me | R⁷ Et | R⁹ H | R⁹ Me | R⁹ Et | R⁹ i-Pr |
|---|---|---|---|---|---|---|---|---|---|---|---|---|---|---|---|
| 5-393 | X | | | | X | | X | | X | | | | X | | |
| 5-394 | X | | | | X | | X | | X | | | | | X | |
| 5-395 | X | | | | X | | X | | X | | | | | | X |
| 5-396 | X | | | | X | | X | | | X | | X | | | |
| 5-397 | X | | | | X | | X | | | X | | | X | | |
| 5-398 | X | | | | X | | X | | | X | | | | X | |
| 5-399 | X | | | | X | | X | | | X | | | | | X |
| 5-400 | X | | | | X | | X | | | X | | | | | |
| 5-401 | X | | | | X | | X | | | | X | X | | | |
| 5-402 | X | | | | X | | X | | | | X | | X | | |
| 5-403 | X | | | | X | | X | | | | X | | | X | |
| 5-404 | X | | | | X | | X | | | | X | | | | X |
| 5-405 | X | | | | X | | X | | | | X | | | | |
| 5-406 | X | | | | X | | | X | X | | | X | | | |
| 5-407 | X | | | | X | | | X | X | | | | X | | |
| 5-408 | X | | | | X | | | X | X | | | | | X | |
| 5-409 | X | | | | X | | | X | X | | | | | | X |
| 5-410 | X | | | | X | | | X | X | | | | | | |
| 5-411 | X | | | | X | | | X | | X | | X | | | |
| 5-412 | X | | | | X | | | X | | X | | | X | | |
| 5-413 | X | | | | X | | | X | | X | | | | X | |
| 5-414 | X | | | | X | | | X | | X | | | | | X |
| 5-415 | X | | | | X | | | X | | X | | | | | |
| 5-416 | X | | | | X | | | X | | | X | X | | | |
| 5-417 | X | | | | X | | | X | | | X | | X | | |
| 5-418 | X | | | | X | | | X | | | X | | | X | |
| 5-419 | X | | | | X | | | X | | | X | | | | X |
| 5-420 | X | | | | X | | | X | | | X | | | | |
| 5-421 | X | | | X | | | X | | X | | | X | | | |
| 5-422 | X | | | X | | | X | | X | | | | X | | |
| 5-423 | X | | | X | | | X | | X | | | | | X | |
| 5-424 | X | | | X | | | X | | X | | | | | | X |
| 5-425 | X | | | X | | | X | | X | | | | | | |
| 5-426 | X | | | X | | | X | | | X | | X | | | |
| 5-427 | X | | | X | | | X | | | X | | | X | | |
| 5-428 | X | | | X | | | X | | | X | | | | X | |
| 5-429 | X | | | X | | | X | | | X | | | | | X |
| 5-430 | X | | | X | | | X | | | X | | | | | |
| 5-431 | X | | | X | | | X | | | | X | X | | | |
| 5-432 | X | | | X | | | X | | | | X | | X | | |
| 5-433 | X | | | X | | | X | | | | X | | | X | |
| 5-434 | X | | | X | | | X | | | | X | | | | X |
| 5-435 | X | | | X | | | X | | | | X | | | | |
| 5-436 | X | | | X | | | | X | X | | | X | | | |
| 5-437 | X | | | X | | | | X | X | | | | X | | |
| 5-438 | X | | | X | | | | X | X | | | | | X | |
| 5-439 | X | | | X | | | | X | X | | | | | | X |
| 5-440 | X | | | X | | | | X | X | | | | | | |
| 5-441 | X | | | X | | | | X | | X | | X | | | |

TABLE 5-continued

Exemplary compounds of the invention of Formula V-A1.

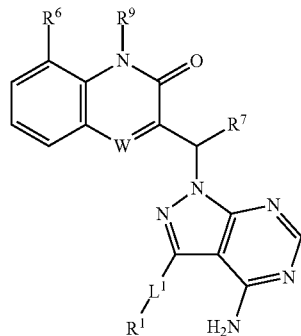

Formula V-A1

| No | R¹ OH(F-phenyl) | R¹ HO-alkyne | R¹ I | R⁶ H | R⁶ Me | W C | W N | R⁷ H | R⁷ Me | R⁷ Et | R⁹ H | R⁹ Me | R⁹ Et | R⁹ i-Pr |
|---|---|---|---|---|---|---|---|---|---|---|---|---|---|---|
| 5-442 | X |   |   |   | X | X |   | X |   |   |   | X |   |   |
| 5-443 | X |   |   |   | X | X |   | X |   |   |   |   | X |   |
| 5-444 | X |   |   |   | X | X |   | X |   |   |   |   |   | X |
| 5-445 | X |   |   |   | X | X |   | X |   |   |   |   |   |   |
| 5-446 | X |   |   |   | X | X |   |   | X | X |   |   |   |   |
| 5-447 | X |   |   |   | X | X |   |   | X |   |   | X |   |   |
| 5-448 | X |   |   |   | X | X |   |   | X |   |   |   | X |   |
| 5-449 | X |   |   |   | X | X |   |   | X |   |   |   |   | X |
| 5-450 | X |   |   |   | X | X |   |   | X |   |   |   |   |   |
| 5-451 |   | X | X | X |   | X |   | X |   |   | X |   |   |   |
| 5-452 |   | X | X | X |   | X |   | X |   |   |   | X |   |   |
| 5-453 |   | X | X | X |   | X |   | X |   |   |   |   | X |   |
| 5-454 |   | X | X | X |   | X |   | X |   |   |   |   |   | X |
| 5-455 |   | X | X | X |   | X |   | X |   |   |   |   |   |   |
| 5-456 |   | X | X | X |   | X |   |   | X | X |   |   |   |   |
| 5-457 |   | X | X | X |   | X |   |   | X |   |   | X |   |   |
| 5-458 |   | X | X | X |   | X |   |   | X |   |   |   | X |   |
| 5-459 |   | X | X | X |   | X |   |   | X |   |   |   |   | X |
| 5-460 |   | X | X | X |   | X |   |   | X |   |   |   |   |   |
| 5-461 |   | X | X | X |   | X |   |   |   | X | X |   |   |   |
| 5-462 |   | X | X | X |   | X |   |   |   | X |   | X |   |   |
| 5-463 |   | X | X | X |   | X |   |   |   | X |   |   | X |   |
| 5-464 |   | X | X | X |   | X |   |   |   | X |   |   |   | X |
| 5-465 |   | X | X | X |   | X |   |   |   | X |   |   |   |   |
| 5-466 |   | X | X |   |   |   | X | X |   |   | X |   |   |   |
| 5-467 |   | X | X |   |   |   | X | X |   |   |   | X |   |   |
| 5-468 |   | X | X |   |   |   | X | X |   |   |   |   | X |   |
| 5-469 |   | X | X |   |   |   | X | X |   |   |   |   |   | X |
| 5-470 |   | X | X |   |   |   | X | X |   |   |   |   |   |   |
| 5-471 |   | X | X |   |   |   | X |   | X |   | X |   |   |   |
| 5-472 |   | X | X |   |   |   | X |   | X |   |   | X |   |   |
| 5-473 |   | X | X |   |   |   | X |   | X |   |   |   | X |   |
| 5-474 |   | X | X |   |   |   | X |   | X |   |   |   |   | X |
| 5-475 |   | X | X |   |   |   | X |   | X |   |   |   |   |   |
| 5-476 |   | X | X |   |   |   | X |   |   | X | X |   |   |   |
| 5-477 |   | X | X |   |   |   | X |   |   | X |   | X |   |   |
| 5-478 |   | X | X |   |   |   | X |   |   | X |   |   | X |   |
| 5-479 |   | X | X |   |   |   | X |   |   | X |   |   |   | X |
| 5-480 |   | X | X |   |   |   | X |   |   | X |   |   |   |   |
| 5-481 |   | X |   | X | X | X |   | X |   |   | X |   |   |   |
| 5-482 |   | X |   | X | X | X |   | X |   |   |   | X |   |   |
| 5-483 |   | X |   | X | X | X |   | X |   |   |   |   | X |   |
| 5-484 |   | X |   | X | X | X |   | X |   |   |   |   |   | X |
| 5-485 |   | X |   | X | X | X |   | X |   |   |   |   |   |   |
| 5-486 |   | X |   | X | X | X |   |   | X |   | X |   |   |   |
| 5-487 |   | X |   | X | X | X |   |   | X |   |   | X |   |   |
| 5-488 |   | X |   | X | X | X |   |   | X |   |   |   | X |   |
| 5-489 |   | X |   | X | X | X |   |   | X |   |   |   |   | X |
| 5-490 |   | X |   | X | X | X |   |   | X |   |   |   |   |   |

TABLE 5-continued

Exemplary compounds of the invention of Formula V-A1.

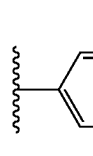

Formula V-A1

| | R¹ | | | R⁶ | | W | | R⁷ | | | R⁹ | | |
|---|---|---|---|---|---|---|---|---|---|---|---|---|---|---|
| No | OH | HO | I | H | Me | X | C | N | H | Me | Et | H | Me | Et | i-Pr |
| 5-491 | | | X | X | X | X | | | | X | | X | | | |
| 5-492 | | | X | X | X | X | | | | X | | | X | | |
| 5-493 | | | X | X | X | X | | | | X | | | | X | |
| 5-494 | | | X | X | X | X | | | | X | | | | | X |
| 5-495 | | | X | X | X | X | | | | X | | | | | |
| 5-496 | | | X | X | X | | X | X | | X | | X | | | |
| 5-497 | | | X | X | X | | X | X | | X | | | X | | |
| 5-498 | | | X | X | X | | X | X | | X | | | | X | |
| 5-499 | | | X | X | X | | X | X | | X | | | | | X |
| 5-500 | | | X | X | X | | X | X | | X | | | | | |
| 5-501 | | | X | X | X | | X | | X | | | X | | | |
| 5-502 | | | X | X | X | | X | | X | | | | X | | |
| 5-503 | | | X | X | X | | X | | X | | | | | X | |
| 5-504 | | | X | X | X | | X | | X | | | | | | X |
| 5-505 | | | X | X | X | | X | | X | | | | | | |
| 5-506 | | | X | X | X | | X | | | X | X | X | | | |
| 5-507 | | | X | X | X | | X | | | X | X | | X | | |
| 5-508 | | | X | X | X | | X | | | X | X | | | X | |
| 5-509 | | | X | X | X | | X | | | X | X | | | | X |
| 5-510 | | | X | X | X | | X | | | X | X | | | | |
| 5-511 | | | X | X | | X | X | | X | | | X | | | |
| 5-512 | | | X | X | | X | X | | X | | | | X | | |
| 5-513 | | | X | X | | X | X | | X | | | | | X | |
| 5-514 | | | X | X | | X | X | | X | | | | | | X |
| 5-515 | | | X | X | | X | X | | X | | | | | | |
| 5-516 | | | X | X | | X | X | | | X | | X | | | |
| 5-517 | | | X | X | | X | X | | | X | | | X | | |
| 5-518 | | | X | X | | X | X | | | X | | | | X | |
| 5-519 | | | X | X | | X | X | | | X | | | | | X |
| 5-520 | | | X | X | | X | X | | | X | | | | | |
| 5-521 | | | X | X | | X | X | | | | X | X | | | |
| 5-522 | | | X | X | | X | X | | | | X | | X | | |
| 5-523 | | | X | X | | X | X | | | | X | | | X | |
| 5-524 | | | X | X | | X | X | | | | X | | | | X |
| 5-525 | | | X | X | | X | X | | | | X | | | | |
| 5-526 | | | X | X | | X | | X | X | | | X | | | |
| 5-527 | | | X | X | | X | | X | X | | | | X | | |
| 5-528 | | | X | X | | X | | X | X | | | | | X | |
| 5-529 | | | X | X | | X | | X | X | | | | | | X |
| 5-530 | | | X | X | | X | | X | X | | | | | | |
| 5-531 | | | X | X | | X | | X | | X | | X | | | |
| 5-532 | | | X | X | | X | | X | | X | | | X | | |
| 5-533 | | | X | X | | X | | X | | X | | | | X | |
| 5-534 | | | X | X | | X | | X | | X | | | | | X |
| 5-535 | | | X | X | | X | | X | | X | | | | | |
| 5-536 | | | X | X | | X | | X | | | X | X | | | |
| 5-537 | | | X | X | | X | | X | | | X | | X | | |

TABLE 5-continued

Exemplary compounds of the invention of Formula V-A1.

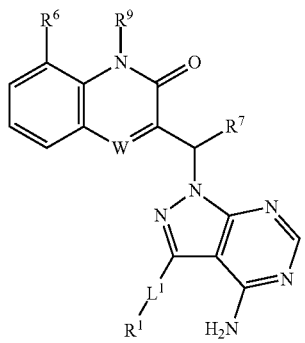

Formula V-A1

| No | R¹ | | | | R⁶ | | W | | R⁷ | | R⁹ | | |
|---|---|---|---|---|---|---|---|---|---|---|---|---|---|
| | F-/OH phenyl | HO-alkyne | alkyne | H | Me | X | C | N | H | Me | Et | H | Me | Et | i-Pr |
| 5-538 | | | X | | | X | X | | | X | | X | | | |
| 5-539 | | | X | | | X | X | | | X | | | | X | |
| 5-540 | | | X | | | X | X | | | X | | | | | |

X represents a halo group (Cl, Br, I or F).

Additional non-limiting examples of compounds of the invention are described in Table 6 along with several biological properties.

| No. | Compound | PI3K δ IC₅₀ | PI3K γ IC₅₀ | PI3K α IC₅₀ | PI3K β IC₅₀ | B cell proliferation EC₅₀ |
|---|---|---|---|---|---|---|
| 1 | 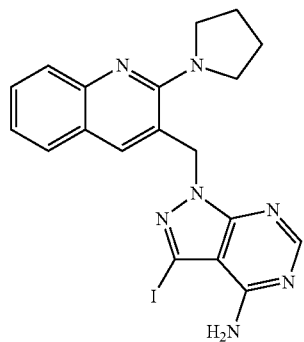 [SMILES: Nc1ncnc2c1c(I)nn2Cc1cc2ccccc2nc1N1CCCC1] | +++ | +++ | + | + | ++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 2 | 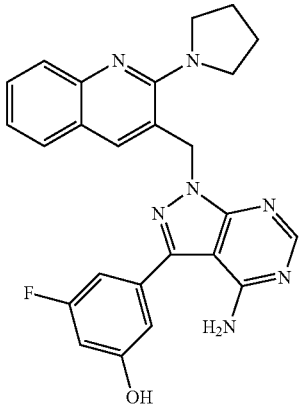 [SMILES: Nc1ncnc2c1c(-c1cc(O)cc(F)c1)nn2Cc1cc2ccccc2nc1N1CCCC1] | +++ | +++ | + | ++ | +++ |
| 3 | 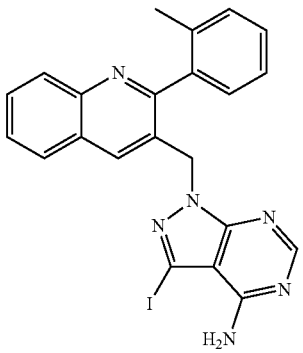 [SMILES: Cc1ccccc1-c1nc2ccccc2cc1Cn1nc(I)c2c(N)ncnc21] | +++ | ++ | + | + | ++ |
| 4 | 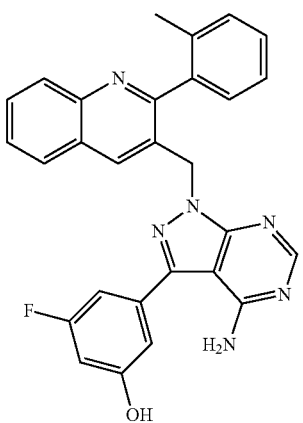 [SMILES: Cc1ccccc1-c1nc2ccccc2cc1Cn1nc(-c2cc(O)cc(F)c2)c2c(N)ncnc21] | +++ | +++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 5 | | +++ | ++ | + | + | ++ |
| 6 | | +++ | + | + | + | ++ |
| 7 | | +++ | +++ | + | + | ++ |
| 8 | | +++ | +++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 9 | | +++ | | + | + | +++ |
| 10 | | +++ | | + | + | ++ |
| 11 | | +++ | | | | +++ |
| 12 | | +++ | | | | +++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 13 | | +++ | | | | +++ |
| 14 | | ++ | | | | |
| 15 | | +++ | | | | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 16 | | +++ | | | | ++ |
| 17 | | +++ | +++ | ++ | ++ | +++ |
| 18 | | + | | | | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 19 | 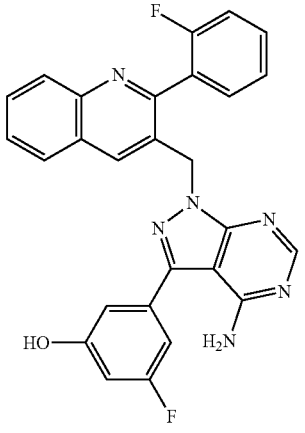 [SMILES: Nc1ncnc2c1c(-c1cc(O)cc(F)c1)nn2Cc1cc2ccccc2nc1-c1ccccc1F] | +++ | | | | +++ |
| 20 | 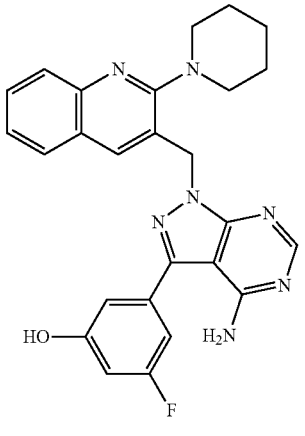 [SMILES: Nc1ncnc2c1c(-c1cc(O)cc(F)c1)nn2Cc1cc2ccccc2nc1N1CCCCC1] | +++ | | | | +++ |
| 21 | 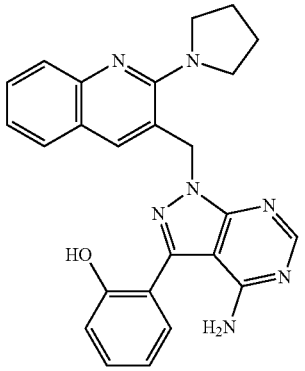 [SMILES: Nc1ncnc2c1c(-c1ccccc1O)nn2Cc1cc2ccccc2nc1N1CCCC1] | + | | | | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 22 | | + | | | | |
| 23 | | +++ | | | | +++ |
| 24 | | +++ | +++ | ++ | + | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 25 | 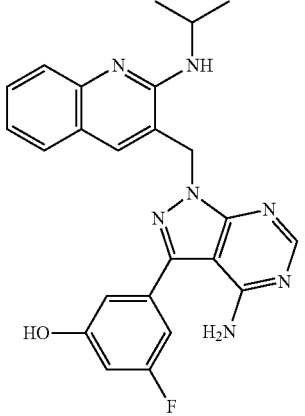 [SMILES: CC(C)Nc1nc2ccccc2cc1Cn1nc(-c2cc(O)cc(F)c2)c2c(N)ncnc21] | ++ | + | | | + |
| 26 | 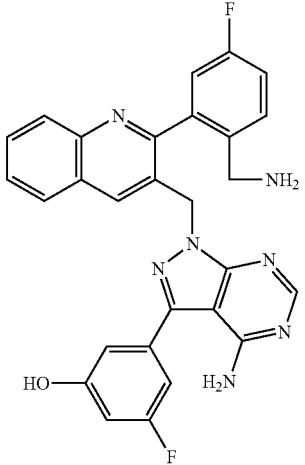 [SMILES: NCc1ccc(F)cc1-c1nc2ccccc2cc1Cn1nc(-c2cc(O)cc(F)c2)c2c(N)ncnc21] | +++ | + | | | +++ |
| 27 | 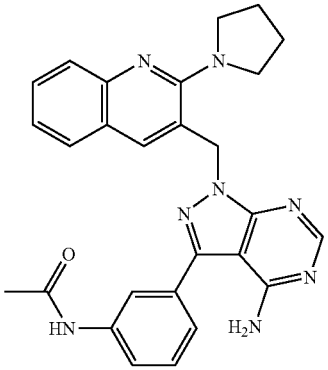 [SMILES: CC(=O)Nc1cccc(-c2nn(Cc3cc4ccccc4nc3N3CCCC3)c3ncnc(N)c23)c1] | | + | | | |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 28 | 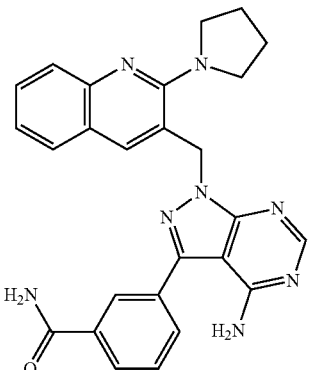 | + | | | | |
| 29 | 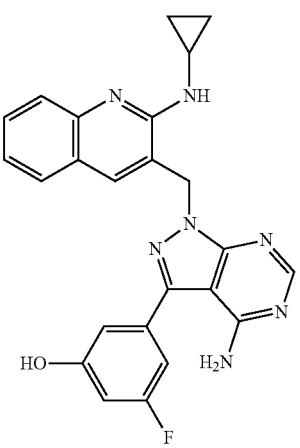 [SMILES: Nc1ncnc2c1c(-c1cc(O)cc(F)c1)nn2Cc1cc2ccccc2nc1NC1CC1] | ++ | + | + | + | |
| 30 | 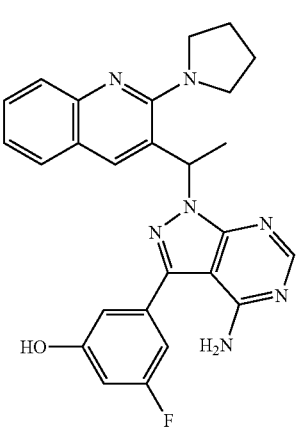 [SMILES: CC(c1cc2ccccc2nc1N1CCCC1)n1nc(-c2cc(O)cc(F)c2)c2c(N)ncnc21] | +++ | +++ | | | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 31 | | +++ | + | | | ++ |
| 32 | | +++ | ++ | | | +++ |
| 33 | | ++ | | | | |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 34 | 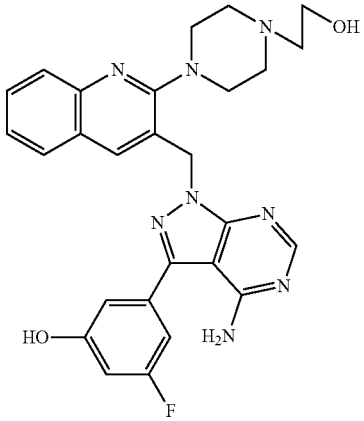 [SMILES: Nc1ncnc2c1c(-c1cc(O)cc(F)c1)nn2Cc1cc2ccccc2nc1N1CCN(CCO)CC1] | +++ | ++ | | | +++ |
| 35 | 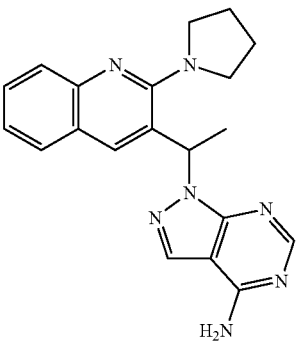 [SMILES: CC(c1cc2ccccc2nc1N1CCCC1)n1ncc2c(N)ncnc21] | + | + | | | |
| 36 | 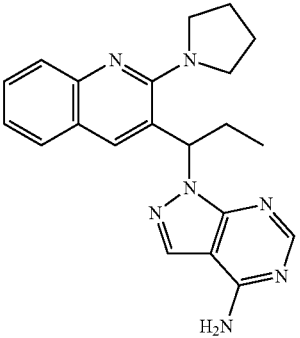 [SMILES: CCC(c1cc2ccccc2nc1N1CCCC1)n1ncc2c(N)ncnc21] | + | + | | | |
| 37 | 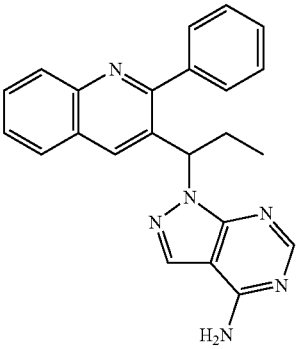 [SMILES: CCC(c1cc2ccccc2nc1-c1ccccc1)n1ncc2c(N)ncnc21] | + | + | | | |

-continued
| No. | Compound | PI3K δ IC₅₀ | PI3K γ IC₅₀ | PI3K α IC₅₀ | PI3K β IC₅₀ | B cell proliferation EC₅₀ |
|---|---|---|---|---|---|---|
| 38 | 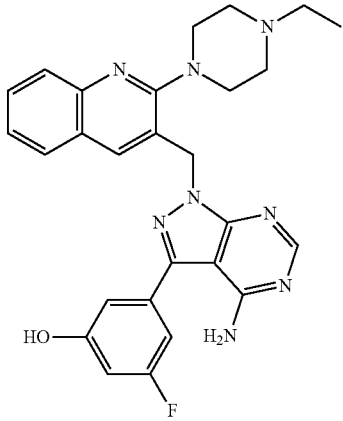 [SMILES: CCN1CCN(c2nc3ccccc3cc2Cn2nc(-c3cc(O)cc(F)c3)c3c(N)ncnc32)CC1] | +++ | + | + | +++ | +++ |
| 39 | 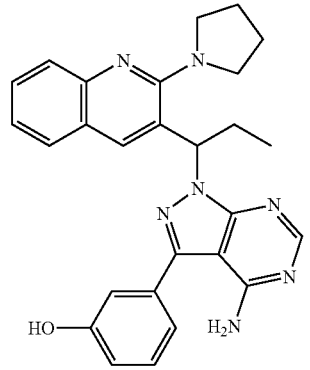 [SMILES: CCC(c1cc2ccccc2nc1N1CCCC1)n1nc(-c2cccc(O)c2)c2c(N)ncnc21] | +++ | + | + | + | +++ |
| 40 | 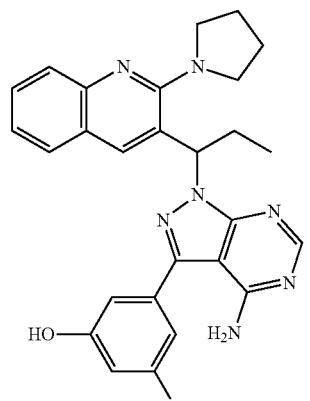 | +++ | ++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 41 | | +++ | | | | ++ |
| 42 | | +++ | | | | +++ |
| 43 | | +++ | + | + | ++ | ++ |
| 44 | | ++ | + | | | |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 45 | 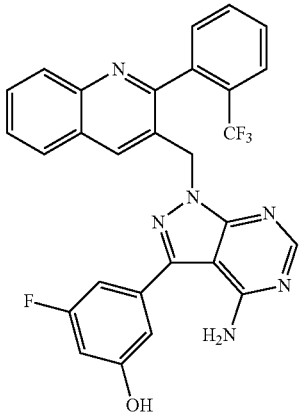 [SMILES: Nc1ncnc2c1c(-c1cc(O)cc(F)c1)nn2Cc1cc2ccccc2nc1-c1ccccc1C(F)(F)F] | +++ | ++ | | | +++ |
| 46 | 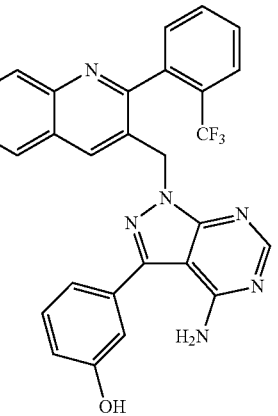 | +++ | ++ | | | ++ |
| 47 | 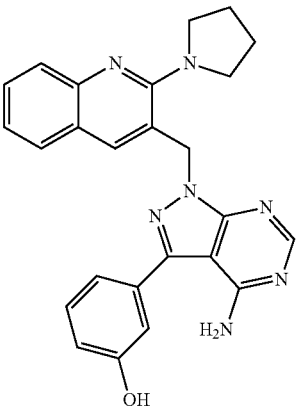 [SMILES: Nc1ncnc2c1c(-c1cccc(O)c1)nn2Cc1cc2ccccc2nc1N1CCCC1] | +++ | +++ | | | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 48 | 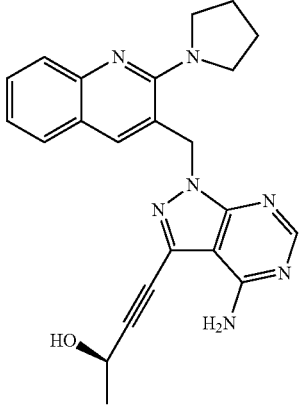 [SMILES: C[C@@H](O)C#Cc1nn(Cc2cc3ccccc3nc2N2CCCC2)c2ncnc(N)c12] | ++ | + | | | ++ |
| 49 | 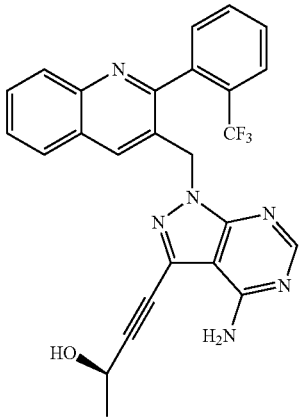 [SMILES: C[C@@H](O)C#Cc1nn(Cc2cc3ccccc3nc2-c2ccccc2C(F)(F)F)c2ncnc(N)c12] | ++ | + | | | ++ |
| 50 | 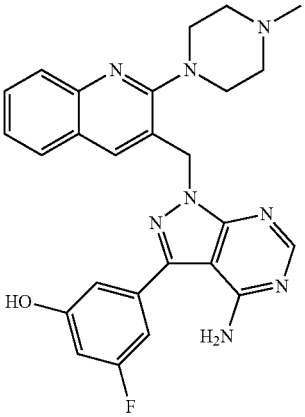 [SMILES: CN1CCN(c2nc3ccccc3cc2Cn2nc(-c3cc(O)cc(F)c3)c3c(N)ncnc32)CC1] | +++ | + | + | +++ | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 51 | | + | | | | |
| 52 | | +++ | ++ | ++ | ++ | +++ |
| 53 | | ++ | + | | | |
| 54 | | +++ | ++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 55 | | +++ | ++ | + | + | +++ |
| 56 | | +++ | +++ | + | + | +++ |
| 57 | | +++ | +++ | ++ | ++ | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 58 | 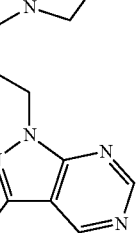 | ++ | ++ | | | |
| 59 | 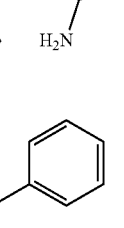 | +++ | ++ | + | + | +++ |
| 60 | 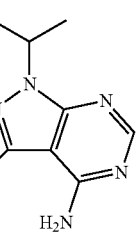 | + | + | | | + |
| 61 | 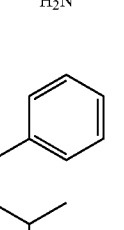 | +++ | +++ | | | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 62 | | ++ | ++ | | | |
| 63 | | +++ | ++ | + | + | +++ |
| 64 | | +++ | ++ | + | + | +++ |
| 65 | | +++ | +++ | ++ | ++ | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 66 | 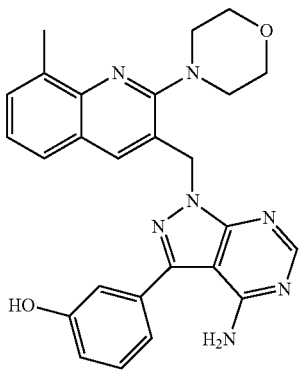 [SMILES: Cc1cccc2cc(Cn3nc(-c4cccc(O)c4)c4c(N)ncnc43)c(N3CCOCC3)nc12] | +++ | +++ | + | ++ | |
| 67 | 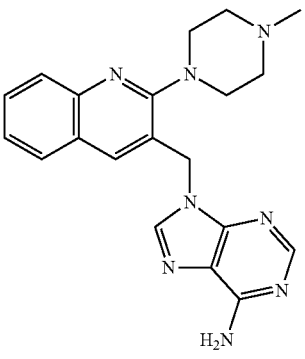 [SMILES: CN1CCN(c2nc3ccccc3cc2Cn2cnc3c(N)ncnc32)CC1] | + | + | + | + | |
| 68 | 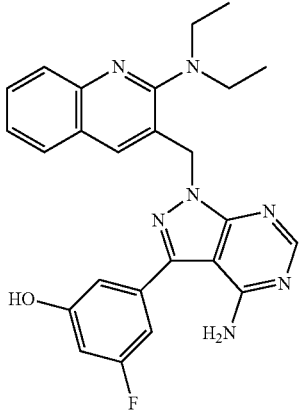 [SMILES: CCN(CC)c1nc2ccccc2cc1Cn1nc(-c2cc(O)cc(F)c2)c2c(N)ncnc21] | +++ | ++ | + | ++ | +++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 69 | 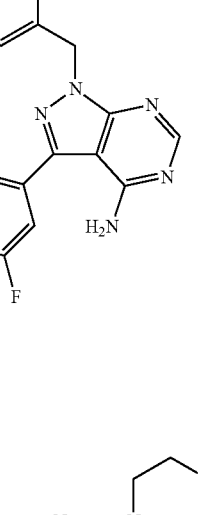 | +++ | + | + | + | +++ |
| 70 | 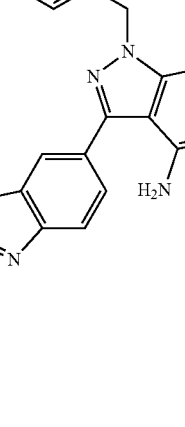 | +++ | ++ | ++ | +++ | +++ |
| 71 | 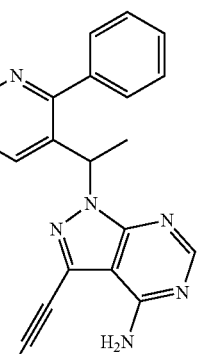 | +++ | + | + | + | ++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 72 | | +++ | + | + | ++ | +++ |
| 73 | | +++ | + | + | +++ | +++ |
| 74 | | +++ | + | + | ++ | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 75 | 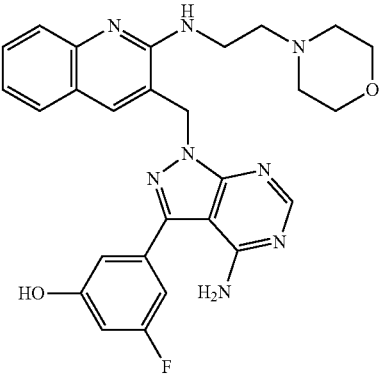 [SMILES: Nc1ncnc2c1c(-c1cc(O)cc(F)c1)nn2Cc1cc2ccccc2nc1NCCN1CCOCC1] | +++ | + | + | + | +++ |
| 76 | 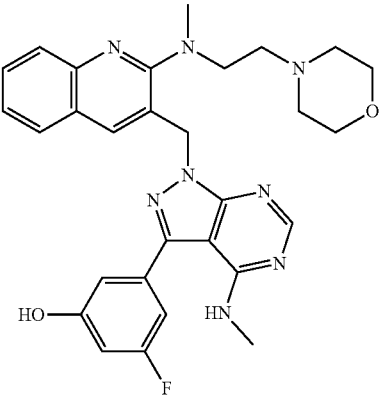 [SMILES: CNc1ncnc2c1c(-c1cc(O)cc(F)c1)nn2Cc1cc2ccccc2nc1N(C)CCN1CCOCC1] | + | + | + | + | |
| 77 | 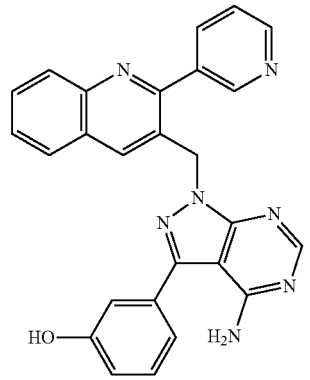 [SMILES: Nc1ncnc2c1c(-c1cccc(O)c1)nn2Cc1cc2ccccc2nc1-c1cccnc1] | +++ | + | + | + | +++ |
| 78 | 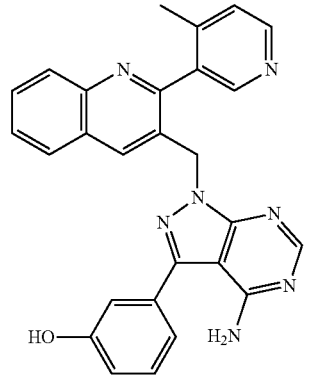 [SMILES: Cc1ccncc1-c1nc2ccccc2cc1Cn1nc(-c2cccc(O)c2)c2c(N)ncnc21] | +++ | + | + | + | ++ |

| No. | Compound | PI3K δ IC₅₀ | PI3K γ IC₅₀ | PI3K α IC₅₀ | PI3K β IC₅₀ | B cell proliferation EC₅₀ |
|---|---|---|---|---|---|---|
| 79 | | +++ | +++ | +++ | + | +++ |
| 80 | | +++ | +++ | +++ | +++ | +++ |
| 81 | | +++ | + | + | + | ++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 82 | | +++ | + | + | + | +++ |
| 83 | | +++ | +++ | + | + | +++ |
| 84 | | +++ | +++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 85 | | +++ | +++ | ++ | + | +++ |
| 86 | | +++ | +++ | + | + | ++ |
| 87 | | + | + | + | + | |
| 88 | | ++ | + | + | + | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 89 | | ++ | + | + | + | |
| 90 | | ++ | + | + | + | |
| 91 | | ++ | ++ | + | + | |
| 92 | | +++ | +++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 93 | | +++ | ++ | + | + | |
| 94 | | +++ | +++ | + | + | ++ |
| 95 | | +++ | + | + | + | |
| 96 | | +++ | ++ | + | + | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 97 | | +++ | ++ | + | ++ | |
| 98 | | +++ | +++ | + | + | |
| 99 | | +++ | +++ | ++ | ++ | |
| 100 | | + | | | | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 101 | 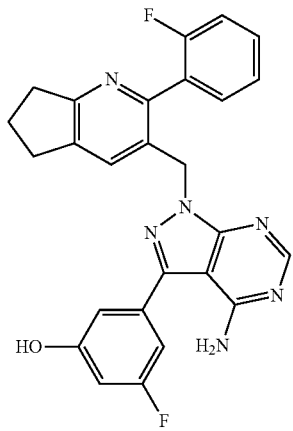 [SMILES: Nc1ncnc2c1c(-c1cc(O)cc(F)c1)nn2Cc1cc2c(nc1-c1ccccc1F)CCC2] | ++ | + | + | + | ++ |
| 102 | 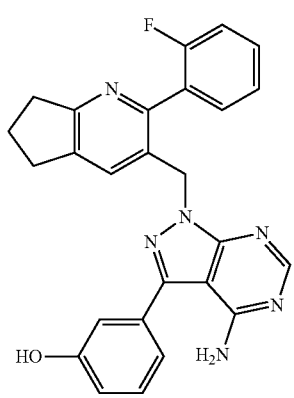 [SMILES: Nc1ncnc2c1c(-c1cccc(O)c1)nn2Cc1cc2c(nc1-c1ccccc1F)CCC2] | + | | | | |
| 103 | 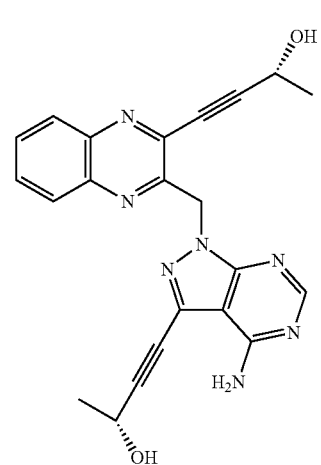 [SMILES: C[C@@H](O)C#Cc1nc2ccccc2nc1Cn1nc(C#C[C@@H](C)O)c2c(N)ncnc21] | + | + | | | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 104 | 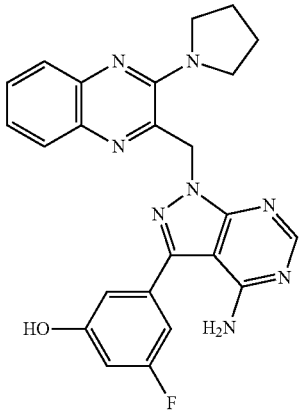 [SMILES: Nc1ncnc2c1c(-c1cc(O)cc(F)c1)nn2Cc1nc2ccccc2nc1N1CCCC1] | +++ | ++ | + | + | +++ |
| 105 | 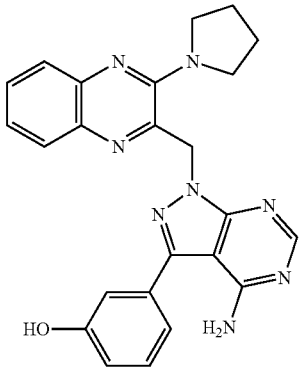 [SMILES: Nc1ncnc2c1c(-c1cccc(O)c1)nn2Cc1nc2ccccc2nc1N1CCCC1] | +++ | ++ | + | + | ++ |
| 106 | 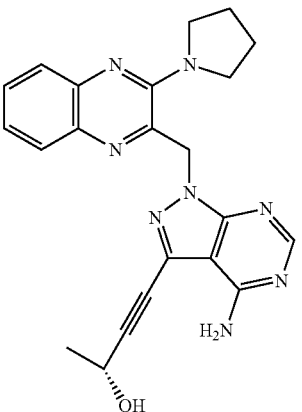 [SMILES: C[C@@H](O)C#Cc1nn(Cc2nc3ccccc3nc2N2CCCC2)c2ncnc(N)c12] | ++ | + | | | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 107 | | +++ | + | + | + | +++ |
| 108 | | ++ | + | + | + | |
| 109 | | ++ | + | + | + | |
| 110 | | ++ | + | + | + | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 111 | | ++ | + | + | + | |
| 112 | | +++ | ++ | + | + | |
| 113 | | +++ | + | + | + | |
| 114 | | +++ | + | + | + | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 115 | | ++ | + | + | + | |
| 116 | | ++ | + | + | + | |
| 117 | | +++ | + | + | + | |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 118 | 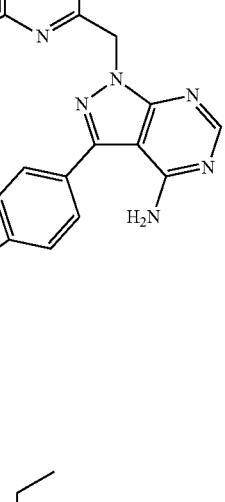 | +++ | ++ | + | + | |
| 119 |  | +++ | +++ | ++ | + | |
| 120 | 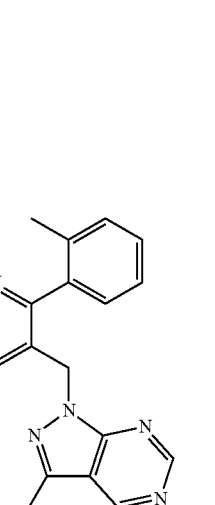 | | | | + | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 121 | | + | | | | |
| 122 | | + | | | | |
| 123 | | + | | | | |
| 124 | | + | | | | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 125 | 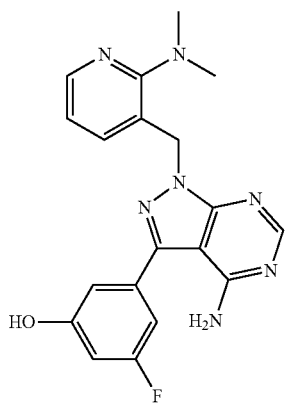 [SMILES: CN(C)c1ncccc1Cn1nc(-c2cc(O)cc(F)c2)c2c(N)ncnc21] | + | | | | |
| 126 | 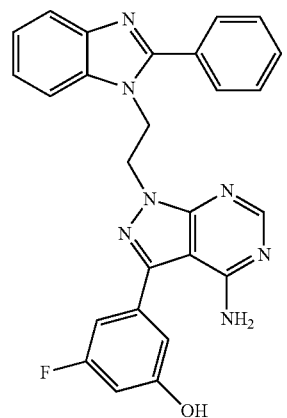 [SMILES: Nc1ncnc2c1c(-c1cc(O)cc(F)c1)nn2CCn1c(-c2ccccc2)nc2ccccc21] | + | | | | |
| 127 | 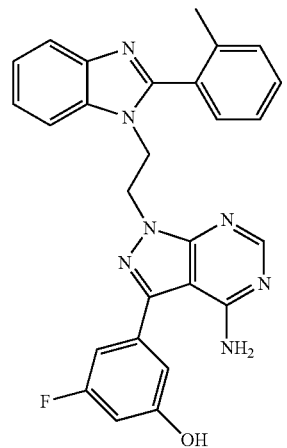 [SMILES: Cc1ccccc1-c1nc2ccccc2n1CCn1nc(-c2cc(O)cc(F)c2)c2c(N)ncnc21] | +++ | + | | | ++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 128 | 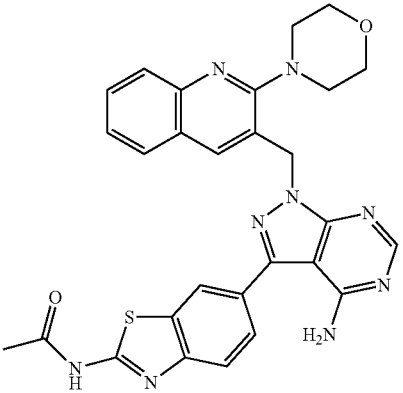 [SMILES: CC(=O)Nc1nc2ccc(-c3nn(Cc4cc5ccccc5nc4N4CCOCC4)c4ncnc(N)c34)cc2s1] | +++ | +++ | +++ | | +++ |
| 129 | 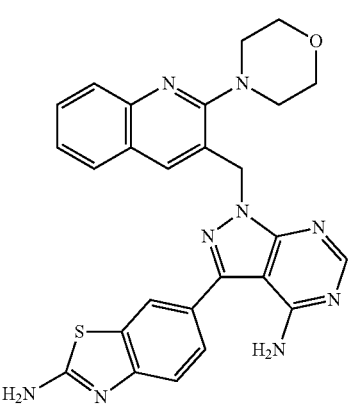 [SMILES: Nc1nc2ccc(-c3nn(Cc4cc5ccccc5nc4N4CCOCC4)c4ncnc(N)c34)cc2s1] | +++ | +++ | +++ | ++ | +++ |
| 130 | 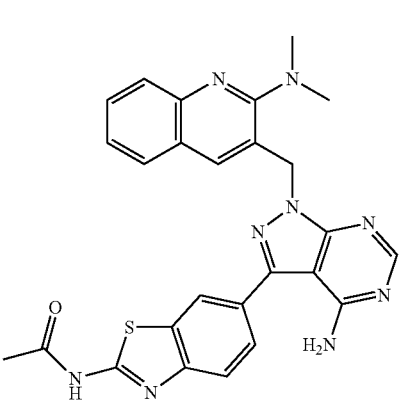 [SMILES: CC(=O)Nc1nc2ccc(-c3nn(Cc4cc5ccccc5nc4N(C)C)c4ncnc(N)c34)cc2s1] | +++ | +++ | +++ | +++ | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 131 | | +++ | +++ | ++ | + | ++ |
| 132 | | +++ | +++ | +++ | ++ | +++ |
| 133 | | +++ | +++ | + | + | ++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 134 | | +++ | +++ | + | + | ++ |
| 135 | | +++ | +++ | ++ | + | +++ |
| 136 | | +++ | +++ | + | + | ++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 137 | | +++ | +++ | + | + | ++ |
| 138 | | +++ | +++ | + | + | ++ |
| 139 | | +++ | +++ | +++ | +++ | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 140 | | +++ | +++ | +++ | ++ | +++ |
| 141 | | +++ | +++ | ++ | + | +++ |
| 142 | | +++ | +++ | ++ | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 143 | | +++ | +++ | ++ | + | +++ |
| 144 | | +++ | +++ | ++ | + | +++ |
| 145 | | +++ | +++ | + | + | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 146 | | +++ | +++ | + | + | ++ |
| 147 | | +++ | +++ | ++ | | ++ |
| 148 | | +++ | +++ | + | | +++ |

-continued

| No. | Compound | PI3K δ IC₅₀ | PI3K γ IC₅₀ | PI3K α IC₅₀ | PI3K β IC₅₀ | B cell proliferation EC₅₀ |
|---|---|---|---|---|---|---|
| 149 | | +++ | +++ | | + | +++ |
| 150 | | +++ | +++ | | + | +++ |
| 151 | | +++ | +++ | | ++ | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 152 | 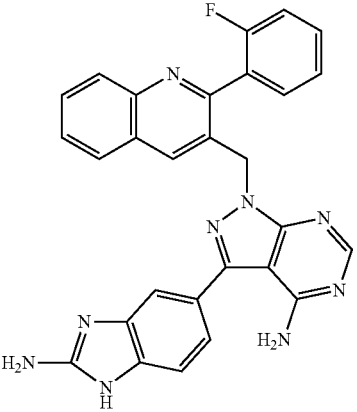 [SMILES: Nc1nc2cc(-c3nn(Cc4cc5ccccc5nc4-c4ccccc4F)c4ncnc(N)c34)ccc2[nH]1] | +++ | +++ | ++ | + | ++ |
| 153 | 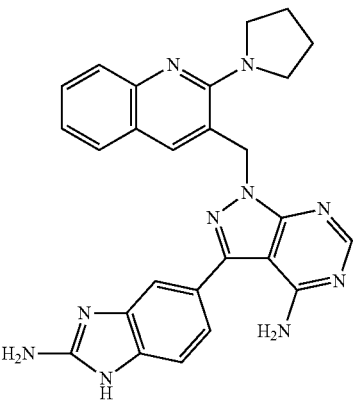 [SMILES: Nc1nc2cc(-c3nn(Cc4cc5ccccc5nc4N4CCCC4)c4ncnc(N)c34)ccc2[nH]1] | +++ | +++ | +++ | ++ | ++ |
| 154 | 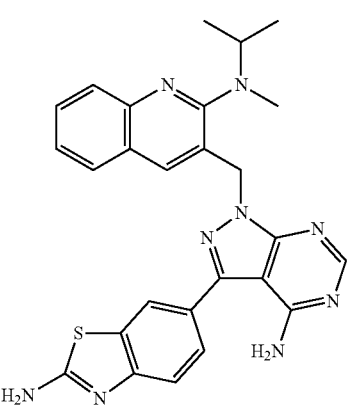 [SMILES: CC(C)N(C)c1nc2ccccc2cc1Cn1nc(-c2ccc3nc(N)sc3c2)c2c(N)ncnc21] | +++ | ++ | +++ | | +++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 155 | | +++ | + | + | | ++ |
| 156 | | +++ | ++ | + | + | ++ |
| 157 | | ++ | + | + | + | + |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 158 | | + | + | + | + | + |
| 159 | | +++ | +++ | ++ | + | + |
| 160 | | ++ | | + | + | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 161 | 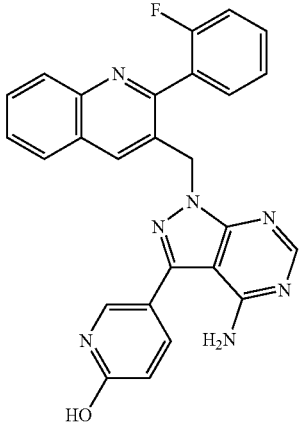 [SMILES: Nc1ncnc2c1c(-c1ccc(O)nc1)nn2Cc1cc2ccccc2nc1-c1ccccc1F] | | | + | + | |
| 162 | 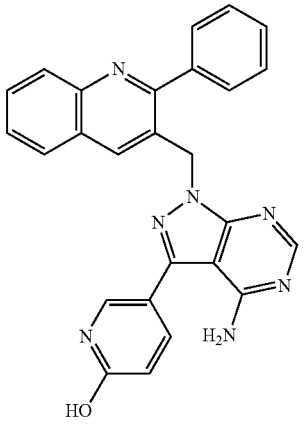 [SMILES: Nc1ncnc2c1c(-c1ccc(O)nc1)nn2Cc1cc2ccccc2nc1-c1ccccc1] | | | + | + | |
| 163 | 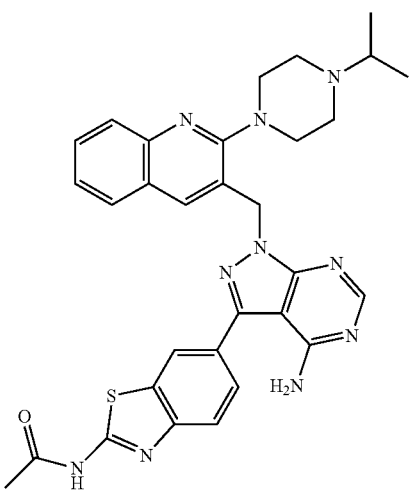 [SMILES: CC(=O)Nc1nc2ccc(-c3nn(Cc4cc5ccccc5nc4N4CCN(C(C)C)CC4)c4ncnc(N)c34)cc2s1] | | | ++ | +++ | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 164 | | | | +++ | +++ | |
| 165 | | +++ | + | + | ++ | +++ |
| 166 | | +++ | ++ | ++ | + | +++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 167 | 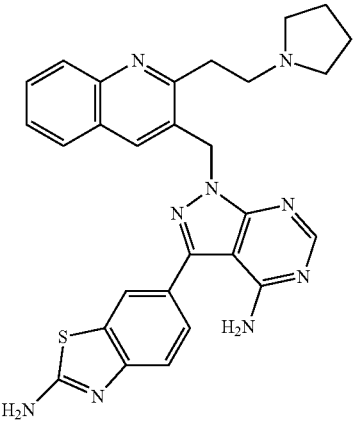 [SMILES: Nc1nc2ccc(-c3nn(Cc4cc5ccccc5nc4CCN4CCCC4)c4ncnc(N)c34)cc2s1] | +++ | +++ | +++ | ++ | +++ |
| 168 | 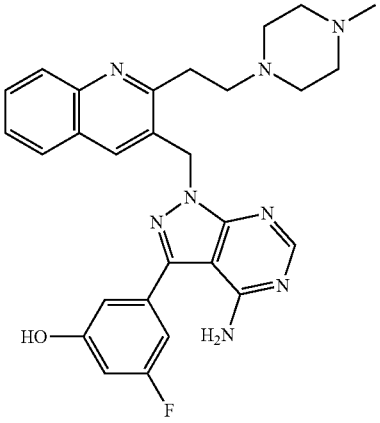 [SMILES: CN1CCN(CCc2nc3ccccc3cc2Cn2nc(-c3cc(O)cc(F)c3)c3c(N)ncnc32)CC1] | +++ | + | + | ++ | +++ |
| 169 | 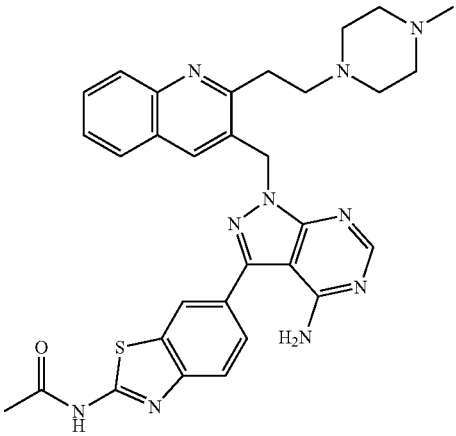 [SMILES: CC(=O)Nc1nc2ccc(-c3nn(Cc4cc5ccccc5nc4CCN4CCN(C)CC4)c4ncnc(N)c34)cc2s1] | +++ | ++ | ++ | ++ | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 170 | 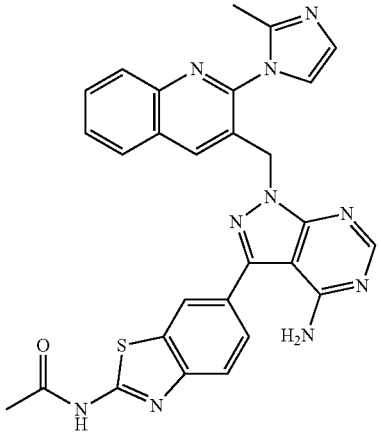 [SMILES: CC(=O)Nc1nc2ccc(-c3nn(Cc4cc5ccccc5nc4-n4ccnc4C)c4ncnc(N)c34)cc2s1] | +++ | ++ | + | + | |
| 171 | 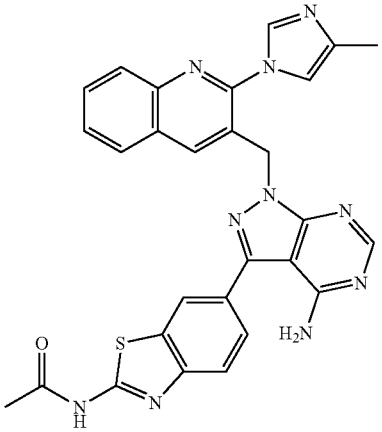 [SMILES: CC(=O)Nc1nc2ccc(-c3nn(Cc4cc5ccccc5nc4-n4cnc(C)c4)c4ncnc(N)c34)cc2s1] | +++ | +++ | ++ | + | +++ |
| 172 | 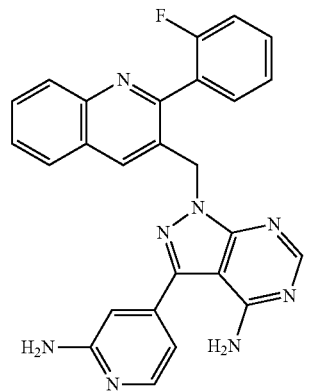 [SMILES: Nc1cc(-c2nn(Cc3cc4ccccc4nc3-c3ccccc3F)c3ncnc(N)c23)ccn1] | + | | + | + | |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 173 | 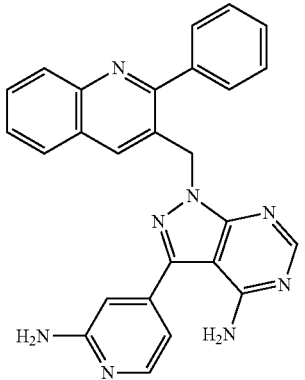 [SMILES: Nc1cc(-c2nn(Cc3cc4ccccc4nc3-c3ccccc3)c3ncnc(N)c23)ccn1] | + |  | + | + |  |
| 174 | 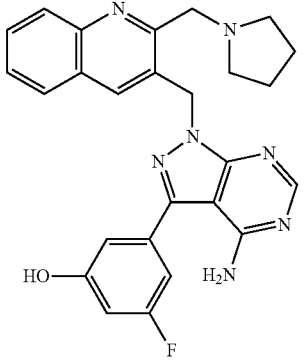 [SMILES: Nc1ncnc2c1c(-c1cc(O)cc(F)c1)nn2Cc1cc2ccccc2nc1CN1CCCC1] | +++ | + | +++ | +++ |  |
| 175 | 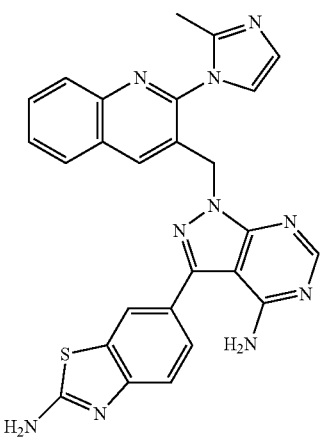 [SMILES: Cc1nccn1-c1nc2ccccc2cc1Cn1nc(-c2ccc3nc(N)sc3c2)c2c(N)ncnc21] | +++ | ++ | + | +++ |  |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 176 | 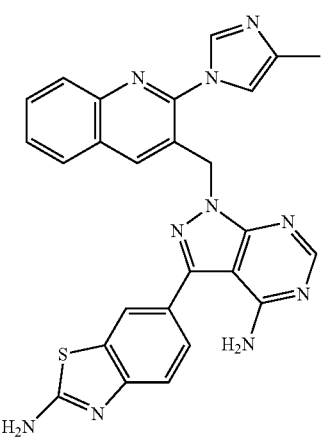 [SMILES: Cc1cn(-c2nc3ccccc3cc2Cn2nc(-c3ccc4nc(N)sc4c3)c3c(N)ncnc32)cn1] | +++ | | ++ | + | +++ |
| 177 | 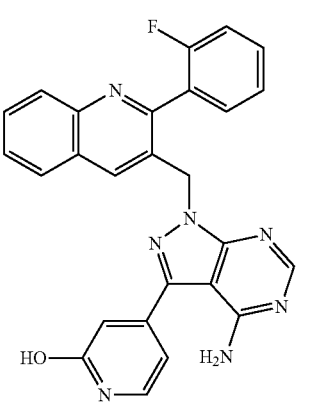 [SMILES: Nc1ncnc2c1c(-c1ccnc(O)c1)nn2Cc1cc2ccccc2nc1-c1ccccc1F] | + | | + | + | |
| 178 | 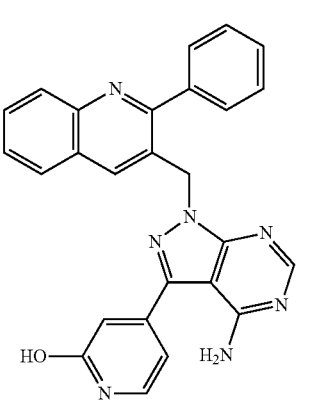 [SMILES: Nc1ncnc2c1c(-c1ccnc(O)c1)nn2Cc1cc2ccccc2nc1-c1ccccc1] | + | | + | + | |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 179 | | ++ | + | + | + | ++ |
| 180 | | +++ | ++ | + | + | ++ |
| 181 | | +++ | +++ | + | + | ++ |

-continued

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 182 | | +++ | +++ | + | | ++ |
| 183 | | ++ | ++ | + | | |
| 184 | | +++ | +++ | + | + | ++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 185 | 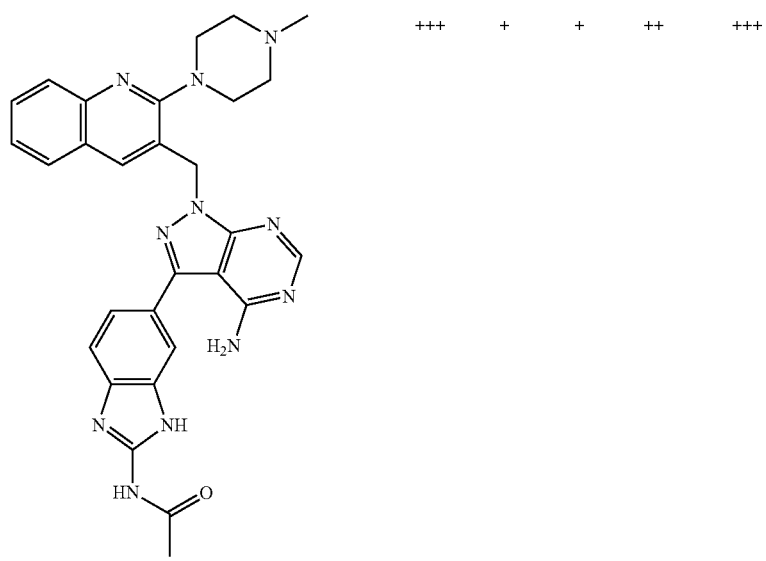 | +++ | + | + | ++ | +++ |
| 186 | 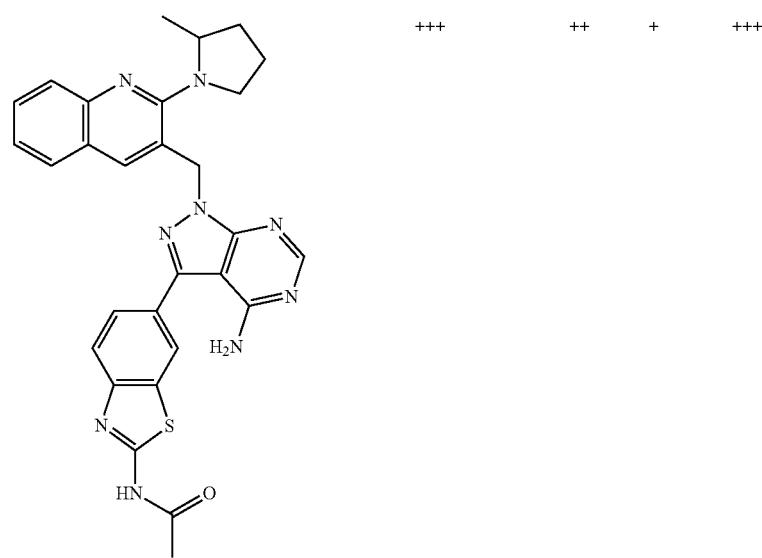 | +++ |  | ++ | + | +++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 187 | 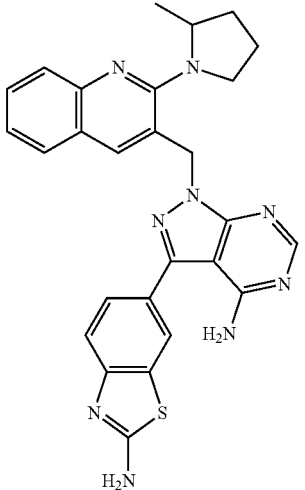 [SMILES: CC1CCCN1c1nc2ccccc2cc1Cn1nc(-c2ccc3nc(N)sc3c2)c2c(N)ncnc21] | +++ | | +++ | ++ | +++ |
| 188 | 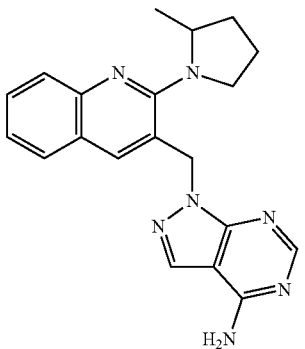 [SMILES: CC1CCCN1c1nc2ccccc2cc1Cn1ncc2c(N)ncnc21] | + | | + | + | |
| 189 | 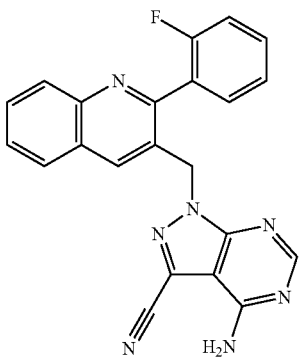 [SMILES: N#Cc1nn(Cc2cc3ccccc3nc2-c2ccccc2F)c2ncnc(N)c12] | + | | + | + | |
| 190 | 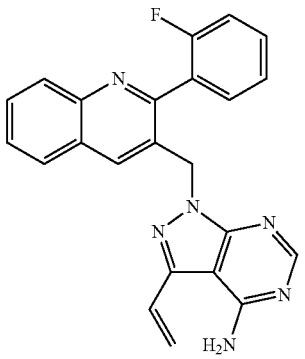 [SMILES: C=Cc1nn(Cc2cc3ccccc3nc2-c2ccccc2F)c2ncnc(N)c12] | + | + | + | + | |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 191 | 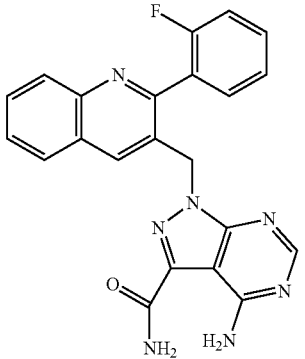 [SMILES: NC(=O)c1nn(Cc2cc3ccccc3nc2-c2ccccc2F)c2ncnc(N)c12] | ++ | + | + | + | |
| 192 | 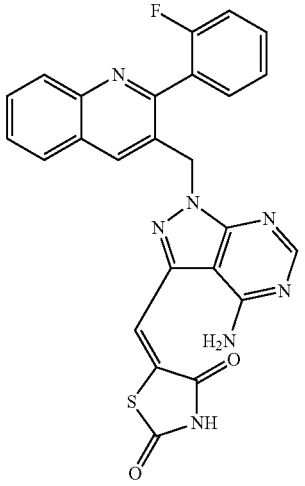 [SMILES: Nc1ncnc2c1c(/C=C1/SC(=O)NC1=O)nn2Cc1cc2ccccc2nc1-c1ccccc1F] | +++ | +++ | + | + | ++ |
| 193 | 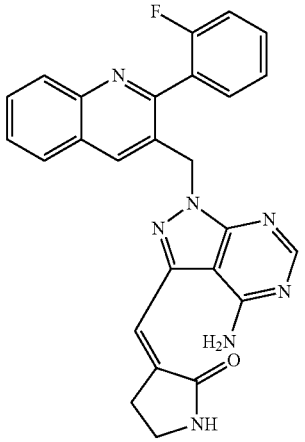 [SMILES: Nc1ncnc2c1c(/C=C1/CCNC1=O)nn2Cc1cc2ccccc2nc1-c1ccccc1F] | + | + | + | + | |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 194 | 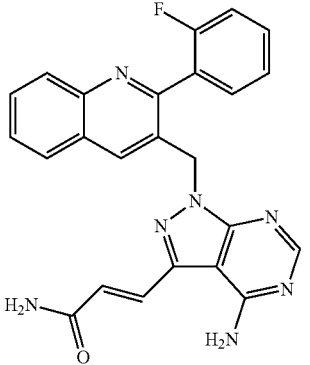 [SMILES: NC(=O)/C=C/c1nn(Cc2cc3ccccc3nc2-c2ccccc2F)c2ncnc(N)c12] | ++ | + | + | + | |
| 195 | 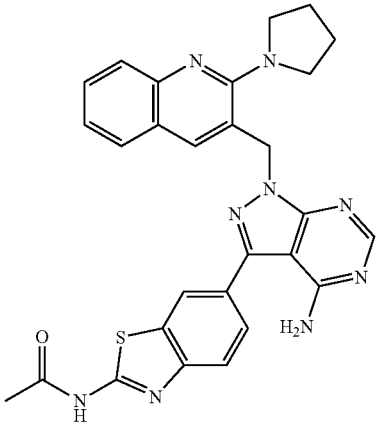 [SMILES: CC(=O)Nc1nc2ccc(-c3nn(Cc4cc5ccccc5nc4N4CCCC4)c4ncnc(N)c34)cc2s1] | +++ | +++ | +++ | + | +++ |
| 196 | 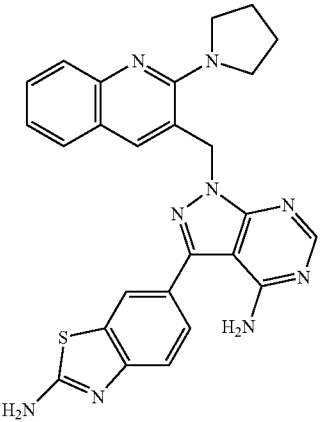 [SMILES: Nc1nc2ccc(-c3nn(Cc4cc5ccccc5nc4N4CCCC4)c4ncnc(N)c34)cc2s1] | +++ | +++ | ++ | + | ++ |

-continued
| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 197 | 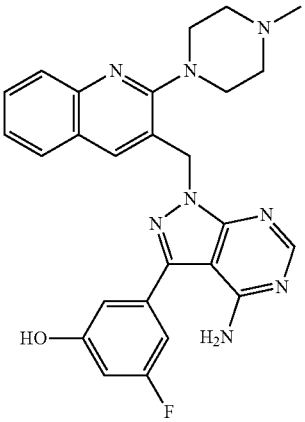 [SMILES: CN1CCN(c2nc3ccccc3cc2Cn2nc(-c3cc(O)cc(F)c3)c3c(N)ncnc32)CC1] | +++ | + | + | ++ | +++ |
| 198 | 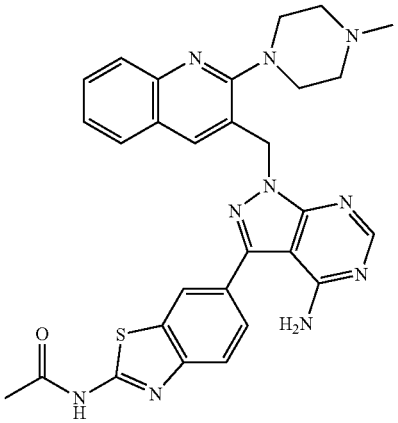 [SMILES: CC(=O)Nc1nc2ccc(-c3nn(Cc4cc5ccccc5nc4N4CCN(C)CC4)c4ncnc(N)c34)cc2s1] | +++ | ++ | ++ | +++ | +++ |
| 199 | 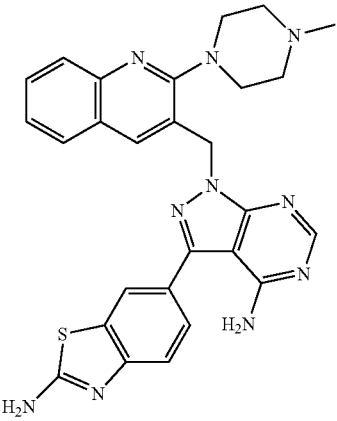 [SMILES: CN1CCN(c2nc3ccccc3cc2Cn2nc(-c3ccc4nc(N)sc4c3)c3c(N)ncnc32)CC1] | +++ | +++ | ++ | +++ | +++ |

| No. | Compound | PI3K δ IC$_{50}$ | PI3K γ IC$_{50}$ | PI3K α IC$_{50}$ | PI3K β IC$_{50}$ | B cell proliferation EC$_{50}$ |
|---|---|---|---|---|---|---|
| 200 | 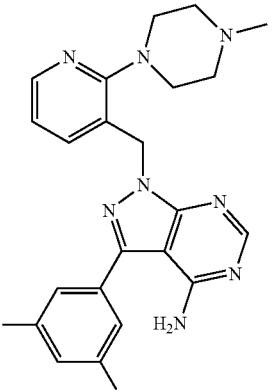 | +++ | + | + | | ++ |
Additional compounds of the invention are described below:
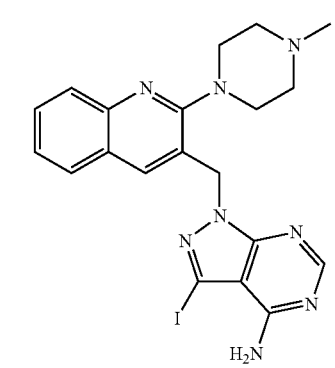
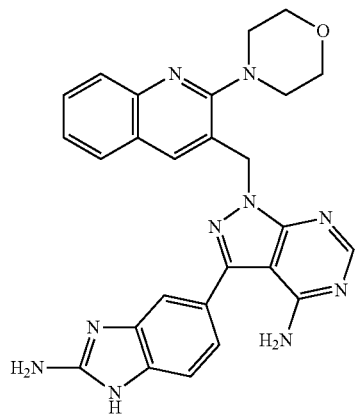
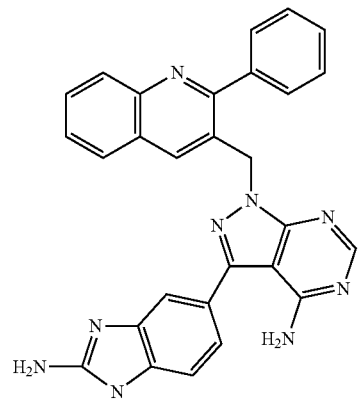
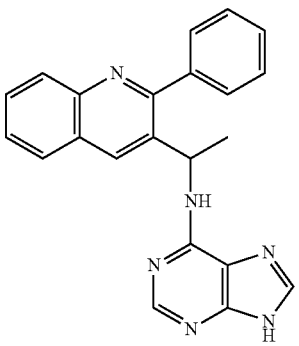
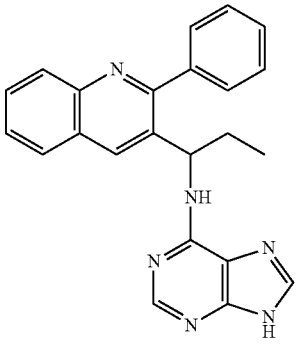

-continued

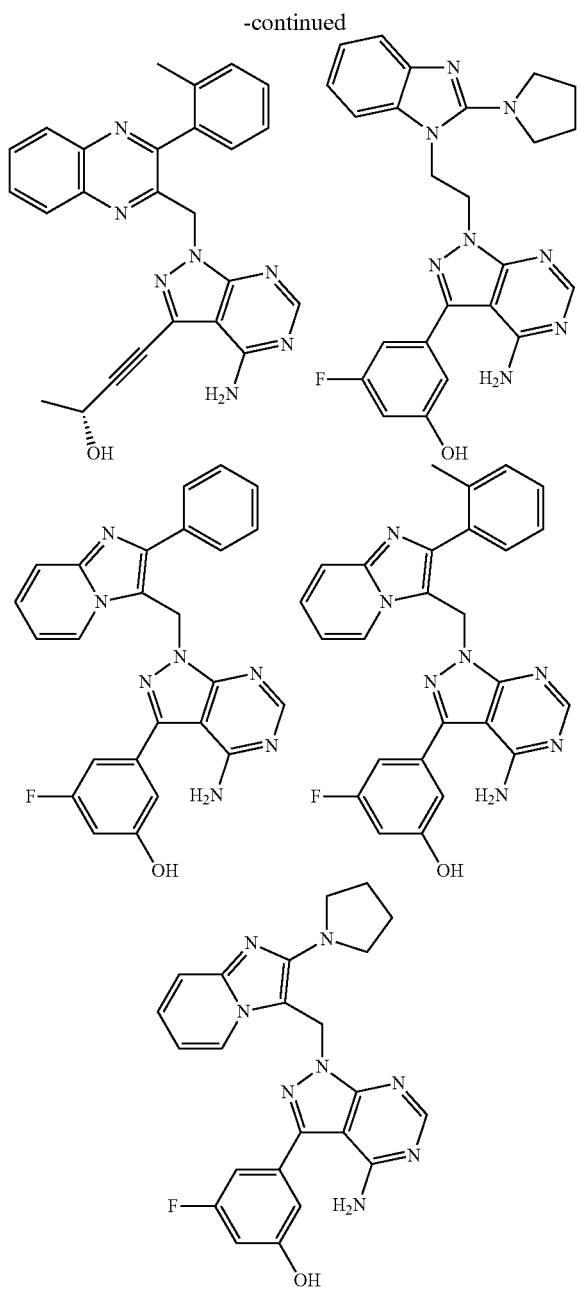

Preparation of the Compounds of the Invention

Compounds of the invention may be synthesized by the general synthetic Schemes 1 and 2 illustrated below. In general synthetic scheme 1, an aromatic group comprising two reactive groups X and Y is first coupled to the $R^9$ group via the reactive group X. The introduction of the linker L and the heteroaromatic moiety Z is performed in a subsequent step. In general scheme 2, the linker L and heteroaromatic moiety Z are first coupled to the aromatic group comprising two reactive groups X and Y. The coupling step to introduce the $R^9$ moiety is performed subsequently.

Varioius reagents may be used to perform the coupling reactions necessary to introduce the $R^9$, L and Z moieties. X and Y are reactive groups which can react with precursors of $R^9$ and L or Z moieties. Alternatively, X and Y are latent or protected reaction groups which are converted to reactive groups during or prior to the coupling reactions. Various coupling reactions may be suitable for this purpose. Some known types of coupling reactions which can involve aromatic ring compounds include the Heck reactions and Suzuki reactions. Such reactions are described, for example, in N. Miyaura and A. Suzuki, Chem. Rev. 1995, 95, 2457-2483.

For example, X may be a halogen atom. If $R^9$ comprises a primary or secondary amino group, it may be attached to the aryl group via an amination reaction. Such a reaction may be performed in the presence of a base and/or a catalyst such as a palladium catalyst. In other embodiments, X is a halogen atom and $R^9$ is an aryl group. A coupling may be effected between X and a precursor compound of $R^9$, such as a boronic acid (Suzuki coupling) or stannane precursor (Stille coupling).

General Scheme 1

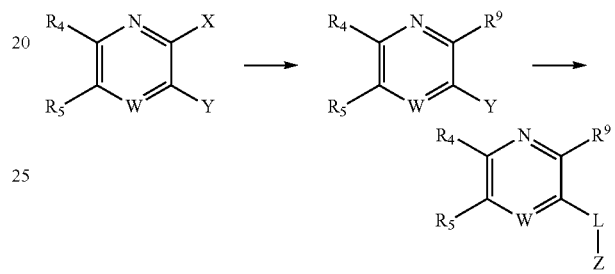

General Scheme 2

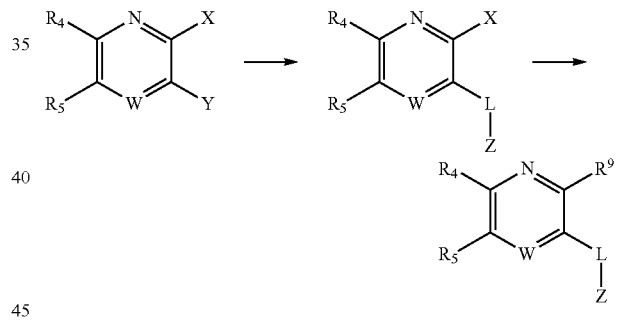

The synthesis of several compounds of the invention is illustrated in Synthetic Schemes 3-15. The general synthetic strategy employed in these schemes is believed to be widely applicable to synthesize the compounds of the invention, and the specific compounds and reagents describe serve merely to exemplify the general synthetic approaches disclosed herein. Scheme 3 shows the preparation of a compound of the invention by reduction of a starting aldehyde 3a to an alcohol in step 1. Such a reaction may be performed, for example, by sodium borohydride reduction in methanol. In step 2, compound 3b is coupled to pyrrolidine in the presence of a solvent such as 1,4-dioxane. The alcohol 3c is converted to a reactive halide in step 3 by reaction with a reagent such as $CBr_4/PPh_3$ in a solvent such as dichloromethane. A heterocyclic moiety such as a pyrazolopyrimide (e.g. 3-iodo-1H-pyrazolo[3,4-d]pyrimidin-4-amine) may be coupled to the halide 3d (e.g. in a base such as potassium carbonate and a solvent such as dimethylformamide) to form the compound 3e in step 4. In step 5, the pyrazolopyrimidine subunit is further derivatized via a reaction such as a Suzuki coupling (e.g. using $Pd(PPh_3)_4$ as a catalyst) to yield compound 3f.

Scheme 3: Synthesis of 3-(4-amino-1-((2-(pyrrolidin-1-yl)quinolin-3-yl)methyl)-1H-pyrazolo[3,4-d]pyrimidin-3-yl)-5-fluorophenol (3f)

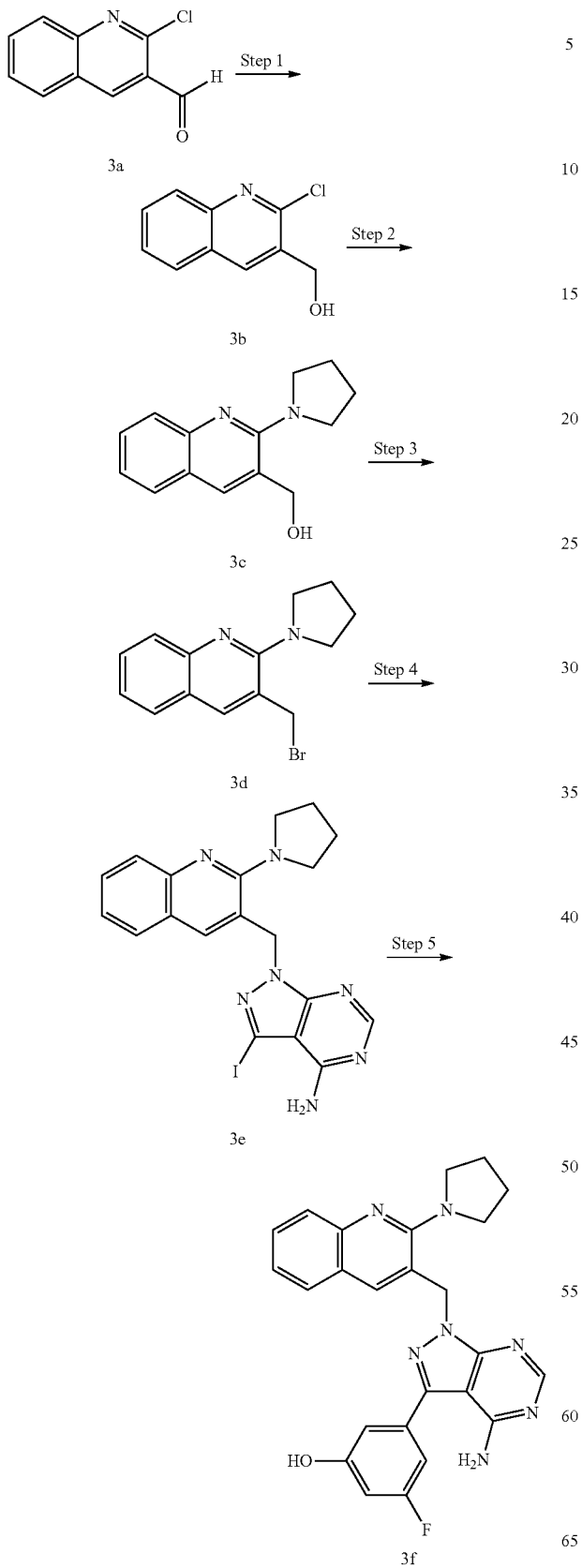

Scheme 4 shows an alternative synthesis of the compound 3f. In Step 1, a starting aldehyde 3a is reduced to an alcohol. Such a reaction may be performed, for example, by sodium borohydride reduction in methanol. In Step 2, compound 3b is converted to a reactive halide 4a by reaction with a reagent such as CBr$_4$/PPh$_3$ in a solvent such as dichloromethane. Coupling to a heterocyclic moiety such as a pyrazolopyrimide (e.g. 3-iodo-1H-pyrazolo[3,4-d]pyrimidin-4-amine) is performed in step 3, for example in a base such as potassium carbonate and a solvent such as dimethylformamide) to yield compound 4b. Compound 4b is then coupled to pyrrolidine in Step 4 in the presence of a solvent such as 1,4-dioxane to produce compound 3e. In step 5, compound 3e is further derivatized via a reaction such as a Suzuki coupling (e.g. using Pd(PPh$_3$)$_4$ as a catalyst) to yield compound 3f.

Scheme 4: Synthesis of 3-(4-amino-1-((2-(pyrrolidin-1-yl)quinolin-3-yl)methyl)-1H-pyrazolo[3,4-d]pyrimidin-3-yl)-5-fluorophenol (3f)

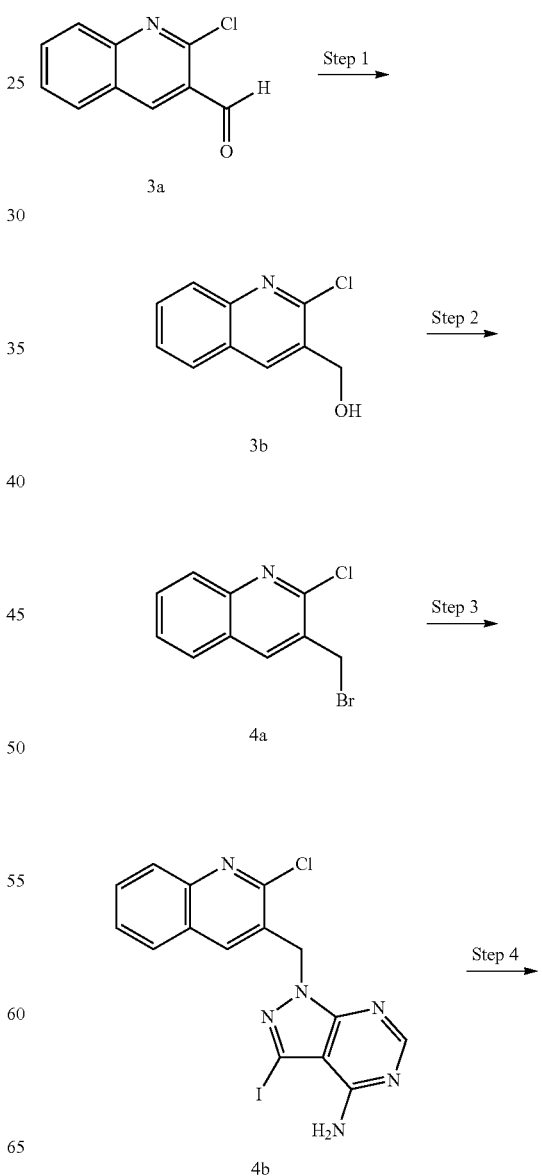

301
-continued

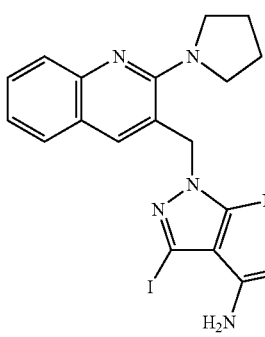

3e

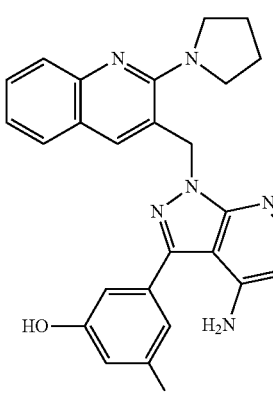

3f

Scheme 5 shows an additional alternative synthesis of the compound 3f. In step 1, a starting aldehyde 3a is reduced to an alcohol. Such a reaction may be performed, for example, by sodium borohydride reduction in methanol. In step 2, compound 3b is converted to a reactive halide 4b by reaction with a reagent such as $CBr_4/PPh_3$ in a solvent such as dichloromethane. Coupling to a heterocyclic moiety such as a derivatized pyrazolopyrimide (e.g. 3-(3-fluoro-5-methoxyphenyl)-1H-pyrazolo[3,4-d]pyrimidin-4-amine) is performed in step 3, for example in a base such as potassium t-butoxide and a solvent such as dimethylformamide) to yield compound 5a. If necessary, the resulting compound 5a is deprotected, for example by removal of a methoxy group by a reagent such as $BBr_3$ in dichloromethane. The resulting compound 5b is then coupled to pyrrolidine in the presence of a solvent such as 1,4-dioxane to yield compound 3f.

Scheme 5: Synthesis of 3-(4-amino-1-((2-(pyrrolidin-1-yl)quinolin-3-yl)methyl)-1H-pyrazolo[3,4-d]pyrimidin-3-yl)-5-fluorophenol (3f)

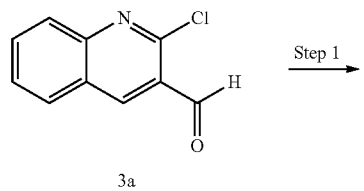

3a

302
-continued

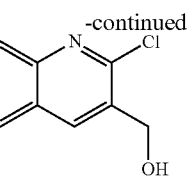

3b

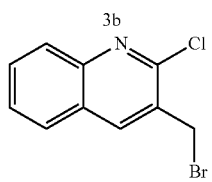

4a

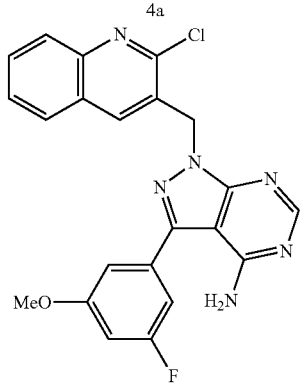

5a

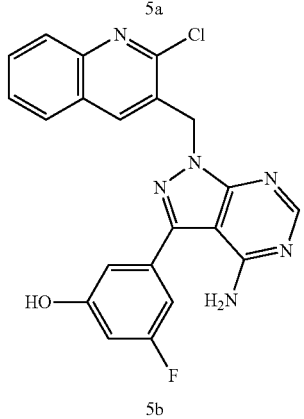

5b

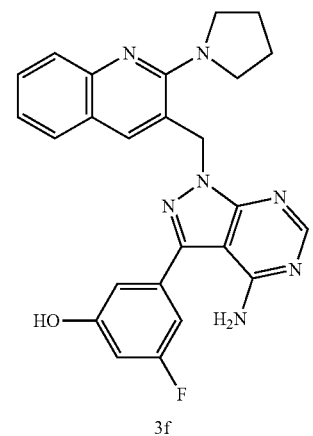 [SMILES: Nc1ncnc2c1c(-c1cc(O)cc(F)c1)nn2Cc1cc2ccccc2nc1N1CCCC1]

3f

Scheme 6 shows the preparation of a compound of the invention by reduction of a starting aldehyde 6a to an alcohol in step 1. Such a reaction may be performed, for example, by sodium borohydride reduction in methanol. In step 2, compound 6b is coupled to an aryl group via, for example, a Suzuki coupling. In the example shown, o-tolylboronic acid is reacted with 6b in the presence of Pd(PPh₃)₄, a base such as Na₂CO₃ and a solvent such as DMF. The resulting alcohol 6c is converted to a reactive halide in step 3 by reaction with a reagent such as CBr₄/PPh₃ in a solvent such as dichloromethane. A heterocyclic moiety such as a pyrazolopyrimide (e.g. 3-iodo-1H-pyrazolo[3,4-d]pyrimidin-4-amine) may be coupled to the halide 6d (e.g. in a base such as potassium carbonate and a solvent such as dimethylformamide) to form the compound 6e in step 4. In step 5, the pyrazolopyrimidine subunit is further derivatized via a reaction such as a Suzuki coupling (e.g. using Pd(PPh₃)₄ as a catalyst) to yield compound 6f.

Scheme 6: Synthesis of 3-(4-amino-1-((2-o-tolylquinolin-3-yl)methyl)-1H-pyrazolo[3,4-d]pyrimidin-3-yl)-5-fluorophenol (6f)

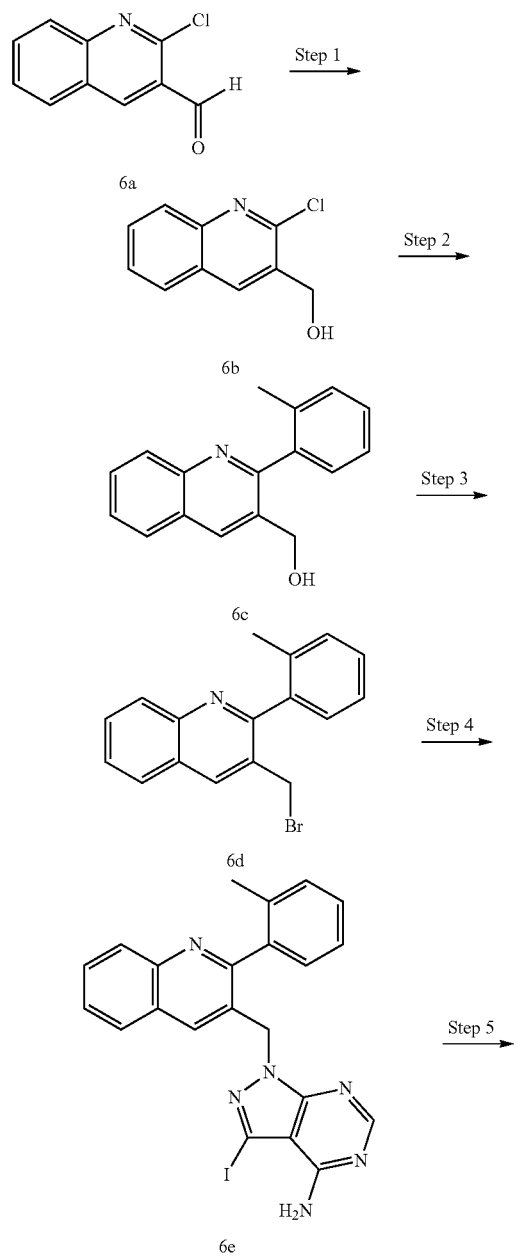

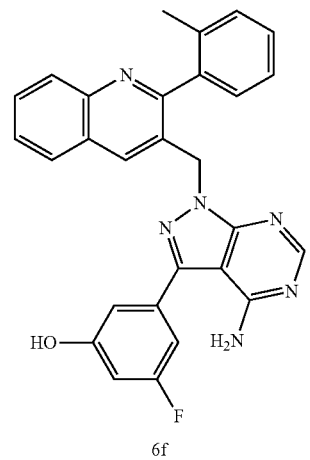 [SMILES: Cc1ccccc1-c1nc2ccccc2cc1Cn1nc(-c2cc(O)cc(F)c2)c2c(N)ncnc21]

Scheme 7 shows an alternative synthesis of the compound 6f. In step 1, a starting aldehyde 6a is reduced to an alcohol. Such a reaction may be performed, for example, by sodium borohydride reduction in methanol. In step 2, compound 6b is converted to a reactive halide 7a by reaction with a reagent such as CBr₄/PPh₃ in a solvent such as dichloromethane. Coupling to a heterocyclic moiety such as a derivatized pyrazolopyrimide (e.g. 3-(3-fluoro-5-methoxyphenyl)-1H-pyrazolo[3,4-d]pyrimidin-4-amine) is performed in step 3, for example in a base such as potassium t-butoxide and a solvent such as dimethylformamide). The resulting compound 7b is then coupled to an aryl group via, for example, a Suzuki coupling. In the example shown, o-tolylboronic acid is reacted with 7b in the presence of Pd(PPh₃)₄, a base such as Na₂CO₃ and a solvent such as DMF. If necessary, the resulting compound 7c is deprotected, for example by removal of a methoxy group by a reagent such as BBr₃ in dichloromethane to yield compound 6f.

Scheme 7: Synthesis of 3-(4-amino-1-((2-o-tolylquinolin-3-yl)methyl)-1H-pyrazolo[3,4-d]pyrimidin-3-yl)-5-fluorophenol (6f)

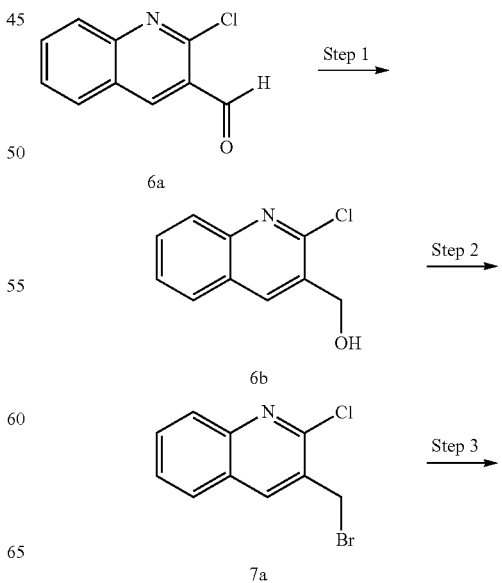

-continued

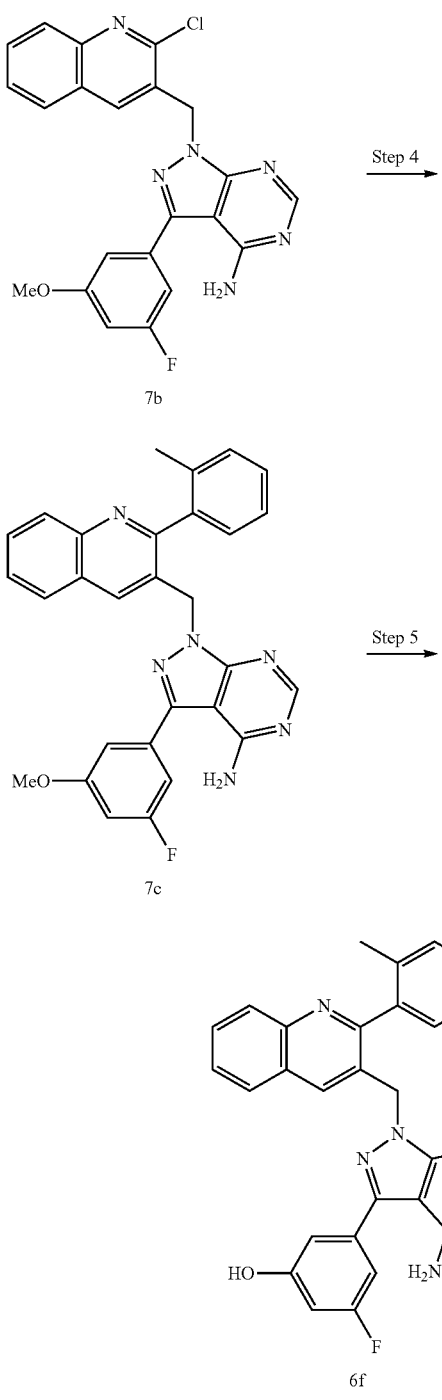

7b

7c

6f

Scheme 8 shows the preparation of a compound of the invention by reduction of a starting acid 8a to an alcohol in step 1. Such a reaction may be performed, for example, by LiAlH$_4$ reduction in methanol. In step 2, compound 8b is coupled to an aryl group via, for example, a Suzuki coupling. In the example shown, 2-fluorophenylboronic acid is reacted with 8b in the presence of Pd(PPh$_3$)$_4$, a base such as Na$_2$CO$_3$ and a solvent such as DME-water. The resulting alcohol 8c is converted to a reactive halide in step 3 by reaction with a reagent such as CBr$_4$/PPh$_3$ in a solvent such as dichloromethane. A heterocyclic moiety such as a pyrazolopyrimide (e.g. 3-iodo-1H-pyrazolo[3,4-d]pyrimidin-4-amine) may be coupled to the halide 8d (e.g. in a base such as potassium carbonate and a solvent such as dimethylformamide) to form the compound 8e in step 4. In step 5, the pyrazolopyrimidine subunit is further derivatized via a reaction such as a Suzuki coupling (e.g. using Pd(PPh$_3$)$_4$ as a catalyst) to yield compound 8f.

Scheme 8: Synthesis of 3-(4-amino-1-((2-(2-fluorophenyl)-6,7-dihydro-5H-cyclopenta[b]pyridin-3-yl)methyl)-1H-pyrazolo[3,4-]pyrimidin-3-yl)-5-fluorophenol (8f)

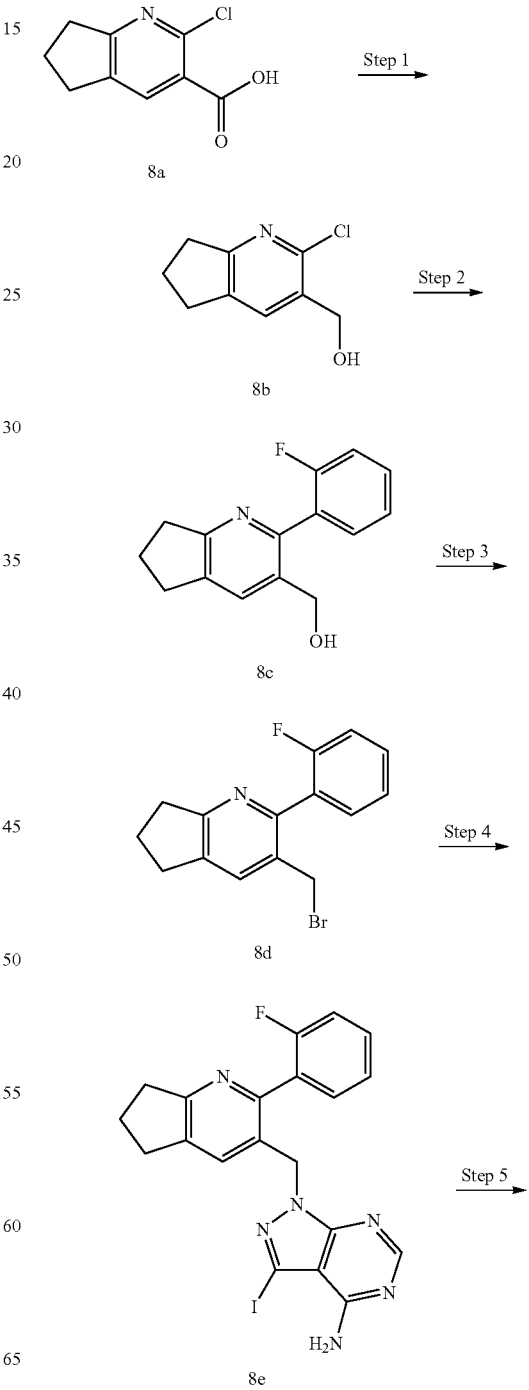

-continued

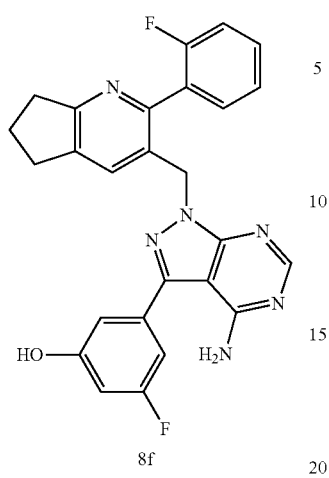

8f

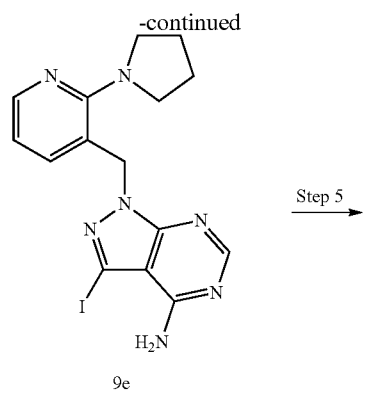

9e

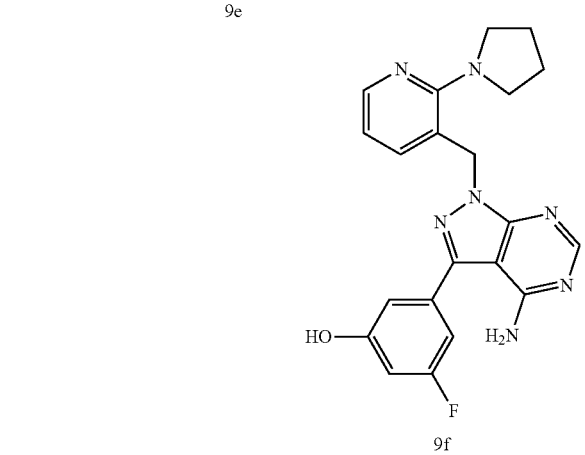

9f

Scheme 9 shows the preparation of a compound of the invention by reduction of a starting aldehyde 9a to an alcohol in step 1. Such a reaction may be performed, for example, by sodium borohydride reduction in methanol. In step 2, compound 9b is coupled to pyrrolidine in the presence of a solvent such as 1,4-dioxane. The resulting alcohol 9c is converted to a reactive halide in step 3 by reaction with a reagent such as $CBr_4/PPh_3$ in a solvent such as acetonitrile. A heterocyclic moiety such as a pyrazolopyrimide (e.g. 3-iodo-1H-pyrazolo[3,4-d]pyrimidin-4-amine) may be coupled to the halide 9d (e.g. in a base such as potassium carbonate and a solvent such as dimethylformamide) to form the compound 9e in step 4. In step 5, the pyrazolopyrimidine subunit is further derivatized via a reaction such as a Suzuki coupling (e.g. using $Pd(PPh_3)_4$ as a catalyst) with 3-fluoro-5-hydroxyphenylboronic acid to yield compound 9f.

Scheme 9: Synthesis of 3-(4-amino-1-((2-(pyrrolidin-1-yl)pyridin-3-yl)methyl)-1H-pyrazolo[3,4-d]pyrimidin-3-yl)-5-fluorophenol (9f)

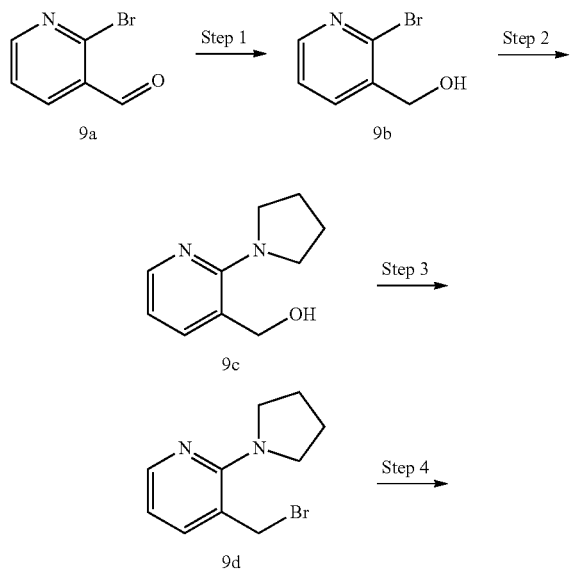

Scheme 10 illustrates a synthesis of the compound 10f. In step 1, a starting aldehyde 10a is converted to an alcohol, for example, by Grignard addition of an alkylmagnesium halide reagent. In step 2, compound 10b is converted to a reactive halide by reaction with a reagent such as $CBr_4/PPh_3$ in a solvent such as acetonitrile. Coupling to a heterocyclic moiety such as a pyrazolopyrimide (e.g. 3-iodo-1H-pyrazolo[3,4-d]pyrimidin-4-amine) is performed in step 3, for example in a base such as potassium t-butoxide and a solvent such as dimethylformamide). The resulting compound 10d is then coupled to pyrrolidine in the presence of a solvent such as 1,4-dioxane. In step 5, the pyrazolopyrimidine subunit is further derivatized via a reaction such as a Suzuki coupling (e.g. using $Pd(PPh_3)_4$ as a catalyst) to yield compound 10f.

Scheme 10: Synthesis of 3-(4-amino-1-(1-(2-(pyrrolidin-1-yl)quinolin-3-yl)ethyl)-1H-pyrazolo[3,4-d]pyrimidin-3-yl)-5-fluorophenol (10f)

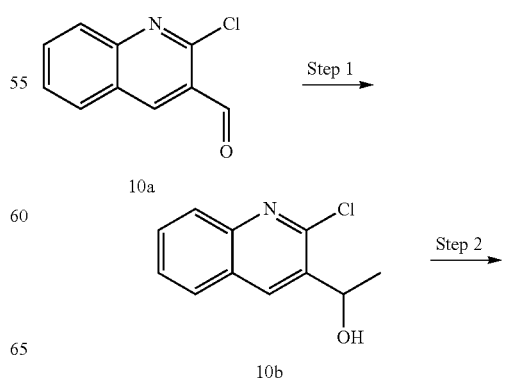

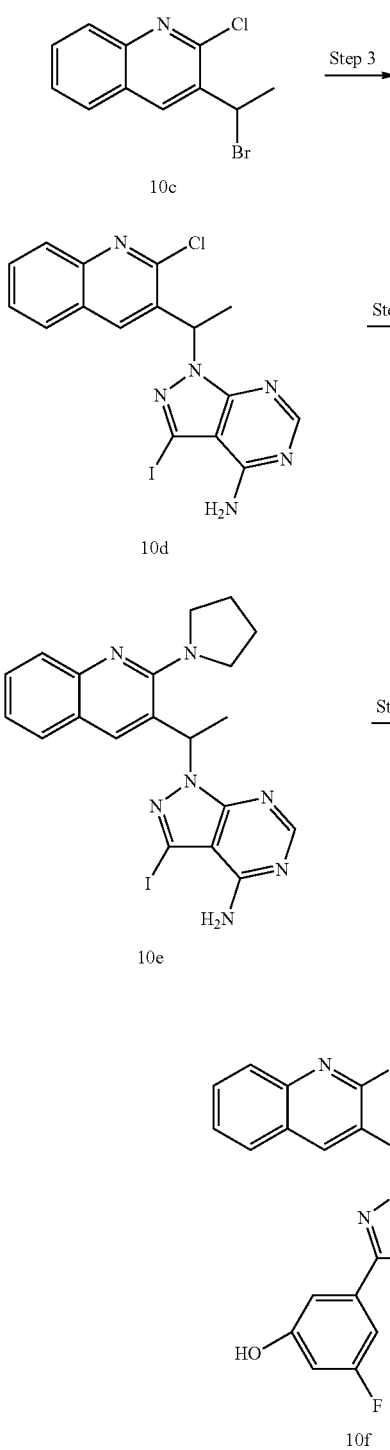

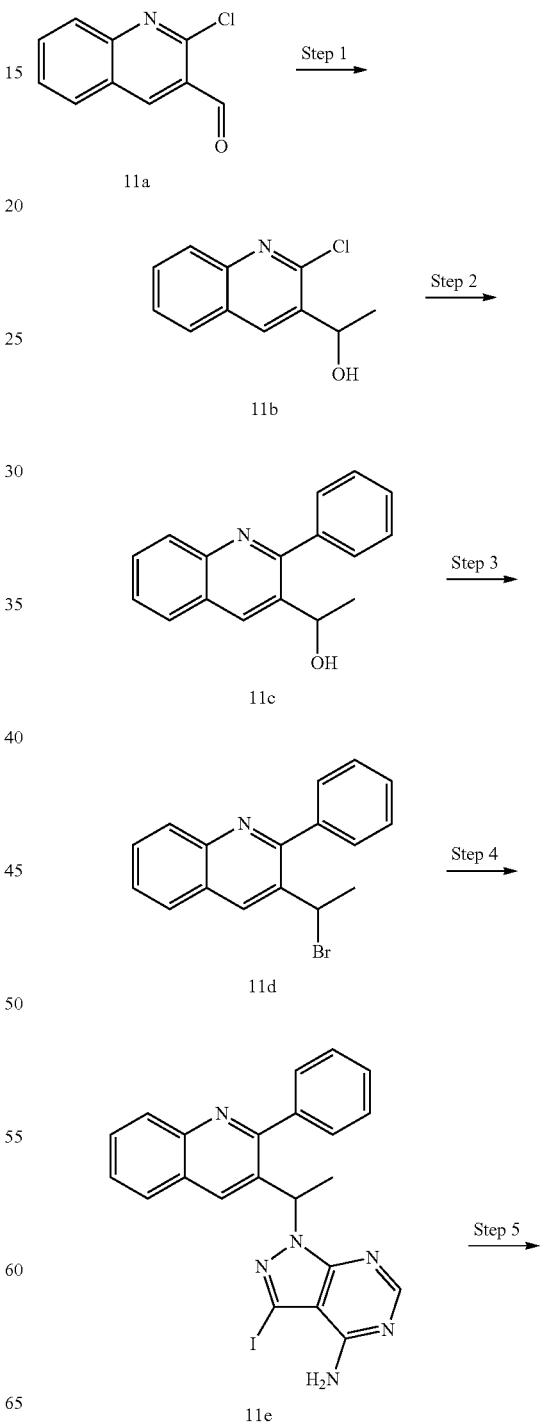

acetonitrile. Coupling to a heterocyclic moiety such as a pyrazolopyrimide (e.g. 3-iodo-1H-pyrazolo[3,4-d]pyrimidin-4-amine) is performed in step 3, for example in a base such as potassium t-butoxide and a solvent such as dimethylformamide. In step 5, the resulting compound 11d is further derivatized via a reaction such as a Suzuki coupling (e.g. using Pd(PPh$_3$)$_4$ as a catalyst) to yield compound 11f.

Scheme 11: Synthesis of 3-(4-amino-1-(1-(2-phenylquinolin-3-yl)ethyl)-1H-pyrazolo[3,4-d]pyrimidin-3-yl)phenol (11f)

Scheme 11 exemplifies a synthesis of the compound 11f. In step 1, a starting aldehyde 11a is converted to an alcohol, for example, by Grignard addition of an alkylmagnesium halide reagent. In step 2, compound 11b is coupled to to an aryl group via, for example, a Suzuki coupling using phenylboronic acid in the presence of Pd(OAc)$_2$, a base such as Na$_2$CO$_3$ and a solvent such as ethanol/DMF/water. The resulting compounds 11c is converted to a reactive halide by reaction with a reagent such as CBr$_4$/PPh$_3$ in a solvent such as

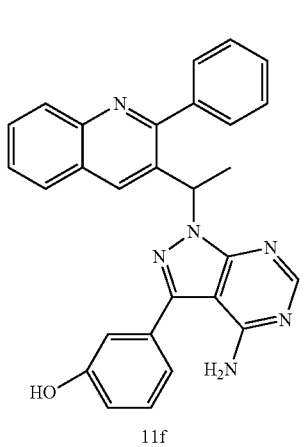

11f

Scheme 12 shows a synthesis of the compound 12e. In step 1, a starting aldehyde 12a is converted to an alcohol, for example, by Grignard addition of an alkylmagnesium halide reagent. In step 2, compound 12b is converted to a reactive halide by reaction with a reagent such as CBr$_4$/PPh$_3$ in a solvent such as acetonitrile. Subsequent reaction with a heterocyclic compound such as 9H-purin-6-amine leads to formation of the intermediate 12d. This intermediae is then coupled to an aryl group via, for example, a Suzuki coupling using phenylboronic acid in the presence of Pd(OAc)$_2$, a base such as Na$_2$CO$_3$ and a solvent such as ethanol/DMF/water. Alternatively, compound 12d is reacted with pyrrolidine in the presence of a solvent such as 1,4-dioxane, leading to formation of product 12f.

Scheme 12: Synthesis of 9-(1-(2-phenylquinolin-3-yl)ethyl)-9H-purin-6-amine (12e) and 9-(1-(2-(pyrrolidin-1-yl)quinolin-3-yl)ethyl)-9H-purin-6-amine (12f)

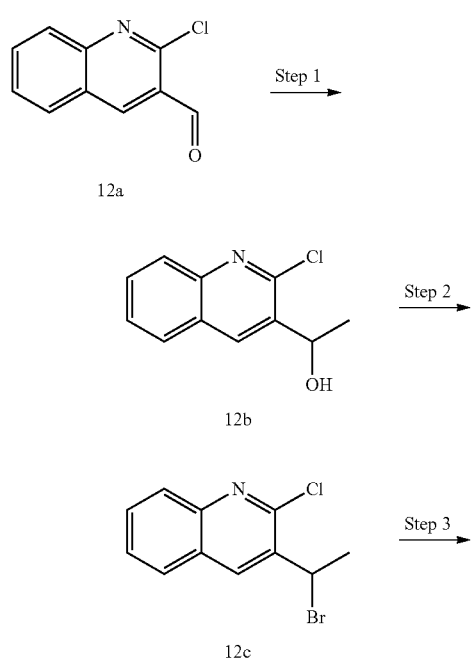

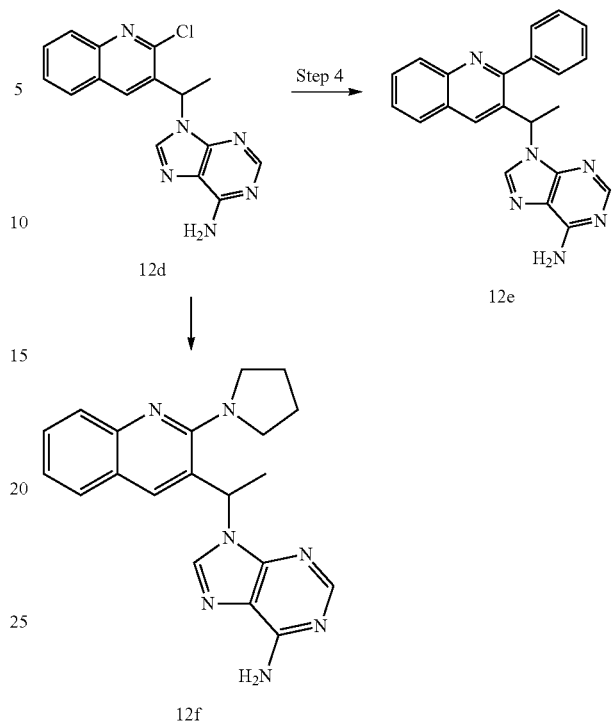

Scheme 13 describes the synthesis of additional compounds comprising heteroaromatic residues. The starting material is the intermediate 12c prepared as described above. Coupling with a derivatized bicyclic heteroaromatic residue (in the example shown, 9-(tetrahydro-2H-pyran-2-yl)-9H-purin-6-amine) results in compound 13b, which is further reacted with a group such as pyrrolidine (shown) to yield compounds 13c. Deprotection of the purine moiety in HCl/ethanol results in compound 13d.

Scheme 13: Synthesis of N-(1-(2-(pyrrolidin-1-yl)quinolin-3-yl)ethyl)-9H-purin-6-amine (13d)

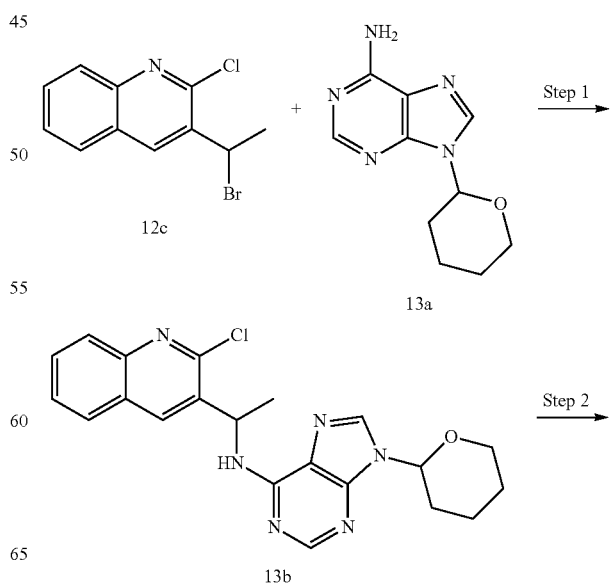

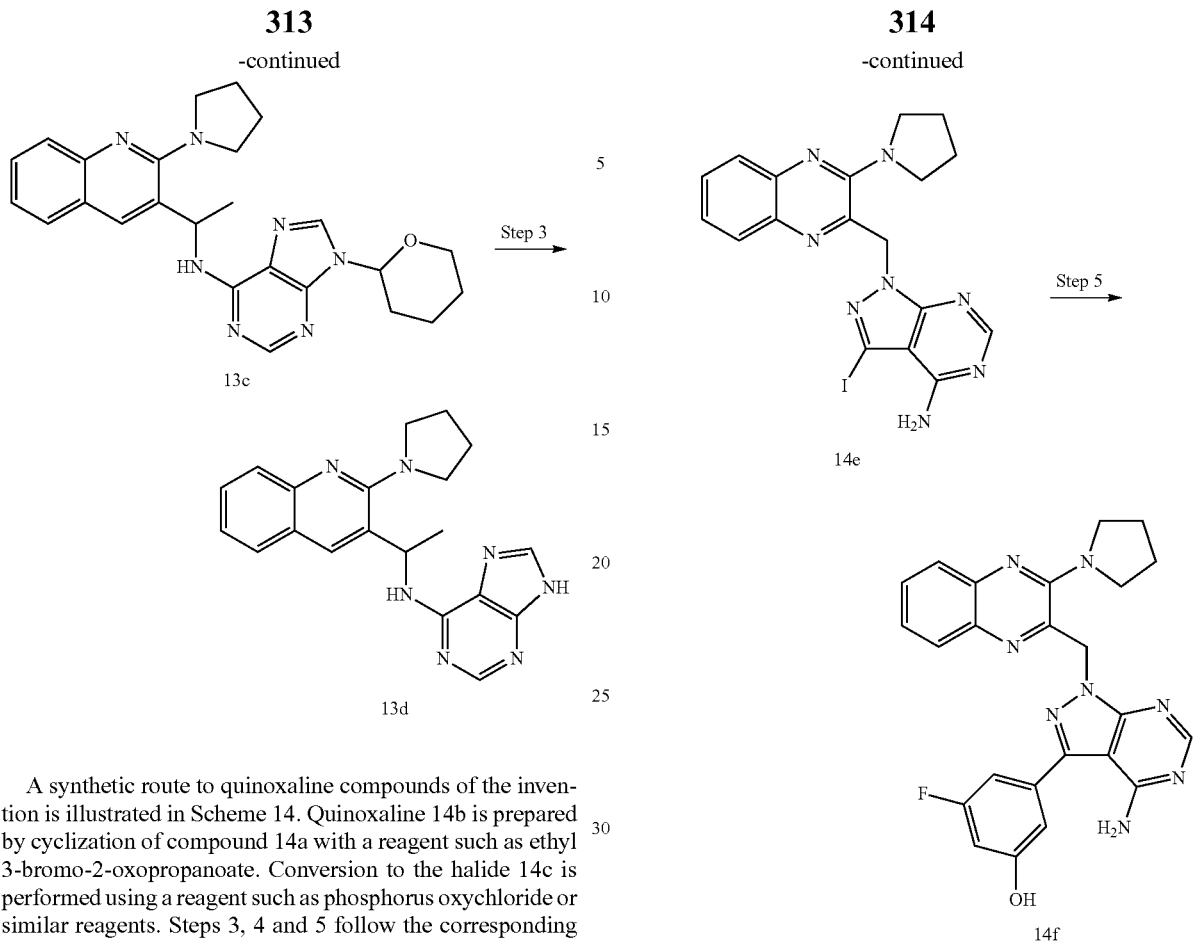

A synthetic route to quinoxaline compounds of the invention is illustrated in Scheme 14. Quinoxaline 14b is prepared by cyclization of compound 14a with a reagent such as ethyl 3-bromo-2-oxopropanoate. Conversion to the halide 14c is performed using a reagent such as phosphorus oxychloride or similar reagents. Steps 3, 4 and 5 follow the corresponding steps in Scheme 10, yielding compound 14f.

Scheme 14: Synthesis of 3-(4-amino-1-((3-(pyrrolidin-1-yl)quinoxalin-2-yl)methyl)-1H-pyrazolo[3,4-d]pyrimidin-3-yl)-5-fluorophenol (14f)

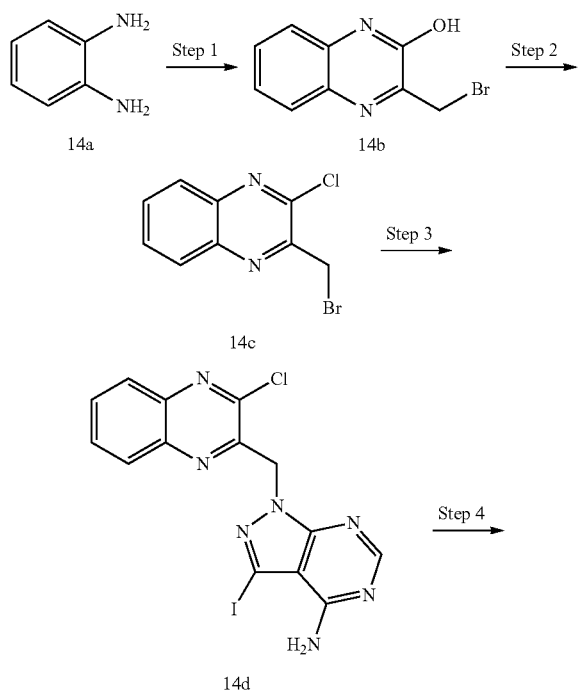

Scheme 15 describes the synthesis of compounds such as 15g. Intermediate 15d is prepared as described for compound 4b. Treatment with NaOH in a solvent such as 1,4-dioxane at 80C yields 15e, which is further alkylated using a reagent such as methyl iodide in potassium t-butoxide/DMF to yield 15f. Compound 15g is obtained following Suzuki coupling as described above.

Scheme 15: Synthesis of 3-((4-amino-3-(3-fluoro-5-hydroxyphenyl)-1H-pyrazolo[3,4-d]pyrimidin-1-yl)methyl)-1-methylquinolin-2(1H)-one (15g)

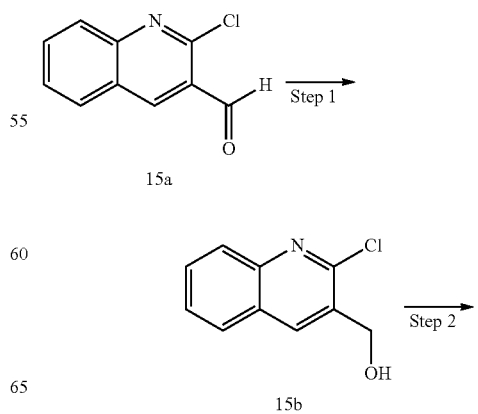

315

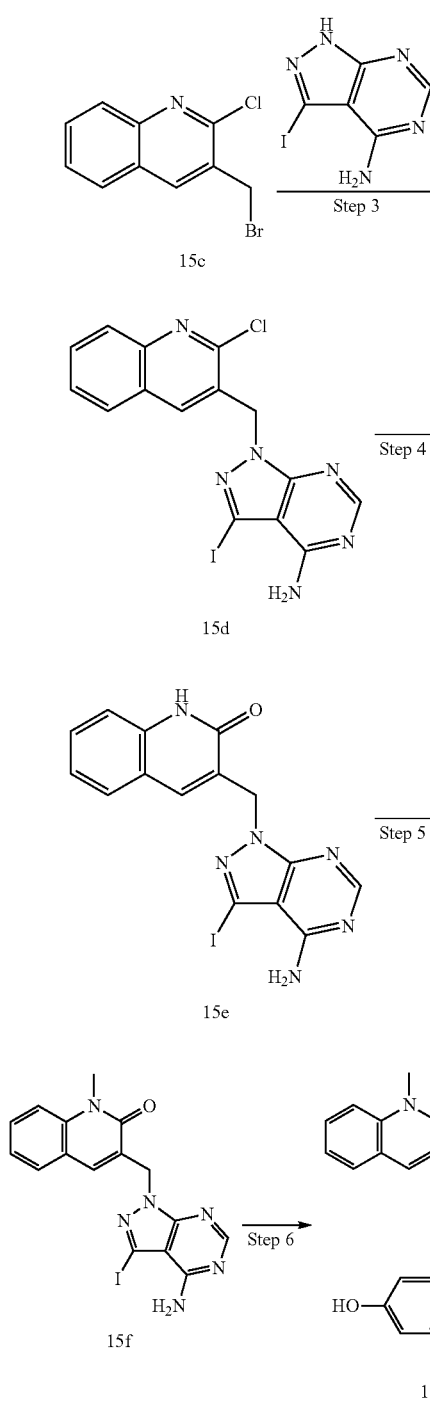

316

Scheme 16: Synthesis of 3-((4-amino-3-(3-fluoro-5-hydroxyphenyl)-1H-pyrazolo[3,4-d]pyrimidin-1-yl)methyl)-1-methylquinoxalin-2(1H)-one

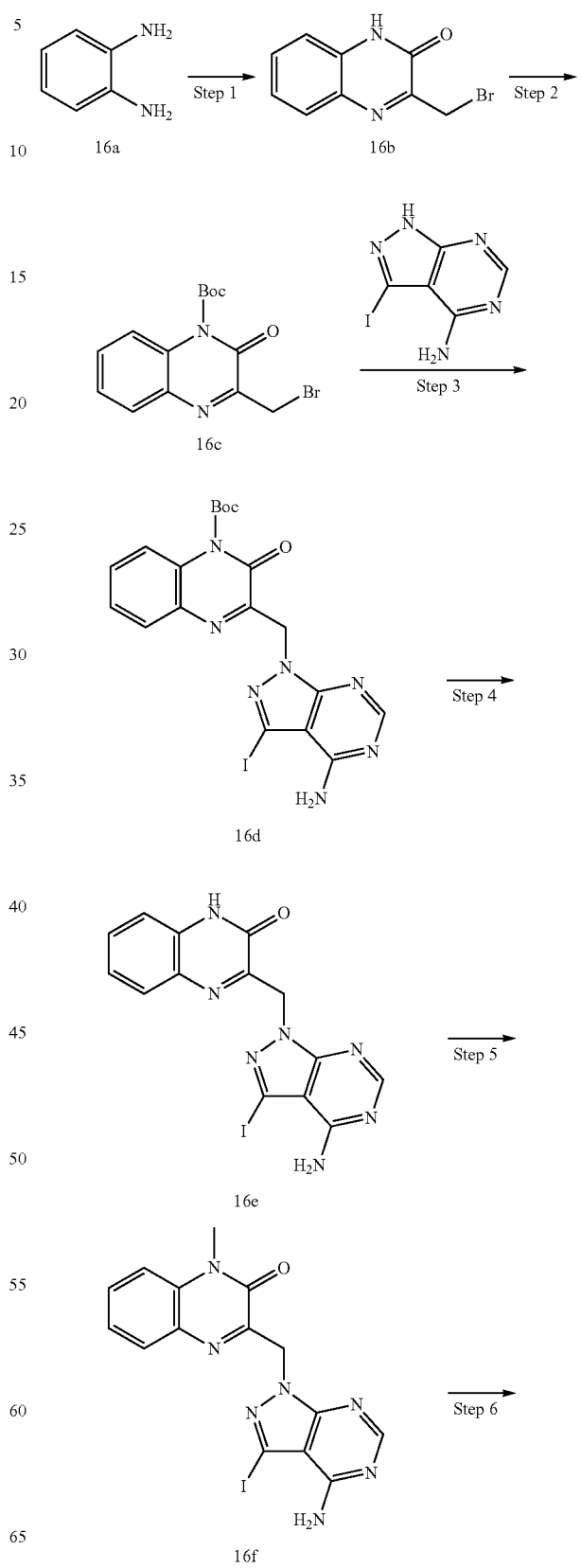

A synthetic route to additional quinoxaline compounds of the invention is illustrated in Scheme 16. Quinoxaline 16b is prepared by cyclization of compound 16a with a reagent such as ethyl 3-bromo-2-oxopropanoate in ethanol. Reaction with Boc anhydride in DMAP/CH$_2$Cl$_2$ leads to the protected intermediate 16c. Coupling to a heterocyclic moiety such as a pyrazolopyrimide is performed in step 3. Deprotection and alkylation, e.g. using methyl iodide, results in compound 16g.

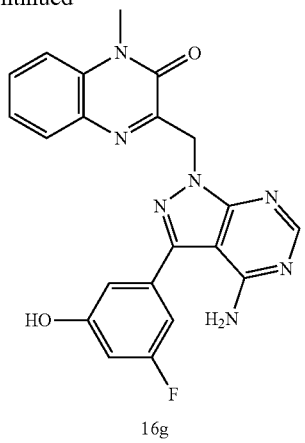

16g

In some embodiments, one or more subject compounds bind specifically to a PI3 kinase or a protein kinase selected from the group consisting of mTor, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other protein kinases listed in the appended tables and figures, as well as any functional mutants thereof. In some embodiments, the IC50 of a subject compound for p110α, p110β, p110γ, or p110δ is less than about 1 uM, less than about 100 nM, less than about 50 nM, less than about 10 nM, less than 1 nM or even less than about 0.5 nM. In some embodiments, the IC50 of a subject compound for mTor is less than about 1 uM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an IC50 value less than about 1 uM, less than about 100 nM, less than about 50 nM, less than about 10 nM, less than 1 nM or even less than about 0.5 nM. One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, the compounds of the present invention exhibits one or more functional characteristics disclosed herein. For example, one or more subject compounds bind specifically to a PI3 kinase. In some embodiments, the IC50 of a subject compound for p110α, p110β, p110γ, or p110δ is less than about 1 uM, less than about 100 nM, less than about 50 nM, less than about 10 nM, less than about 1 nM, less than about 0.5 nM, less than about 100 pM, or less than about 50 pM.

In some embodiments, one or more of the subject compounds may selectively inhibit one or more members of type I or class I phosphatidylinositol 3-kinases (PI3-kinase) with an IC50 value of about 100 nM, 50 nM, 10 nM, 5 nM, 100 pM, 10 pM or 1 pM, or less as measured in an in vitro kinase assay.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration (IC50) with respect to a given type I PI3-kinase, that is at least at least 10-fold, at least 20-fold, at least 50-fold, at least 100-fold, at least 1000-fold, at least 10,100-fold, or lower, than the inhibitor's IC50 with respect to the rest of the other type I PI3-kinases.

The invention provides pharmaceutical compositions comprising one or more compounds of the present invention. In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxsis, auto-immune diseases, rhuematoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25% 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

Described below are non-limiting exemplary pharmaceutical compositions and methods for preparing the same.

Pharmaceutical compositions for oral administration In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters;

propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation.

Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, the invention provides a pharmaceutical composition for injection containing a compound of the present invention and a pharmaceutical excipient suitable for injection. Components and amounts of agents in the compositions are as described herein. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also abe administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of the compounds of the present invention may be determined by the following procedure, as well as the procedure described in the examples below. The activity of the kinase is assessed by measuring the incorporation of $\gamma$-$^{33}$P-phosphate from $\gamma$-$^{33}$P-ATP onto N-terminal His tagged substrate, which is expressed in E. coli and is purified by conventional methods, in the presence of the kinase. The assay is carried out in 96-well polypropylene plate. The incubation mixture (100 µL) comprises of 25 mM Hepes, pH 7.4, 10 mM MgCl$_2$, 5 mM β-glycerolphosphate, 100 µM Na-orthovanadate, 5 mM DTT, 5 nM kinase, and 1 µM substrate. Inhibitors are suspended in DMSO, and all reactions, including controls are performed at a final concentration of 1% DMSO. Reactions are initiated by the addition of 10 µM ATP (with 0.5 µCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 μL/well of Packard Microscint 20, and plates are counted using a Packard TopCount.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The invention also provides methods of using the compounds or pharmaceutical compositions of the present invention to treat disease conditions, including but not limited to diseases associated with malfunctioning of one or more types of PI3 kinase. A detailed description of conditions and disorders mediated by p110δ kinase activity is set forth in Sadu et al., WO 01/81346, which is incorporated herein by reference in its entirety for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rhuematoid arthritis, psoriasis, lupus erythematosus, or graft versus host disease. Selective inhibition of PI3K-δ may further provide for a reduction in the inflammatory or undesirable immune response without a concomitant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rhuematoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma iuch as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quartemary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 1, 5, 10, 20, 30, 40, 50, 60, 70, 80 90, 95, or 99% of the kinase activity in the absence of said contacting step.

In some embodiments, the kinase is a lipid kinase or a protein kinase. In some embodiments, the kinase is selected from the group consisting of PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, the invention provides methods of inhibiting PI3 kinase activity in an animal (including mammal such as humans) by contacting said animal with an amount of a compound of the invention sufficient to inhibit the activity of the PI3 kinase in said animal.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of PI3Kδ or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering to a PI3Kδ inhibitor and an agent that inhibits IgE production or activity. Other exemplary PI3Kδ inhibitors are applicable and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseaseses, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB398/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Administration of the compounds of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent. Compounds can also be administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

The compound may be applied as a sole therapy or may involve one or more other anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl) propionanilide). Such conjoint treatment may be achieved by way of the simultaneous, sequential or separate dosing of the individual components of treatment.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO- PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053; 4,762,129; 6,152,946; 6,663,652; 6,027,520 6,676,682; 6,663,652; 6,872,216; 6,027,520; 6,114,653; 5,852,277; 5,843,120; 5,643,312; 5,733,303; 5,597,378; 5,653,727; 4,762,129; 5,922,021; 3,657,744; 4,739,762; 5,195,984; 5,451,233; 3,657,744; 4,739,762; 5,195,984; 4,739,762; 3,657,744; 4,739,762; 5,195,984; 5,292,331; 5,674,278; 5,643,312; 5,879,370; 5,421,955; 5,514,154; 5,603,721; 5,421,955; 5,514,154; 5,603,721; 5,292,331; 5,674,278; 5,879,382; 6,344,053; 5,728,067; 5,980,486; 6,129,708; 5,733,303; 5,843,120; 5,972,018; 5,972,018; 5,733,303; 5,843,120; 4,739,762; 5,195,984; 5,902,332; 5,156,594; 5,395,334; 6,090,083; 5,639,278; 6,051,020; 6,117,167; 5,632,772; 6,165,213; 4,762,129; 5,156,594; 5,217,482; 5,395,334; 4,641,653; 4,739,762; 5,922,021; 5,895,406; 6,251,920; 6,120,536; 5,292,331; 5,674,278; 5,879,382; 6,344,053; 5,609,627; 6,251,920; 5,733,303; 5,843,120; 5,972,018; 6,344,053; 5,292,331; 5,674,278; 5,879,382; 5,653,760; 6,190,358; 6,210,364; 6,283,939; 6,605,057; 5,292,331; 5,674,278; 5,879,382; 6,344,053; 5,423,851; 6,007,575; 5,501,759; 5,674,208; 5,843,032; 5,961,765; 6,027,477; 6,319,228; 6471673; 6,190,358; 6,605,057; 6,858,037; 7,001,358; 5,156,594; 5,217,482; 5,395,334; 5,702,439; 5,501,759; 5,674,208; 5,843,032; 5,961,765; 6,027,477; 6,319,228; 6,471,673; 5,759,192; 6,527,789; 5,147,302; 5,342,307; 6,290,485; 6,352,551; 6,402,778; 6,488,694; 6,511,505; 6,613,073; 6,582,458; 5,820,594; 5,824,173; 5,538,510; 4,323,071; 4,762,129; 4,846,186; 5,156,594; 5,217,482; 5,395,334; 5,156,594; 4,323,071; 5,040,548; 5,061,273; 5,451,233; 5,496,346; 5,496,275; 5,496,346; 5,040,548; 5,061,273; 5,451,233; 5,496,346; 4,596,563; 5,040,548; 5,061,273; 5,350,395; 5,451,233; 5,445,625; 6,083,213; 6,475,195; 5,421,955; 5,514,154; 5,603,721; 5,292,331; 5,674,278; 5,879,382; 6,344,053; 6,238,415; 5,421,955; 5,514,154; and 5,603,721.

The compounds of the invention may be administered in dosages as described herein (see, e.g., Compositions). It is known in the art that due to intersubject variability in compound pharmacokinetics, individualization of dosing regimen is necessary for optimal therapy. Dosing for a compound of the invention may be found by routine experimentation.

When a compound of the invention, is administered in a composition that comprises one or more agents, and the agent has a shorter half-life than the compound of the invention unit dose forms of the agent and the compound of the invention may be adjusted accordingly. See e.g., Compositions.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of the compounds of the present invention may be determined by the following procedure, as well as the procedure described in the examples below. N-terminal 6 His-tagged, constitutively active kinase is expressed in *E. coli* and protein is purified by conventional methods (Ahn et al. *Science* 1994, 265, 966-970). The activity of the kinase is assessed by measuring the incorporation of $\gamma$-$^{33}$P-phosphate from $\gamma$-$^{33}$P-ATP onto N-terminal His tagged substrate, which is expressed in *E. coli* and is purified by conventional methods, in the presence of the kinase. The assay is carried out in 96-well polypropylene plate. The incubation mixture (100, µL) comprises of 25 mM Hepes, pH 7.4, 10 mM MgCl2, 5 mM β-glycerolphosphate, 100 µM Na-orthovanadate, 5 mM DTT, 5 nM kinase, and 1 µM substrate. Inhibitors are suspended in DMSO, and all reactions, including controls are performed at a final concentration of 1% DMSO. Reactions are initiated by the addition of 10 µM ATP (with 0.5 µCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 µL/well of Packard Microscint 20, and plates are counted using a Packard TopCount.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHCl3:MeOH (1:1). The biphasic mixture is vortexed, briefly centrifuged, and the organic phase is transferred to a new tube using a gel loading pipette tip precoated with $CHCl_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are avaiable. The commercially available kits or systems can be used to screen for inhibitors and/or agonists of PI3-Ks including but not limited to PI 3-Kinase α, β, δ, and γ. Anr exemplary system is PI 3-Kinase (human) HTRFT™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 2

Expression and Inhibition Assays of Abl

The compounds described herein can be assayed in triplicate against recombinant full-length Abl or Abl (T315I) (Upstate) in an assay containing 25 mM HEPES, pH 7.4, 10 mM MgCl2, 200 μM ATP (2.5 μCi of γ-32P-ATP), and 0.5 mg/mL BSA. The optimized Abl peptide substrate EAIYAAP-FAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 3

Expression and Inhibition Assays of Hck

The compounds described herein can be assayed in triplicate against recombinant full-length Hck in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 4

Expression and Inhibition Assays of Inulsin Receptor (IR)

The compounds described herein can be assayed in triplicate against recombinant insulin receptor kinase domain (Upstate) in an assay containing 25 mM HEPES, pH 7.4, 10 mM MgCl2, 10 mM MnCl2, 200 ATP (2.5 μCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 5

Expression and Inhibition Assays of Src

The compounds described herein can be assayed in triplicate against recombinant full-length Src or Src (T338I) in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 6

Expression and Inhibition Assays of DNA-PK (DNAK)

DNA-PK can be purchased from Promega and assayed using the DNA-PK Assay System (Promega) according to the manufacturer's instructions.

Example 7

Expression and Inhibition Assays mTOR

The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 μM ATP (2.5 μCi of μ-32P-ATP), and 3 μg/mL BSA. Rat recombinant PHAS-1/4EBP1 (Calbiochem; 2 mg/mL) is used as a substrate. Reactions are terminated by spotting onto nitrocellulose, which is washed with 1M NaCl/ 1% phosphoric acid (approximately 6 times, 5-10 minutes each). Sheets are dried and the transferred radioactivity quantitated by phosphorimaging.

Other kits or systems for assaying mTOR activity are commercially avaiable. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 8

Expression and Inhibition Assays of Vascular Endothelial Growth Receptor

The compounds described herein can be tested against recombinant KDR receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 9

Expression and Inhibition Assays of Ephrin Receptor B4 (EphB4)

The compounds described herein can be tested against recombinant Ephrin receptor B4 kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 10

Expression and Inhibition Assays of Epidermal Growth Factor Receptor (EGFR)

The compounds described herein can be tested against recombinant EGF receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 11

Expression and Inhibition Assays of KIT Assay

The compounds described herein can be tested against recombinant KIT kinase domain (Invitrogen) in an assay containing 25 mM HEPES, pH 7.4, 10 mM MgCl2, 1 mM DTT, 10 mM MnCl$_2$, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 12

Expression and Inhibition Assays of RET

The compounds described herein can be tested against recombinant RET kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 13

Expression and Inhibition Assays of Platelet Derived Growth Factor Receptor (PDGFR)

The compounds described herein can be tested against recombinant PDG receptor kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAP-FAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 14

Expression and Inhibition Assays of Fms-related Tyrosine Kinase 3 (Flt-3)

The compounds described herein can be tested against recombinant FLT-3 kinase domain (Invitrogen) in an assay containing 25 mM HEPES, pH 7.4, 10 mM MgCl2, 2.5 mM DTT, 10 μM ATP (2.5 μCi of μ-32P-ATP), and 3 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 15

Expression and Inhibition Assays of TEK Receptor Tyrosine Kinase (TIE2)

The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 ul volume. Plates are incubated for 30 min at 37C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 uL of Alamar Blue reagent is added to each well and plates are incubated for 5 hours at 37C and 5% $CO_2$. Alamar Blue fluoresce is read at 560Ex/590Em, and IC50 or EC50 values are calculated using GraphPad Prism 5.

Example 17

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37C and 5% $CO_2$. A volume of 10 uL of Alamar Blue reagent is added to each well and plates are incubated for 3 hours at 37C and 5% $CO_2$. Alamar Blue fluoresce is read at 560Ex/590Em, and IC50 values are calculated using GraphPad Prism 5.

Example 18

Antitumor Activity in Vivo

The compounds described herein can be evaluated in a panel of human and murine tumor models.
Paclitaxel-refractory Tumor Models
1. Clinically-derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days×5 schedule.
3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel.
The compounds described herein can be administered to mice bearing staged tumors on an every 2 days×5 schedule.
5. M5076 Murine Sarcoma Model
M5076 is a mouse fibrosarcoma that is inherently refractory to paclitaxel in vivo.
The compounds described herein can be administered to mice bearing staged tumors on an every 2 days×5 schedule.
One or more compounds of the invention can be used in combination other therapeutic agents in vivo in the multidrug resistant human colon carcinoma xenografts HCT/VM46 or any other model known in the art including those described herein.

Example 19

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL of 10.0 mg/ml NADPH; 75 μL, of 20.0 mg/ml mouse, rat or human liver microsome; 0.4 μL of 0.2 M phosphate buffer, and 425 μL of dd$H_2$O, Negative control (without NADPH) tube contains 75 μL of 20.0 mg/ml mouse, rat or human liver microsome; 0.4 μL of 0.2 M phosphate buffer, and 525 μL of ddH$_2$O. The reaction is started by adding 1.0 μL of 10.0 mM tested compound. The reaction tubes are incubated at 37° C. 100 μL sample is collected into new Eppendorf tube containing 300 μL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 20

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 μM stock solution to an aliquot of pre-warmed plasma to give a final assay volume of 400 μL (or 800 μL for half-life determination), containing 5 μM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 μL of the incubation mixture to 200 μL of ice-cold acetonitrile and mixed by shaking for 5 minutes. The samples are centrifuged at 6000×g for 15 minutes at 4° C. and 120 μL of supernatant removed into clean tubes. The samples are then evaporated to dryness and submitted for analysis by HPLC-MS/MS.

Where desired, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 21

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 μM stock solution to an aliquot of PBS (in duplicate) to give a final assay volume of 400 μL, containing 5 μM test compound and 1% DMSO (for half-life determination a total sample volume of 700 μL is prepared). Reactions are incubated, with shaking, for 0 minutes and 24 hours at 37° C.; for half-life determination samples are incubated for 0, 2, 4, 6, and 24 hours. Reactions are stopped by adding immediately 100 μL of the incubation mixture to 100 μL of acetonitrile and vortexing for 5 minutes. The samples are then stored at −20° C. until analysis by HPLC-MS/MS. Where desired, a control compound or a reference compound such as chlorambucil (5 μM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 22

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, philadelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

The results demonstrate that one or more compounds of the present disclosure inhibit insulin stimulated phosphorylation of Akt at S473. Alternatively, some compounds disclosed herein additionally inhibit insulin stimulated phosphorylation of Akt at T308. Such class of compounds can inhibit Akt more effectively than rapamycin and may be indicative of mTORC2 inhibitors or inhibitors of upstream kinases such as PI3K or Akt.

Example 23

Kinase Signaling in Blood

PI3K/ Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent dinstinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphrylation of kinase substrates such as Akt and S6 are then measured by incubating the fixed cells with labeled antibodies specific to the phosphorylated isoforms of these proteins. The population of cells are then analyzed by flow cytometry.

Example 24

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+H4435, Stem Cell Tehcnologies) suplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 25

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g. Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevac) alone under the conditions tested.

Example 26

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to demonstrate that the kinase inhibitors disclosed herein can suppress or delay the onset of lupus symptoms in lupus disease model mice.

Example 27

Murine Bone Marrow Transplant Assay

Female recipient mice are lethally irradiated from a γ ray source. About 1 hr after the radiation dose, mice are injected with about $1 \times 1006$ leukemic cells from early passage p190 transduced cultures (e.g. as described in *Cancer Genet Cytogenet.* 2005 August; 161(1):51-6). These cells are administered together with a radioprotective dose of approximately $5 \times 106$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to demonstrate that effective therapeutic doses of the compounds disclosed herein can be used for inhibiting the proliferation of leukemic cells.

What is claimed is:
1. A compound having a structure of Formula I-E:

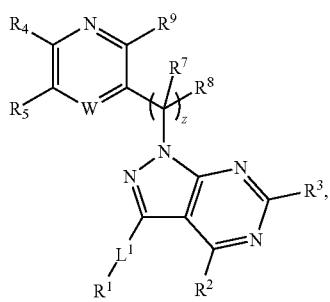

I-E or a pharmaceutically acceptable salt thereof, wherein:
$R^1$ is halogen, —CN, —$OR^{10}$, —$S(O)_nR^{11}$, —$NR^{12}R^{13}$, —$C(O)R^{14}$, alkenyl, alkynyl, heteroalkyl, cycloalkyl, heterocycloalkyl, aryl, or heteroaryl;
n is an integer from 0 to 2;
$L^1$ is a bond, alkylene, heteroalkylene, alkenylene, alkynylene, cycloalkylene, heterocycloalkylene, arylene, or heteroarylene;
$R^2$ is —$NR^{12}R^{13}$;
$R^3$ is hydrogen;
$R^4$ and $R^5$ are independently hydrogen or $R^6$, or $R^4$ and $R^5$ are taken together to form a 5, 6 or 7 membered ring, wherein the 5, 6, or 7 membered ring is optionally substituted with $(R^6)_q$;
z is 1;
q is an integer from 0 to 5;
each of $R^6$ is independently hydrogen, halogen, —CN, —$OR^{10}$, —$S(O)_nR^{11}$, —$NR^{12}R^{13}$, —$C(O)R^{14}$, alkyl, alkenyl, alkynyl, heteroalkyl, cycloalkyl, heterocycloalkyl, aryl, or heteroaryl;
each of $R^7$ and $R^8$ is independently hydrogen, alkyl, heteroalkyl, cycloalkyl, heterocyclyalkyl, or $R^7$ and $R^8$ taken together form a cycloalkyl, heterocycloalkyl or aryl ring;
$R^9$ is —$NR^{12}R^{13}$, where $R^{12}$ and $R^{13}$ are taken together to form a 5, 6, 7 or 8 membered ring, wherein the 5, 6, 7, or 8 membered ring contains 0, 1, 2 or 3 ring heteroatoms selected from N, S, or O in addition to the nitrogen atom of —$NR^{12}R^{13}$; and further wherein the 5, 6, 7, or 8 membered ring is optionally substituted;
each $R^{10}$ is independently hydrogen, —$C(O)R^{15}$, alkyl, heteroalkyl, cycloalkyl, heterocycloalkyl, aryl, or heteroaryl;
each $R^{11}$ is independently —$NR^{16}R^{17}$, alkyl, heteroalkyl, cycloalkyl, heterocycloalkyl, aryl, or heteroaryl;
each $R^{12}$ is independently hydrogen, alkyl, heteroalkyl, cycloalkyl, heterocycloalkyl, aryl, or heteroaryl;
each $R^{13}$ is independently hydrogen, —$S(O)_nR^{18}$, —$C(O)R^{19}$, alkyl, heteroalkyl, cycloalkyl, heterocycloalkyl, aryl, or heteroaryl;
or $R^{12}$ and $R^{13}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{12}R^{13}$; and further wherein the 5, 6, 7, or 8 membered ring is optionally substituted;
each $R^{14}$ is independently —$NR^{20}R^{21}$, hydrogen, alkyl, heteroalkyl, cycloalkyl, heterocycloalkyl, aryl, or heteroaryl;
each $R^{15}$ is independently —$NR^{22}R^{23}$, hydrogen, alkyl, heteroalkyl, cycloalkyl, heterocycloalkyl, aryl, or heteroaryl;
each of $R^{16}$ and $R^{17}$ is independently hydrogen, alkyl, heteroalkyl, cycloalkyl, heterocycloalkyl, aryl, or heteroaryl; or $R^{16}$ and $R^{17}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{16}R^{17}$; and further wherein the 5, 6, 7, or 8 membered ring is optionally substituted;
each $R^{18}$ is independently hydrogen, alkyl, heteroalkyl, cycloalkyl, heterocycloalkyl, aryl, or heteroaryl;
each $R^{19}$ is independently —$NR^{24}R^{25}$, hydrogen, alkyl, heteroalkyl, cycloalkyl, heterocycloalkyl, aryl, or heteroaryl;
each of $R^{20}$ and $R^{21}$ is independently hydrogen, alkyl, heteroalkyl, cycloalkyl, heterocycloalkyl, aryl, or heteroaryl, or $R^{20}$ and $R^{21}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —$NR^{20}R^{21}$; and further wherein the 5, 6, 7, or 8 membered ring is optionally substituted;
each $R^{22}$ and $R^{23}$ are independently hydrogen, alkyl, heteroalkyl, cycloalkyl, heterocycloalkyl, aryl, or heteroaryl, or $R^{22}$ and $R^{23}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —NR$^{22}$R$^{23}$; and further wherein the 5, 6, 7, or 8 membered ring is optionally substituted;

each R$^{24}$ and R$^{25}$ are independently hydrogen, alkyl, heteroalkyl, cycloalkyl, heterocycloalkyl, aryl, or heteroaryl, or R$^{24}$ and R$^{25}$ are taken together to form a 5, 6, 7, or 8 membered ring, wherein the 5, 6, 7, or 8 membered ring contains 0, 1, 2 or 3 ring heteroatoms selected from N, S, or O in addition to the nitrogen atom of —NR$^{24}$R$^{25}$; and further wherein the 5, 6, 7, or 8 membered ring is optionally substituted; and W is CR$^6$ or N.

2. The compound of claim 1, wherein R$^1$ is alkynyl, aryl, or heteroaryl.

3. The compound of claim 1, wherein L$^1$ is a bond, and R$^1$ is alkynyl, aryl, or heteroaryl.

4. The compound of claim 1, wherein R$^1$ is bicyclic heteroaryl.

5. The compound of claim 1, wherein R$^4$ and R$^5$ are taken together to form a 6-membered ring.

6. The compound of claim 1, wherein R$^2$ is —NH$_2$.

7. The compound of claim 1, wherein R$^7$ is alkyl.

8. The compound of claim 1, wherein R$^7$ and R$^8$ are hydrogen.

9. The compound of claim 1, wherein W is CH.

10. The compound of claim 1, wherein the compound has a structure of one of the following formulae:

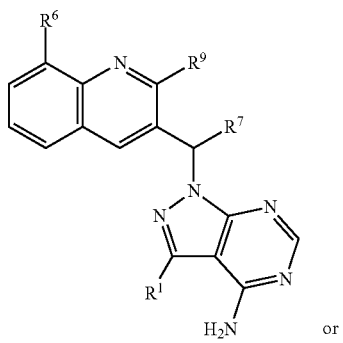

Formula II-A1 or

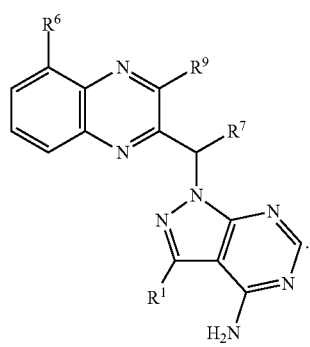

Formula II-A2

11. The compound of claim 1, or a pharmaceutically acceptable salt thereof, wherein the compound is:

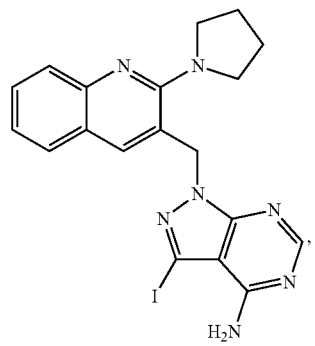

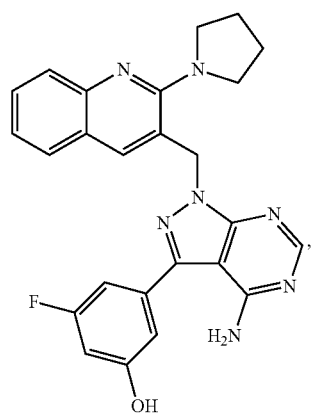

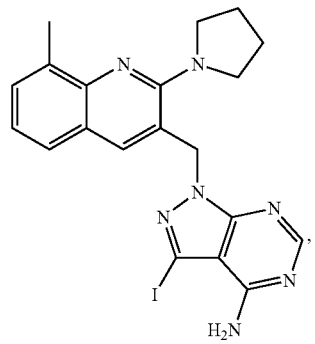

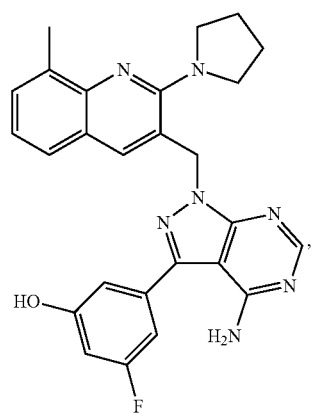

361
-continued

362
-continued

363
-continued
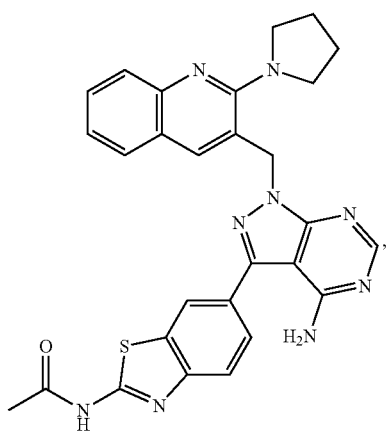,
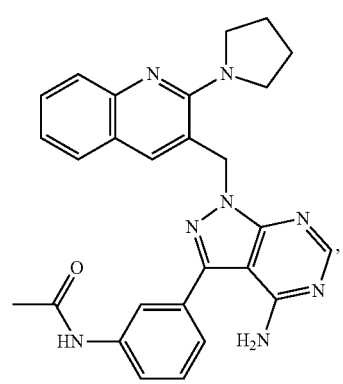,
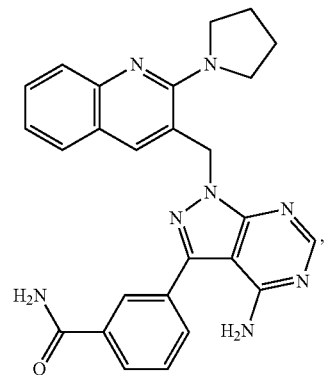,
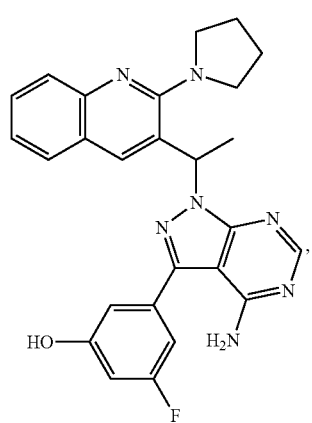,
364
-continued
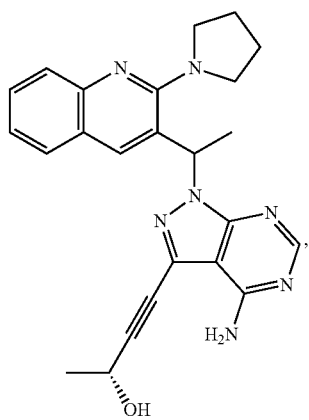,
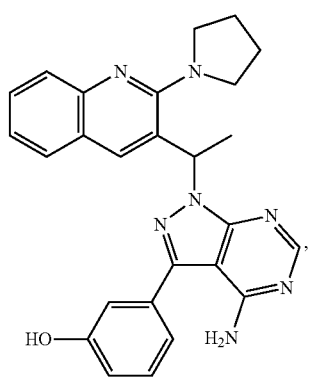, 365
-continued
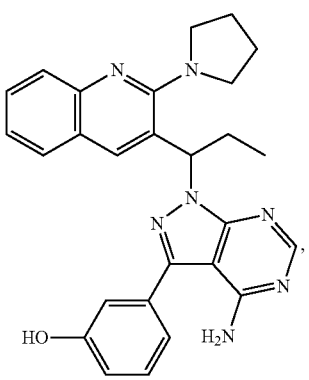
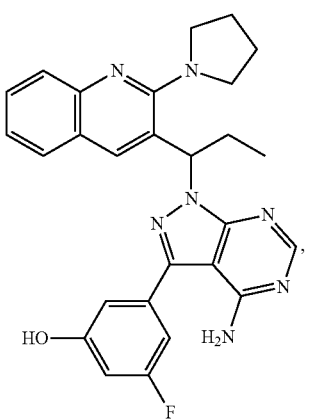
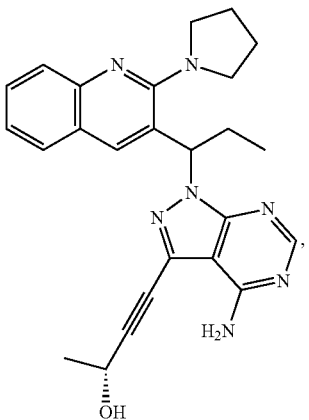
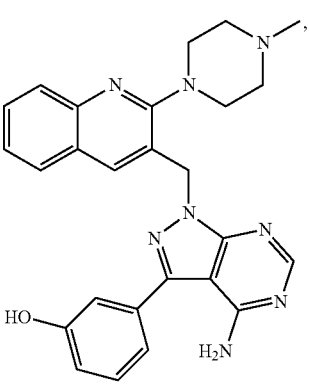
366
-continued
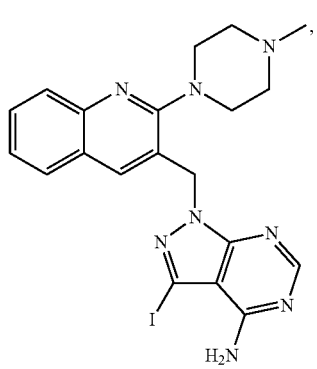
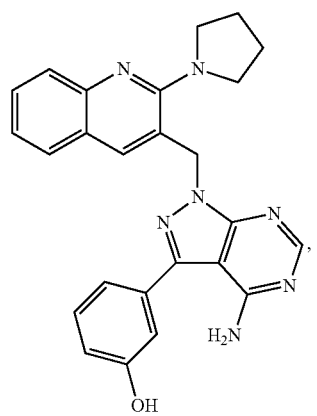
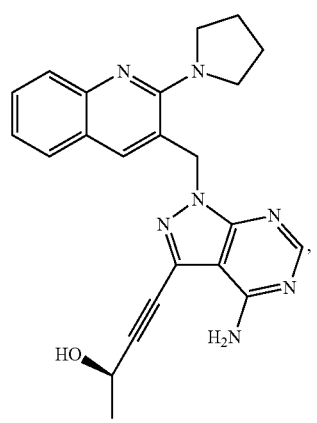
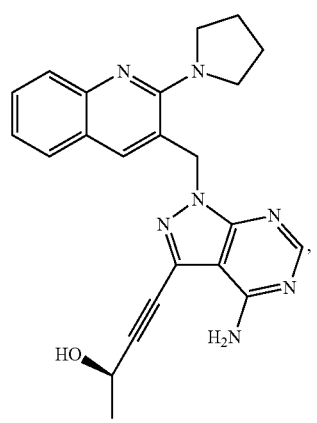
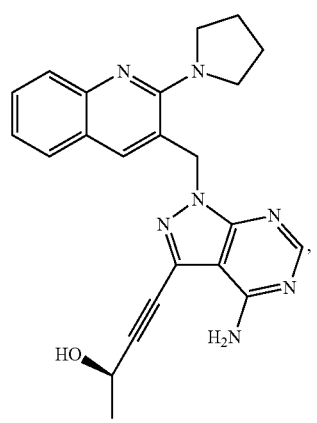

367
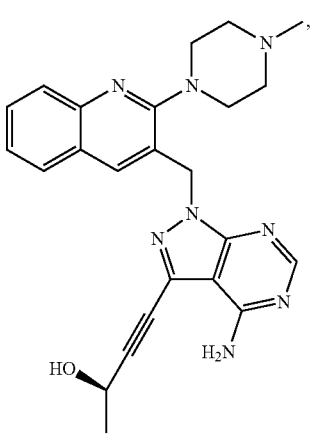
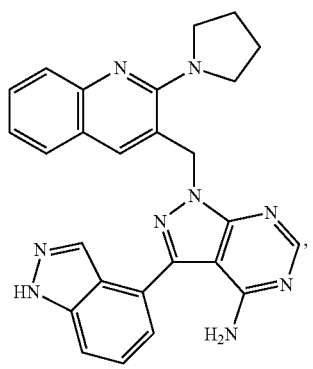
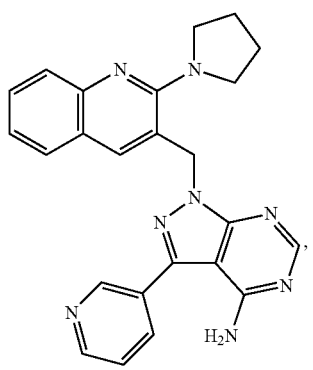
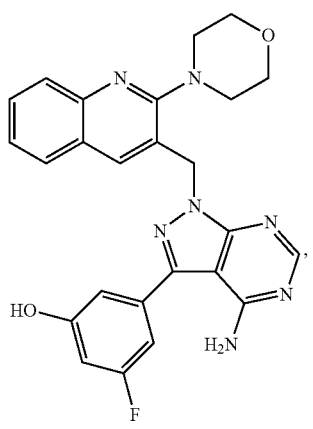
368
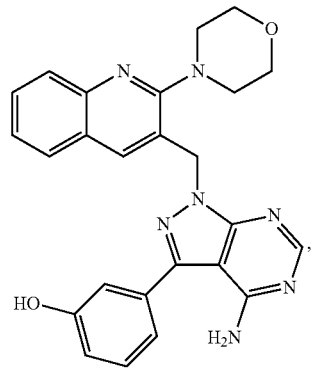
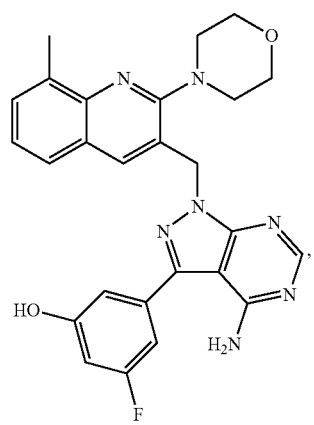
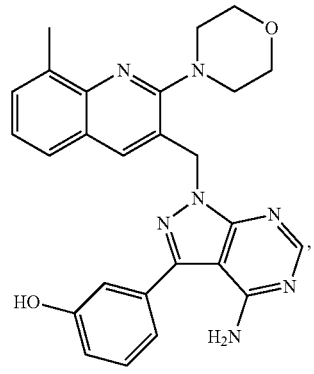
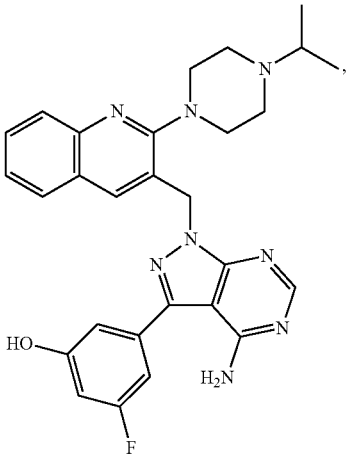

369
-continued
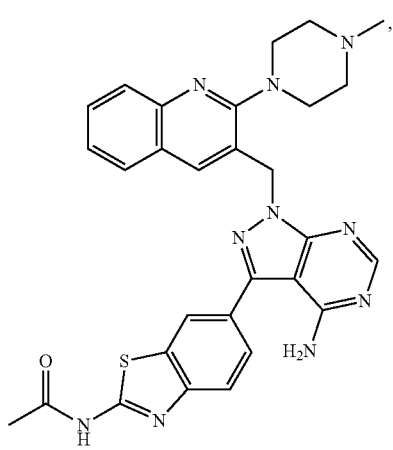
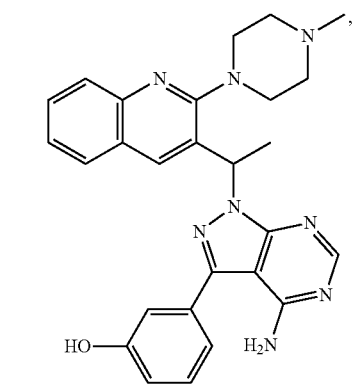
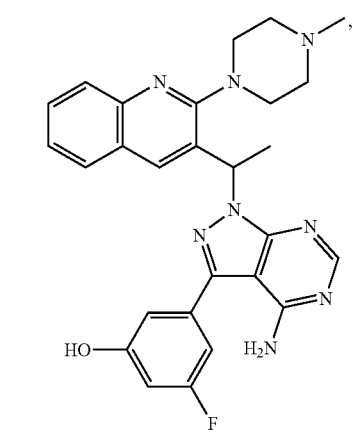
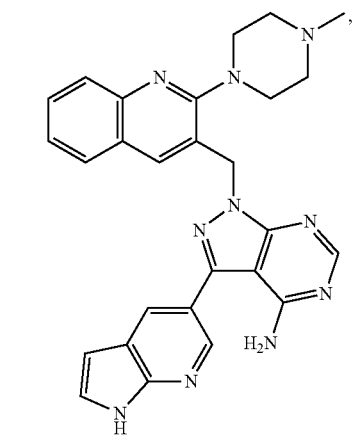
370
-continued
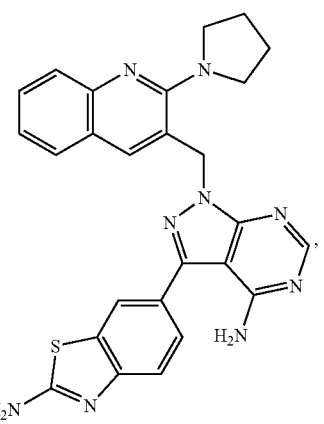
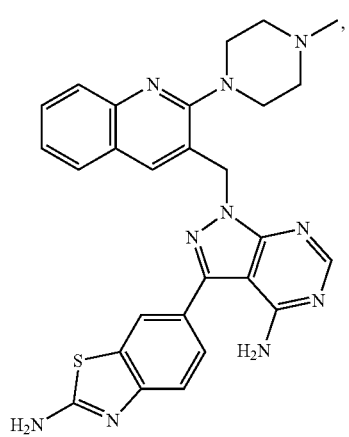
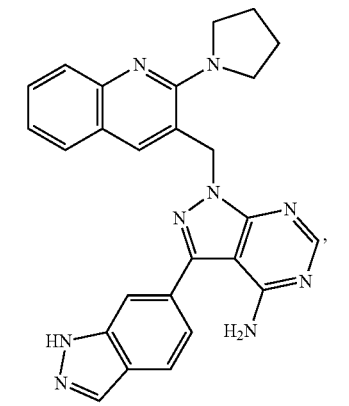
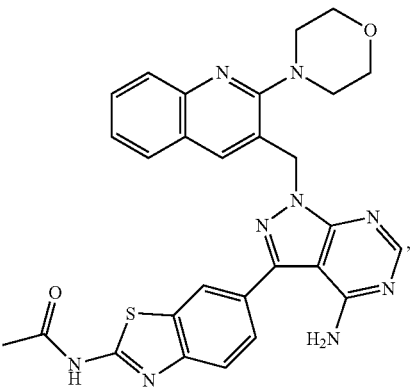

371
-continued
372
-continued
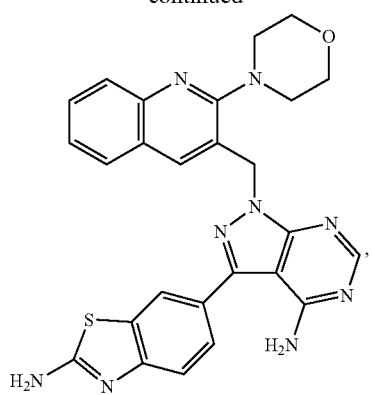
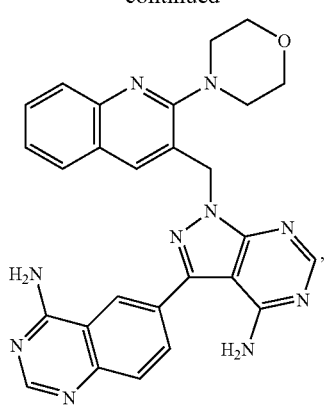

373
-continued
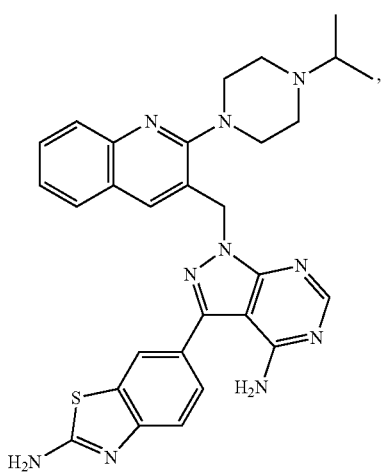
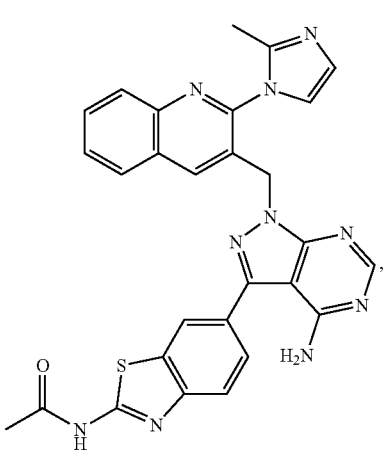
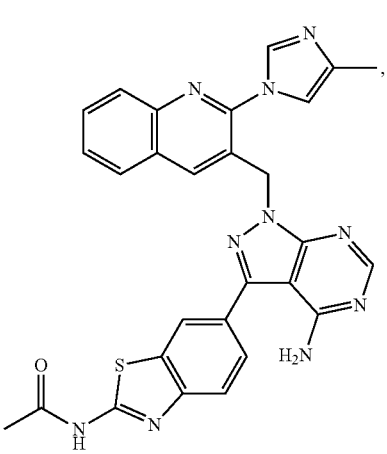
374
-continued
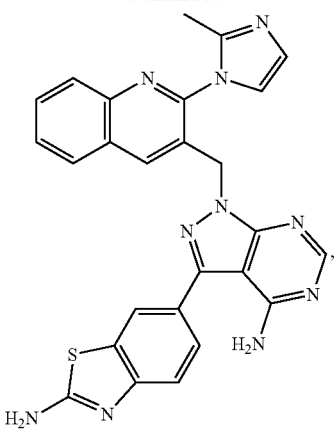
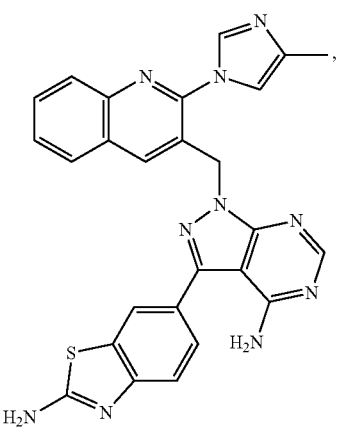
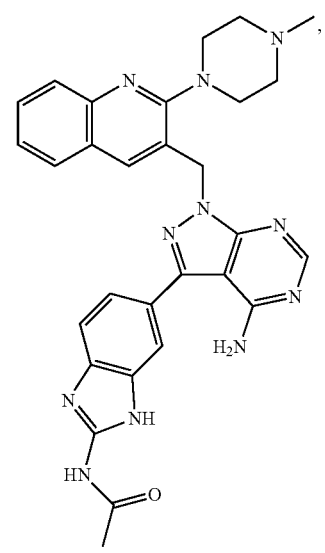

375
-continued
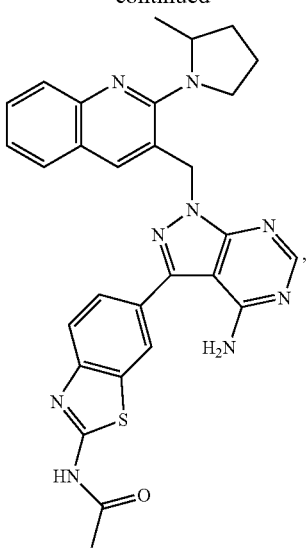
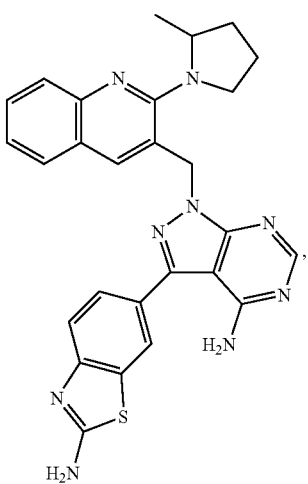
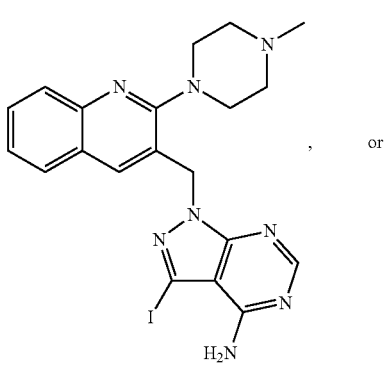
376
-continued
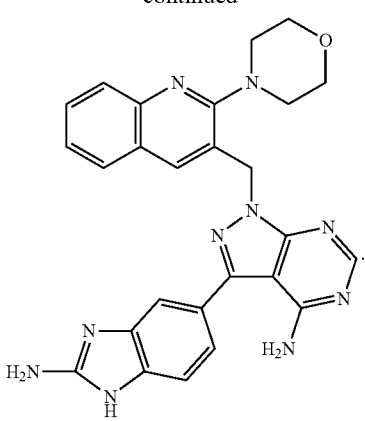
12. The compound of claim 1, or a pharmaceutically acceptable salt thereof, wherein the compound is:
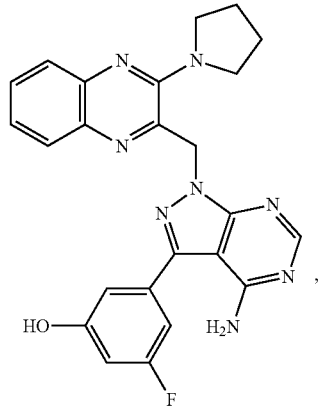

377
-continued
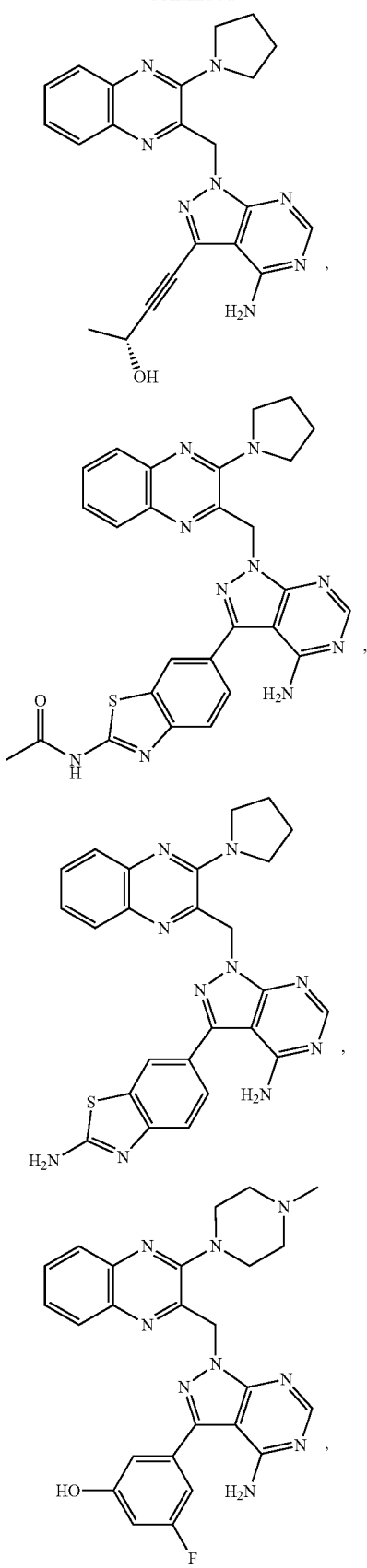
378
-continued
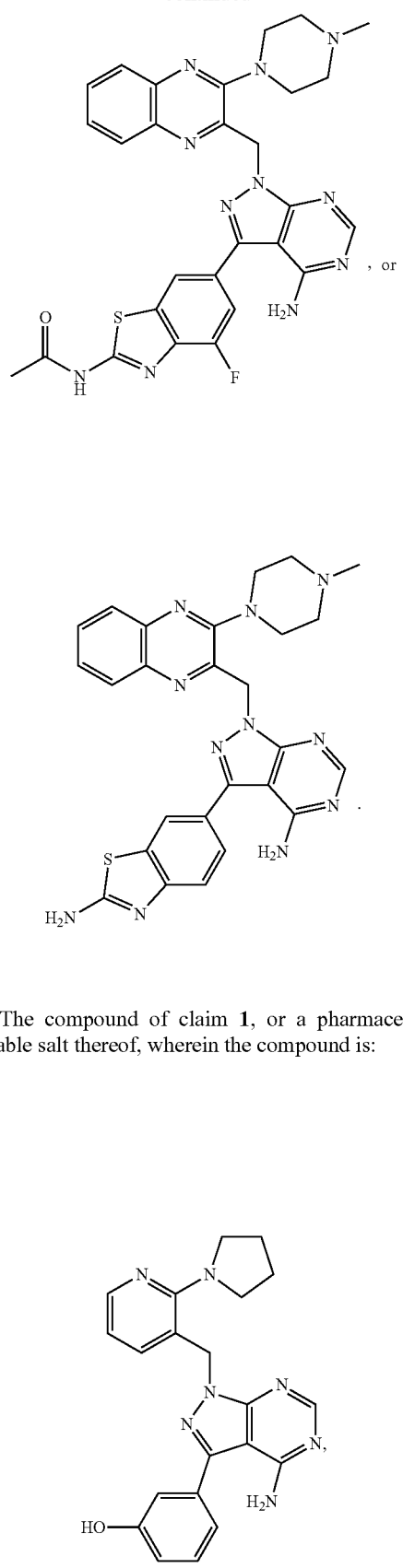
13. The compound of claim 1, or a pharmaceutically acceptable salt thereof, wherein the compound is:

-continued
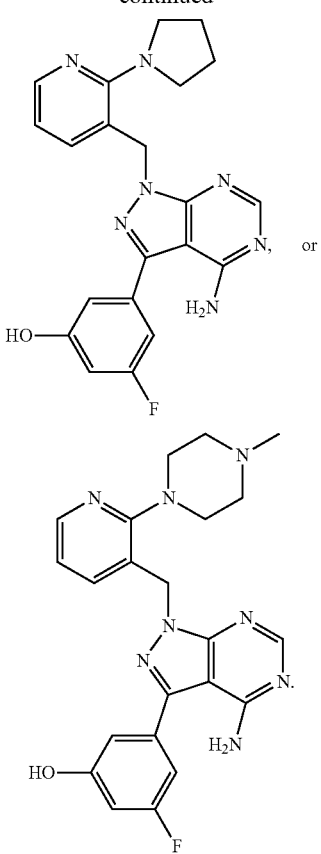
14. The compound of claim 11, or a pharmaceutically acceptable salt thereof, wherein the compound is:
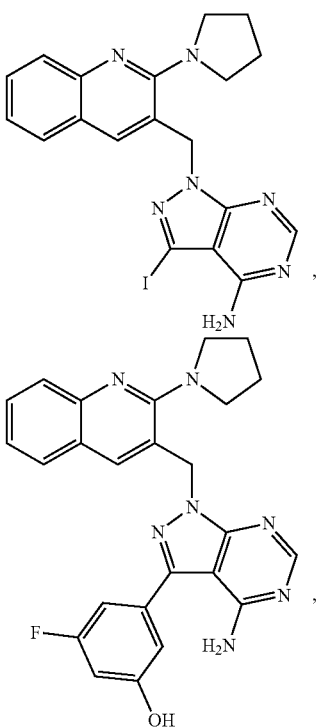
-continued
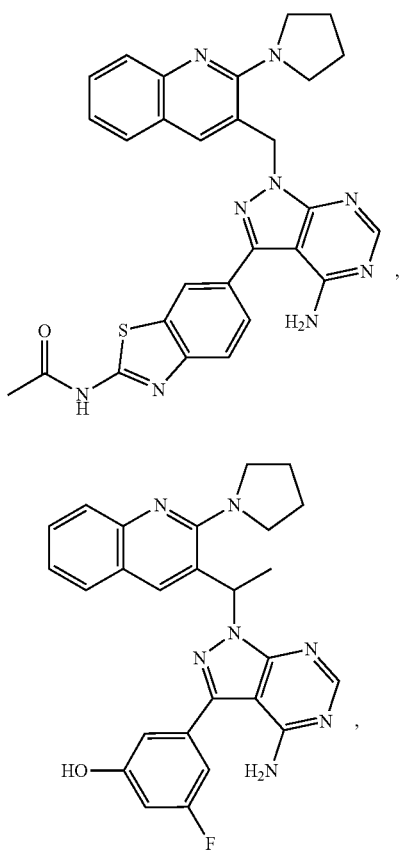
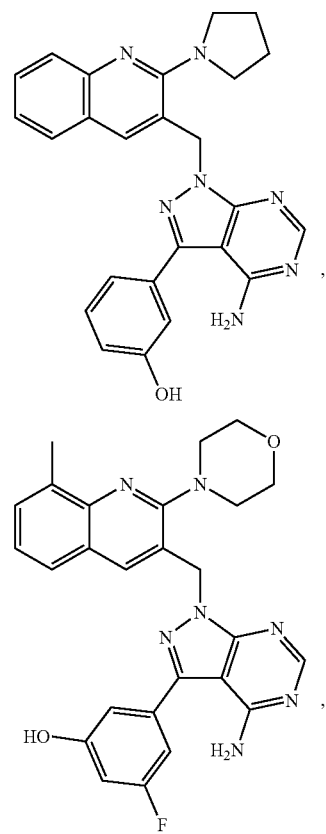

381
-continued
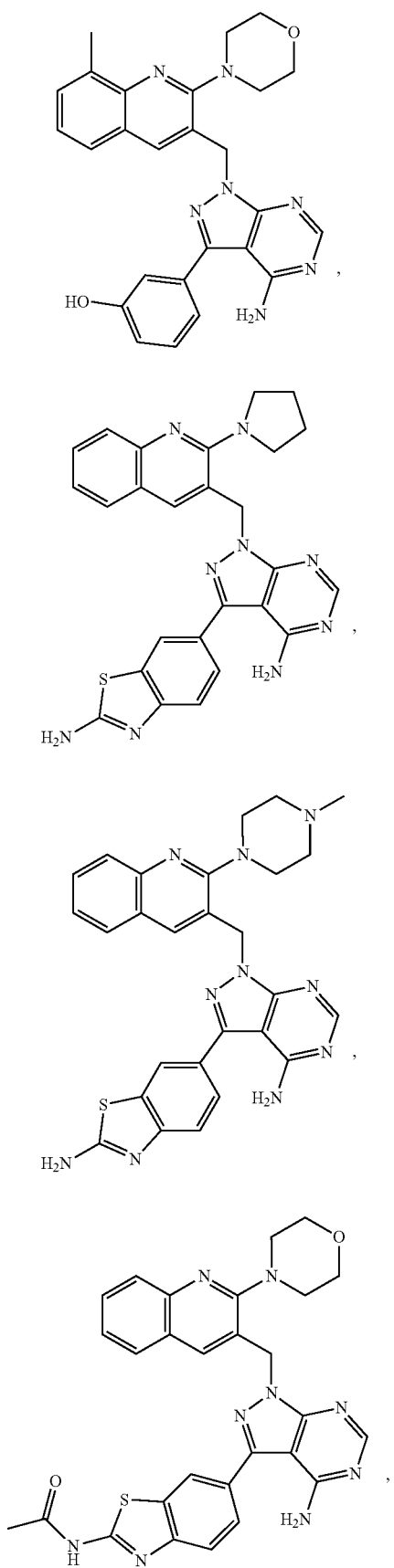
382
-continued
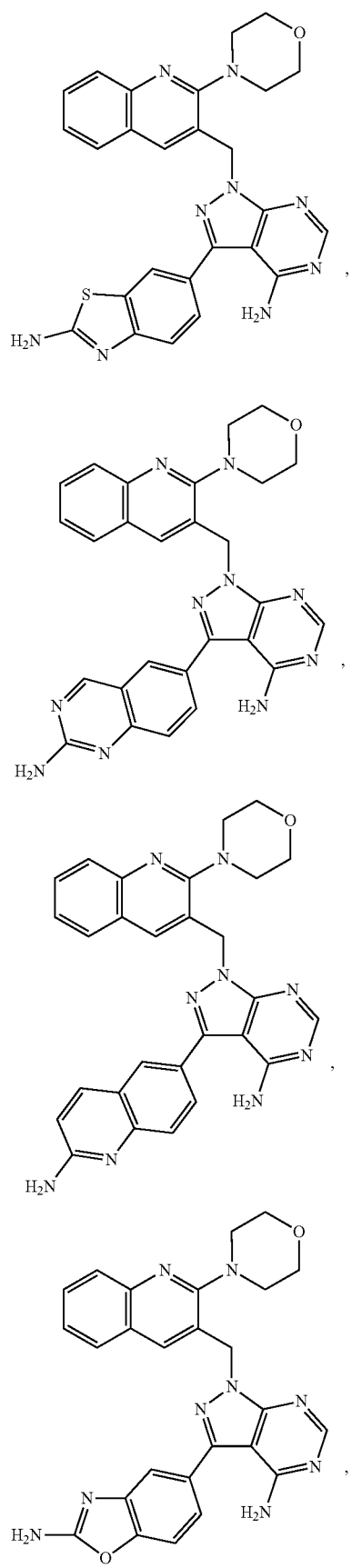

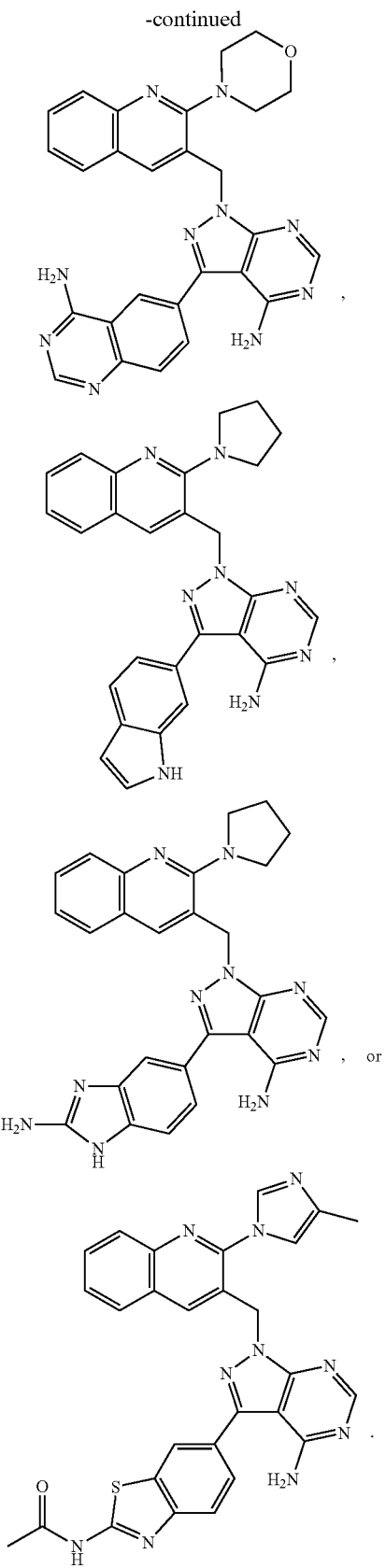
15. The compound of claim 12, or a pharmaceutically acceptable salt thereof, wherein the compound is:
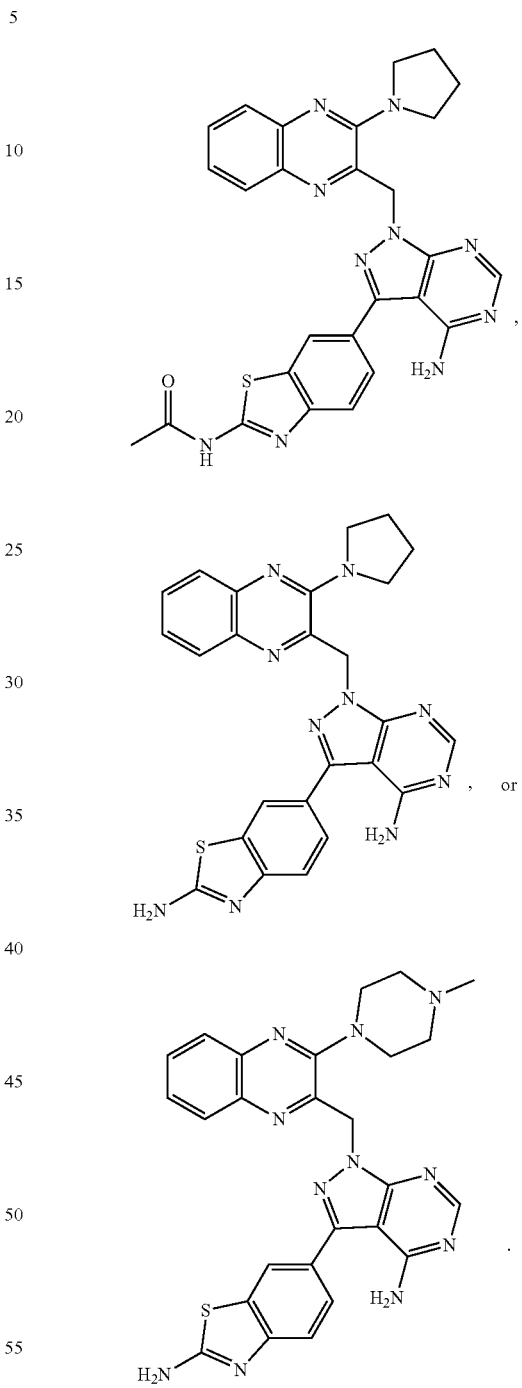
16. A pharmaceutical composition comprising a compound of any one of claim 1, 2, 3, 4, 5, 6, 7, 8, 9, 10, 11, 12, 13, 14, or 15 or a pharmaceutically acceptable salt thereof, and a pharmaceutically acceptable excipient.
* * * * *

UNITED STATES PATENT AND TRADEMARK OFFICE
CERTIFICATE OF CORRECTION

| | | |
|---|---|---|
| PATENT NO. | : 8,703,778 B2 | Page 1 of 1 |
| APPLICATION NO. | : 13/121157 | |
| DATED | : April 22, 2014 | |
| INVENTOR(S) | : Ren et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 215 days.

Signed and Sealed this
Fifth Day of May, 2015

Michelle K. Lee
*Director of the United States Patent and Trademark Office*